US007563443B2

(12) United States Patent
Grant et al.

(10) Patent No.: US 7,563,443 B2

(45) Date of Patent: Jul. 21, 2009

(54) MONOVALENT ANTI-CD40L ANTIBODY POLYPEPTIDES AND COMPOSITIONS THEREOF

(75) Inventors: Steven Grant, Cambridge (GB); Haiqun Liu, Cambridge (GB); Kevin Moulder, Cambridge (GB)

(73) Assignee: Domantis Limited, Cambridge (GB)

( * ) Notice: Subject to any disclaimer, the term of this patent is extended or adjusted under 35 U.S.C. 154(b) by 335 days.

(21) Appl. No.: 11/102,512

(22) Filed: Apr. 8, 2005

(65) Prior Publication Data

US 2006/0062784 A1 Mar. 23, 2006

Related U.S. Application Data

(60) Provisional application No. 60/610,819, filed on Sep. 17, 2004.

(51) Int. Cl.
*A61K 39/395* (2006.01)
*C07K 16/28* (2006.01)

(52) U.S. Cl. .............. 424/154.1; 424/130.1; 424/133.1; 424/135.1; 424/136.1; 424/141.1; 424/143.1; 424/144.1; 424/153.1; 424/173.1; 530/387.1; 530/387.3; 530/388.1; 530/388.2; 530/388.22; 530/388.7; 530/388.73; 530/388.75

(58) Field of Classification Search ....................... None
See application file for complete search history.

(56) References Cited

U.S. PATENT DOCUMENTS

| | | | | |
|---|---|---|---|---|
| 5,474,771 | A | 12/1995 | Lederman et al. | |
| 5,747,037 | A | 5/1998 | Noelle et al. | |
| 5,759,808 | A | 6/1998 | Casterman et al. | |
| 5,800,988 | A | 9/1998 | Casterman et al. | |
| 5,831,012 | A | 11/1998 | Nilsson et al. | |
| 5,840,526 | A | 11/1998 | Casterman et al. | |
| 5,843,440 | A | 12/1998 | Pouletty et al. | |
| 5,869,049 | A | 2/1999 | Noelle et al. | |
| 5,874,541 | A | 2/1999 | Casterman et al. | |
| 5,876,718 | A | 3/1999 | Noelle et al. | |
| 5,876,950 | A | 3/1999 | Siadak et al. | |
| 5,922,545 | A | 7/1999 | Mattheakis et al. | |
| 5,977,307 | A | 11/1999 | Friden et al. | |
| 6,005,079 | A | 12/1999 | Casterman et al. | |
| 6,015,695 | A | 1/2000 | Casterman et al. | |
| 6,297,053 | B1 | 10/2001 | Stemmer | |
| 6,328,964 | B1 | 12/2001 | Noelle et al. | |
| 6,340,459 | B1 | 1/2002 | Yellin et al. | |
| 6,375,950 | B1 | 4/2002 | Noelle et al. | |
| 6,696,245 | B2 | 2/2004 | Winter et al. | |
| 2003/0219437 | A1* | 11/2003 | Yellin et al. | 424/144.1 |
| 2004/0062746 | A1* | 4/2004 | Martinez et al. | 424/78.38 |
| 2005/0043519 | A1 | 2/2005 | Dooley et al. | |
| 2005/0089932 | A1 | 4/2005 | Kolkman et al. | |
| 2006/0063921 | A1* | 3/2006 | Moulder et al. | 530/387.3 |

FOREIGN PATENT DOCUMENTS

| | | |
|---|---|---|
| EP | 0368684 | 5/1990 |
| EP | 0721469 | 7/1996 |
| EP | 0742721 | 11/1996 |
| EP | 0831906 | 4/1998 |
| EP | 1005372 | 6/2000 |
| WO | WO90/05144 | 5/1990 |
| WO | WO-9005144 | 5/1990 |
| WO | WO90/14430 | 11/1990 |
| WO | WO-9014430 | 11/1990 |
| WO | WO 91/01743 | 2/1991 |
| WO | WO92/01047 | 1/1992 |
| WO | WO-9201047 | 1/1992 |
| WO | WO92/20791 | 11/1992 |
| WO | WO-9220791 | 11/1992 |
| WO | WO-9305236 | 3/1993 |
| WO | WO93/11236 | 6/1993 |
| WO | WO 95/06481 A | 3/1995 |
| WO | WO-95/06666 | 3/1995 |
| WO | WO-9506480 | 3/1995 |
| WO | WO-9506481 | 3/1995 |
| WO | WO-9606213 | 2/1996 |
| WO | WO-9640246 | 6/1996 |

(Continued)

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Lund et al., The Journal of Immunology 157: 4963-4969, 1996.*
Abuchowski et al., J. Biol. Chem. 1977, 252:3578.
Alderson et al., 1994, Cytokine, 6(4):407-13.
Aggarwal et al., 2003, J Biol Chem., 278(3):1910-4.
Andoh et al., 2002, Int J Mol Med., 10(5):631-4.
Armitage et al., 1992, Nature 357: 80-82.
Asadullah et al., 2000, Exp Dermatol., 9(4):248-51.

(Continued)

*Primary Examiner*—Phillip Gambel
(74) *Attorney, Agent, or Firm*—Edwards Angell Palmer & Dodge LLP; Kathleen Williams; Amy DeCloux

(57) ABSTRACT

The invention relates to antibody polypeptides that monovalently bind CD40L. Antibody polypeptides that are monovalent for binding of CD40L can inhibit CD40L activity while avoiding potential undesirable effects that can occur with antibodies capable of divalent or multivalent binding of CD40L. In one aspect, a monovalent anti-CD40L antibody polypeptide consists of or comprises a single immunoglobulin variable domain that specifically binds and antagonizes the activity of CD40L, preferably without substantially agonizing CD40 activity. In another aspect, the monovalent anti-CD40L antibody polypeptide is a human antibody polypeptide. The invention further encompasses methods of antagonizing CD40/CD40L interactions in an individual and methods of treating diseases or disorders involving CD40/CD40L interactions, the methods involving administering a monovalent anti-CD40L antibody polypeptide to the individual.

40 Claims, 15 Drawing Sheets

FOREIGN PATENT DOCUMENTS

| | | | |
|---|---|---|---|
| WO | WO-9708320 | | 3/1997 |
| WO | WO-98/58965 | | 12/1998 |
| WO | WO 99/00143 | A | 1/1999 |
| WO | WO-9900143 | | 1/1999 |
| WO | WO-9920749 | | 4/1999 |
| WO | WO-9923221 | | 5/1999 |
| WO | WO-0029004 | | 5/2000 |
| WO | WO-0069907 | | 11/2000 |
| WO | WO 01/68860 | A | 9/2001 |
| WO | WO-0168860 | | 9/2001 |
| WO | WO-0190192 | | 11/2001 |
| WO | WO 01/94586 | A | 12/2001 |
| WO | WO-0194586 | | 12/2001 |
| WO | WO 02/06485 | A | 1/2002 |
| WO | WO-0206485 | | 1/2002 |
| WO | WO 02/18445 | A | 3/2002 |
| WO | WO-0218445 | | 3/2002 |
| WO | WO-0248193 | | 6/2002 |
| WO | WO-03002609 | | 1/2003 |
| WO | WO-03031611 | | 4/2003 |
| WO | WO-03035694 | | 5/2003 |
| WO | WO 2004/003019 | A | 1/2004 |
| WO | WO-2004003019 | | 1/2004 |
| WO | WO-2004041862 | | 5/2004 |
| WO | WO-2004041865 | | 5/2004 |
| WO | WO-2004044011 | | 5/2004 |
| WO | WO 2004/058821 | A | 7/2004 |
| WO | WO 2004/058822 | A | 7/2004 |
| WO | WO-2004058821 | | 7/2004 |
| WO | WO-2004058822 | | 7/2004 |
| WO | WO 2005/035572 | A | 4/2005 |
| WO | WO-2005035572 | | 5/2005 |
| WO | WO-2005040229 | | 5/2005 |

OTHER PUBLICATIONS

Azuma, M. et al., 1993, Nature 366, 76-79.
Balasa et al., 1997, J. Immunol. 159: 1420.
Bennett et al., 1998, Nature 393: 478-480.
Beuken et al., J. Mol. Biol. (2001) 310, 591-601.
Blair et al., 2000, J. Exp. Med. 191: 651-660.
Blazar et al., 1997, J. Immunol. 158: 29-39.
Bird et al., 1988, Science 242:423-426.
Borset et al.,1994, Eur J Haematol., 53(1):31-7.
Boumpas et al., 2003, Arthritis Rheum. 48: 719-727.
Brach et al. 1992, Cancer Res., 52(8):2197-2201.
Brenner et al., 1997, FEBS Lett. 417: 301-306.
Burchill et al., 2003 Infect Immun., 71(6):3437-42.
Chess, C., 2001, in Therapeutic Immunology, 2nd edition, Austen, K.F., Burakoff, S., Rosen, F. and Strom. T., eds., Blackwell Sciences, pp. 441-456.
Chiswell et al., 1992, Trends Biotech. 10: 80.
Caryanniotis et al., 1997, Immunology 90: 421-426.
Chegini et al., 2003, Am J Reprod Immunol. 49(2):75-83.
Chen et al., 2003, J Biol Chem. 278(19):17036-43.
Cheng et al., 2002, Am J Respir Crit Care Med., 166(3):409-16.
Chess, 2001, "Blockade of the CD40L/CD40 Pathway," in Therapeutic Immunology 2nd Edition, Austen, Burakof, Rosen and Strom, Eds., Blackwell Sciences (Pubs.), pp. 441-456.
Chothia et al., 1992, J. Mol. Biol. 227: 799.
Chothia et al., 1989, Nature 342: 877.
Chothia et al., 1985, J. Mol. Biol. 186: 651-663.
Chothia and Lesk, 1987, J. Mol. Biol. 196(4):901-917.
Clark & Ledbetter, 1986, Proc. Natl. Acad. Sci. U.S.A. 83: 4494.
Kuperman et al., 2002, Nat Med., 8(8):885-9.
Corre et al., 1999, Exp Hematol., 27(1):28-36.
Covey et al., 1994, Mol. Immunol. 31: 471-484.
Cox et al., 1994, Eur. J. Immunol. 24: 827.
Crameri et al., 1996, Nature Med., 2: 100.
Croft et al., 1999, Am J Pathol., 154(4):1149-58.
Cua et al., 2003, Nature, 421(6924):744-8.
Davies & Riechmann, 1995, Biotechnology N.Y. 13: 475-479.
Davies & Reichmann, 1994, FEBS Lett. 339: 285-290.
Davis et al., 2001, J. Rheumatol. 28: 95-101.
DeBlaker-Hohe, 1995, Cell Immunol., 165(1):33-43.
Delgado et al., 1996 Br. J. Cancer, 73: 175.
Dellinger, 2003, Clin Infect Dis., 36(10):1259-65.
Deng et al., 1994, J. Biol. Chem., 269: 9533.
Denning, 1996, J. Immunol., 156(12):4807-14.
Durie et al., 1993, Science 261: 132 [p. 122].
Early et al., 1996, J. Immunol. 157: 3159-3164.
Eckenberg et al., 2000, Immunol., 165(8): 4312-8.
Eum et al., 2003, J Allergy Clin Immunol., 111(5):1049-61.
Feliciani et al., 1999, Int J Immunopathol Pharmacol., 12(2):55-61.
Ferretti et al,. 2003, J Immunol. 170(4):2106-12.
Francis et al., Pharmaceutical Biotechnology vol. 3 (Borchardt, R. T. ed.); and Stability of Protein Pharmaceuticals: in vivo Pathways of Degradation and Strategies for Protein Stabilization 1991 pp. 235-263, Plenum, NY.
Freedman, A. S. et al., 1987, J. Immunol. 137, 3260-3267.
Freeman, G. J. et al., 1993, J. Exp. Med. 178, 2185-2192.
Freeman, G. J. et al., 1993, Science 262, 909-911.
Freeman, G. J. et al., 1991, J. Exp. Med. 174, 625-631.
Freeman, G. J. et al., 1989, J. Immunol. 143, 2714-2722.
Fukao et al., 2000, J Immunol., 164(1):64-71.
Gahroudi et al., 1997, FEBS Lett. 414: 521-526.
Garn et al., 2002, Immunobiology, 2005(3):321-34.
Garrone et al., 1995, J Exp Med 182, 1265-1273.
Gastinel et al., 1992, PNAS, 89:638.
Gerritse, 1996, Proc. Natl. Acad. Sci. U.S.A. 93: 2494.
Gobburu, et al., 1998, JPET, 286, 925-930.
Gordon et al., 1988, J. Immunol. 140: 1425.
Gordon et al., 1987, Eur. J. Immunol. 17: 1535.
Gounni et al., 2000, Blood, 96(6):2163-71.
Graf et al., 1992, Eur. J. Immunol. 22: 3191-3194.
Greenberg et al. Nature 374: 168-173 1995.
Greenwald et al., 2000, Crit. Rev. Ther. Drug Carrier Syst. 17:101.
Gregory et al., 2003, J. Immunol., 170(11):5359-66.
Grewal et al., 1996, Science 273: 186.
Hahn et al., 2003, J Allergy Clin Immunol., 111(6):1361-1369.
Halász et al., 2003, Allergy Asthma Proc., 24(2):111-8.
Hamers-Casterman et al., 1993, Nature 363: 446-448.
Hellings et al., 2003, Am J Respir Cell Mol Biol., 28(1):42-50.
Herbelin et al., 1992, J Immunol., 148(1):99-105.
Herman et al., 1994, Macromol. Chem. Phys. 195:203.
Hermouet et al., 2002, Cytokine, 20(4):178-83.
Hershfield et al., 1991, PNAS 88:7185.
Holliger and Hudson, 2005, Nature Biotechnol., 23:1126-1136.
Holliger et al, Nat. Biotechnol. 1997, 15(7):632-6.
Holliger et al., 1993, PNAS (USA) 90:6444-6448.
Holt et al., 2003, Trends Biotech., 21(11):484-490 [ISR].
Hood et al. (1967) Cold Spring Harbor Symp. Quant. Biol., 48: 133.
Hoogenboom et al., 1991, Nucleic Acids Res. 19: 4133-4137.
Hoogenboom & Winter, 1992, J. Mol. Biol., 227: 381.
Honorati et al., 2002, Osteoarthritis Cartilage, 10(10):799-807.
Howard et al., 1999, J. Clin . Invest. 103: 281-290.
Howells et al., 1991, Eur J Immunol., 21(1):97-101.
Huang et al., 2002, Arthritis Rheum. 46: 1554-1562.
Hudson et al., Journal Immunol Methods 231 (1999) 177-189.
Hurst et al., 2002, J Immunol., 169(1):443-53.
Ikeda et al., 2003 Blood, 101(9):3594-6.
Itoh et al., 1994, Cell Immunol., 157(2):478-88.
Jones and Chan, 2002, Am J Respir Cell Mol Biol., 26(6):748-53.
Joosten et al., 2003, Arthritis Rheum., 48(2):339-47.
Jutel et al., 2003, Eur J Immunol., 33(5):1205-14.
Kabat et al., 1991, Sequences of proteins of immunological interest, U.S. Department of Health and Human Services.
Kalled et al., 1998, J. Immunol. 160: 2158-2165.
Kalunian et al., 2002, Arthritis Rheum. 46: 3251-3258.
Kaneda et al., 2003, J Interferon Cytokine Res., 23(3):155-62.
Kaufmann, 2001, Rheumatology (Oxford)., 40(4):474-5.
Keates et al, 2000, Gastroenterology., 119(4):972-82.
Kelly-Welch, 2003, Science, 300(5625):1527-8.
Kirk et al., 1997, Proc. Natl. Acad Sci. U.S.A. 94: 8789-8794.

Kitamura et al., 1991, Cancer Res. 51:4310.
Kong et al., 1999, Nature, 402:304-309.
Kotake and Kamatani, 2002, Drug News Perspect., 15(1):17-23.
Kudo et al., 2003, Bone, 32(1):1-7.
Laan et al., 2003, Eur Respir J. 21(3):387-93.
Larsen et al., 1996, Nature 381: 434-438.
Laman et al., 1998, Mult. Scler. 4: 14.
Lankford and Frucht, 2003, J Leukoc Biol. 73(1):49-56.
Larsen et al., 1996, Transplantation 61: 4.
Lauwerys et al., 1999, Cytokine, 11(11):822-30.
Lauwerys et al., 1998, Eur J Immunol., 28(6):2017-24.
Lazenby et al., 1992, Cytokine, 4(6):479-87.
Lederman et al., 1993, Curr. Opin. Immunol. 5: 439-444.
Lederman et al., 1992, J. Exp. Med., 175: 1091-1101.
Lederman et al., 1992, J. Immunol. 149: 3817-3826.
LeGrand et al., 2001, Arthritis Rheum., 44(9):2078-83.
Li et al., 2001, Nat Med., 7(1):114-8.
Liao et al., 2002, J. Immunol., 169(8):4288-97.
Ling and Mattiasson, 1983, Immunol. Methods 59:327.
Linsley & Ledbetter, 1993, Ann. Rev. Immunol. 11: 191-212; Jenkins et al., 1993, Curr Opin. Immunol. 5: 361-367; and Boussiotis et al., 1996, Immunol. Rev. 153: 5-26.
Little et al., 2003, Am J Respir Cell Mol Biol., 28(3):354-62.
Lorenz and Bischoff, 2001, Immunol Rev., 179:57-60.
Low et al., 1996, J. Mol. Biol., 260: 359.
Lowry et al., 1951, J. Biol. Chem. 193: 265-275.
Lubberts et al., 2003, J Immunol., 170(5):2655-62.
Mach et al., 1998, Nature 394: 200-203.
Martin et al., 1996, J. Mol. Biol. 263: 800.
Mathy et al., 2000, Immunology., 100(1):63-9.
Matthews et al., 2003, Am. J. Transplantation, 3:794-803.
Mehrota et al., 1995, J Immunol., 154(10):5093-102.
Minshall and Hamid, 2000, Clin Exp Allergy., 30(3):301-303.
Mohan et al., 1995, J. Immunol. 154: 1470-1480.
Moriwaki et al., 2003, Metabolism, 52(5):605-8.
Musashi et al., 1991, Blood, 78(6):1448-51.
Mulydermans et al., 2001, Trends Biochem. Sci., 26(4):230-235 [ISR].
Mysliwiec et al., 2003, Int Immunopharmacol., 3(4):549-52.
Nielsen et al., 2003, Scand J Gastroenterol., 38(2):180-5.
Nucci et al., Adv. Drug Delivery Reviews 1991, 6:133.
Okamoto et al., 2002, Blood, 99(4):1289-98.
Padian et al., 1994, Mol. Immunol. 31: 169-217.
Pankow et al., 2000, J. Immunol. 165(1):263-70.
Parada et al., 1998, J. Immunol., 1;160(5):2115-20.
Parker et al., 1995, Proc. Natl. Acad. Sci. U.S.A. 92: 9560-9564.
Pedley et al., 1994, Br. J. Cancer, 70:1126.
Pflanz et al., 2002, Immunity., 16(6):779-90.
Plenum, NY; Goodson and Katre, 1990, Bio/Technology, 8:343.
Qin et al., 2001, Blood., 98(9):2778-83.
Ragab et al., 2002, Am J Physiol Cell Physiol., 283(3):C679-87.
Riechmann et al., 1995, Bio/Technology, 13: 475.
Reiter et al., 1994, Proetin Eng. 7:697-704.
Rich and Kupper, 2001, Curr Biol., 11(13):R531-4.
Ridge et al., 1998, Nature 393: 474-478.
Ridgeway et al., 1996, Protein Eng. 7:617-621.
Roopenian et al., 2003 J. Immunol. 170:3528.
Salmaggi et al., 2003, J. Neurooncol., 62(3):297-303.
Shirai et al., 1996, FEBS Letters 399: 1.
Schoenberger et al., 1998, Nature 393: 480-483.
Scott & Smith, 1990, Science 249: 386.
Sinah et al., 2002, Blood, 100(7):2642-9.
Smith, 1985, Science 228: 1315.
Spadaro et al., 2003, Clin Rheumatol., 22(2):107-11.
Stemmer, 1994, Nature 370: 389-39.
Strengell et al., 2003, J Immunol., 170(11):5464-9.
Stuber et al., 1996, J. Exp. Med. 183: 693-698.
Tahar et al., 1994, Eur Cytokine Netw., 5(5):455-60.
Tain et al., 2003, Cytokine. 2003, 21(3):155-9.
Temann et al., 2002, J Clin Invest., 109(1):29-39.
Terada et al., 2000, Clin Exp Allergy., 30(3):348-55.
Thomas and Heywood, 2000, Thorax, 57(9):774-8.
Toda, 2003, J Allergy Clin Immunol., 111(4):875-81.
Tomlinson et al., 1996 J. Mol. Biol., 256: 813.
Tomlinson et al., 1995, EMBO J. 14: 4628.
Tomlinson et al., 1992, J. Mol. Biol. 227: 7768.
Uckun et al., 1991, J. Biol. Chem. 266:17478.
Ward et al., 1989, Nature 341: 544-546.
Wilkinson et al., 1987, Immunol. Letters, 15: 17.
Winter et al., 1994, Ann. Rev. Immunology 12, 433-55.
Yellin et al., 1995, J. Exp. Med. 182: 1857-1864.
Yellin et al., 1995, J. Leuko. Biol. 58: 209-216.
Yellin et al., 1991, J. Immunol. 147: 3389-3395.
Yoshida et al., 2001, Cell Immunol., 207(2):75-80.
Zalipsky, 1995, Bioconjug. Chem. 6:150.
Zhu et al., 1997, Protein Science 6:781-788.
Zhang, 1995, J Exp Med., 182(3):699-709.
Zhou et al., 2001, Respir Res., 2(2):80-4.
Bram, Peter et al. "A humanized anti-human CD154 monoclonal antibody blocks CD154-CD40 mediated human B cell activation" *International Immunopharmacology*, vol. 1, No. 2, Feb. 2001.
Muyldermans S. et al. "Recognition of antigens by single-domain antibody fragments: the superfluous luxury of paired domains" *Trends in Biochemical Sciences, Elsevier*, Haywards, GB, vol. 26, No. 4, Apr. 2001.
Holt L.J. et al. "Domain antibodies: proteins for therapy" *Trends in Biotechnology, Elsevier, Publications*, Cambridge, GB, vol. 21, No. 11, Nov. 2003.
Durie F. et al. "Prevention of Collagen-induced arthritis with an antibody to gp39, the ligand for CD40" *Science, American Assoication for the Advancement of Science*, US, vol. 261, No. 5126, Sep. 3, 1993.
International Search Report, PCT/GB2005/003562, Nov. 23, 2005.
Hoogenboom, H. R.; Nature Biotechnology; "Mix and Match: Building Manifold Binding Sites"; vol. 15, p. 125-126, Feb. 1997.
Conrath, K. et al., The Journal of Biological Chemistry, "Camel Single-domain Antibodies as Modular Building Units in Bispecific and Bivalent Antibody Constructs", vol. 276, No. 10, Issue of Mar. 9, 2001, p. 7346-7350.
Smith, B. et al., Bioconjugate Chem, "Prolonged in Vivo Residence Times of antibody Fragments Associated with Albumin"; vol. 12 p. 750-756; 2001.
Reiter, Y. et al., J. Mol. Biol, "An Antibody Single-domain Phage Display Library of a Native Heavy Chain Variable Region: Isolation of Functional Single-doamin VH Molecules with a Unique Interface", 1999, vol. 290, p. 685-698.
Nygren, P. et al., Vaccines, "In Vivo Stabilization of a Human Recombinant CD4 Derivative by Fusion to a Serum-albumin-binding Receptor", vol. 91, 1991, p. 363-368.
Ghahroudi, et al., Federation of European Biochemical Societies, "Selection and Identification of Single Domain Antibody Fragments from Camel Heavey-chain Antibodies"; 1997, p. 521-526.
Van der Linden, R. et al., Journal of Immunological Methods "Induction of Immune Responses and Molecular Cloning of the Heavy Chain Antibody Repertoire of Lama Glama", 2000, p. 185-195.
Stahl, et al. Biomedische Bibl, "The Use of Gene Fusions to Protein a And Protein G In Immunology and Biotechnology", 1997, p. 66-76.
Waldmann, et al., The Journal of Clinical Investigation, "The Renal Handling of Low Molecular Weight Proteins"; vol. 51, 1972, p. 2162-2174.
Gale Encyclopedia of Medicine, Gale Research, 1999, p. 419.
Hulme & Hardwicke, Proc Royal Soc. Medicine, "Kidney Function and Structure", vol. 59, 1966, p. 509-512.
Birkett, D. "Pharmacokinetics Made Easy", 1998, p. 16-24.
Cortez-Retamozo, V., Int. J. Cancer, Efficient Tumor Targeting By Single-Domain Antibody Fragments of Camels; 2002, p. 456-462.
Patentee's $25^{th}$ Sep. 2006 letter regarding EP05076402.6.
Patentee's $23^{rd}$ Dec. 2005 letter regarding EP03776677.1.
Ward, et al., Letters to Nature; "Binding Activities of a Repertoire of Single Immunoglobulin Variable Domains Secreted from *Escherichia coli*"; vol. 341, 1989; p. 544-546.
Van den Beucken, et al., J. Mol. Biol.; "Building Novel Binding Ligands to B7.1 and B7.2 Based on Human Antibody Sinigle Variable Light Chain Domains", 2001, vol. 310, p. 591-601.

Holliger et al., Nature Biotechnology, "Retargeting Serum Immunoglobulin with Bispecific Diabodies", 1997, vol. 15, p. 632-638.

Mulyldermans, S., Molecular Biotechnology, "Single Domain Camel Antibodies: Current Status", 2001, vol. 74, p. 277-302.

Conrath, K. et al.; β-Lactamase Inhibitors Derived from Single-Domain Antibody Fragments Elicited in the *Camelidae* Antimicrobial Agents and Chemotherapy, Oct. 2001, p. 2807-2812 vol. 45, No. 10.

* cited by examiner

Figure 5

```
     E   V   Q   L   L   E   S   G   G   G   L   V   Q   P   G   G
1    GAG GTG CAG CTG TTG GAG TCT GGG GGA GGC TTG GTA CAG CCT GGG GGG
     CTC CAC GTC GAC AAC CTC AGA CCC CCT CCG AAC CAT GTC GGA CCC CCC

     S   L   R   L   S   C   A   A   S   G   F   T   F   S   S   Y
49   TCC CTG CGT CTC TCC TGT GCA GCC TCC GGA TTC ACC TTT AGC AGC TAT
     AGG GAC GCA GAG AGG ACA CGT CGG AGG CCT AAG TGG AAA TCG TCG ATA
                                                             HCDR1
     A   M   S   W   V   R   Q   A   P   G   K   G   L   E   W   V
97   GCC ATG AGC TGG GTC CGC CAG GCT CCA GGG AAG GGT CTA GAG TGG GTC
     CGG TAC TCG ACC CAG GCG GTC CGA GGT CCC TTC CCA GAT CTC ACC CAG

     S   A   I   S   G   S   G   G   S   T   Y   Y   A   D   S   V
145  TCA GCT ATT AGT GGT AGT GGT GGT AGC ACA TAC TAC GCA GAC TCC GTG
     AGT CGA TAA TCA CCA TCA CCA CCA TCG TGT ATG ATG CGT CTG AGG CAC
                                 HCDR2
     K   G   R   F   T   I   S   R   D   N   S   K   N   T   L   Y
193  AAG GGC CGG TTC ACC ATC TCC CGT GAC AAT TCC AAG AAC ACG CTG TAT
     TTC CCG GCC AAG TGG TAG AGG GCA CTG TTA AGG TTC TTG TGC GAC ATA

     L   Q   M   N   S   L   R   A   E   D   T   A   V   Y   Y   C
241  CTG CAA ATG AAC AGC CTG CGT GCC GAG GAC ACC GCG GTA TAT TAC TGT
     GAC GTT TAC TTG TCG GAC GCA CGG CTC CTG TGG CGC CAT ATA ATG ACA
```

FIGURE 5 (continued)

```
         A   K   S   Y   G   A   F   D   Y   W   G   Q   G   T   L   V
289     GCG AAA AGT TAT GGT GCT TTT GAC TAC TGG GGC CAG GGA ACC CTG GTC
        CGC TTT TCA ATA CCA CGA AAA CTG ATG ACC CCG GTC CCT TGG GAC CAG
                          HCDR3

         T   V   S   S
337     ACC GTC TCG AGC
        TGG CAG AGC TCG
```

Figure 6

```
       D   I   Q   M   T   Q   S   P   S   S   L   S   A   S   V   G
1      GAC ATC CAG ATG ACC CAG TCT CCA TCC TCC CTG TCT GCA TCT GTA GGA
       CTG TAG GTC TAC TGG GTC AGA GGT AGG AGG GAC AGA CGT AGA CAT CCT

       D   R   V   T   I   T   C   R   A   S   Q   S   I   S   S   Y
49     GAC CGT GTC ACC ATC ACT TGC CGG GCA AGT CAG AGC ATT AGC AGC TAT
       CTG GCA CAG TGG TAG TGA ACG GCC CGT TCA GTC TCG TAA TCG TCG ATA
                                                LCDR1
       L   N   W   Y   Q   Q   K   P   G   K   A   P   K   L   L   I
97     TTA AAT TGG TAC CAG CAG AAA CCA GGG AAA GCC CCT AAG CTC CTG ATC
       AAT TTA ACC ATG GTC GTC TTT GGT CCC TTT CGG GGA TTC GAG GAC TAG

       Y   A   A   S   S   L   Q   S   G   V   P   S   R   F   S   G
145    TAT GCT GCA TCC AGT TTG CAA AGT GGG GTC CCA TCA CGT TTC AGT GGC
       ATA CGA CGT AGG TCA AAC GTT TCA CCC CAG GGT AGT GCA AAG TCA CCG
                    LCDR2
       S   G   S   G   T   D   F   T   L   T   I   S   S   L   Q   P
193    AGT GGA TCT GGG ACA GAT TTC ACT CTC ACC ATC AGC AGT CTG CAA CCT
       TCA CCT AGA CCC TGT CTA AAG TGA GAG TGG TAG TCG TCA GAC GTT GGA

       E   D   F   A   T   Y   Y   C   Q   Q   S   Y   S   T   P   N
241    GAA GAT TTT GCT ACG TAC TAC TGT CAA CAG AGT TAC AGT ACC CCT AAT
       CTT CTA AAA CGA TGC ATG ATG ACA GTT GTC TCA ATG TCA TGG GGA TTA
                                                    LCDR3
       T   F   G   Q   G   T   K   V   E   I   K   R
289    ACG TTC GGC CAA GGG ACC AAG GTG GAA ATC AAA CGG
       TGC AAG CCG GTT CCC TGG TTC CAC CTT TAG TTT GCC
```

Figure 8. GAS1 secretion signal coding sequences

```
                   (1) 1        ,10           ,20           ,30           ,40           ,50            66
GAS wt             (1) ATGTTGTTTAAATCCCTTTCAAAGTTAGCAACCGCTGCTGCTTTTTTTGCTGGCGTCGCAACTGCG
GAS leader e.coli  (1) ATGCTGTTTAAAAGCCTGAGCAAACTGGCGACCGCGGCGGCGTTTTTTGCGGGCGTGGCGACCGCG
GAS leaderAT       (1) ATGTTATTTAAATCATTATCAAAATTAGCAACCGCAGCAGCATTTTTTGCAGGCGTGGCAACAGCG
```

MONOVALENT ANTI-CD40L ANTIBODY POLYPEPTIDES AND COMPOSITIONS THEREOF

RELATED APPLICATIONS

This application is claims priority under 35 U.S.C. § 119(e) to U.S. patent application Ser. No. 60/610,819 filed Sep. 17, 2004, the entirety of which is incorporated herein by reference.

BACKGROUND OF THE INVENTION

CD40 is a 50 kD cell surface glycoprotein molecule expressed on the surface of mature and immature B cells, macrophages, follicular dendritic cells, thymic epithelium, normal basal epithelium, and some tumor-derived cell lines. The CD40 molecule is a member of the TNF receptor family, and has important signaling functions leading to a variety of downstream effects in various cell types. Early studies showed that cross-linking of CD40 on the B cell surface with an antibody resulted in B cell proliferation and activation. Antibody cross linking of CD40 in the presence of IL-4 induces proliferation and class switching in vitro, B cell aggregation via LFA-1 (Gordon et al., 1988, J. Immunol. 140: 1425), and serine/threonine and tyrosine phosphorylation of a number of intracellular substrates (Gordon et al., 1988, supra; Uckun et al., 1991, J. Biol. Chem. 266:17478). Anti-CD40 monoclonal antibodies also prime B cells to proliferate in response to agents such as PMA (Gordon et al., 1987, Eur. J. Immunol. 17: 1535) and anti-CD20 antibody (Clark & Ledbetter, 1986, Proc. Natl. Acad. Sci. U.S.A. 83: 4494).

The receptor homology of CD40 and the antibody cross-linking studies showing a central role for CD40 in B cell activation prompted the search for a natural ligand. A mutant of the Jurkat T cell line was found to constitutively activate human B cells to secrete immunoglobulin (Yellin et al., 1991, J. Immunol. 147: 3389-3395). A monoclonal antibody, termed 5c8, was raised which specifically reacted with the mutant line, but not with the parental Jurkat cell line. The 5c8 antibody immunoprecipitated a 30 kD (more accurately, 29.3 kD, 261 amino acids) cell surface polypeptide and was found to specifically inhibit the B cell helper function of the mutant cell line. (Lederman et al., 1992, J. Exp. Med., 175: 1091-1101; Lederman et al., 1992, J. Immunol. 149: 3817-3826; Lederman et al., 1993, Curr. Opin. Immunol. 5: 439-444;). The 30 kD polypeptide ligand of the 5c8 antibody was termed T-BAM, for T-B-cell Activating Molecule. A second line of studies used molecular cloning techniques to identify polypeptides that specifically bind the CD40 molecule. cDNA clones for a specific ligand of CD40 were identified in a CD40 binding assay and alternately termed CD40 Ligand (CD40L), gp39, CD154, or TRAP (Graf et al., 1992, Eur. J. Immunol. 22: 3191-3194; Armitage et al., 1992, Nature 357: 80-82; and Aruffo et al., 1993, Cell 72: 291-300). Subsequently, the CD40L clone was found to have the same structure as T-BAM (Covey et al., 1994, Mol. Immunol. 31: 471-484). Human CD40L protein shows 82.8% and 77.4% identity at the nucleic acid and amino acid levels, respectively, to a similar protein isolated from murine EL4 thymoma cells. Both of these proteins are ligands for CD40 cell surface antigen expressed on resting B cells. CD40L has also been described as IMD3, a protein involved in hyper-IgM immunodeficiency syndrome.

The human gene encoding CD40L maps to chromosome Xq26.3-q27. The gene contains five exons. Deletions, point mutations and frameshift mutations clustering within a limited region of the CD40L extracellular domain have been found to be the basis of a rare X-linked immunodeficiency syndrome (Hyper-IgM immunodeficiency syndrome, HIGM1) characterized by recurrent bacterial infections, very low or absent IgG, IgA and IgE, and normal to increased IgM and IgD serum levels. Causally-related mutations have been found to consist of clustered deletions arising by splice-donor mutations with exon skipping, splice-acceptor mutations with utilization of a cryptic splice site, and deletion/insertion events with the creation of a new splice site.

CD40L is expressed on activated, but not resting CD4+ T cells, and was found to play a particularly important role in the humoral immune response, being linked to B cell proliferation, antibody and cytokine production, and cell viability. In vivo, deletion or mutation of CD40L leads to severe immunodeficiency, both in mice and in humans, characterized by hypogammaglobulinemia and T cell deficits in cell-mediated immunity (Chess, C., 2001, in Therapeutic Immunology, $2^{nd}$ edition, Austen, K. F., Burakoff, S., Rosen, F. and Strom, T., eds., Blackwell Sciences, pp. 441-456). Human CD4+ T cells infected by HIV1, which causes severe dysfunction of cellular immunity, but paradoxically results in intense polyclonal activation of B cells, do not express CD40L. Gene and cell surface expression of the CD40L by activated T cells has been shown to be depressed in a subgroup of patients with common variable immunodeficiency (CVI). Thus, inefficient signaling via CD40 may be responsible, at least in part, for the failure of B cell differentiation in these patients.

The functional consequences of CD40L binding to CD40 include, for example, a) rescuing B cells from apoptosis induced by Fas or cross-linking of IgM, b) induction of the co-stimulator molecules CD80 (B7-1) and CD86 (B7-2) which interact with CD28 and CD152 (CTLA-4) on the surface of activated T cells; c) increased expression of other cell surface activation molecules including CD23, CD54, CD95 and lymphotoxin-a; and d) inducing immunoglobulin class switching (see Chess, supra, and references 25, 44, and 47-60 cited therein). CD40L binding to CD40 also augments the antigen-presenting functions of dendritic cells, inducing maintenance of high levels of MHC class II antigens and upregulation of accessory molecules including CD58 (LFA-3). CD40L induces cytokine production and tumoricidal activity in peripheral blood monocytes. CD40L also co-stimulates the proliferation of activated T cells, and the co-stimulation is accompanied by the production of IFN-γ, TNF-α and IL2. The expression of CD40L on murine T-helper cells and CD4+ T cells is inhibited by IFN-γ, and is inhibited on T-helper-type 2 cells by TGF-β.

CD40L upregulates the expression of CD54 by cultured Hodgkin and Reed-Sternberg cells. The increased CD54 surface expression is accompanied by increased shedding of surface-bound CD54.

CD40L has also been suggested to be important in the induction of tolerance—CD80 and CD86, which are upregulated by CD40L, interact with CD28 to provide essential co-stimulation of T cells, in concert with T cell receptor activation, that results in full activation of T cells. In the absence of CD80 and CD86-triggered activation of CD28, anergy or tolerance occurs as a consequence of antigen triggering (Linsley & Ledbetter, 1993, Ann. Rev. Immunol. 11: 191-212; Jenkins et al., 1993, Curr Opin. Immunol. 5: 361-367; and Boussiotis et al., 1996, Immunol. Rev. 153: 5-26).

The CD40L/CD40 pathway has been implicated in the in vivo priming of CD8+ cytotoxic T lymphocytes (CTSs) by CD4+ T cells. As noted, CD40L expressed on the surface of activated CD4+ T cells interacts with CD40 expressed on dendritic cells, inducing the dendritic cells to express more MHC, and signaling through CD40 can replace the requirement for CD4+ T-helper cells in priming CD8+ CTL responses. Blockade of CD40L inhibits CTL priming, emphasizing the vital role of CD40L/CD40 interactions in CTL priming by helper T cells (Ridge et al., 1998, Nature 393: 474-478; Schoenberger et al., 1998, Nature 393: 480-483; Bennett et al., 1998, Nature 393: 478-480).

CD40L can also mediate functional interactions of CD4+ T cells with other cells that express CD40, such as fibroblasts, synovial cells and endothelial cells (Yellin et al., 1995, J. Leuko. Biol. 58: 209-216; Yellin et al., 1995, J. Exp. Med. 182: 1857-1864). CD40L induces the expression of CD54 (ICAM-1) and CD106 (VCAM-1) by fibroblasts, as well as increasing fibroblast IL-6, collagenase and collagen production and inducing fibroblast proliferation. Thus, CD40L/CD40 interactions may be involved in the induction of fibrosis associated with autoimmunity and immune responses.

CD40L interaction with CD40 induces endothelial cells to express CD62E (E-selectin), ICAM-1 and VCAM-1. The upregulation of these adhesion molecules may be involved in the binding of inflammatory cells to vascular endothelium and the subsequent migration of the inflammatory cells to sites of inflammation. CD40L blockade retards the migration of leukocytes through endothelial cell barriers. In animal models of autoimmunity, antibodies to CD40L interfere with the accumulation of inflammatory cells at the site of inflammation.

CD40/CD40L interactions have been implicated in diseases having an immune or autoimmune connection. Animal models of immune-related disease in which the CD40L/CD40 pathway has been demonstrated to play a role in the pathology include, for example, murine models of systemic lupus erythematosis (Lupus or SLE; see, e.g., Kalled et al., 1998, J. Immunol. 160: 2158-2165), arthritis (collagen-induced arthritis, see, e.g., Durie et al., 1993, Science 261: 1328-1330), multiple sclerosis (experimental autoimmune encephalomyelitis, EAE; see, e.g., Howard et al., 1999, J. Clin. Invest. 103: 281-290), autoimmune thyroiditis (experimental autoimmune thyroiditis, EAT; see, e.g., Caryanniotis et al., 1997, Immunology 90: 421-426), colitis (hapten-induced colitis; see, e.g., Stuber et al., 1996, J. Exp. Med. 183: 693-698), atherosclerosis and coronary artery disease (see, e.g., Mach et al., 1998, Nature 394: 200-203), and allograft rejection (see, e.g., Parker et al., 1995, Proc. Natl. Acad. Sci. U.S.A. 92: 9560-9564; Kirk et al., 1997, Proc. Natl. Acad. Sci. U.S.A. 94: 8789-8794; Larsen et al., 1996, Nature 381: 434-438 and Blazar et al., 1997, J. Immunol. 158: 29-39).

CD40L antibody trials for treatment of human immune-related diseases include studies in patients with Lupus (see, e.g., Huang et al., 2002, Arthritis Rheum. 46: 1554-1562). A phase I trial demonstrated that anti-CD40L humanized monoclonal antibody (IDEC-131) is safe and well tolerated by patients with Lupus (Davis et al., 2001, J. Rheumatol. 28: 95-101). A phase II study with the IDEC-131 antibody showed improvement in clinical symptoms, but efficacy of the drug over placebo controls was not demonstrated (Kalunian et al., 2002, Arthritis Rheum. 46: 3251-3258). In a phase II study with BG9588 anti-CD40L antibody, clinical efficacy was demonstrated, but the study was terminated due to the occurrence of thromboembolic events (Boumpas et al., 2003, Arthritis Rheum. 48: 719-727).

U.S. Pat. Nos. 5,474,771 (Lederman et al.) and 5,876,950 (Siadak et al.) disclose murine monoclonal antibodies specific for different epitopes of human gp39. WO95/06666 (Noelle & Foy) discloses murine anti-gp39 antibodies.

U.S. Pat. No. 6,328,964 (Noelle & Claassen) discloses methods for the treatment of multiple sclerosis using gp39-specific antibodies.

U.S. Pat. No. 5,747,037 (Noelle et al.), and EP0721469B1 (Ledbetter et al.) and its U.S. counterpart U.S. Pat. No. 5,869,049 disclose anti-human monoclonal (mouse) antibodies specific for gp39. U.S. Pat. No. 5,876,718 (Noelle et al.) discloses methods of inducing T cell non-responsiveness to transplanted tissues and of treating graft-versus-host disease with anti-gp39 monoclonal (mouse) antibodies. EP0742721B1 (Noelle et al.) discloses methods of inhibiting a humoral immune response to a thymus-dependent antigen that use anti-gp39 monoclonal (mouse) antibodies. U.S. Pat. No. 6,375,950 describes methods for inducing T cell unresponsiveness to donor tissue or organs in a transplant recipient through use of anti-gp39 monoclonal (murine) antibodies.

EP1005372B1 (De Boer et al.) describes methods for the selective killing of autoreactive CD40L+ T cells using anti-CD40L monoclonal (mouse) antibody-toxin fusion proteins.

U.S. Pat. No. 6,340,459 (Yellin et al.) describes the use of murine anti gp39 monoclonal antibody 5c8 for the treatment or prevention of reperfusion injury.

EP0831906B1 (Claassen et al.) describes methods for the treatment of T cell-mediated tissue destruction in autoimmune diseases such as multiple sclerosis using anti-gp39 monoclonal (mouse) antibodies. Antibodies used in therapeutic approaches in the prior art have been divalent antibodies of murine origin.

A number of smaller antigen binding fragments of naturally occurring antibodies have been identified following protease digestion. These include, for example, the "Fab fragment" ($V_L$-$C_L$-$C_H1$-$V_H$), "Fab' fragment" (a Fab with the heavy chain hinge region) and "F(ab')$_2$ fragment" (a dimer of Fab' fragments joined by the heavy chain hinge region). Recombinant methods have been used to generate even smaller antigen-binding fragments, referred to as "single chain Fv" (variable fragment) or "scFv," consisting of $V_L$ and $V_H$ joined by a synthetic peptide linker.

While the antigen binding unit of a naturally-occurring antibody (e.g., in humans and most other mammals) is generally known to be comprised of a pair of V regions ($V_L$/$V_H$), camelid species express a large proportion of fully functional, highly specific antibodies that are devoid of light chain sequences. The camelid heavy chain antibodies are found as homodimers of a single heavy chain, dimerized via their constant regions. The variable domains of these camelid heavy chain antibodies are referred to as $V_HH$ domains and retain the ability, when isolated as fragments of the $V_H$ chain, to bind antigen with high specificity ((Hamers-Casterman et al., 1993, Nature 363: 446-448; Gahroudi et al., 1997, FEBS Lett. 414: 521-526). Antigen binding single $V_H$ domains have also been identified from, for example, a library of murine $V_H$ genes amplified from genomic DNA from the spleens of immunized mice and expressed in *E. coli* (Ward et al., 1989, Nature 341: 544-546). Ward et al. named the isolated single $V_H$ domains "dAbs," for "domain antibodies." The term "dAb" will refer herein to an antibody single variable domain ($V_H$ or $V_L$) polypeptide that specifically binds antigen. A "dAb" binds antigen independently of other V domains; however, as the term is used herein, a "dAb" can be present in a homo- or heteromultimer with other $V_H$ or $V_L$ domains where the other domains are not required for antigen binding by the dAb, i.e., where the dAb binds antigen independently of the additional $V_H$ or $V_L$ domains.

Antibody single variable domains, for example, $V_HH$, are the smallest antigen-binding antibody unit known. For use in therapy, human antibodies are preferred, primarily because they are not as likely to provoke an immune response when administered to a patient. As noted above, isolated non-camelid $V_H$ domains tend to be relatively insoluble and are often poorly expressed. Comparisons of camelid $V_{HH}$ with the $V_H$ domains of human antibodies reveals several key differences in the framework regions of the camelid $V_{HH}$ domain corresponding to the $V_H/V_L$ interface of the human $V_H$ domains. Mutation of these residues of human $V_H3$ to more closely resemble the $V_{HH}$ sequence (specifically Gly 44→Glu, Leu 45→Arg and Trp 47→Gly) has been performed to produce "camelized" human $V_H$ domains that retain antigen binding activity (Davies & Riechmann, 1994, FEBS Lett. 339: 285-290) yet have improved expression and solubility. (Variable domain amino acid numbering used herein is consistent with the Kabat numbering convention (Kabat et al., 1991, Sequences of Immunological Interest, $5^{th}$ ed. U.S. Dept. Health & Human Services, Washington, D.C.)) WO 03/035694 (Muyldermans) reports that the Trp 103→Arg mutation improves the solubility of non-camelid $V_H$ domains. Davies & Riechmann (1995, Biotechnology N.Y. 13: 475-479) also report production of a phage-displayed repertoire of camelized human $V_H$ domains and selection of clones that bind hapten with affinities in the range of 100-400 nM, but clones selected for binding to protein antigen had weaker affinities.

While many antibodies and their derivatives are useful for diagnosis and therapy, the ideal pharmacokinetics of antibodies are often not achieved for a particular application. In order to provide improvement in the pharmacokinetics of antibody molecules, the present invention provides single domain variable region polypeptides that are linked to polymers which provide increased stability and half-life. The attachment of polymer molecules (e.g., polyethylene glycol; PEG) to proteins is well established and has been shown to modulate the pharmacokinetic properties of the modified proteins. For example, PEG modification of proteins has been shown to alter the in vivo circulating half-life, antigenicity, solubility, and resistance to proteolysis of the protein (Abuchowski et al., *J. Biol. Chem.* 1977, 252:3578; Nucci et al., *Adv. Drug Delivery Reviews* 1991, 6:133; Francis et al., *Pharmaceutical Biotechnology* Vol. 3 (Borchardt, R. T. ed.); and Stability of Protein Pharmaceuticals: in vivo Pathways of Degradation and Strategies for Protein Stabilization 1991 pp 235-263, Plenum, NY).

Both site-specific and random PEGylation of protein molecules is known in the art (See, for example, Zalipsky and Lee, *Poly(ethylene glycol) Chemistry: Biotechnical and Biomedical Applications* 1992, pp 347-370, Plenum, NY; Goodson and Katre, 1990, *Bio/Technology,* 8:343; Hershfield et al., 1991, *PNAS* 88:7185). More specifically, random PEGylation of antibody molecules has been described at lysine residues and thiolated derivatives (Ling and Mattiasson, 1983, *Immunol. Methods* 59: 327; Wilkinson et al., 1987, *Immunol. Letters,* 15: 17; Kitamura et al., 1991, *Cancer Res.* 51:4310; Delgado et al., 1996 *Br. J. Cancer,* 73: 175; Pedley et al., 1994, *Br. J. Cancer,* 70:1126).

SUMMARY OF THE INVENTION

The invention relates to antibody polypeptides that monovalently bind CD40L. Because of the clear importance of CD40L in the production of antibodies, the CD40/CD40L interaction and pathways present important targets for the development of therapeutic approaches for the treatment of diseases and disorders that involve inappropriate or excessive antibody responses, such as autoimmune diseases. Antibody polypeptides that are monovalent for binding of CD40L can inhibit CD40L activity, including binding and activation of CD40 on the B cell surface and downstream effects, while avoiding potential undesirable effects that can occur with antibodies capable of divalent or multivalent binding of CD40L. Monovalent anti-CD40L antibody polypeptides can also be applied to any of a number of uses for which standard divalent antibodies are also used, e.g., in vivo imaging and diagnosis.

In one aspect, the antibody polypeptide consists of or comprises a single immunoglobulin variable domain that specifically binds and antagonizes the activity of CD40L, preferably without substantially agonizing CD40 activity. In another aspect, because human antibodies will avoid the generation of an immune response to the antibodies when administered to human subjects for the treatment or prevention of disease, the antibody polypeptide is a human antibody polypeptide that monovalently binds CD40L, preferably without substantially agonizing CD40 activity.

In summary then, in one embodiment, the invention provides a human antibody polypeptide that is monovalent for binding to CD40L (gp39).

In one embodiment, the human antibody polypeptide dissociates from human CD40L with a $K_d$ in the range of 50 nM to 20 pM, inclusive, as measured by surface plasmon resonance. For example, the $K_d$ for human CD40L can be 25 nM to 20 pM, 10 nM to 20 pM, 5 nm to 20 pM, 1 nM to 20 pM, 0.5 nM to 20 pM, 0.1 nM to 20 pM, 0.1 nM to 50 nM, 75 pM to 20 pM or even 50 pM to 20 pM.

Unless otherwise stated, all ranges described herein are inclusive of the specific endpoints.

In another embodiment, the antibody polypeptide inhibits the binding of CD40L to CD40.

In another embodiment, the binding of the antibody polypeptide to CD40L does not substantially agonize CD40 activity.

In another embodiment, the human antibody polypeptide inhibits the binding of CD40 to CD40L, and does not substantially agonize signaling by CD40.

In another embodiment, the binding of the antibody polypeptide to CD40L does not substantially induce JNK phosphorylation in Jurkat T-cells.

In another embodiment, the binding of the antibody polypeptide to CD40L does not substantially induce IFN-γ secretion by Jurkat T-cells co-stimulated with anti-CD3 antibody.

In another embodiment, the presence of the antibody polypeptide in a standard platelet aggregation assay does not result in aggregation of more than 25% over the aggregation observed in a negative control assay performed without the addition of antibody.

In another embodiment, the human antibody polypeptide comprises a single immunoglobulin variable domain that binds CD40L. In a preferred embodiment, the single immunoglobulin variable domain is a $V_H$ or a $V_L$ domain.

In another embodiment, the antibody polypeptide is selected from the group consisting of a dAb, a FAb, an scFv, an Fv, or a disulfide-bonded Fv.

In another embodiment, the human antibody polypeptide is PEG-linked. In one embodiment, the PEG is covalently linked to the human antibody polyepeptide. In one preferred embodiment, the PEG-linked human antibody polypeptide has a hydrodynamic size of at least 24 kD. In another preferred embodiment, the PEG is linked to the antibody polypeptide at a cysteine or lysine residue. In another preferred embodiment, the total PEG size is from 20 to 60 kD, inclusive. In another preferred embodiment, the PEG-linked human antibody polypeptide has a hydrodynamic size of at least 200 kD.

In one embodiment, the antibody polypeptide has an increased in vivo half-life relative to the same antibody polypeptide composition lacking polyethylene glycol.

In another embodiment, the tα-half life of the antibody polypeptide composition is increased by 10% or more. In another embodiment, the tα-half life of the antibody polypeptide composition is increased by 50% or more. In another embodiment, the tα-half life of the antibody polypeptide composition is increased by 2× or more. In another embodiment, the tα-half life of the antibody polypeptide composition is increased by 5× or more, e.g., 10×, 15×, 20×, 25×, 30×, 40×, or more. In another embodiment, the tα-half life of the antibody polypeptide composition is increased by 50× or more.

In another embodiment, the PEG-linked antibody polypeptide has a tα half-life of 0.25 to 6 hours, inclusive. In another embodiment, the tα half-life is in the range of 30 minutes to 12 hours, inclusive. In another embodiment, the tα-half life of the antibody polypeptide composition is in the range of 1 to 6 hours.

In another embodiment, the tβ-half life of the antibody polypeptide composition is increased by 10% or more. In another embodiment, the tβ-half life of the antibody polypeptide composition is increased by 50% or more. In another embodiment, the tβ-half life of the antibody polypeptide composition is increased by 2× or more. In another embodiment, the tβ-half life of the antibody polypeptide composition is increased by 5× or more, e.g., 10×, 15×, 20×, 25×, 30×, 40×, or more. In another embodiment, the tβ-half life of the antibody polypeptide composition is increased by 50× or more.

In another embodiment, the antibody polypeptide composition has a tβ half-life of 1 to 170 hours, inclusive. In another embodiment, the tβ-half life is in the range of 12 to 48 hours, inclusive. In another embodiment, the tβ-half life is in the range of 12 to 26 hours, inclusive.

In addition, or alternatively to the above criteria, the present invention provides a dAb containing composition comprising a ligand according to the invention having an AUC value (area under the curve) in the range of 1 mg.min/ml or more. In one embodiment, the lower end of the range is 5, 10, 15, 20, 30, 100, 200 or 300 mg.min/ml. In addition, or alternatively, a ligand or composition according to the invention has an AUC in the range of up to 600 mg.min/ml. In one embodiment, the upper end of the range is 500, 400, 300, 200, 150, 100, 75 or 50 mg.min/ml. Advantageously a ligand according to the invention will have an AUC in the range selected from the group consisting of the following: 15 to 150 mg.min/ml, 15 to 100 mg.min/ml, 15 to 75 mg.min/ml, and 15 to 50 mg.min/ml.

In another embodiment, the antibody polypeptides described herein can be linked to human serum albumin (HSA), which also has the effect of increasing the in vivo half life of the molecule. The human serum albumin coding sequences can be obtained by PCR using primers derived from the cDNA sequence available at GenBank Accession No. NM000477. Such coding sequences can be fused to the coding sequence for a monovalent anti-CD40L antibody polypeptide as described herein, and the fusion can be expressed by one of skill in the art.

In another embodiment, the tα-half life of the HSA-linked human antibody polypeptide composition is increased by 10% or more.

In another embodiment, the tα-half life of the HSA-linked human antibody polypeptide composition is in the range of 0.25 hours to 6 hours.

In another embodiment, the tβ-half life of the HSA-linked human antibody polypeptide composition is increased by 10% or more.

In another embodiment, the tβ-half life of the HSA-linked human antibody polypeptide composition is in the range of 12 to 48 hours.

In another embodiment, the human antibody polypeptide comprises an amino acid sequence selected from the group consisting of SEQ ID NOs 7-82.

In another embodiment, the human antibody polypeptide inhibits binding of CD40L to CD40 with an $IC_{50}$ in the range of 20 pM to 1.5 μM, inclusive; $IC_{50}$ for inhibition of CD40L binding to CD40 in any embodiment described herein is preferably measured as described herein in Example 6. The $IC_{50}$ can preferably be in the range of 20 pM to 1 μM, 20 pM to 900 nM, 20 pM to 800 nM, 20 pM to 700 nM, 20 pM to 600 nM, 20 pM to 500 nM, 20 pM to 400 nM, 20 pM to 300 nM, 20 pM to 200 nM, 20 pM to 100 nM, or 20 pM to 50 nM. Further acceptable or preferred ranges include, for example, 50 pM to 1 μM, 100 pM to 500 nM, 125 pM to 250 nM, 150 pM to 200 nM, 150 pM to 100 nM and 200 pM to 50 nM.

In another embodiment, the antibody polypeptide is fused to a second antibody polypeptide which binds a ligand other than CD40L. In a preferred embodiment, the antibody polypeptide which binds a ligand other than CD40L binds a ligand selected from the group consisting of HSA, TNFα, IL-1, IL-2, IL-4, IL-6, IL-8, IL-12, IL-18, IFN-γ, CD2, CD4, CD8, CTLA4, LFA1, LFA3 and VLA4.

In another embodiment, the human antibody polypeptide is free of an Fc domain. The limits of an Fc domain are set out in Kabat et al. (1991, Sequences of Immunological Interest, $5^{th}$ ed. U.S. Dept. Health & Human Services, Washington, D.C.; incorporated herein by reference). In the alternative, an Fc domain consists of the CH2-CH3 regions, optionally including a hinge region linked to the CH2. In a preferred embodiment, the human antibody polypeptide does not mediate platelet aggregation in a standard platelet aggregation assay.

The invention further encompasses a human antibody polypeptide which has an amino acid sequence at least 85% identical to a sequence selected from the group consisting of SEQ ID NOs 7-82, which antibody polypeptide specifically and monovalently binds CD40L.

The invention further encompasses an antigen-binding polypeptide, the polypeptide comprising a single immunoglobulin variable domain which specifically and monovalently binds CD40L. Recited differently, the invention further encompasses a polypeptide comprising a moiety which specifically binds CD40L, which moiety consists of a single immunoglobulin variable domain.

In one embodiment, the polypeptide consists of a human single immunoglobulin variable domain.

In another embodiment, the polypeptide has a Kd for human CD40L in the range of 50 nM to 20 pM, inclusive, as determined by surface plasmon resonance. For example, the Kd for human CD40L can be 25 nM to 20 pM, 10 nM to 20 pM, 5 nm to 20 pM, 1 nM to 20 pM, 0.5 nM to 20 pM, 0.1 nM to 20 pM, 75 pM to 20 pM or even 50 pM to 20 pM.

In another embodiment, the polypeptide inhibits the binding of CD40L to CD40.

In another embodiment, the polypeptide inhibits the binding of CD40 to CD40L and has an $IC_{50}$ in the range of 20 pM to 1.5 μM, inclusive. For example, the $IC_{50}$ can be in the range of 20 pM to 1 μM, 20 pM to 900 nM, 20 pM to 800 nM, 20 pM to 700 nM, 20 pM to 600 nM, 20 pM to 500 nM, 20 pM to 400 nM, 20 pM to 300 nM, 20 pM to 200 nM, 20 pM to 100 nM, or 20 pM to 50 nM. Further acceptable or preferred ranges include, for example, 50 pM to 1 μM, 100 pM to 500 nM, 125 pM to 250 nM, 150 pM to 200 nM, 150 pM to 100 nM and 200 pM to 50 nM.

In another embodiment, the binding of the polypeptide to CD40L does not substantially agonize CD40 activity.

In another embodiment, the binding of the polypeptide to CD40L does not substantially induce JNK phosphorylation in Jurkat T-cells.

In another embodiment, the binding of the polypeptide to CD40L does not substantially induce IFN-γ secretion by Jurkat T-cells co-stimulated with anti-CD3 antibody.

In another embodiment, the presence of the antibody polypeptide in a standard platelet aggregation assay does not result in aggregation more than 25% over the aggregation observed in a negative control assay lacking antibody polypeptide.

In another embodiment, the single immunoglobulin variable domain is a human single immunoglobulin variable domain.

In another embodiment, the single immunoglobulin variable domain is a $V_H$ or a $V_L$ domain.

In one embodiment, the polypeptide is PEG-linked. In one embodiment, the PEG is covalently linked. In one preferred embodiment, the PEG-linked antigen-binding polypeptide has a hydrodynamic size of at least 24 kD. In another preferred embodiment, the PEG is linked to the antigen-binding polypeptide at a cysteine or lysine residue. In another preferred embodiment, the total PEG size is from 20 to 60 kD, inclusive. In another preferred embodiment, the PEG-linked antigen-binding polypeptide has a hydrodynamic size of at least 200 kD.

In another embodiment, the PEG-linked polypeptide has an increased in vivo half-life relative to the same polypeptide composition lacking linked polyethylene glycol. In another embodiment, the tα-half life of the polypeptide composition is increased by 10% or more. In another embodiment, the tα-half life of the polypeptide composition is increased by 50% or more. In another embodiment, the tα-half life of the polypeptide composition is increased by 2× or more. In another embodiment, the tα-half life of the polypeptide composition is increased by 5× or more, e.g., 10×, 15×, 20×, 25×, 30×, 40×, or more. In another embodiment, the tα-half life of the polypeptide composition is increased by 50× or more.

In another embodiment, the PEG-linked antibody polypeptide has a tα half-life of 0.25 to 6 hours, inclusive. In another embodiment, the tα half-life is in the range of 30 minutes to 12 hours, inclusive. In another embodiment, the tα-half life of the polypeptide composition is in the range of 1 to 6 hours.

In another embodiment, the tβ-half life of the polypeptide composition is increased by 10% or more. In another embodiment, the tβ-half life of the polypeptide composition is increased by 50% or more. In another embodiment, the tβ-half life of the polypeptide composition is increased by 2× or more. In another embodiment, the tβ-half life of the polypeptide composition is increased by 5× or more, e.g., 10×, 15×, 20×, 25×, 30×, 40×, or more. In another embodiment, the tβ-half life of the polypeptide composition is increased by 50× or more.

In another embodiment, the antibody polypeptide composition has a tβ half-life of 1 to 170 hours, inclusive. In another embodiment, the tβ-half life is in the range of 12 to 48 hours, inclusive. In another embodiment, the tβ-half life is in the range of 12 to 26 hours, inclusive.

In another embodiment, the composition has an AUC value (area under the curve) in the range of 1 mg.min/ml or more. In one embodiment, the lower end of the range is 5, 10, 15, 20, 30, 100, 200 or 300 mg.min/ml. In addition, or alternatively, a ligand or composition according to the invention has an AUC in the range of up to 600 mg.min/ml. In one embodiment, the upper end of the range is 500, 400, 300, 200, 150, 100, 75 or 50 mg.min/ml. Advantageously a ligand according to the invention will have an AUC in the range selected from the group consisting of the following: 15 to 150 mg.min/ml, 15 to 100 mg.min/ml, 15 to 75 mg.min/ml, and 15 to 50 mg.min/ml.

In another embodiment, the antibody polypeptide is linked to human serum albumin (HSA). In another embodiment, the antibody polypeptide has an increased in vivo half-life relative to the same polypeptide composition lacking linked HSA. In another embodiment, the antibody polypeptide has a tα-half life that is increased by 10% or more relative to a molecule lacking linked HSA. In another embodiment, the tα-half life of the polypeptide composition is in the range of 0.25 minutes to 6 hours. In another embodiment, the tβ-half life of the polypeptide composition is increased by 10% or more. In another embodiment, the tβ-half life is in the range of 12 to 48 hours.

In another embodiment, the antigen-binding polypeptide comprises an amino acid sequence selected from the group consisting of SEQ ID NOs 7-82.

In another embodiment, the antigen-binding polypeptide is free of an Fc domain.

In another aspect, the invention encompasses an immunoglobulin variable domain polypeptide which has an amino acid sequence at least 85% identical to a sequence selected from the group consisting of SEQ ID NOs 7-82, which polypeptide specifically and monovalently binds CD40L.

In one embodiment, the immunoglobulin variable domain polypeptide antagonizes the binding of CD40L to CD40.

In another embodiment, the immunoglobulin variable domain polypeptide inhibits the binding of CD40 to CD40L and has an $IC_{50}$ in the range of 20 pM to 1.5 μM, inclusive. For example, the $IC_{50}$ can be in the range of 20 pM to 1 μM, 20 pM to 900 nM, 20 pM to 800 nM, 20 pM to 700 nM, 20 pM to 600 nM, 20 pM to 500 nM, 20 pM to 400 nM, 20 pM to 300 nM, 20 pM to 200 nM, 20 pM to 100 nM, or 20 pM to 50 nM. Further acceptable or preferred ranges include, for example, 50 pM to 1 μM, 100 pM to 500 nM, 125 pM to 250 nM, 150 pM to 200 nM, 150 pM to 100 nM and 200 pM to 50 nM.

In another embodiment, the immunoglobulin variable domain polypeptide inhibits the interaction of CD40 with CD40L, but does not substantially agonize intracellular signaling by CD40. In a preferred embodiment, the binding of the polypeptide to CD40L does not substantially induce JNK phosphorylation in Jurkat T-cells. In another preferred embodiment, the binding of the polypeptide to CD40L does not substantially induce IFN-γ secretion by Jurkat T-cells co-stimulated with anti-CD3 antibody. In another preferred embodiment, the binding of the antibody polypeptide to CD40L does not substantially induce platelet aggregation in a platelet aggregation assay.

In another embodiment, the antigen-binding polypeptide further comprises a second antibody polypeptide which binds a ligand other than CD40L. In a preferred embodiment, the second antibody polypeptide binds a ligand selected from the group consisting of HSA, TNFα, IL-1, IL-2, IL-4, IL-6, IL-8, IL-12, IL-18, IFN-γ, CD2, CD4, CD8, CTLA4, LFA1, LFA3 and VLA4.

The invention further encompasses a method of antagonizing the binding of CD40 to CD40L in an individual, the method comprising administering a monovalent anti-CD40L antibody polypeptide as described herein to the individual, wherein the polypeptide antagonizes the binding of CD40 to CD40L in the individual.

The invention further encompasses a method of antagonizing an activity of CD40 or CD40L in an individual, the method comprising administering a a monovalent anti-CD40L antibody polypeptide as described herein to the individual, wherein the polypeptide antagonizes an activity of CD40 or CD40L or both.

The invention further encompasses a composition comprising an extended release formulation comprising a monovalent anti-CD40L antibody polypeptide, preferably, but not limited to, a polypeptide comprising a single immunoglobulin variable domain that binds CD40L. In one embodiment, the single immunoglobulin variable domain is a non-human mammalian single immunoglobulin variable domain. In another embodiment, the single immunoglobulin variable domain is a human single immunoglobulin variable domain.

The invention further encompasses a method of treating or preventing a disease or disorder mediated by CD40L in an individual in need of such treatment, the method comprising administering to the individual a therapeutically effective amount of a composition comprising a monovalent anti-CD40L antibody polypeptide, preferably a composition comprising a single human immunoglobulin variable domain that binds CD40L. In one embodiment, the disease or disorder is an autoimmune disease or disorder.

The invention further encompasses a method of treating or preventing a symptom of systemic lupus erythematosus (SLE) in an individual, the method comprising administering a monovalent anti-CD40L antibody polypeptide to said individual in an amount effective to treat or prevent a symptom of SLE.

The invention further encompasses an antibody polypeptide that is monovalent for binding to CD40L, wherein the antibody polypeptide comprises a universal framework.

In one embodiment, the universal framework comprises a VH framework selected from the group consisting of DP47, DP45 and DP38, and/or the VL framework is DPK9.

In another embodiment, the antibody polypeptide comprises a generic ligand binding site. In another embodiment, the generic ligand binding site binds a generic ligand selected from the group consisting of protein A, protein L and protein G.

In another embodiment, the antibody polypeptide comprises a variable domain having one or more framework regions comprising an amino acid sequence that is the same as the amino acid sequence of a corresponding framework region encoded by a human germline antibody gene segment, or the amino acid sequences of one or more of the framework regions collectively comprises up to 5 amino acid differences relative to the amino acid sequence of the corresponding framework region encoded by a human germline antibody gene segment.

In another embodiment, the antibody polypeptide comprises a variable domain, wherein the amino acid sequences of FW1, FW2, FW3 and FW4 are the same as the amino acid sequences of corresponding framework regions encoded by a human germline antibody gene segment, or the antibody sequences of FW1, FW2, FW3 and FW4 collectively contain up to 10 amino acid differences relative to the amino acid sequences of corresponding framework regions encoded by the human germline antibody gene segment.

In another embodiment, the antibody polypeptide comprises an antibody variable domain comprising FW1, FW2 and FW3 regions, and the amino acid sequence of said FW1, FW2 and FW3 are the same as the amino acid sequences of corresponding framework regions encoded by human germline antibody gene segments. In another embodiment, the human germline antibody gene segment is selected from the group consisting of DP47, DP45, DP48 and DPK9.

Definitions:

As used herein, the term "human" when applied to an antibody polypeptide or to an immunoglobulin variable domain means that the polypeptide has a sequence derived from a human immunoglobulin. A sequence is "derived from" a human immunoglobulin coding sequence when the sequence is either: a) isolated from a human individual or from cells or a cell line from a human individual; b) isolated from a library of cloned human antibody gene sequences (or a library of human antibody V domain sequences); or c) when a cloned human antibody gene sequence (or a cloned human V region sequence (including, e.g., a germline V gene segment)) was used to generate one or more diversified sequences that were then selected for binding to a desired target antigen. The term "human" as applied herein to an antibody polypeptide or to an immunoglobulin variable domain does not encompass an immunoglobulin from another species, e.g., mouse, camel, etc., that has been "humanized" through grafting of human constant region sequences onto an antibody polypeptide (i.e., replacing non-human constant regions with human constant regions) or through grafting of human V region framework sequences onto an immunoglobulin variable domain from a non-human mammal (i.e., replacing non-human framework regions of a V domain with human framework regions).

At a minimum, a human variable domain has at least 85% amino acid similarity (including, for example, 87%, 90%, 93%, 95%, 97%, 99% or higher similarity) to a naturally-occurring human immunoglobulin variable domain sequence.

As used herein, the term "domain" refers to a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain.

By "single immunoglobulin variable domain" is meant a folded polypeptide domain which comprises a sequence characteristic of immunoglobulin variable domains and which specifically binds an antigen (e.g., dissociation constant of 500 nM or less). A "single immunoglobulin variable domain" therefore includes complete antibody variable domains as well as modified variable domains, for example in which one or more loops have been replaced by sequences which are not characteristic of antibody variable domains, or antibody variable domains which have been truncated or comprise N- or C-terminal extensions, as well as folded fragments of variable domains which retain a dissociation constant of 500 nM or less (e.g., 450 nM or less, 400 nM or less, 350 nM or less, 300 nM or less, 250 nM or less, 200 nM or less, 150 nM or less, 100 nM or less) and the target antigen specificity of the full-length domain. Where necessary or in case of any doubt, the numbering convention and boundaries set forth by Kabat et al. (1991, supra) are applicable to immunoglobulin variable and constant domains referred to herein.

An antibody single variable domain polypeptide, as used herein refers to a mammalian single immunoglobulin variable domain polypeptide, preferably human, but also includes rodent (for example, as disclosed in WO00/29004, the contents of which are incorporated herein in their entirety) or camelid $V_{HH}$ dAbs. Camelid dAbs are antibody single variable domain polypeptides which are derived from species including camel, llama, alpaca, dromedary, and guanaco, and comprise heavy chain antibodies naturally devoid of light chain: $V_{HH}$. $V_{HH}$ molecules are about 10× smaller than IgG molecules, and as single polypeptides, they are very stable, resisting extreme pH and temperature conditions. Moreover, camelid antibody single variable domain polypeptides are resistant to the action of proteases. Camelid antibodies are described in, for example, U.S. Pat. Nos. 5,759,808; 5,800,988; 5,840,526; 5,874,541; 6,005,079; and 6,015,695, the contents of each of which are incorporated herein in their entirety. Camelid $V_{HH}$ antibody single variable domain polypeptides useful according to the invention include a class of camelid antibody single variable domain polypeptides having human-like sequences, wherein the class is characterized in that the $V_{HH}$ domains carry an amino acid from the group consisting of glycine, alanine, valine, leucine, isoleucine, proline, phenylalanine, tyrosine, tryptophan, methionine, serine, threonine, asparagine, or glutamine at position 45, such as for example L45, and further comprise a tryptophan at position 103 according to the Kabat numbering. Humanized camelid $V_{HH}$ polypeptides are taught, for example in WO04/041862, the teachings of which are incorporated herein in their entirety. It will be understood by one of skill in the art that naturally occurring camelid antibody single variable domain polypeptides may be modified according to the teachings of WO04/041862 (e.g., amino acid substitutions at positions 45 and 103) to generate humanized camelid $V_{HH}$ polypeptides.

The phrase "single immunoglobulin variable domain polypeptide" encompasses not only an isolated single immunoglobulin variable domain polypeptide, but also larger polypeptides that comprise a monomer of a single immunoglobulin variable domain polypeptide sequence. A "domain antibody" or "dAb" is equivalent to a "single immunoglobulin variable domain polypeptide" as the term is used herein. With regard to a single immunoglobulin variable domain polypeptide, the binding to antigen, e.g., CD40L, is mediated by the single immunoglobulin V domain without a requirement for a complementary V domain.

According to the invention, the terms "antibody single variable domain polypeptide", "antibody single variable domain", "single antibody variable domain", and "immunoglobulin single variable domain" are understood to be equivalent.

As used herein, the phrase "sequence characteristic of immunoglobulin variable domains" refers to an amino acid sequence that is homologous, over 20 or more, 25 or more, 30 or more, 35 or more, 40 or more, 45 or more, or even 50 or more contiguous amino acids, to a sequence comprised by an immunoglobulin variable domain sequence.

As used herein, the terms "homology" or "similarity" refer to the degree with which two nucleotide or amino acid sequences structurally resemble each other. As used herein, sequence "similarity" is a measure of the degree to which amino acid sequences share similar amino acid residues at corresponding positions in an alignment of the sequences. Amino acids are similar to each other where their side chains are similar. Specifically, "similarity" encompasses amino acids that are conservative substitutes for each other. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical amino acids or conservative substitutions. Optimal global alignments can be performed using the following parameters in the Needleman-Wunsch alignment algorithm:

For polypeptides:

Substitution matrix: blosum62.

Gap scoring function: −A−B*LG, where A=11 (the gap penalty), B=1 (the gap length penalty) and LG is the length of the gap.

For nucleotide sequences:

Substitution matrix: 10 for matches, 0 for mismatches.

Gap scoring function: −A−B*LG where A=50 (the gap penalty), B=3 (the gap length penalty) and LG is the length of the gap.

Typical conservative substitutions are among Met, Val, Leu and Ile; among Ser and Thr; among the residues Asp, Glu and Asn; among the residues Gln, Lys and Arg; or aromatic residues Phe and Tyr.

As used herein, two sequences are "homologous" or "similar" to each other where they have at least 85% sequence similarity to each other, including, e.g., 90%, 95%, 97%, 99% or even 100% sequence similarity, when aligned using either the Needleman-Wunsch algorithm or the "BLAST 2 sequences" algorithm described by Tatusova & Madden, 1999, FEMS Microbiol Lett. 174:247-250. Where amino acid sequences are aligned using the "BLAST 2 sequences algorithm," the Blosum 62 matrix is the default matrix.

As used herein, the terms "inhibit," "inhibits" and "inhibited" refer to a decrease in a given measurable activity by at least 10% relative to a reference. Where inhibition is desired, such inhibition is preferably at least 20%, 30%, 40%, 50%, 60%, 70%, 80%, 90% or more, up to and including 100%, i.e., complete inhibition or absence of the given activity. One way that inhibition of CD40L binding to CD40 is measured is as described in Example 6 herein.

As used herein, the terms "activate," "activates" and "activated" refer to an increase in a given measurable activity by at least 5% relative to a reference, for example, at least 10%, 25%, 50%, 75% or even 100%.

As used herein, the term "antagonist" refers to an agent that inhibits at least one activity mediated by CD40L. An activity is "antagonized" if the activity is reduced by at least 10%, and preferably at least 20%, 30%, 40%, 50%, 60%, 70%, 80%, 90%, 95%, 97% or even 100% (i.e., no activity) in the presence, relative to the absence of an antagonist. An antagonist as the term is used herein preferably comprises a single immunoglobulin variable domain that binds monovalently to CD40L.

As used herein, the term "agonist" refers to an agent that activates at least one activity mediated by CD40L, either alone or when combined with another co-stimulus, relative to a reference. An activity is "agonized" if the activity is increased by at least 10%, e.g., 50%, in the presence, relative to the absence of an agonist.

As used herein, the term "epitope" refers to a unit of structure conventionally bound by an immunoglobulin $V_H/V_L$ pair. Epitopes define the minimum binding site for an antibody, and thus represent the target of specificity of an antibody. In the case of a single immunoglobulin variable domain, an epitope represents the unit of structure bound by a single variable domain in isolation. That is, the binding site is provided by one, single immunoglobulin variable domain.

As used herein, the term "extended release" or the equivalent terms "controlled release" or "slow release" refer to drug formulations that release active drug, such as a polypeptide drug, over a period of time following administration to an individual. Extended release of polypeptide drugs, which can occur over a range of desired times, e.g., minutes, hours, days, weeks or longer, depending upon the drug formulation, is in contrast to standard formulations in which substantially the entire dosage unit is available for immediate absorption or immediate distribution via the bloodstream. Preferred extended release formulations result in a level of circulating drug from a single administration that is sustained, for example, for 8 hours or more, 12 hours or more, 24 hours or more, 36 hours or more, 48 hours or more, 60 hours or more, 72 hours or more 84 hours or more, 96 hours or more, or even, for example, for 1 week or 2 weeks or more, for example, 1 month or more.

As used herein, a "CD40L activity" is an activity involving or resulting from the binding of CD40L to CD40, and includes, but is not limited to binding to CD40 (assayed, for example, according to the method described in Example 6), activation of Jun-N-terminal Kinase (JNK), the induction of T cells to produce and secrete cytokines including, for example, IL-10, IFN-γ and TNF-α, and the mediation of platelet aggregation. Assays for these activities are provided herein below.

As used herein, the term "does not substantially agonize" means that a given agent, e.g., an anti-CD40L antibody polypeptide, does not activate one or more of the CD40L activities including Jun-N-terminal kinase activation (phosphorylation) in Jurkat T cells and induction of IFN-γ production or secretion in anti-CD3-stimulated Jurkat T cells, as the term "activate" is defined herein.

As used herein, the term "antibody polypeptide" refers to a polypeptide which either is an antibody or is a part of an antibody, modified or unmodified, which retains the ability to specifically bind antigen. Thus, the term antibody polypeptide includes an antigen-binding heavy chain, light chain, heavy chain-light chain dimer, Fab fragment, F(ab')2 fragment, dAb, or an Fv fragment, including a single chain Fv (scFv). The phrase "antibody polypeptide" is intended to encompass recombinant fusion polypeptides that comprise an antibody polypeptide sequence that retains the ability to specifically bind antigen in the context of the fusion.

As used herein, the term "monovalent" means that a given antibody polypeptide or single immunoglobulin variable domain polyepeptide can bind only a single molecule of its target. Naturally-occurring antibodies are generally divalent, in that they have two functional antigen-binding arms, each comprising a VH and a VL domain. Where steric hindrance is not an issue, a divalent antibody can bind two separate molecules of the same antigen. In contrast, a "monovalent" antibody has the capacity to bind only one such antigen molecule. As the term is used herein, a "monovalent" antibody can also comprise more than one antigen binding site, e.g., two antigen binding sites, but the binding sites must be for different antigens, such that the antibody can only bind one molecule of CD40L at a time. The antigen-binding domain of a monovalent antibody can comprise a $V_H$ and a $V_L$ domain, but preferably comprises only a single immunoglobulin variable domain, i.e., a $V_H$ or a $V_L$ domain, that has the capacity to bind CD40L without the need for a corresponding $V_L$ or $V_H$ domain, respectively. A monovalent antibody lacks the capacity to cross link molecules of a single antigen.

As used herein, the term "standard platelet aggregation assay" means the assay described in the section herein below, entitled "Platelet Aggregation Assay."

As used herein, the terms "$V_H$ domain" and "$V_L$ domain" refer to immunoglobulin variable regions as defined by Kabat et al. (supra), which is incorporated herein by reference.

As used herein, "linked" refers to the attachment of a polymer moiety, such as PEG to an amino acid residue of an antibody polypeptide. Attachment of a PEG polymer to an amino acid residue of an antibody polypeptide, e.g., an anti-CD40L dAb, is referred to as "PEGylation" and may be achieved using several PEG attachment moieties including, but not limited to N-hydroxylsuccinimide (NHS) active ester, succinimidyl propionate (SPA), maleimide (MAL), vinyl sulfone (VS), or thiol. A PEG polymer, or other polymer, can be linked to an antibody polypeptide at either a predetermined position, or may be randomly linked to the an antibody polypeptide molecule. It is preferred, however, that the PEG polymer be linked to an antibody polypeptide at a predetermined position. A PEG polymer may be linked to any residue in the an antibody polypeptide, however, it is preferable that the polymer is linked to either a lysine or cysteine, which is either naturally occurring in the antibody polypeptide, or which has been engineered into the antibody polypeptide, for example, by mutagenesis of a naturally occurring residue in the antibody polypeptide to either a cysteine or lysine. PEG-linkage can also be mediated through a peptide linker attached to an antibody polypeptide. That is, the PEG moiety can be attached to a peptide linker fused to an antibody polypeptide, where the linker provides the site, e.g., a free cysteine or lysine, for PEG attachment. As used herein, "linked" can also refer to the association of two or more antibody polypeptides, e.g., dAb monomers, to form a dimer, trimer, tetramer, or other multimer. Antibody polypeptide monomers can be linked to form a multimer by several methods known in the art, including, but not limited to, expression of the antibody polypeptide monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). While dAb multimers are specifically contemplated herein, e.g., in the context of dual- or multi-specific antibody polypeptide constructs, it is emphasized that for any given antibody polypeptide construct, the construct should only be able to bind one molecule of CD40L, i.e., the constructs can have only one CD40L-binding element, and cannot cross link CD40L.

As used herein, "polymer" refers to a macromolecule made up of repeating monomeric units, and can refer to a synthetic or naturally occurring polymer such as an optionally substituted straight or branched chain polyalkylene, polyalkenylene, or polyoxyalkylene polymer or a branched or unbranched polysaccharide. A "polymer" as used herein, specifically refers to an optionally substituted or branched chain poly(ethylene glycol), poly(propylene glycol), or poly(vinyl alcohol) and derivatives thereof.

As used herein, "PEG" or "PEG polymer" refers to polyethylene glycol, and more specifically can refer to a derivitized form of PEG, including, but not limited to N-hydroxylsuccinimide (NHS) active esters of PEG such as succinimidyl propionate, benzotriazole active esters, PEG derivatized with maleimide, vinyl sulfones, or thiol groups. Particular PEG formulations can include PEG-O—$CH_2CH_2CH_2$—$CO_2$—NHS; PEG-O—$CH_2$—NHS; PEG-O—$CH_2CH_2$—$CO_2$—NHS; PEG-S—$CH_2CH_2$—CO—NHS; PEG-$O_2$CNH—CH(R)—$CO_2$—NHS; PEG-NHCO—$CH_2CH_2$—CO—NHS; and PEG-O—$CH_2$—$CO_2$—NHS; where R is $(CH_2)_4)NHCO_2$(mPEG). PEG polymers useful in the invention may be linear molecules, or may be branched wherein multiple PEG moieties are present in a single polymer. Some particularly preferred PEG conformations that are useful in the invention include, but are not limited to the following:

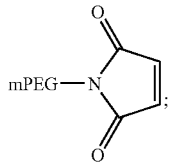

mPEG-MAL

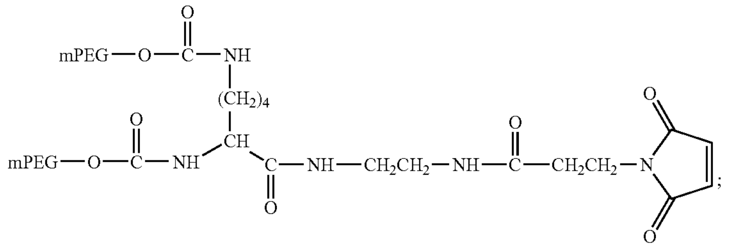

mPEG2-MAL

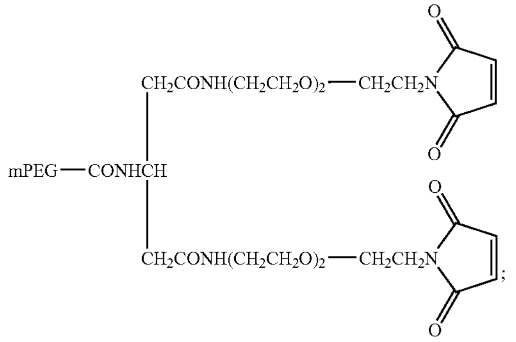

mPEG-(MAL)[2]

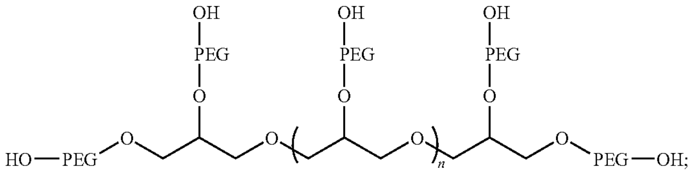

$n$ = O-4 multi-arm PEG

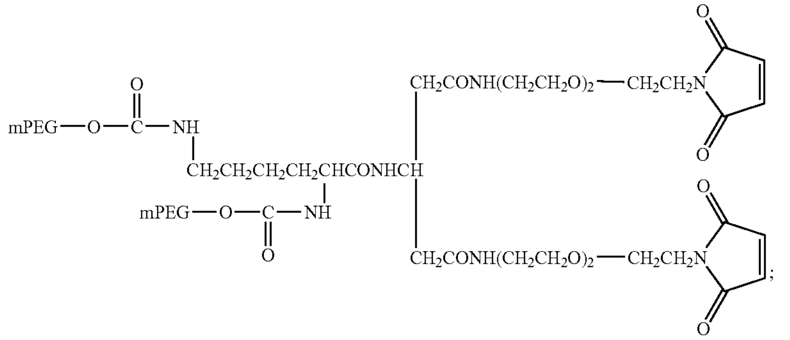

mPEG2-(MAL)[2]

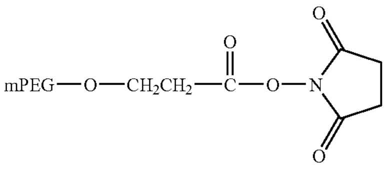

mPEG-SPA

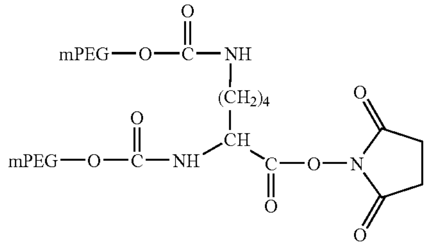

mPEG2-NHS

As used herein, a "sulfhydryl-selective reagent" is a reagent which is useful for the attachment of a PEG polymer to a thiol-containing amino acid. Thiol groups on the amino acid residue cysteine are particularly useful for interaction with a sulfhydryl-selective reagent. Sulfhydryl-selective reagents which are useful for such attachment include, but are not limited to maleimide, vinyl sulfone, and thiol. The use of sulfhydryl-selective reagents for coupling to cysteine residues is known in the art and may be adapted as needed according to the present invention (See Eg., Zalipsky, 1995, *Bioconjug. Chem.* 6:150; Greenwald et al., 2000, *Crit. Rev. Ther. Drug Carrier Syst.* 17:101; Herman et al., 1994, *Macromol. Chem. Phys.* 195:203).

The attachment of PEG or another agent, e.g., HSA, to an antibody polypeptide or to a single immunoglobulin variable domain polypeptide as described herein will preferably not impair the ability of the polypeptide to specifically bind CD40L. That is, the PEG-linked antibody polypeptide or single immunoglobulin variable domain polypeptide will retain its binding activity relative to a non-PEG-linked counterpart. As used herein, "retains activity" refers to a level of activity of a PEG-linked antibody polypeptide which is at least 10% of the level of activity of a non-PEG-linked antibody polypeptide, preferably at least 20%, 30%, 40%, 50%, 60%, 70%, 80% and up to 90%, preferably up to 95%, 98%, and up to 100% of the activity of a non-PEG-linked antibody polypeptide comprising the same antigen-binding domain or domains. More specifically, the activity of a PEG-linked antibody polypeptide compared to a non-PEG linked antibody variable domain should be determined on an antibody polypeptide molar basis; that is equivalent numbers of moles of each of the PEG-linked and non-PEG-linked antibody polypeptides should be used in each trial. In determining whether a particular PEG-linked antibody polypeptide "retains activity", it is preferred that the activity of a PEG-linked antibody polypeptide be compared with the activity of the same antibody polypeptide in the absence of PEG.

As used herein, the term "in vivo half-life" refers to the time taken for the serum concentration of a ligand (e.g., a single immunoglobulin variable domain) to reduce by 50%, in vivo, for example due to degradation of the ligand and/or clearance or sequestration of the ligand by natural mechanisms. The anti CD40L antibody polypeptides or single immunoglobulin variable domain polypeptides described herein can be stabilized in vivo and their half-life increased by binding to molecules, such as PEG, which resist degradation and/or clearance or sequestration. The half-life of an antibody polypeptide is increased if its functional activity persists, in vivo, for a longer period than a similar antibody polypeptide which is not linked to a PEG polymer. Typically, the half life of a PEGylated antibody polypeptide is increased by 10%, 20%, 30%, 40%, 50% or more relative to a non-PEGylated antibody polypeptide. Increases in the range of 2×, 3×, 4×, 5×, 10×, 20×, 30×, 40×, 50× or more of the half life are possible. Alternatively, or in addition, increases in the range of up to 30×, 40×, 50×, 60×, 70×, 80×, 90×, 100×, 150× of the half life are possible. According to the invention, a PEG-linked antibody single variable domain has a half-life of between 0.25 and 170 hours, preferably between 1 and 100 hours, more preferably between 30 and 100 hours, and still more preferably between 50 and 100 hours, and up to 170, 180, 190, and 200 hours or more.

As used herein, "resistant to degradation" or "resists degradation" with respect to a PEG or other polymer-linked antibody polypeptide monomer or multimer means that the PEG- or other polymer-linked antibody polypeptide monomer or multimer is degraded by no more than 10% when exposed to pepsin at pH 2.0 for 30 minutes and preferably not degraded at all.

As used herein, "hydrodynamic size" refers to the apparent size of a molecule (e.g., a protein molecule) based on the diffusion of the molecule through an aqueous solution. The diffusion, or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein. Hydrodynamic size is measured, for example, by size exclusion chromatography. The hydrodynamic size of a PEG-linked antibody polypeptide, e.g., a single immunoglobulin variable domain (including antibody variable domain multimers as described herein), can be in the range of 24 kDa to 500 kDa; 30 to 500 kDa; 40 to 500 kDa; 50 to 500 kDa; 100 to 500 kDa; 150 to 500 kDa; 200 to 500 kDa; 250 to 500 kDa; 300 to 500 kDa; 350 to 500 kDa; 400 to 500 kDa and 450 to 500 kDa. Preferably the hydrodynamic size of a PEGylated antibody polypeptide of the invention is 30 to 40 kDa; 70 to 80 kDa or 200 to 300 kDa. Where a single immunoglobulin variable domain polypeptide is desired for use in imaging applications, the polypeptide should have a hydrodynamic size of between 50 and 100 kDa. Alternatively, where a single immunoglobulin variable domain polypeptide is desired for therapeutic applications, the polypeptide preparation should have a hydrodynamic size of greater than 200 kDa.

As used herein, the term "$IC_{50}$" refers to the concentration of an inhibitor necessary to inhibit a given activity by 50%. $IC_{50}$ is determined by assaying a given activity, e.g., binding of CD40L to CD40, in the presence of varying amounts of the inhibitor (e.g., monovalent anti-CD40L antibody polypeptide), and plotting the inhibitor concentration versus the activity being targeted. Binding of CD40L to CD40 is measured herein by the method described in Example 6. Alternatively, SPR can be used.

As used herein, the term "fused to an antibody polypeptide" means that a polypeptide is fused to a given antibody through use of recombinant DNA techniques. Thus, an antibody "fused to" another polypeptide, e.g., to another antibody of different binding specificity, does not exist in nature and is generated through recombinant means. The term "fused to an antibody polypeptide" also encompasses the linkage of a polypeptide to a given antibody polypeptide through, for example, disulfide or other chemical linkages, where the fused polypeptide is not naturally found fused to the antibody polypeptide. Recombinant and chemical methods of fusing a polypeptide to another polypeptide, e.g., to an antibody, are well known in the art.

As used herein, the term "Fc domain" refers to the constant region antibody sequences comprising CH2 and CH3 constant domains as delimited according to Kabat et al., supra. The Fc portion of the heavy chain polypeptide has the ability to self-associate, a function which facilitates the formation of divalent antibodies. The term "lacks an Fc domain" means that a given antibody polypeptide lacks at least the portion of an immunoglobulin Fc domain (as such domains are defined according to Kabat et al., supra) sufficient to mediate the dimerization of Fc-containing antibody polypeptides. Dimerization of Fc-containing antibody polypeptides is measured, for example, by chromatographic methods or by surface plasmon resonance. An antibody polypeptide lacking an Fc domain avoids Fc-platelet interactions and therefore avoids induction of platelet aggregation.

As used herein, the term "symptom of systemic lupus erythematosus" refers to any of the clinically relevant symptoms of SLE known to those of skill in the art. Non-limiting examples include the accumulation of IgG autoantibodies (e.g., against nuclear antigens such as chromatin, snRNPs (especially U1, Sm, Ro/SSA and La/SSB), phospholipids and cell surface molecules), hemolytic anemia, thrombocytopenia, leukopenia, glomerulonephritis, vasculitis, arthritis, and serositis). A reduction in such a symptom is a reduction by at least 10% in a clinically measurable parameter, or by at least one point on a clinically-accepted scale of disease severity.

As used herein, the phrase "specifically binds" refers to the binding of an antigen by an immunoglobulin variable domain with a dissociation constant ($K_d$) of 1 μM or lower as measured by surface plasmon resonance analysis using, for example, a BIAcore™ surface plasmon resonance system and BIAcore™ kinetic evaluation software (e.g., version 2.1). The affinity or $K_d$ for a specific binding interaction is preferably about 500 nM or lower, more preferably about 300 nM or lower.

As used herein, a "generic ligand" is a ligand that binds a substantial proportion of functional members in a given repertoire, e.g., in a phage display library. Thus, the same generic ligand can bind many members of the repertoire regardless of their target ligand specificities. In general, the presence of a functional generic ligand binding site indicates that the repertoire member is expressed and folded correctly. Thus, binding of the generic ligand to its binding site provides a method for preselecting functional polypeptides from a repertoire of polypeptides. Generic ligands include, for example, Protein A, Protein G and Protein L.

As used herein, the term "universal framework" refers to a single antibody framework sequence corresponding to the regions of an antibody conserved in sequence as defined by Kabat (supra) or corresponding to the human germline immunoglobulin repertoire or structure as defined by Chothia and Lesk, (1987) J. Mol. Biol. 196:910-917. The invention provides for the use of a single framework, or a set of such frameworks, which has been found to permit the derivation of virtually any binding specificity though variation in the hypervariable regions alone.

BRIEF DESCRIPTION OF THE FIGURES

FIG. 5 shows the sequence of the $V_H$ framework based on germline sequence DP47-JH4b (SEQ ID NO: 1, amino acid sequence; SEQ ID NO: 2, nucleotide sequence—both sense and antisense strands are shown—SEQ ID NO: 2 is the top strand). HCDRs 1-3 are indicated by underlining.

FIG. 6 shows the sequence of the $V_\kappa$ framework based on germline sequence DPK9-$J_K$1 (SEQ ID NO: 3, amino acid sequence; SEQ ID NO: 4, nucleotide sequence—both sense and antisense strands are shown—SEQ ID NO: 4 is the top strand). LCDRs 1-3 are indicated by underlining.

FIG. 8 shows various GAS1 secretion signal peptide coding sequences. GAS we: The natural occurring sequence in yeast. GAS *E. Coli:* The nucleotide sequence according to optimal *E. Coli* codon usage (Wada et al. 1992 NAR 20 p 2111). GAS leader AT: AT rich nucleotide sequence. All nucleotide sequences encode the same amino acid sequence. Yellow indicates nucleotides that are similar for all sequences. Blue indicates nucleotides that are similar to the wt sequence. White indicates nucleotides that are different from the wt sequence.

DETAILED DESCRIPTION

Figure 1A:
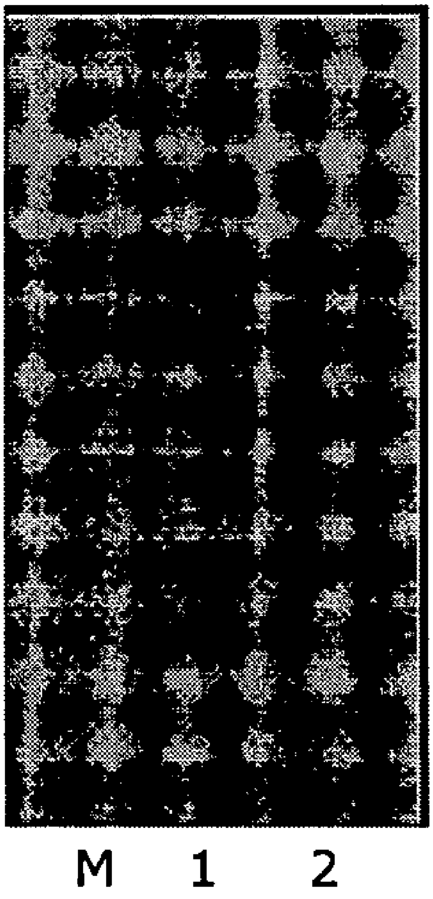
FIG. 1 shows gel analysis of the quality of biotin-labeled CD40L used in the screening procedures described herein. (a) 1 μg of non-biotinylated-CD40L (Lane 1) and 0.3 μg of biotin-CD40L (Lane 2) were analysed on SDS-PAGE and detected by Simply Blue Safe-Stain. (b) 0.1 μg of biotin-CD40L (Lane 1) and 0.02 μg of biotin-CD40L (Lane 2) were detected by Western-blot probing with 1:5000 Streptavidin-HRP.

The invention provides antibody polypeptides that are monovalent for binding to CD40L. Monovalency for CD40L binding removes the possibility for cross-linking that occurs with prior art antibodies, and which plays a role in undesirable side effects observed with anti-CD40L monoclonal antibodies. Further, while not wishing to be limited to any specific mechanism or theory, because antibody polypeptides monovalent for CD40L cannot cross link CD40L, the possibility is eliminated that cross-linked CD40L may in turn cross-link cell surface CD40 and result in agonism of CD40 signaling activity. Thus, in a preferred aspect, the anti-CD40L antibodies disclosed herein not only inhibit or antagonize the binding of CD40L to CD40, they do not substantially agonize CD40 activity.

In one aspect, the antibodies monovalent for CD40L binding are human antibody polypeptides. Human antibody polypeptides can be administered to human patients while largely avoiding the anti-antibody immune response often provoked by the administration of antibodies from other species, e.g., mouse. While murine antibodies can be "humanized" by grafting human constant domains onto the murine antigen-binding domains, human antibodies as disclosed herein are produced without the need for laborious and time-consuming genetic manipulation of a murine antibody sequence.

Monovalent Antibody Polypeptides:

The heavy and light polypeptide chains of antibodies comprise variable (V) regions that directly participate in antigen interactions, and constant (C) regions that provide structural support and function in non-antigen-specific interactions with immune effectors. The antigen binding domain of a conventional antibody is comprised of two separate domains: a heavy chain variable domain ($V_H$) and a light chain variable domain ($V_L$: which can be either $V_\kappa$ or $V_\lambda$). The antigen binding site itself is formed by six polypeptide loops: three from the $V_H$ domain (H1, H2 and H3) and three from the $V_L$ domain (L1, L2 and L3). In vivo, a diverse primary repertoire of V genes that encode the $V_H$ and $V_L$ domains is produced by the combinatorial rearrangement of gene segments. C regions include the light chain C regions (referred to as $C_L$ regions) and the heavy chain C regions (referred to as $C_H1$, $C_H2$ and $C_H3$ regions). A naturally-occurring antibody generally comprises two antigen binding domains and is therefore divalent.

A number of smaller antigen binding fragments of naturally occurring antibodies have been identified following protease digestion. These include, for example, the "Fab fragment" ($V_L$-$C_L$-$C_H$1-$V_H$), "Fab' fragment" (a Fab with the heavy chain hinge region), and "F(ab')$_2$ fragment" (a dimer of Fab' fragments joined by the heavy chain hinge region). Recombinant methods have been used to generate such fragments and to generate even smaller antigen-binding fragments, e.g., those referred to as "single chain Fv" (variable fragment) or "scFv," consisting of $V_L$ and $V_H$ joined by a synthetic peptide linker ($V_L$-linker-$V_H$). Fab fragments, Fab' fragments and scFv fragments are monovalent for antigen binding, as they each comprise only one antigen binding domain comprising one $V_H/V_L$ dimer. Even smaller monovalent antibody fragments are the "domain antibodies," or "dAbs," which comprise only a single immunoglobulin variable domain, e.g., $V_H$ or $V_L$, that alone specifically binds antigen, i.e., without the need for a complementary $V_L$ or $V_H$ domain, respectively.

The term "dAb" will refer herein to a single immunoglobulin variable domain ($V_H$ or $V_L$) polypeptide that specifically binds antigen. A "dAb" binds antigen independently of other V domains; however, a "dAb" can be present in a homo- or heteromultimer with other $V_H$ or $V_L$ domains where the other domains are not required for antigen binding by the dAb, i.e., where the dAb binds antigen independently of the additional $V_H$ or $V_L$ domains. The preparation of single immunoglobulin variable domains is described and exemplified herein below.

Monovalent antibody polypeptides can be generated in several different ways. For example, the nucleic acid sequence encoding heavy and light chains of an antibody known to bind CD40L can be manipulated to generate a number of different antibody polypeptides that are monovalent for CD40L binding. Thus, given the sequences encoding the heavy and light chain polypeptides that constitute an antibody and standard molecular cloning methodologies, one can generate monovalent antigen-binding polypeptide constructs such as Fab fragments, scFv, dAbs, or even bispecific antibodies (i.e., antibodies that comprise two different antigen-binding moieties and can therefore bind two separate antigens, preferably simultaneously) that are monovalent for CD40L.

Thus, one means of generating monovalent antibody polypeptides specific for CD40L is is to amplify and express the $V_H$ and $V_L$ regions of the heavy chain and light chain gene sequences isolated, for example, from a hybridoma (e.g., a mouse hybridoma) that expresses anti-CD40L monoclonal antibody. The boundaries of $V_H$ and $V_L$ domains are set out by Kabat et al. (1991, supra). The information regarding the boundaries of the $V_H$ and $V_L$ domains of heavy and light chain genes is used to design PCR primers that amplify the V domain from a heavy or light chain coding sequence encoding an antibody known to bind CD40L. The amplified V domains are inserted into a suitable expression vector, e.g., pHEN-1 (Hoogenboom et al., 1991, Nucleic Acids Res. 19: 4133-4137) and expressed, e.g., as a fusion of the $V_H$ and $V_L$ in an scFv or other suitable monovalent format. The resulting polypeptide is then screened for high affinity monovalent binding to CD40L. For all aspects of the present invention, screening for binding is performed as known in the art or as described herein below.

Alternatively, library screening methods can be used to identify monovalent CD40L-specific binding proteins. Phage display technology (see, e.g., Smith, 1985, Science 228: 1315; Scott & Smith, 1990, Science 249: 386; McCafferty et al., 1990, Nature 348: 552) provides an approach for the selection of antibody polypeptides which bind a desired target from among large, diverse repertoires of antibody polypeptides. These phage-antibody libraries can be grouped into two categories: natural libraries which use rearranged V genes harvested from human B cells (Marks et al., 1991, J. Mol. Biol., 222: 581; Vaughan et al., 1996, Nature Biotech., 14: 309) or synthetic libraries whereby germline V gene segments or other antibody polypeptide coding sequences are 'rearranged' in vitro (Hoogenboom & Winter, 1992, J. Mol. Biol., 227: 381; Nissim et al., 1994, EMBO J., 13: 692; Griffiths et al., 1994, EMBO J., 13: 3245; De Kruif et al., 1995, J. Mol. Biol., 248: 97) or where synthetic CDRs are incorporated into a single rearranged V gene (Barbas et al., 1992. Proc. Natl. Acad. Sci. USA, 89: 4457). Methods involving genetic display packages (e.g., phage display, polysome display) are well-suited for the selection of monovalent CD40L-specific antibody constructs because they generally express only monovalent fragments, rather than whole, divalent antibodies, on the display packages. Methods for the preparation of phage display libraries displaying various antibody fragments are described in the preceding references. Such methods are also described, for example, in U.S. Pat. No. 6,696,245, which is incorporated herein by reference. The methods described in the '245 patent generally involve the randomization of selected regions of immunoglobulin gene coding regions, in particular $V_H$ and $V_L$ coding regions, while leaving other regions non-randomized (see below). The '245 patent also describes the generation of scFv constructs comprising individually randomized $V_H$ and $V_L$ domains.

The $V_H$ gene is produced by the recombination of three gene segments, $V_H$, D and $J_H$. In humans, there are approximately 51 functional $V_H$ segments (Cook and Tomlinson (1995) Immunol Today 16: 237), 25 functional D segments (Corbett et al. (1997) J. Mol. Biol. 268: 69) and 6 functional $J_H$ segments (Ravetch et al. (1981) Cell 27: 583), depending on the haplotype. The $V_H$ segment encodes the region of the polypeptide chain which forms the first and second antigen binding loops of the $V_H$ domain (H1 and H2), while the $V_H$, D and $J_H$ segments combine to form the third antigen binding loop of the $V_H$ domain (H3).

The $V_L$ gene is produced by the recombination of only two gene segments, $V_L$ and $J_L$. In humans, there are approximately 40 functional $V_\kappa$ segments (Schäble and Zachau (1993) Biol. Chem. Hoppe-Seyler 374: 1001), 31 functional $V_\lambda$ segments (Williams et al. (1996) J. Mol. Biol. 264: 220; Kawasaki et al. (1997) Genome Res. 7: 250), 5 functional $J_\kappa$ segments (Hieter et al. (1982) J. Biol. Chem. 257: 1516) and 4 functional $J_\lambda$ segments (Vasicek and Leder (1990) J. Exp. Med. 172: 609), depending on the haplotype. The $V_L$ segment encodes the region of the polypeptide chain which forms the first and second antigen binding loops of the $V_L$ domain (L1 and L2), while the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced in vivo by "affinity maturation" of the rearranged genes, in which point mutations are generated and selected by the immune system on the basis of improved binding.

Analysis of the structures and sequences of antibodies has shown that five of the six antigen binding loops (H1, H2, L1, L2, L3) possess a limited number of main-chain conformations or canonical structures (Chothia and Lesk (1987) J. Mol. Biol. 196: 901; Chothia et al. (1989) Nature 342: 877). The main-chain conformations are determined by (i) the length of the antigen binding loop, and (ii) particular residues, or types of residue, at certain key positions in the antigen binding loop and the antibody framework. Analysis of the loop lengths and key residues has enabled the prediction of the main-chain conformations of H1, H2, L1, L2 and L3 encoded by the majority of human antibody sequences (Chothia et al. (1992) J. Mol. Biol. 227: 799; Tomlinson et al. (1995) EMBO J. 14: 4628; Williams et al. (1996) J. Mol. Biol. 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) J. Mol. Biol. 263: 800; Shirai et al. (1996) FEBS Letters 399: 1.

While, in one approach, diversity can be added to synthetic repertoires at any site in the CDRs of the various antigen-binding loops, this approach results in a greater proportion of V domains that do not properly fold and therefore contribute to a lower proportion of molecules with the potential to bind antigen. An understanding of the residues contributing to the main chain conformation of the antigen-binding loops permits the identification of specific residues to diversify in a synthetic repertoire of $V_H$ or $V_L$ domains. That is, diversity is best introduced in residues that are not essential to maintaining the main chain conformation. As an example, for the diversification of loop L2, the conventional approach would be to diversify all the residues in the corresponding CDR (CDR2) as defined by Kabat et al. (1991, supra), some seven residues. However, for L2, it is known that positions 50 and 53 are diverse in naturally occurring antibodies and are observed to make contact with the antigen. The preferred approach would be to diversify only those two residues in this loop. This represents a significant improvement in terms of the functional diversity required to create a range of antigen binding specificities.

Immunoglobulin polypeptide libraries can advantageously be designed to be based on predetermined variable domain main chain conformation. Such libraries may be constructed as described in International Patent Application WO 99/20749, the contents of which are incorporated herein by reference. Thus, in one aspect, an antibody polypeptide comprises the amino acid sequence of a given human germline V region gene segment, e.g., $V_H$ germline gene segment DP-47, or $V_\kappa$ germline gene segment DPK9. Such variable region polypeptides can be used for the production of scFvs or Fabs, e.g., an scFv or Fab comprising (i) an antibody heavy chain variable domain ($V_H$), or antigen binding fragment thereof, which comprises the amino acid sequence of germline $V_H$ segment DP-47 and (ii) an antibody light chain variable domain ($V_L$), or antigen binding fragment thereof, which comprises the amino acid sequence of germline $V_\kappa$ segment DPK9. Diversification of sequences within the context of the selected heavy and light chain germline gene segments, e.g., DP-47, DPK 9, DP45, DP38, etc. can generate a repertoire of diverse immunoglobulin coding sequences. One approach to diversification is described below in the context of generating a library of diversified dAb or scFv sequences. These variable region polypeptides can also be expressed as dAbs and screened for high affinity binding to CD40L. The repertoire can be cloned into or generated in a vector suitable for phage display, e.g., a lambda or filamentous bacteriophage display vector and is then screened for binding to a given target antigen, e.g., CD40L.

Preparation of Human Single Immunoglobulin Variable Domain Polypeptides:

A single immunoglobulin variable domain is a folded polypeptide domain which comprises sequences characteristic of immunoglobulin variable domains and which specifically binds an antigen (e.g., dissociation constant of 500 nM or less), and which binds antigen as a single variable domain; that is, there is one binding site provided by a single immunoglobulin variable domain without any complementary variable domain. A single immunoglobulin variable domain therefore includes complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains which retain a dissociation constant of 500 nM or less (e.g., 450 nM or less, 400 nM or less, 350 nM or less, 300 nM or less, 250 nM or less, 200 nM or less, 150 nM or less, 100 nM or less) and the target antigen specificity of the full-length domain. Preferably an antibody single variable domain useful in the invention is selected from the group of $V_H$ and $V_L$, including $V_{kappa}$ and $V_{lambda}$. The single immunoglobulin variable domains of use herein are preferably "human" as that term is defined herein.

Preparation of Single Immunoglobulin Variable Domains:

Single immunoglobulin variable domains are prepared in a number of ways. For each of these approaches, well-known methods of preparing (e.g., amplifying, mutating, etc.) and manipulating nucleic acid sequences are applicable.

One means of preparing single immunoglobulin variable domains is to amplify and express the $V_H$ or $V_L$ region of a heavy chain or light chain gene for a cloned antibody known to bind the desired antigen. That is, the $V_H$ or $V_L$ domain of a known anti-CD40L antibody coding region can be amplified and expressed as a single domain (or as a fusion of a single domain) and evaluated for binding to CD40L. The boundaries of $V_H$ and $V_L$ domains are set out by Kabat et al. (1991, supra). The information regarding the boundaries of the $V_H$ and $V_L$ domains of heavy and light chain genes is used to design PCR primers that amplify the V domain from a cloned heavy or light chain coding sequence encoding an antibody known to bind CD40L. The amplified V domain is inserted into a suitable expression vector, e.g., pHEN-1 (Hoogenboom et al., 1991, Nucleic Acids Res. 19: 4133-4137) and expressed, either alone or as a fusion with another polypeptide sequence.

In a preferred approach, a repertoire of $V_H$ or $V_L$ domains, preferably human $V_H$ or $V_L$ domains, is screened by, for example, phage display, panning against the desired antigen. Methods for the construction of bacteriophage display libraries and lambda phage expression libraries are well known in the art, and taught, for example, by: McCafferty et al., 1990, Nature 348: 552; Kang et al., 1991, Proc. Natl. Acad. Sci. U.S.A., 88: 4363; Clackson et al., 1991, Nature 352: 624; Lowman et al., 1991, Biochemistry 30: 10832; Burton et al., 1991, Proc. Natl. Acad. Sci U.S.A. 88: 10134; Hoogenboom et al., 1991, Nucleic Acids Res. 19: 4133; Chang et al., 1991, J. Immunol. 147: 3610; Breitling et al., 1991, Gene 104: 147; Marks et al., 1991, J. Mol. Biol. 222: 581; Barbas et al., 1992, Proc. Natl. Acad. Sci. U.S.A. 89: 4457; Hawkins and Winter (1992) J. Immunol., 22: 867; Marks et al. (1992) J. Biol. Chem., 267: 16007; and Lerner et al. (1992) Science, 258: 1313. Fab phage display libraries are taught, for example, by U.S. Pat. No. 5,922,545. scFv phage libraries are taught, for example, by Huston et al., 1988, Proc. Natl. Acad. Sci U.S.A. 85: 5879-5883; Chaudhary et al., 1990, Proc. Natl. Acad. Sci U.S.A. 87: 1066-1070; McCafferty et al., 1990, supra; Clackson et al., 1991, supra; Marks et al., 1991, supra; Chiswell et al., 1992, Trends Biotech. 10: 80; and Marks et al., 1992, supra. Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra).

The repertoire of $V_H$ or $V_L$ domains can be a naturally-occurring repertoire of immunoglobulin sequences or a synthetic repertoire. A naturally-occurring repertoire is one prepared, for example, from immunoglobulin-expressing cells harvested from one or more individuals. Such repertoires can be "naïve," i.e., prepared, for example, from human fetal or newborn immunoglobulin-expressing cells, or rearranged, i.e., prepared from, for example, adult human B cells. Natural repertoires are described, for example, by Marks et al., 1991, J. Mol. Biol. 222: 581 and Vaughan et al., 1996, Nature Biotech. 14: 309. If desired, clones identified from a natural repertoire, or any repertoire, for that matter, that bind the target antigen are then subjected to mutagenesis and further screening in order to produce and select variants with improved binding characteristics.

Synthetic repertoires of single immunoglobulin variable domains are prepared by artificially introducing diversity into a cloned V domain. Synthetic repertoires are described, for example, by Hoogenboom & Winter, 1992, J. Mol. Biol. 227: 381; Barbas et al., 1992, Proc. Natl. Acad. Sci. U.S.A. 89: 4457; Nissim et al., 1994, EMBO J. 13: 692; Griffiths et al., 1994, EMBO J. 13: 3245; DeKriuf et al., 1995, J. Mol. Biol. 248: 97; and WO 99/20749.

In one aspect, synthetic variable domain repertoires are prepared in $V_H$ or $V_\kappa$ backgrounds, based on artificially diversified germline $V_H$ or $V_\kappa$ sequences. For example, the $V_H$ domain repertoire can be based on cloned germline $V_H$ gene segments V3-23/DP47 (Tomlinson et al., 1992, J. Mol. Biol. 227: 7768) and JH4b. The $V_\kappa$ domain repertoire can be based, for example, on germline $V_\kappa$ gene segments O2/O12/DPK9 (Cox et al., 1994, Eur. J. Immunol. 24: 827) and $J_\kappa 1$. Diversity is introduced into these or other gene segments by, for example, PCR mutagenesis. Diversity can be randomly introduced, for example, by error prone PCR (Hawkins, et al., 1992, J. Mol. Biol. 226: 889) or chemical mutagenesis. As discussed above, however it is preferred that the introduction of diversity is targeted to particular residues. It is further preferred that the desired residues are targeted by introduction of the codon NNK using mutagenic primers (using the IUPAC nomenclature, where N=G, A, T or C, and K=G or T), which encodes all amino acids and the TAG stop codon. Other codons which achieve similar ends are also of use, including the NNN codon (which leads to the production of the additional stop codons TGA and TAA), DVT codon ((A/G/T)(A/G/C)T), DVC codon ((A/G/T)(A/G/C)C), and DVY codon ((A/G/T)(A/G/C)(C/T). The DVT codon encodes 22% serine and 11% tyrosine, aspargine, glycine, alanine, aspartate, threonine and cysteine, which most closely mimics the distribution of amino acid residues for the antigen binding sites of natural human antibodies. Repertoires are made using PCR primers having the selected degenerate codon or codons at each site to be diversified. PCR mutagenesis is well known in the art.

In one aspect, diversity is introduced into the sequence of human germline $V_H$ gene segments V3-23/DP47 (Tomlinson et al., 1992, J. Mol. Biol. 227: 7768) and JH4b using the NNK codon at sites H30, H31, H33, H35, H50, H52, H52a, H53, H55, H56, H58, H95, H97 and H98, corresponding to diversity in CDRs 1, 2 and 3, with the numbering as used in U.S. Pat. No. 6,696,245.

In another aspect, diversity is also introduced into the sequence of human germline $V_H$ gene segments V3-23/DP47 and JH4b, for example, using the NNK codon at sites H30, H31, H33, H35, H50, H52, H52a, H53, H55, H56, H58, H95, H97, H98, H99, H100, H100a and H100b, corresponding to diversity in CDRs 1, 2 and 3, with the numbering as used in U.S. Pat. No. 6,696,245.

In another aspect, diversity is introduced into the sequence of human germline $V_\kappa$ gene segments O2/O12/DPK9 and $J_\kappa 1$, for example, using the NNK codon at sites L30, L31, L32, L34, L50, L53, L91, L92, L93, L94 and L96, corresponding to diversity in CDRs 1, 2 and 3, with the numbering as used in U.S. Pat. No. 6,696,245.

Diversified repertoires are cloned into phage display vectors as known in the art and as described, for example, in WO 99/20749. In general, the nucleic acid molecules and vector constructs required for the performance of the present invention are available in the art and are constructed and manipulated as set forth in standard laboratory manuals, such as Sambrook et al. (1989). Molecular Cloning: A Laboratory Manual, Cold Spring Harbor, USA.

The manipulation of nucleic acids in the present invention is typically carried out in recombinant vectors. As used herein, "vector" refers to a discrete element that is used to introduce heterologous DNA into cells for the expression and/or replication thereof. Methods by which to select or construct and, subsequently, use such vectors are well known to one of skill in the art. Numerous vectors are publicly available, including bacterial plasmids, bacteriophage, artificial chromosomes and episomal vectors. Such vectors may be used for simple cloning and mutagenesis; alternatively, as is typical of vectors in which repertoire (or pre-repertoire) members of the invention are carried, a gene expression vector is employed. A vector of use according to the invention is selected to accommodate a polypeptide coding sequence of a desired size, typically from 0.25 kilobase (kb) to 40 kb in length. A suitable host cell is transformed with the vector after in vitro cloning manipulations. Each vector contains various functional components, which generally include a cloning (or "polylinker") site, an origin of replication and at least one selectable marker gene. If a given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector also contains a selection gene also referred to as selectable marker.

This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Because the replication of vectors according to the present invention is most conveniently performed in *E. coli*, an *E. coli*-selectable marker, for example, the β-lactamase gene that confers resistance to the antibiotic ampicillin, is of use. These can be obtained from *E. coli* plasmids, such as pBR322 or a pUC plasmid such as pUC18 or pUC19.

Expression vectors usually contain a promoter that is recognized by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Dalgarno sequence operably linked to the coding sequence.

In libraries or repertoires as described herein, the preferred vectors are expression vectors that enable the expression of a nucleotide sequence corresponding to a polypeptide library member. Thus, selection is performed by separate propagation and expression of a single clone expressing the polypeptide library member or by use of any selection display system. As described above, a preferred selection display system uses bacteriophage display. Thus, phage or phagemid vectors can be used. Preferred vectors are phagemid vectors, which have an *E. coli* origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector contains a β-lactamase or other selectable marker gene to confer selectivity on the phagemid, and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tags (for detection), optionally, one or more TAG stop codons and the phage protein pIII. In one embodiment, the vector encodes, rather than the pelB leader sequence, a eukaryotic GAS1 leader sequence which serves to direct the secretion of the fusion polypeptide to the periplasmic space in *E. coli* or to the medium in eukaryotic cell systems. Using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only, or produce phage, some of which contain at least one copy of the polypeptide-pIII fusion on their surface.

An example of a preferred vector is the pHEN1 phagemid vector (Hoogenboom et al., 1991, Nucl. Acids Res. 19: 4133-4137; sequence is available, e.g., as SEQ ID NO: 7 in WO 03/031611), in which the production of pIII fusion protein is under the control of the LacZ promoter, which is inhibited in the presence of glucose and induced with IPTG. When grown in suppressor strains of *E. coli*, e.g., TG1, the gene III fusion protein is produced and packaged into phage, while growth in non-suppressor strains, e.g., HB2151, permits the secretion of soluble fusion protein into the bacterial periplasm and into the culture medium. Because the expression of gene III prevents later infection with helper phage, the bacteria harboring the phagemid vectors are propagated in the presence of glucose before infection with VCSM13 helper phage for phage rescue.

Construction of vectors according to the invention employs conventional ligation techniques. Isolated vectors or DNA fragments are cleaved, tailored, and re-ligated in the form desired to generate the required vector. If desired, sequence analysis to confirm that the correct sequences are present in the constructed vector is performed using standard methods. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridization, immunocytochemistry or sequence analysis of nucleic acid or protein molecules. Those skilled in the art will readily envisage how these methods may be modified, if desired.

Screening Single Immunoglobulin Variable Domains for Antigen Binding:

Following expression of a repertoire of single immunoglobulin variable domains on the surface of phage, selection is performed by contacting the phage repertoire with immobilized target antigen, washing to remove unbound phage, and propagation of the bound phage, the whole process frequently referred to as "panning." This process is applicable to the screening of single immunoglobulin variable domains as well as other antibody fragments that can be expressed on a display library, e.g., scFv, Fab, etc. Alternatively, phage are pre-selected for the expression of properly folded member variants by panning against an immobilized generic ligand (e.g., protein A or protein L) that is only bound by folded members. This has the advantage of reducing the proportion of non-functional members, thereby increasing the proportion of members likely to bind a target antigen. Pre-selection with generic ligands is taught in WO 99/20749. The screening of phage antibody libraries is generally described, for example, by Harrison et al., 1996, Meth. Enzymol. 267: 83-109.

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks et al., 1993, BioTechnology 11: 1145; de Kruif et al., 1995, Proc. Natl. Acad. Sci. U.S.A. 92: 3938). Another alternative involves selection by binding biotinylated antigen in solution, followed by capture on streptavidin-coated beads.

In a preferred aspect, panning is performed by immobilizing antigen (generic or specific) on tubes or wells in a plate, e.g., Nunc MAXISORP™ immunotube 8 well strips. Wells are coated with 150 μl of antigen (100 μg/ml in PBS) and incubated overnight. The wells are then washed 3 times with PBS and blocked with 400 μl PBS-2% skim milk (2% MPBS) at 37° C. for 2 hr. The wells are rinsed 3 times with PBS and phage are added in 2% MPBS. The mixture is incubated at room temperature for 90 minutes and the liquid, containing unbound phage, is removed. Wells are rinsed 10 times with PBS-0.1% tween 20, and then 10 times with PBS to remove detergent. Bound phage are eluted by adding 200 μl of freshly prepared 100 mM triethylamine, mixing well and incubating for 10 min at room temperature. Eluted phage are transferred to a tube containing 100 μl of 1M Tris-HCl, pH 7.4 and vortexed to neutralize the triethylamine. Exponentially-growing *E. coli* host cells (e.g., TG1) are infected with, for example, 150 ml of the eluted phage by incubating for 30 min at 37° C. Infected cells are spun down, resuspended in fresh medium and plated in top agarose. Phage plaques are eluted or picked into fresh cultures of host cells to propagate for analysis or for further rounds of selection. One or more rounds of plaque purification are performed if necessary to ensure pure populations of selected phage. Other screening approaches are described by Harrison et al., 1996, supra.

Following identification of phage expressing a single immunoglobulin variable domain that binds a desired target, if a phagemid vector such as pHEN1 has been used, the variable domain fusion proteins are easily produced in soluble form by infecting non-suppressor strains of bacteria, e.g., HB2151 that permit the secretion of soluble gene III fusion protein. If a GAS1 secretion signal peptide is encoded by the vector, the fusion polypeptide can be secreted by eukaryotic (e.g., yeast or mammalian) or prokaryotic (e.g., *E. coli*) cells. Alternatively, the V domain sequence can be subcloned into an appropriate expression vector to produce soluble protein according to methods known in the art.

Purification and Concentration of Single Immunoglobulin Variable Domains:

Single immunoglobulin variable domain polypeptides or other monovalent antibody polypeptides secreted into the periplasmic space or into the medium of bacteria are harvested and purified according to known methods (Harrison et al., 1996, supra). Skerra & Pluckthun (1988, Science 240: 1038) and Breitling et al. (1991, Gene 104: 147) describe the harvest of antibody polypeptides from the periplasm, and Better et al. (1988, Science 240: 1041) describes harvest from the culture supernatant. For some antibody polypeptides, purification can also be achieved by binding to generic ligands, such as protein A or Protein L. Alternatively, the variable domains can be expressed with a peptide tag, e.g., the Myc, HA or 6×-His tags, which facilitates purification by affinity chromatography.

If necessary, monovalent anti-CD40L antibody polypeptides are concentrated by any of several methods well known in the art, including, for example, ultrafiltration, diafiltration and tangential flow filtration. The process of ultrafiltration uses semi-permeable membranes and pressure to separate molecular species on the basis of size and shape. The pressure is provided by gas pressure or by centrifugation. Commercial ultrafiltration products are widely available, e.g., from Millipore (Bedford, Mass.; examples include the Centricon™ and Microcon™ concentrators) and Vivascience (Hannover, Germany; examples include the Vivaspin™ concentrators). By selection of a molecular weight cutoff smaller than the target polypeptide (usually ⅓ to ⅙ the molecular weight of the target polypeptide, although differences of as little as 10 kD can be used successfully), the polypeptide is retained when solvent and smaller solutes pass through the membrane. Thus, a molecular weight cutoff of about 5 kD is useful for concentration of anti-CD40L single immunoglobulin variable domain polypeptides described herein.

Diafiltration, which uses ultrafiltration membranes with a "washing" process, is used where it is desired to remove or exchange the salt or buffer in a polypeptide preparation. The polypeptide is concentrated by the passage of solvent and small solutes through the membrane, and remaining salts or buffer are removed by dilution of the retained polypeptide with a new buffer or salt solution or water, as desired, accompanied by continued ultrafiltration. In continuous diafiltration, new buffer is added at the same rate that filtrate passes through the membrane. A diafiltration volume is the volume of polypeptide solution prior to the start of diafiltration—using continuous diafiltration, greater than 99.5% of a fully permeable solute can be removed by washing through six diafiltration volumes with the new buffer. Alternatively, the process can be performed in a discontinuous manner, wherein the sample is repeatedly diluted and then filtered back to its original volume to remove or exchange salt or buffer and ultimately concentrate the polypeptide. Equipment for diafiltration and detailed methodologies for its use are available, for example, from Pall Life Sciences (Ann Arbor, Mich.) and Sartorius AG/Vivascience (Hannover, Germany).

Tangential flow filtration (TFF), also known as "cross-flow filtration," also uses ultrafiltration membrane. Fluid containing the target polypeptide is pumped tangentially along the surface of the membrane. The pressure causes a portion of the fluid to pass through the membrane while the target polypeptide is retained above the filter. In contrast to standard ultrafiltration, however, the retained molecules do not accumulate on the surface of the membrane, but are carried along by the tangential flow. The solution that does not pass through the filter (containing the target polypeptide) can be repeatedly circulated across the membrane to achieve the desired degree of concentration. Equipment for TFF and detailed methodologies for its use are available, for example, from Millipore (e.g., the ProFlux M12™ Benchtop TFF system and the Pellicon™ systems), Pall Life Sciences (e.g., the Minim™ Tangential Flow Filtration system).

Protein concentration is measured in a number of ways that are well known in the art. These include, for example, amino acid analysis, absorbance at 280 nm, the "Bradford" and "Lowry" methods, and SDS-PAGE. The most accurate method is total hydrolysis followed by amino acid analysis by HPLC, concentration is then determined then comparison with the known sequence of the single immunoglobulin variable domain polypeptide. While this method is the most accurate, it is expensive and time-consuming. Protein determination by measurement of UV absorbance at 280 nm faster and much less expensive, yet relatively accurate and is preferred as a compromise over amino acid analysis. Absorbance at 280 nm was used to determine protein concentrations reported in the Examples described herein.

"Bradford" and "Lowry" protein assays (Bradford, 1976, Anal. Biochem. 72: 248-254; Lowry et al., 1951, J. Biol. Chem. 193: 265-275) compare sample protein concentration to a standard curve most often based on bovine serum albumin (BSA). These methods are less accurate, tending to underestimate the concentration of single immunoglobulin variable domains. Their accuracy could be improved, however, by using a $V_H$ or $V_\kappa$ single domain polypeptide as a standard.

An additional protein assay method is the bicinchoninic acid assay described in U.S. Pat. No. 4,839,295 (incorporated herein by reference) and marketed by Pierce Biotechnology (Rockford, Ill.) as the "BCA Protein Assay" (e.g., Pierce Catalog No. 23227).

The SDS-PAGE method uses gel electrophoresis and Coomassie Blue staining in comparison to known concentration standards, e.g., known amounts of a single immunoglobulin variable domain polypeptide. Quantitation can be done by eye or by densitometry.

Single human immunoglobulin variable domain antigen-binding polypeptides described herein retain solubility at high concentration (e.g., at least 4.8 mg (~400 μM) in aqueous solution (e.g., PBS), and preferably at least 5 mg/ml (~417 μM), 10 mg/ml (~833 μM), 20 mg/ml (~1.7 mM), 25 mg/ml (~2.1 mM), 30 mg/ml (~2.5 mM), 35 mg/ml (~2.9 mM), 40 mg/ml (~3.3 mM), 45 mg/ml (~3.75 mM), 50 mg/ml (~4.2 mM), 55 mg/ml (~4.6 mM), 60 mg/ml (~5.0 mM), 65 mg/ml (~5.4 mM), 70 mg/ml (~5.8 mM), 75 mg/ml (~6.3 mM), 100 mg/ml (~8.33 mM), 150 mg/ml (~12.5 mM), 200 mg/ml (~16.7 mM), 240 mg/ml (~20 mM) or higher). One structural feature that promotes high solubility is the relatively small size of the single immunoglobulin variable domain polypeptides. A full length conventional four chain antibody, e.g., IgG is about 150 kD in size. In contrast, single immunoglobulin variable domains, which all have a general structure comprising 4 framework (FW) regions and 3 CDRs, have a size of approximately 12 kD, or less than 1/10 the size of a conventional antibody. Similarly, single immunoglobulin variable domains are approximately ½ the size of an scFv molecule (~26 kD), and approximately ⅕ the size of a Fab molecule (~60 kD). It is preferred that the size of a single immunoglobulin variable domain-containing structure disclosed herein is 100 kD or less, including structures of, for example, about 90 kD or less, 80 kD or less, 70 kD or less, 60 kD or less, 50 kD or less, 40 kD or less, 30 kD or less, 20 kD or less, down to and including about 12 kD, or a single immunoglobulin variable domain in isolation.

The solubility of a polypeptide is primarily determined by the interactions of the amino acid side chains with the surrounding solvent. Hydrophobic side chains tend to be localized internally as a polypeptide folds, away from the solvent-interacting surfaces of the polypeptide. Conversely, hydrophilic residues tend to be localized at the solvent-interacting surfaces of a polypeptide. Generally, polypeptides having a primary sequence that permits the molecule to fold to expose more hydrophilic residues to the aqueous environment are more soluble than one that folds to expose fewer hydrophilic residues to the surface. Thus, the arrangement and number of hydrophobic and hydrophilic residues is an important determinant of solubility. Other parameters that determine polypeptide solubility include solvent pH, temperature, and ionic strength. In a common practice, the solubility of polypeptides can be maintained or enhanced by the addition of glycerol (e.g., ~10% v/v) to the solution.

As discussed above, specific amino acid residues have been identified in conserved residues of human $V_H$ domains that vary in the $V_H$ domains of camelid species, which are generally more soluble than human $V_H$ domains. These include, for example, Gly 44 (Glu in camelids), Leu 45 (Arg in camelids) and Trp 47 (Gly in camelids). Amino acid residue 103 of $V_H$ is also implicated in solubility, with mutation from Trp to Arg tending to confer increased $V_H$ solubility.

In preferred aspects of the invention, single immunoglobulin variable domain polypeptides are based on the DP47 germline $V_H$ gene segment or the DPK9 germline $V_\kappa$ gene segment. Thus, these germline gene segments are capable, particularly when diversified at selected structural locations described herein, of producing specific binding single immunoglobulin variable domain polypeptides that are highly soluble. In particular, the four framework regions, which are preferably not diversified, can contribute to the high solubility of the resulting proteins.

It is expected that a single human immunoglobulin variable domain that is highly homologous to one having a known high solubility will also tend to be highly soluble. Thus, as one means of prediction or recognition that a given single immunoglobulin variable domain would have the high solubility recited herein, one can compare the sequence of a single immunoglobulin variable domain polypeptide to one or more single immunoglobulin variable domain polypeptides having known solubility. Thus, when a single immunoglobulin variable domain polypeptide is identified that has high binding affinity but unknown solubility, comparison of its amino acid sequence with that of one or more (preferably more) human single immunoglobulin variable domain polypeptides known to have high solubility (e.g., a dAb sequence disclosed herein) can permit prediction of its solubility. While it is not an absolute predictor, where there is a high degree of similarity to a known highly soluble sequence, e.g., 90-95% or greater similarity, and particularly where there is a high degree of similarity with respect to hydrophilic amino acid residues, or residues likely to be exposed at the solvent interface, it is more likely that a newly identified binding polypeptide will have solubility similar to that of the known highly soluble sequence.

Molecular modeling software can also be used to predict the solubility of a polypeptide sequence relative to that of a polypeptide of known solubility. For example, the substitution or addition of a hydrophobic residue at the solvent-exposed surface, relative to a molecule of known solubility that has a less hydrophobic or even hydrophilic residue exposed in that position is expected to decrease the relative solubility of the polypeptide. Similarly, the substitution or addition of a more hydrophilic residue at such a location is expected to increase the relative solubility. That is, a change in the net number of hydrophilic or hydrophobic residues located at the surface of the molecule (or the overall hydrophobic or hydrophilic nature of the surface-exposed residues) relative to a single immunoglobulin variable domain polypeptide structure with known solubility can predict the relative solubility of a single immunoglobulin variable domain polypeptide.

Alternatively, or in conjunction with such prediction, one can determine limits of a single immunoglobulin variable domain polypeptide's solubility by simply concentrating the polypeptide.

Affinity Determination:

Isolated single immunoglobulin variable domain- and antibody polypeptide-containing polypeptides as described herein preferably have affinities (dissociation constant, $K_d$, $=K_{off}/K_{on}$) of at least 500 nM or less, and preferably at least 400 nM-50 pM, 300 nM-50 pM, 200 nM-50 pM, and more preferably at least 100 nM-50 pM, 75 nM-50 pM, 50 nM-50 pM, 25 nM-50 pM, 10 nM-50 pM, 5 nM-50 pM, 1 nM-50 pM, 950 pM-50 pM, 900 pM-50 pM, 850 pM-50 pM, 800 pM-50 pM, 750 pM-50 pM, 700 pM-50 pM, 650 pM-50 pM, 600 pM-50 pM, 550 pM-50 pM, 500 pM-50 pM, 450 pM-50 pM, 400 pM-50 pM, 350 pM-50 pM, 300 pM-50 pM, 250 pM-50 pM, 200 pM-50 pM, 150 pM-50 pM, 100 pM-50 pM, 90 pM-50 pM, 80 pM-50 pM, 70 pM-50 pM, 60 pM-50 pM, or even as low as 50 pM.

The antigen-binding affinity of an antibody polypeptide, e.g., a single immunoglobulin variable domain polypeptide or other monovalent antibody polypeptide, can be conveniently measured by SPR using the BIAcore system (Pharmacia Biosensor, Piscataway, N.J.). In this method, antigen is coupled to the BIAcore chip at known concentrations, and variable domain polypeptides are introduced. Specific binding between the variable domain polypeptide and the immobilized antigen results in increased protein concentration on the chip matrix and a change in the SPR signal. Changes in SPR signal are recorded as resonance units (RU) and displayed with respect to time along the Y axis of a sensorgram. Baseline signal is taken with solvent alone (e.g., PBS) passing over the chip. The net difference between baseline signal and signal after completion of antibody polypeptide injection represents the binding value of a given sample. To determine the off rate ($K_{off}$), on rate ($K_{on}$) and dissociation rate ($K_d$) constants, BIAcore kinetic evaluation software (e.g., version 2.1) is used.

Thus, SPR can be used to monitor antagonism of CD40L binding to CD40 by a monovalent anti-CD40L antibody preparation by measuring the displacement or inhibition of binding of CD40L to CD40 caused the the monovalent antibody preparation. SPR can also be used to monitor the dimerization, or preferably, the lack of dimerization, occurring via Fc region in antibody preparations as described herein.

High affinity is dependent upon the complementarity between a surface of the antigen and the CDRs of the antibody or antibody fragment. Complementarity is determined by the type and strength of the molecular interactions possible between portions of the target and the CDR, for example, the potential ionic interactions, van der Waals attractions, hydrogen bonding or other interactions that can occur. CDR3 tends to contribute more to antigen binding interactions than CDRs 1 and 2, probably due to its generally larger size, which provides more opportunity for favorable surface interactions. (See, e.g., Padlan et al., 1994, Mol. Immunol. 31: 169-217; Chothia & Lesk, 1987, J. Mol. Biol. 196: 904-917; and Chothia et al., 1985, J. Mol. Biol. 186: 651-663.) High affinity indicates antibody polypeptide/antigen pairings that have a high degree of complementarity, which is directly related to the structures of the variable domain and the target.

In one aspect, a monovalent anti-CD40L antibody polypeptide, e.g., a single immunoglobulin variable domain polypeptide, is linked to another antibody polypeptide to form a heterodimer in which each individual antibody polypeptide is capable of binding a different cognate antigen. Fusing antibody polypeptides, such as single immunoglobulin variable domains, as heterodimers, wherein each monomer binds a different target antigen, can produce a dual-specific ligand capable, for example, of bridging the respective target antigens. Such dual specific ligands may be used to target cytokines and other molecules which cooperate synergistically in therapeutic situations in the body of an organism. Thus, there is provided a method for synergising the activity of two or more cytokines, comprising administering a dual specific antibody heterodimer capable of binding to the two or more cytokines.

Non-limiting examples of second targets for anti-CD40L dual specific antibody polypeptides include the following: TNF-α; IL-1; IL-2; IL-4; IL-6; IL-8; IL-12; IL-18; IFN-γ; CD2; CD4; CD8; CTLA4; LFA1; LFA3 and VLA4.

Homologous Sequences:

The invention encompasses anti-CD40L antibody polypeptides, e.g., CD40L-binding single immunoglobulin variable domain clones, and clones with substantial sequence similarity or homology to them that also bind target antigen with high affinity. As used herein, "substantial" sequence similarity or homology is at least 85% similarity or homology.

Calculations of "homology" or "sequence identity" between two sequences (the terms are equivalent and used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

As used herein, sequence "similarity" is a measure of the degree to which amino acid sequences share similar amino acid residues at corresponding positions in an alignment of the sequences. Amino acids are similar to each other where their side chains are similar. Specifically, "similarity" encompasses amino acids that are conservative substitutes for each other. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical amino acids or conservative substitutions. Optimal global alignments can be performed using the following parameters in the Needleman-Wunsch alignment algorithm:

For polypeptides:

Substitution matrix: blosum62.

Gap scoring function: $-A-B*LG$, where A=11 (the gap penalty), B=1 (the gap length penalty) and LG is the length of the gap.

For nucleotide sequences:

Substitution matrix: 10 for matches, 0 for mismatches.

Gap scoring function: —A—B*LG where A=50 (the gap penalty), B=3 (the gap length penalty) and LG is the length of the gap.

Typical conservative substitutions are among Met, Val, Leu and Ile; among Ser and Thr; among the residues Asp, Glu and Asn; among the residues Gln, Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

Alternatively, the BLAST (Basic Local Alignment Search Tool) algorithm is employed for sequence alignment, with parameters set to default values. The BLAST algorithm "BLAST 2 Sequences" is available at the world wide web site ("www") of the National Center for Biotechnology Information (".ncbi"), of the National Library of Medicine (".nlm") of the National Institutes of Health (".nih") of the U.S. government (".gov"), in the "/blast/" directory, sub-directories "bl2seqibl2.html." This algorithm aligns two sequences for comparison and is described by Tatusova & Madden, 1999, FEMS Microbiol Lett. 174:247-250.

An additional measure of homology or similarity is the ability to hybridize under highly stringent hybridization conditions. Thus, a first sequence encoding a single immunoglobulin variable domain polypeptide is substantially similar to a second coding sequence if the first sequence hybridizes to the second sequence (or its complement) under highly stringent hybridization conditions (such as those described by Sambrook et al., Molecular Cloning, Laboratory Manuel, Cold Spring, Harbor Laboratory press, New York). "Highly stringent hybridization conditions" refer to hybridization in 6×SSC at about 45° C., followed by one or more washes in 0.2×SSC, 0.1% SDS at 65° C. "Very highly stringent hybridization conditions" refer to hybridization in 0.5M sodium phosphate, 7% SDS at 65° C., followed by one or more washes at 0.2×SSC, 1% SDS at 65° C.

Assays for CD40L Activities:

It is preferred that a monovalent anti-CD40L antibody polypeptides as described herein bind to CD40L yet do not substantially agonize CD40 signaling. Activation of the CD40L/CD40 pathway manifests a number of different outcomes that can be measured in order to assess the effect of a given monovalent anti-CD40L antibody polypeptide on the activity of the pathway. However, for the assessment of the antagonist or agonist function of monovalent anti-CD40L antibody polypeptides described herein, at least one of the following CD40L assays can be used:

1) Activation of Jun-N-Terminal Kinase (JNK):

Stimulation of T-lymphocytes via CD40L induces strong activation of JNK. The ability of a monovalent anti-CD40L antibody polypeptide to activate this signaling pathway is measured as follows. Human leukemic Jurkat cells are stimulated with a positive control agonistic anti-CD40L antibody (2 μg/ml monoclonal anti-human or anti-mouse gp39/CD40L antibody (Pharmingen, San Diego, Calif., USA) or isotype matched hamster or mouse immunoglobulins (Dianova, Hamburg, Germany)), monovalent anti-CD40L antibody polypeptide, or a negative control irrelevant antibody as described by Brenner et al., 1997, FEBS Lett. 417: 301-306, which is incorporated herein by reference. The cells are lysed and the extract assayed for phosphorylated JNK via colorimetric assay (e.g., Titerzyme™ colorimetric (EIA) phospho-JNK1/2 immunoassay kit, by Assay Designs Inc., Catalog # 900-106). An increase in phospho-JNK (e.g., by 5% or more) for anti-CD40L-stimulated cells over non-stimulated cells indicates agonism of CD40L activity by the antibody polypeptide.

2. Induction of Cytokine Secretion:

Co-stimulation of T cells with anti-CD3 Ab and CD40L has been shown to upregulate the production of IL-10, IFN-γ and TNF-α by those cells. The ability of a monovalent anti-CD40L antibody polypeptide to activate this signaling pathway is measured as follows. Human leukemic Jurkat T cells (or freshly isolated CD4+ T cells) are plated into 96 well plates containing immobilized anti-CD3 antibody. The cells are then cultured for 72 hours in the presence of a positive control agonistic anti-CD40L antibody, CD40L, monovalent anti-CD40L antibody polypeptide, or a negative control irrelevant antibody, as described by Blair et al., 2000, J. Exp. Med. 191: 651-660. IFN-γ (or IL-10 of TNF-α) is then quantitated in the supernatant by sandwich ELISA using an IFN-g standard to generate a standard curve from which all other unknowns can be calculated. An increase in IFN-g (e.g., by 5% or more) for anti-CD40L-stimulated cells over non-stimulated cells indicates agonism by the antibody polypeptide.

3. Platelet Aggregation Assay:

Divalent anti-CD40L antibodies tend to cause platelet aggregation, which is likely associated with the thromboembolic events observed in clinical trials of divalent anti-CD40L antibodies in the prior art. Monovalent anti-CD40L antibody polypeptides as described herein preferably do not substantially mediate or agonize CD40L-mediated platelet aggregation. With regard to this aspect, the "standard platelet aggregation assay" is as follows:

Platelets are prepared at $2.5\times10^5$/ml and left stirring in a 500-Ca lumi-aggregometer (or its equivalent, e.g., a Platelet Aggregation Profiler (BioData, Horsham, Pa.)). Platelets are partially activated by the addition of a dilution series of 0.1-10 μM ADP (the 10 μM ADP induces aggregation, and is used as a positive control—lower concentrations activate platelets but do not induce aggregation). CD40L mediated platelet aggregation is stimulated by addition of either anti-CD40L monoclonal antibodies (i.e., divalent monoclonal antibodies, available from, e.g., Pharmingen, San Diego, Calif., USA) or soluble CD40/Fc fusion protein (available from R&D Systems). The reaction is allowed to proceed for between 3 and 5 minutes. Stimulation of platelet aggregation above the minimal aggregation/activation achieved with ADP alone is plotted against stimulating anti-CD40L or CD40/Fc concentration. The percentage of platelet aggregation is measured by the change in light transmittance following addition of antibody polypeptide being tested or positive control peptide. A value greater than that observed for negative control lacking antibody and amounting to 25% or more of the positive control value (divalent anti-CD40L or CD40/Fc fusion) is considered to be indicative of induction of platelet aggregation.

PEGylation of Monovalent Anti-CD40L Antibody Polypeptides

The present invention provides PEGylated monovalent anti-CD40L antibody polypeptides which have increased half-life and preferably also resistance to degradation without a loss in activity (e.g., binding affinity) relative to non-PEGylated antibody polypeptides.

Monovalent anti-CD40L antibody polypeptides according to this aspect can be coupled, using methods known in the art to polymer molecules (preferably PEG) useful for achieving the increased half-life and degradation resistance properties encompassed by the present invention. Polymer moieties which can be utilized in the invention can be synthetic or naturally occurring and include, but are not limited to straight or branched chain polyalkylene, polyalkenylene or polyoxyalkylene polymers, or a branched or unbranched polysaccharide such as a homo- or heteropolysaccharide. Preferred examples of synthetic polymers which may be used in the invention include straight or branched chain poly(ethylene glycol) (PEG), poly(propylene glycol), or poly(vinyl alcohol) and derivatives or substituted forms thereof. Particularly preferred substituted polymers useful in the invention include substituted PEG, including methoxy(polyethylene glycol). Naturally occurring polymer moieties which may be used according to the invention in addition to or in place of PEG include lactose, amylose, dextran, or glycogen, as well as derivatives thereof which would be recognized by one of skill in the art. Derivatized forms of polymer molecules of the invention include, for example, derivatives which have additional moieties or reactive groups present therein to permit interaction with amino acid residues of the dAb polypeptides described herein. Such derivatives include N-hydroxylsuccinimide (NHS) active esters, succinimidyl propionate polymers, and sulfhydryl-selective reactive agents such as maleimide, vinyl sulfone, and thiol. Particularly preferred derivatized polymers include, but are not limited to PEG polymers having the formulae: PEG-O—$CH_2CH_2CH_2$—$CO_2$—NHS; PEG-O—$CH_2$—NHS; PEG-O—$CH_2CH_2$—$CO_2$—NHS; PEG-S—$CH_2CH_2$—CO—NHS; PEG-$O_2$CNH—CH(R)—$CO_2$—NHS; PEG-NHCO—$CH_2CH_2$—CO—NHS; and PEG-O—$CH_2$—$CO_2$—NHS; where R is $(CH_2)_4)NHCO_2$(mPEG). PEG polymers useful in the invention may be linear molecules, or may be branched wherein multiple PEG moieties are present in a single polymer. Some particularly preferred PEG derivatives which are useful in the invention include, but are not limited to the following:

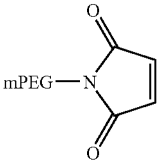

mPEG-MAL

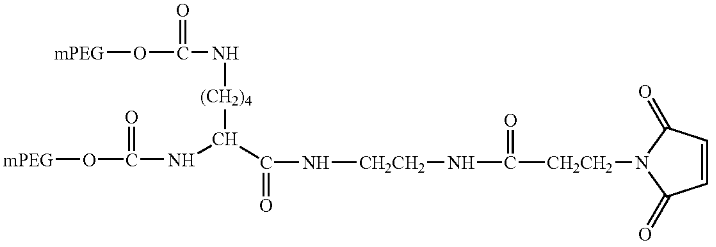

mPEG2-MAL

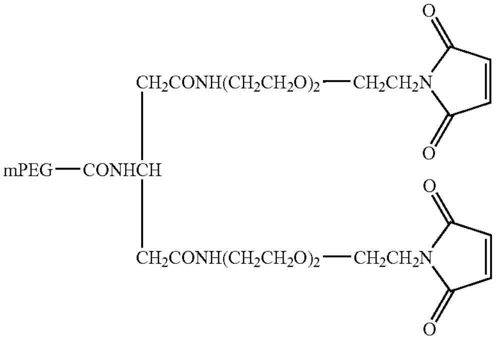

mPEG-(MAL)[2]

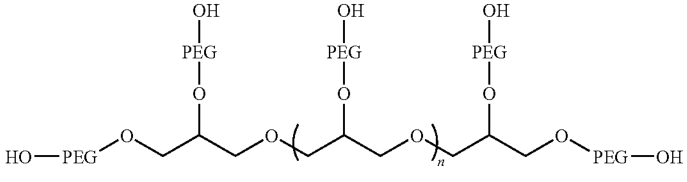

$n$ = 0-4 multi-arm PEG

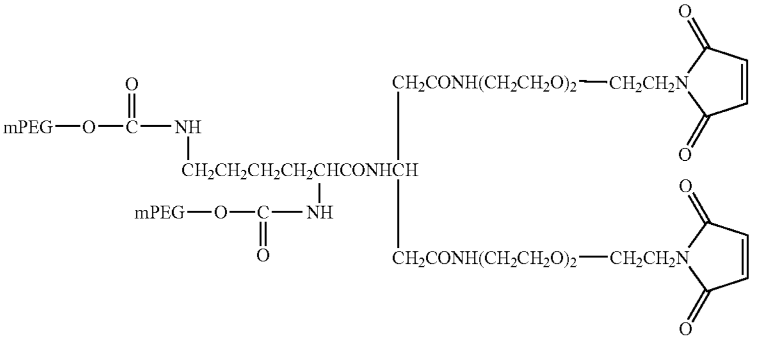

mPEG2-(MAL)[2]

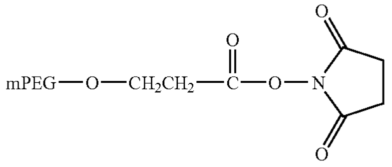

mPEG-SPA

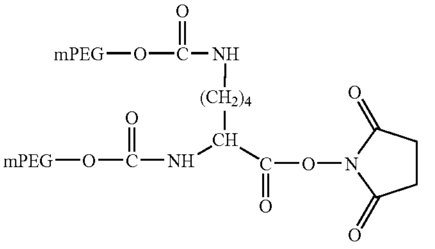

mPEG2-NHS

The reactive group (e.g., MAL, NHS, SPA, VS, or Thiol) may be attached directly to the PEG polymer or may be attached to PEG via a linker molecule.

The size of polymers useful in the invention can be in the range of between 500 Da to 60 kDa, for example, between 1000 Da and 60 kDa, 10 kDa and 60 kDa, 20 kDa and 60 kDa, 30 kDa and 60 kDa, 40 kDa and 60 kDa, and up to between 50 kDa and 60 kDa. The polymers used in the invention, particularly PEG, can be straight chain polymers or can possess a branched conformation. Depending on the combination of molecular weight and conformation, the polymer molecules useful in the invention, when attached to a monovalent anti-CD40L antibody polypeptide, will yield a molecule having an average hydrodynamic size of between 24 and 500 kDa. The hydrodynamic size of a polymer molecule used herein refers to the apparent size of a molecule (e.g., a protein molecule) based on the diffusion of the molecule through an aqueous solution. The diffusion, or motion of a protein through solution can be processed to derive an apparent size of the protein, where the size is given by the Stokes radius or hydrodynamic radius of the protein particle. The "hydrodynamic size" of a protein depends on both mass and shape (conformation), such that two proteins having the same molecular mass may have differing hydrodynamic sizes based on the overall conformation of the protein. The hydrodynamic size of a PEG-linked monovalent anti-CD40L antibody polypeptide, e.g., an anti- CD40L single immunoglobulin variable domain as described herein, can be in the range of 24 kDa to 500 kDa; 30 to 500 kDa; 40 to 500 kDa; 50 to 500 kDa; 100 to 500 kDa; 150 to 500 kDa; 200 to 500 kDa; 250 to 500 kDa; 300 to 500 kDa; 350 to 500 kDa; 400 to 500 kDa and 450 to 500 kDa. Preferably the hydrodynamic size of a PEGylated antibody polypeptide as described herein is 30 to 40 kDa; 70 to 80 kDa or 200 to 300 kDa. The size of a polymer molecule attached to a monovalent anti-CD40L antibody polypeptide may thus be varied depending upon the desired application. For example, where the PEGylated antibody polypeptide is intended to leave the circulation and enter into peripheral tissues, it is desirable to keep the size of the attached polymer low to facilitate extravazation from the blood stream. Alternatively, where it is desired to have the PEGylated antibody polypeptide remain in the circulation for a longer period of time, a higher molecular weight polymer can be used (e.g., a 30 to 60 kDa polymer).

The polymer (PEG) molecules useful in the invention can be attached to antibody polypeptides using methods that are well known in the art. The first step in the attachment of PEG or other polymer moieties to an antibody polypeptide is the substitution of the hydroxyl end-groups of the PEG polymer by electrophile-containing functional groups. Particularly, PEG polymers are attached to either cysteine or lysine residues present in the antibody polypeptide. The cysteine and lysine residues can be naturally occurring, or can be engineered into the antibody polypeptide molecule. For example, cysteine residues can be recombinantly engineered at the C-terminus of antibody polypeptides, or residues at specific solvent accessible locations in the antibody polypeptide can be substituted with cysteine or lysine. In a preferred embodiment, a PEG moiety is attached to a cysteine residue which is present in the hinge region at the C-terminus of an antibody polypeptide.

In a further preferred embodiment a PEG moiety or other polymer is attached to a cysteine or lysine residue which is either naturally occurring at or engineered into the N-terminus of antibody single variable domain polypeptide of the invention. In a still further embodiment, a PEG moiety or other polymer is attached to an antibody single variable domain according to the invention at a cysteine or lysine residue (either naturally occurring or engineered) which is at least 2 residues away from (e.g., internal to) the C- and/or N-terminus of the antibody single variable domain polypeptide.

In one embodiment, the PEG polymer(s) is attached to one or more cysteine or lysine residues present in a framework region (FWs) and one or more heterologous CDRs of a single immunoglobulin variable domain. CDRs and framework regions (e.g., CDR1-CDR3 and FW1-FW4) are those regions of an immunoglobulin variable domain as defined in the Kabat database of Sequences of Proteins of Immunological Interest (Kabat et al., 1991, supra). In a preferred embodiment, a PEG polymer is linked to a cystine or lysine residue in the $V_H$ framework segment DP47, or the $V_k$ framework segment DPK9. Cysteine and/or lysine residues of DP47 which may be linked to PEG according to the invention include the cysteine at positions 22, or 96 and the lysine at positions 43, 65, 76, or 98 of SEQ ID NO: 1 (FIG. 5). Cysteine and/or lysine residues of DPK9 which may be linked to PEG according to the invention include the cysteine residues at positions 23, or 88 and the lysine residues at positions 39, 42, 45, 103, or 107 of SEQ ID NO: 3 (FIG. 6). In addition, specific cysteine or lysine residues may be linked to PEG in the $V_H$ canonical framework region DP38, or DP45.

In addition, specific solvent accessible sites in the antibody molecule which are not naturally occurring cysteine or lysine residues may be mutated to a cysteine or lysine for attachment of a PEG polymer. Solvent accessible residues in any given antibody, e.g., a dAb, can be determined using methods known in the art such as analysis of the crystal structure of the antibody polypeptide. For example, using the solved crystal structure of the $V_H$ dAb HEL4 (SEQ ID NO: 3; a dAb that binds hen egg lysozyme), the residues Gln-13, Pro-14, Gly-15, Pro-41, Gly-42, Lys-43, Asp-62, Lys-65, Arg-87, Ala-88, Glu-89, Gln-112, Leu-115, Thr-117, Ser-119, and Ser-120 have been identified as being solvent accessible, and according to the present invention would be attractive candidates for mutation to cysteine or lysine residues for the attachment of a PEG polymer. In addition, using the solved crystal structure of the $V_k$ dummy dAb (SEQ ID NO: 4), the residues Val-15, Pro-40, Gly-41, Ser-56, Gly-57, Ser-60, Pro-80, Glu-81, Gln-100, Lys-107, and Arg-108 have been identified as being solvent accessible, and according to the present invention would be attractive candidates for mutation to cysteine or lysine residues for the attachment of a PEG polymer. In one embodiment of the invention, a PEG polymer is linked to multiple solvent accessible cysteine or lysine residues, or to solvent accessible residues which have been mutated to a cysteine or lysine residue. Alternatively, only one solvent accessible residue is linked to PEG, either where the particular antibody polypeptide only possesses one solvent accessible cysteine or lysine (or residue modified to a cysteine or lysine) or where a particular solvent accessible residue is selected from among several such residues for PEGylation.

Primary Amino Acid Sequence of HEL4 (SEQ ID NO: 5).

```
  1 EVQLLESGGG LVQPGGSLRL SCAASGFRIS DEDMGWVRQA
    PGKGLEWVSS

 51 IYGPSGSTYY ADSVKGRFTI SRDNSKNTLY LQMNSLRAED
    TAVYYCASAL

101 EPLSEPLGFW GQGTLVTVSS
```

Primary Amino Acid Sequence of $V_k$ Dummy (SEQ ID NO: 6).

```
  1 DIQMTQSPSS LSASVGDRVT ITCRASQSIS SYLNWYQQKP
    GKAPKLLIYA

 51 ASSLQSGVPS RFSGSGSGTD FTLTISSLQP EDFATYYCQQ
    SYSTPNTFGQ

101 GTKVEIKR
```

Several PEG attachment schemes which are useful in the invention are provided by the company Nektar (San Carlos, Calif.). For example, where attachment of PEG or other polymer to a lysine residue is desired, active esters of PEG polymers which have been derivatized with N-hydroxylsuccinimide, such as succinimidyl propionate may be used. Where attachment to a cysteine residue is intended, PEG polymers which have been derivatized with sulfhydryl-selective reagents such as maleimide, vinyl sulfone, or thiols may be used. Other examples of specific embodiments of PEG derivatives which may be used according to the invention to generate PEGylated antibodies can be found in the Nektar Catalog (available on the world wide web at nektar.com). In addition, several derivitized forms of PEG may be used according to the invention to facilitate attachment of the PEG polymer to an antibody polypeptide. PEG derivatives useful in the invention include, but are not limited to PEG-succinimidyl succinate, urethane linked PEG, PEG phenylcarbonate, PEG succinimidyl carbonate, PEG-carboxymethyl azide, dimethylmaleic anhydride PEG, PEG dithiocarbonate derivatives, PEG-tresylates (2,2,2-trifluoroethanesolfonates), mPEG imidoesters, and other as described in Zalipsky and Lee, (1992) ("Use of functionalized poly(ethylene glycol)s for modification of peptides" in *Poly(Ethylene Glycol) Chemistry: Biotechnical and Biomedical Applications*, J. Milton Harris, Ed., Plenum Press, NY).

In one embodiment, the invention provides an anti-CD40L antibody single variable domain composition comprising an antibody single variable domain and PEG polymer wherein the ratio of PEG polymer to antibody single variable domain is a molar ratio of at least 0.25:1. In a further embodiment, the molar ratio of PEG polymer to antibody single variable domain is 0.33:1 or greater. In a still further embodiment the molar ratio of PEG polymer to antibody single variable domain is 0.5:1 or greater.

Increased Half-Life

In vivo, the PEGylated monovalent anti-CD40L antibodies as described herein confer a distinct advantage over over non-PEGylated antibody polypeptides, in that the PEGylated antibody molecules will have a greatly prolonged in vivo half life. Without being bound to one particular theory, it is believed that the increased half-life of the molecules described herein is conferred by the increased hydrodynamic size of the antibody polypeptide resulting from the attachment of PEG polymer(s). More specifically, it is believed that two parameters play an important role in determining the serum half-life of PEGylated antibody polypeptides. The first criterion is the nature and size of the PEG attachment, i.e., if the polymer used is simply a linear chain or a branched/forked chain, wherein the branched/forked chain gives rise to a longer half-life. The second is the location of the PEG moiety or moieties on the antibody polypeptide in the final format and how many "free" unmodified PEG arms the molecule has. The resulting hydrodynamic size of the PEGylated antibody polypeptide, as estimated, for example, by size exclusion chromatography, reflects the serum half-life of the molecule. Accordingly, the larger the hydrodynamic size of the PEGylated molecule, the greater the serum half life.

Increased half-life is useful in in vivo applications of immunoglobulins, especially antibodies and most especially antibody fragments of small size. Such fragments (Fvs, Fabs, scFvs, dAbs) suffer from rapid clearance from the body; thus, while they are able to reach most parts of the body rapidly, and are quick to produce and easier to handle, their in vivo applications have been limited by their only brief persistence in vivo.

In one aspect, a monovalent anti-CD40L antibody polypeptide as described herein is stabilized in vivo by fusion with a moiety, such as PEG, that increases the hydrodynamic size of the antibody polypeptide. Methods for pharmacokinetic analysis and determination of half-life will be familiar to those skilled in the art. Details may be found in Kenneth et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Typically, the half life of a PEGylated antibody polypeptide as described herein is increased by 10%, 20%, 30%, 40%, 50% or more relative to a non-PEGylated dAb (wherein the antibody polypeptide of the PEGylated antibody polypeptide and non-PEGylated antibody polypeptide are the same). Increases in the range of 2×, 3×, 4×, 5×, 7×, 10×, 20×, 30×, 40×, and up to 50× or more of the half life are possible. Alternatively, or in addition, increases in the range of up to 30×, 40×, 50×, 60×, 70×, 80×, 90×, 100×, 150× of the half life are possible.

Half lives (t½ alpha and t½ beta) and AUC can be determined from a curve of serum concentration of ligand against time. The WinNonlin analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The tα half life is the half life of the first phase and the tβ half life is the half life of the second phase. "Half-life" as used herein, unless otherwise noted, refers to the overall half-life of an antibody single variable domain of the invention determined by non-compartment modeling (as contrasted with biphasic modeling, for example). Beta half-life is a measurement of the time it takes for the amount of dAb monomer or multimer to be cleared from the mammal to which it is administered. Thus, advantageously, the present invention provides a dAb-containing composition, e.g., a dAb-effector group composition, having a tα half-life in the range of 0.25 hours to 6 hours or more. In one embodiment, the lower end of the range is 30 minutes, 45 minutes, 1 hour, 1.3 hours, 2 hours, 3 hours, 4 hours, 5 hours, 6 hours, 7 hours, 10 hours, 11 hours or 12 hours. In addition or alternatively, a dAb containing composition will have a tα half-life in the range of up to and including 12 hours. In one embodiment, the upper end of the range is 11, 10, 9, 8, 7, 6, or 5 hours. An example of a suitable range is 1.3 to 6 hours, 2 to 5 hours or 3 to 4 hours.

Advantageously, the present invention provides a dAb containing composition comprising a ligand according to the invention having a tβ half-life in the range of 1-170 hours or more. In one embodiment, the lower end of the range is 2.5 hours, 3 hours, 4 hours, 5 hours, 6 hours, 7 hours, 8 hours, 9 hours, 10 hours, 11 hours or 12 hours. In addition, or alternatively, a dAb containing composition, e.g. a dAb-effector group composition has a tβ half-life in the range of up to and including 21 days. In one embodiment, the upper end of the range is 12 hours, 24 hours, 2 days, 3 days, 5 days, 10 days, 15 days, or 20 days. Advantageously a dAb containing composition according to the invention will have a tβ half-life in the range 2-100 hours, 4-80 hours, and 10-40 hours. In a further embodiment, it will be in the range 12-48 hours. In a further embodiment still, it will be in the range 12-26 hours. The present invention provides a dAb containing composition comprising a ligand according to the invention having a half-life in the range of 1-170 hours or more. In one embodiment, the lower end of the range is 1.3 hours, 2.5 hours, 3 hours, 4 hours, 5 hours, 6 hours, 7 hours, 8 hours, 9 hours, 10 hours, 11 hours or 12 hours. In addition, or alternatively, a dAb containing composition, e.g. a dAb-effector group composition has a half-life in the range of up to and including 21 days. In one embodiment, the upper end of the range is 12 hours, 24 hours, 2 days, 3 days, 5 days, 10 days, 15 days, or 20 days.

In addition, or alternatively to the above criteria, the present invention provides a dAb containing composition comprising a ligand according to the invention having an AUC value (area under the curve) in the range of 1 mg.min/ml or more. In one embodiment, the lower end of the range is 5, 10, 15, 20, 30, 100, 200 or 300 mg.min/ml. In addition, or alternatively, a ligand or composition according to the invention has an AUC in the range of up to 600 mg.min/ml. In one embodiment, the upper end of the range is 500, 400, 300, 200, 150, 100, 75 or 50 mg.min/ml. Advantageously a ligand according to the invention will have an AUC in the range selected from the group consisting of the following: 15 to 150 mg.min/ml, 15 to 100 mg.min/ml, 15 to 75 mg.min/ml, and 15 to 50 mg.min/ml.

Increased Protease Stability

A further advantage of the present invention is that the PEGylated dAbs and dAb multimers described herein possess increased stability to the action of proteases. Depending on the assay conditions, dAbs are generally intrinsically stable to the action of proteases. In the presence of pepsin, however, many dAbs are totally degraded at pH 2 because the protein is unfolded under the acid conditions, thus making the protein more accessible to the protease enzyme. The present invention provides PEGylated dAb molecules, including dAb multimers, wherein it is believed that the PEG polymer provides protection of the polypeptide backbone due the physical coverage of the backbone by the PEG polymer, thereby preventing the protease from gaining access to the polypeptide backbone and cleaving it. In a preferred embodiment a PEGylated dAb having a higher hydrodynamic size (e.g., 200 to 500 kDa) is generated according to the invention, because the larger hydrodynamic size will confirm a greater level of protection from protease degradation than a PEGylated dAb having a lower hydrodynamic size. In one embodiment, a PEG- or other polymer-linked antibody single variable domain monomer or multimer is degraded by no more than 10% when exposed to one or more of pepsin, trypsin, elastase, chymotrypsin, or carboxypeptidase, wherein if the protease is pepsin then exposure is carried out at pH 2.0 for 30 minutes, and if the protease is one or more of trypsin, elastase, chymotrypsin, or carboxypeptidase, then exposure is carried out at pH 8.0 for 30 minutes. In a preferred embodiment, a PEG- or other polymer-linked dAb monomer or multimer is degraded by no more than 10% when exposed to pepsin at pH 2.0 for 30 minutes, preferably no more than 5%, and preferably not degraded at all. In a further preferred embodiment, a PEG- or other polymer-linked dAb multimer (e.g., hetero- or homodimer, trimer, tetramer, octamer, etc.) of the invention is degraded by less than 5%, and is preferably not degraded at all in the presence of pepsin at pH 2.0 for 30 minutes. In a preferred embodiment, a PEG- or other polymer-linked dAb monomer or multimer is degraded by no more than 10% when exposed to trypsin, elastase, chymotrypsin, or carboxypeptidase at pH 8.0 for 30 minutes, preferably no more than 5%, and preferably not degraded at all. In a further preferred embodiment, a PEG- or other polymer-linked dAb multimer (e.g., hetero- or homodimer, trimer, tetramer, octamer, etc.) of the invention is degraded by less than 5%, and is preferably not degraded at all in the presence of trypsin, elastase, chymotrypsin, or carboxypeptidase at pH 8.0 for 30 minutes.

The relative ratios of protease:antibody single variable domain polypeptide may be altered according to the invention to achieve the desired level of degradation as described above. For example the ratio or protease to antibody single variable domain may be from about 1:30, to about 10:40, to about 20:50, to about 30:50, about 40:50, about 50:50, about 50:40, about 50:30, about 50:20, about 50:10, about 50:1, about 40:1, and about 30:1.

Accordingly, the present invention provides a method for decreasing the degradation of an antibody single variable domain comprising linking an antibody single variable domain monomer or multimer to a PEG polymer according to any of the embodiments described herein. According to this aspect of the invention, the antibody single variable domain is degraded by no more than 10% in the presence of pepsin at pH2.0 for 30 minutes. In particular, a PEG-linked dAb multimer is degraded by no more than 5%, and preferably not degraded at all in the presence of pepsin at pH 2.0 for 30 minutes. In an alternate embodiment, the antibody single variable domain is degraded by no more than 10% when exposed to trypsin, elastase, chymotrypsin, or carboxypeptidase at pH 8.0 for 30 minutes, preferably no more than 5%, and preferably not degraded at all.

Degradation of PEG-linked dAb monomers and multimers according to the invention may be measured using methods which are well known to those of skill in the art. For example, following incubation of a PEG-linked dAb with pepsin at pH 2.0 for 30 minutes, or with trypsin, elastase, chymotrypsin, or carboxypeptidase at pH 8.0 for 30 minutes, the dAb samples may be analyzed by gel filtration, wherein degradation of the dAb monomer or multimer is evidenced by a gel band of a smaller molecular weight than an un-degraded (i.e., control dAb not treated with pepsin, trypsin, chymotrypsin, elastase, or carboxypeptidase) dAb. Molecular weight of the dAb bands on the gel may be determined by comparing the migration of the band with the migration of a molecular weight ladder (see FIG. 5). Other methods of measuring protein degradation are known in the art and may be adapted to evaluate the PEG-linked dAb monomers and multimers of the present invention.

Pharmaceutical Compositions, Dosage and Administration

The antibody polypeptides of the invention can be incorporated into pharmaceutical compositions suitable for administration to a subject. Typically, the pharmaceutical composition comprises a monovalent anti-CD40L antibody polypeptide and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The term "pharmaceutically acceptable carrier" excludes tissue culture medium comprising bovine or horse serum. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances include minor amounts of auxiliary substances such as wetting or emulsifying agents, preservatives or buffers, which enhance the shelf life or effectiveness of the antibody polypeptide.

The compositions as described herein may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular).

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants.

The antibody polypeptides described herein can be administered by a variety of methods known in the art, although for many therapeutic applications, the preferred route/mode of administration is intravenous injection or infusion. The polypeptide can also be administered by intramuscular or subcutaneous injection.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Single immunoglobulin variable domains and other relatively small monovalent antibody polypeptides are well suited for formulation as extended release preparations due, in part, to their small size—the number of moles per dose can be significantly higher than the dosage of, for example, full sized antibodies. Biodegradable, biocompatible polymers can be used, such as ethylene vinyl acetate, polyanhydrides, polyglycolic acid, collagen, polyorthoesters, and polylactic acid. Prolonged absorption of injectable compositions can be brought about by including in the composition an agent that delays absorption, for example, monostearate salts and gelatin. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. Additional methods applicable to the controlled or extended release of polypeptide agents such as the monovalent antibody polypeptides disclosed herein are described, for example, in U.S. Pat. Nos. 6,306,406 and 6,346,274, as well as, for example, in U.S. Patent Application Nos. US20020182254 and US20020051808, all of which are incorporated herein by reference.

In certain embodiments, a monovalent anti-CD40L antibody polypeptide can be orally administered, for example, with an inert diluent or an assimilable edible carrier. The compound (and other ingredients, if desired) may also be enclosed in a hard or soft shell gelatin capsule, compressed into tablets, or incorporated directly into the individual's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds can also be incorporated into the compositions. In certain embodiments, a monovalent anti-CD40L antibody polypeptide is coformulated with and/or coadministered with one or more additional therapeutic agents. For example, a monovalent anti-CD40L antibody polypeptide can be coformulated and/or coadministered with one or more additional antibodies that bind other targets (e.g., antibodies that bind other cytokines or that bind cell surface molecules), or, for example, one or more cytokines. Such combination therapies may utilize lower dosages of the administered therapeutic agents, thus avoiding possible toxicities or complications associated with the various monotherapies.

The pharmaceutical compositions of the invention can include a "therapeutically effective amount" or a "prophylactically effective amount" of a monovalent anti-CD40L antibody polypeptide. A "therapeutically effective amount" refers to an amount effective, at dosages and for periods of time necessary, to achieve the desired therapeutic result. A therapeutically effective amount of the antibody polypeptide can vary according to factors such as the disease state, age, sex, and weight of the individual, and the ability of the monovalent anti-CD40L antibody polypeptide to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

A non-limiting range for a therapeutically or prophylactically effective amount of a monovalent anti-CD40L antibody polypeptide is 0.1-20 mg/kg, more preferably 1-10 mg/kg. It is to be noted that dosage values can vary with the type and severity of the condition to be alleviated. It is to be further understood that for any particular subject, specific dosage regimens should be adjusted over time according to the individual need and the professional judgment of the administering clinician.

The efficacy of treatment with a monovalent anti-CD40L antibody polypeptide as described herein is judged by the skilled clinician on the basis of improvement in one or more symptoms or indicators of the disease state or disorder being treated. An improvement of at least 10% (increase or decrease, depending upon the indicator being measured) in one or more clinical indicators is considered "effective treatment," although greater improvements are preferred, such as 20%, 30%, 40%, 50%, 75%, 90%, or even 100%, or, depending upon the indicator being measured, more than 100% (e.g., two-fold, three-fold, ten-fold, etc., up to and including attainment of a disease-free state. Indicators can be physical measurements, e.g., enzyme, cytokine, growth factor or metabolite levels, rate of cell growth or cell death, or the presence or amount of abnormal cells. One can also measure, for example, differences in the amount of time between flare-ups of symptoms of the disease or disorder (e.g., for remitting/relapsing diseases, such as multiple sclerosis). Alternatively, non-physical measurements, such as a reported reduction in pain or discomfort or other indicator of disease status can be relied upon to gauge the effectiveness of treatment. Where non-physical measurements are made, various clinically acceptable scales or indices can be used, for example, the Crohn's Disease Activity Index, or CDAI (Best et al., 1976, Gastroenterology 70: 439), which combines both physical indicators, such as hematocrit and the number of liquid or very soft stools, among others, with patient-reported factors such as the severity of abdominal pain or cramping and general well-being, to assign a disease score.

As the term is used herein, "prophylaxis" performed using a composition as described herein is "effective" if the onset or severity of one or more symptoms is delayed or reduced by at least 10%, or abolished, relative to such symptoms in a similar individual (human or animal model) not treated with the composition.

Whereas the monovalent anti-CD40L antibody polypeptides described herein must bind human CD40L, where one is to evaluate its effect in an animal model system, the polypeptide must cross-react with one or more antigens in the animal model system, preferably at high affinity. One of skill in the art can readily determine if this condition is satisfied for a given animal model system and a given monovalent anti-CD40L antibody polypeptide. If this condition is satisfied, the efficacy of the monovalent anti-CD40L antibody polypeptide can be examined by administering it to an animal model under conditions which mimic a disease state and monitoring one or more indicators of that disease state for at least a 10% improvement.

Animal Models:

Monovalent anti-CD40L antibody polypeptides as described herein are useful for the treatment of autoimmune disorders in which CD40/CD40L signaling is inappropriately active. There are several animal models in which the therapeutic efficacy of a given monovalent anti-CD40L antibody polypeptide can be assessed, as discussed below.

Systemic Lupus Erythematosis (SLE):

Anti-CD40L antibody treatment prevents the development of lupus-like nephritis in NZB/NZW and SNF1 SLE mice. Treatment of SNF1 mice with anti-CD40L antibody reverses established nephritis and preserves kidney function. See, e.g., Mohan et al., 1995, J. Immunol. 154: 1470-1480; Early et al., 1996, J. Immunol. 157: 3159-3164; Kalled et al., 1998, J. Immunol. 160: 2158-2165, and Chess, 2001, "Blockade of the CD40L/CD40 Pathway," in Therapeutic Immunology $2^{nd}$ Edition, Austen, Burakof, Rosen and Strom, Eds., Blackwell Sciences (Pubs.), pp 441-456.

Multiple Sclerosis:

Specific blockade of CD40L at the time of immunization markedly suppresses the incidence, mortality, day of onset, and clinical scores of experimental autoimmune encephalomyelitis (EAE) in B10P1L and (PLJ×SJL)F1 mice induced by either myelin basic protein or PLP myelin antigens. See, for example, Gerritse, 1996, Proc. Natl. Acad. Sci. U.S.A. 93: 2494; Grewal et al., 1996, Science 273: 186; Laman et al., 1998, Mult. Scler. 4: 14; and Chess, 2001, supra.

Rheumatoid Arthritis:

Anti-CD40L blocks the development of joint inflammation, serum antibody titers to collagen, the infiltration of inflammatory cells into the synovial tissue, ant the erosion of cartilage and bone in collagen-induced arthritis. See, e.g., Durie et al., 1993, Science 261: 132; and Chess, 2001, supra.

Insulin-Dependent Type I Diabetes Models:

The non-obese diabetic (NOD) mouse spontaneously develops T cell dependent autoimmune diabetes. Anti-CD40L monoclonal antibody treatment of 3 to 4 week old NOD females (the age at which insulitis typically begins) completely prevented the insulitis and diabetes. Cytokine analysis revealed a dramatic decrease in IFN-g and IL-2 release without a concomitant increase in IL-4 production by T cells from anti-CD40L-treated mice. See, e.g., Balasa et al., 1997, J. Immunol. 159: 1420; and Chess, 2001, supra.

Inhibition of Allograft and Xenograft Transplant Rejection:

Anti-CD40L prevents the development of renal rejection of fully allogeneic grafts in mice. Moreover, the survival of renal allografts transplanted into nephrectomized rehsus monkeys is typically prolonged by anti-CD40L therapy alone. Similarly, anti CD40L therapy has prevented graft rejection of skin, islet cells and cardiac transplants as well as GVHD in rodents. See, e.g., Kirk et al., 1997, Proc. Natl. Acad. Sci. U.S.A. 94: 8789-8794; Parker et al., 1995, Proc. Natl. Acad. Sci. U.S.A. 92: 9560; Larsen et al., 1996, Transplantation 61: 4; and Chess, 2001, supra.

Uses of Monovalent Anti-CD40L Antibody Polypeptides

Monovalent anti-CD40L antibody polypeptides as described herein are useful for the treatment or prevention of diseases or disorders in which inappropriate activation of a CD40L/CD40-mediated pathway is involved. In particular, autoimmune diseases frequently involve inappropriate regulation or activity of CD40L/CD40 pathways. Administration of a monovalent anti-CD40L antibody polypeptide as described herein to an individual suffering from such a disease, can reduce one or more symptoms of the disease. Non-limiting examples of diseases for which the antibody polypeptides described herein can be therapeutically useful include Systemic Lupus Erythematosus (SLE), Idiotypic Thrombocytopenic Purpura (ITP), transplant rejection, Crohn's Disease, Inflammatory Bowel Disease (IBD), colitis, asthma/allergy, atherosclerosis, Myasthenia Gravis, immune response to recombinant drug products, e.g., factor VII in hemophilia, Multiple Sclerosis, Psoriasis, Rheumatoid Arthritis, Ankylosing Spondylitis, Coronary Heart Disease, and Type 2 Diabetes.

The monovalent anti-CD40L antibody polypeptides described herein are additionally useful in the way that generally any antibody preparation is useful, e.g., for in vivo imaging or diagnostic uses, in vitro diagnostic uses, etc. For these and other uses it may be desirable to label the monovalent anti-CD40L antibody polypeptides, e.g., with a fluorescent, colorimetric, enzymatic or radioactive label. Methods of labeling antibody polypeptides are well known in the art.

EXAMPLES

Example 1

Biotinylation of Recombinant CD40L

Recombinant human soluble CD40L (PeproTech) was biotinylated and used during phage selections. Reagents, equipment and sources from which they are available are provided in Table 1.

Biotinylation of CD40L was performed by incubating CD40L (0.5 mg/ml) with EZ-Link™ Sulfo-NHS-LC-Biotin [Sulfosuccinimidyl-6-(biotinamido)hexanoate] (Pierce) at a molar ratio of 5:1 on ice for 2 hours according to the product instructions. The biotinylation reaction mixture was then dialysed against 3 exchanges of PBS (1000× sample volume) in a Slide-A-Lyzer® Dialysis Cassette at 4° C. to remove the unincorporated biotinylation reagent.

Figure 1B:
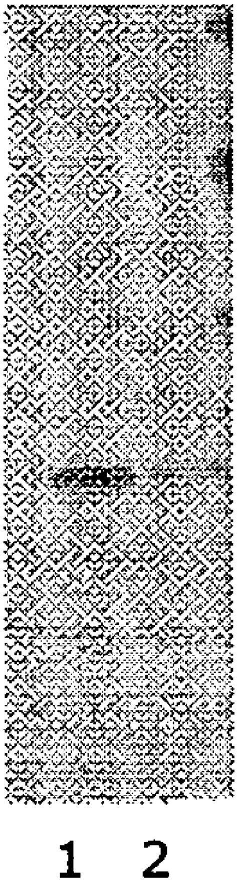

The biotinylated-CD40L was tested by receptor binding assay for binding to CD40/Fc to confirm its biological activity. Quality of biotin-CD40L was also monitored by analysing on a NuPaGE 4-12% Bis-Tris gel and detected by Simply Blue Safe-Stain (Invitrogen) (FIG. 1*a*), and western-blotting by probing with Streptavidin-HRP (FIG. 1*b*). The biotinylated-CD40L was further analysed by mass spectrometry with the majority of CD40L subunits containing 1 or 2 biotin moieties (data not shown).

TABLE 1

| Equipment/Reagent | Suggested or required supplier |
|---|---|
| Recombinant human soluble CD40 ligand/TRAP | PeproTech, Cat No: 310-02 Reconstituted in 5 mM Sodium phosphate, pH5.0 to concentration of 0.5 mg/ml |
| EZ-Link ™ Sulfo-NHS-LC-Biotin | Pierce, Cat No: 21335 |
| Slide-A-Lyzer ® Dialysis Cassette | Pierce, Cat No: 66110 |
| Recombinant human CD40/Fc chimera | R&D Systems, Cat No: 1493-CD |
| NuPAGE ® 4-12% Bis-Tris gel | Invitrogen life technologies Ltd Cat. No NP0322 |
| Streptavidin-HRP | Amersham Biosciences Cat No: 1231V |
| Invitrogen ™ Simply Blue Safe-stain | Invitrogen Cat No: LC6065 |

Example 2

Phage Selections Using Biotinylated Antigen

The Domain Antibody (dAb) libraries are based on a single human framework for the $V_H$ (DP47 and JH4b) and for the VK (DPK9 and JK1) with side chain diversity incorporated at positions in the antigen binding site that make contact with antigen in known molecular structures and mirror residues diversified in the human antibody repertoire. The antibodies are displayed as fusion proteins covalently linked to the N-terminus of the Fd-phage protein pIII, using the phage vector pDOM4 (Fd-Tet) with encodes the Fd phage genome with dAb expression under the control of the gene-III promoter. The dAb cassette consists of (5' to 3'): eukaryotic leader sequence, dAb, myc tag, gIII. The vector contains both the M13 and colE1 origins of replication and is selectable using tetracycline. The $V_H$ and $V_\kappa$ libraries each have a calculated size of over $1\times10^{10}$ molecules. Reagents, equipment and sources from which they are available are provided in Table 2.

Approximately $1\times10^{11}$ phage from the each of the Domantis dAb libraries were incubated in a final volume of 1 ml PBS containing 2% Marvel™ at room temperature for 1 h. Biotinylated antigen was added to the blocked phage such that the phage antigen mixture had a final concentration of 2% Marvel™ in PBS. The antigen concentration used for the first round of selection was 60 nM; the antigen concentration was decreased to 6 nM for round 2, and to 0.6 nM for round 3. The antigen/phage mix was incubated for 1 h at room temperature with rotation at ~40 rpm.

For each selection, 100 μl of streptavidin-coated paramagnetic beads (Dynal Biotech) were prepared by washing once in 1 ml of PBS containing 0.1% Tween-20 followed by a second wash in 1 ml of PBS. The beads were then blocked in 1 ml of PBS containing 2% Marvel™ in a 2 ml eppendorf tube at room temperature on a rotating wheel for 1 h.

The tube containing the blocked streptavidin-coated magnetic beads was placed into a magnetic holder, enabling capture of the magnetic beads. The supernatant was removed and the beads resuspended in the antigen/phage mix. This mixture was rotated for 10 min to allow for bead capture of phage/antigen complexes.

The beads were captured using a magnetic holder and repeatedly washed 19 times using 1 ml of PBS containing 0.1% Tween-20, followed by a final wash of 1 ml PBS. The eppendorf tubes were changed following washing steps 3, 9, 15 and 19 to minimise background phage carryover.

The washed beads were then recaptured and all washing solution removed. The phage were eluted through resuspension in 500 μl of trypsin solution (50 μl of 10 mg/ml trypsin stock solution added to 450 μl PBS, freshly diluted) and rotated for 10 min at room temperature. The eluted phage were recovered by capturing the beads using the magnetic holder and the liquid containing the eluted phage recovered. The eluted phage were used to infect *E. coli* TG1 to prepare phage for a further round of selection.

The eluted phage (250 μl) were mixed with 1.75 ml of log phase *E. coli* TG1 ($OD_{600}$ between 0.3 and 0.6) and infection allowed to occur for 30 min at 37° C. without shaking. The infected *E. coli* TG1 culture was centrifuged at 11,600 g in a micro centrifuge for 1 min at room temperature. The pelleted bacteria were resuspended in 100 μl of 2×TY and plated on regular 9 cm diameter plates containing TYE supplemented with 15 μg/ml tetracycline. Plates were grown at 37° C. overnight.

After overnight growth, 2 ml of 2×TY containing 15% glycerol was added to the culture plates and cells loosened with a spreader, ensuring the cells were thoroughly mixed. Two millilitres of the culture were recovered by pipetting into a cryo-vial, from which 50 μl was used to inoculate 50 ml of 2×TY supplemented with 15 μg/ml tetracycline. The remaining cells in the cryo-vial were stored at −80° C.

The 50 ml culture was grown at 37° C. for 16 to 24 hours with shaking at 250 rpm.

Following overnight growth, the culture was centrifuged at 3,300 g for 15 min to pellet the bacteria. The phage were then precipitated from the supernatant through the addition of 10 ml of PEG/NaCl to 40 ml of clarified supernatant. The phage/PEG solution was mixed and incubated on ice for at least 1 h. To pellet the phage, the solution was centrifuged at 3,300 g for 30 min at 4° C. The supernatant was decanted and any remaining supernatant removed by aspiration.

The resulting phage pellet was resuspended in 2 ml PBS and centrifuged at 11,600 g for 10 min in a micro centrifuge to remove any remaining bacterial debris. The supernatant was filtered through a 0.45 μm filter (Sartorius, Minisart). The resuspended phage solution was used for the next round of selection.

TABLE 2

| Equipment/Reagent | Suggested or required supplier | Instrument setting, reagent preparation |
|---|---|---|
| Dynabeads ® M-280 Streptavidin (Prod. No.: 112.05) | Dynal Biotech UK 11 Bassendale Road, Croft Business Park, Bromborough, Wirral CH62 3QL UK | Resuspend thoroughly through repeated pipetting. |
| Tween 20 | Sigma Chemical Company Ltd. | 0.1% in PBS. |
| 99.5% dried skim milk powder | Marvel ™ (premier brands) from supermarkets. | 2% in PBS (prepare fresh and do not store). |

TABLE 2-continued

| Equipment/Reagent | Suggested or required supplier | Instrument setting, reagent preparation |
|---|---|---|
| Trypsin (T-8642) Type XIII from Bovine Pancreas. | Sigma Chemical Company Ltd. Fancy Road Dorset BH17 7NH U.K Tel +44 1202 733114 Fax +44 1202 715460 | made up in 50 mM Tris-HCl pH7.4; 1 mM $CaCl_2$ and stored at −20° C. The trypsin stock solution should be stored aliquotted at −20° C. to avoid autoproteolysis. |
| PEG/NaCl | Sigma Chemical Company Ltd. | 20% Polyethylene glycol 8000 [formally known as 6000], 2.5 M NaCl pre-chilled to 4° C. |
| Dynal MPC-S magnetic particle concentrator (Prod. No.: 120.20) | Dynal Biotech UK 11 Bassendale Road, Croft Business Park, Bromborough, Wirral CH62 3QL UK | |
| 2xTY | | 16 g Tryptone, 10 g Yeast Extract and 5 g NaCl in 1 litre. Autoclave (121° C., 15 min) and store at RT |

Example 3

Cloning Enriched Phage Selection Outputs into the Soluble dAb Expression Vector pDOM5

Following the second and third rounds of selection, *E. coli* cells infected with the enriched dAb displaying fd-phage populations were obtained. An aliquot of these cells was used to prepare phage DNA and the enriched V-genes excised by digestion using the restriction endonucleases, SalI and NotI. The purified V-genes were ligated into the corresponding sites of pDOM5 (expression vector derived from pUC119 with LacZ promoter, eukaryotic leader, dAb cloning site, myc tag), and the ligated DNA used to electro-transform *E. coli* HB2151 cells which were grown overnight on agar plates containing the antibiotic carbenicillin. The resulting colonies were induced to express dAb protein either as 200 μl microcultures or 50 ml cultures. The resulting dAb was analysed for inhibitory activity using the CD40L receptor binding assay.

Following selection of phage, pDOM4 DNA was purified from the cell pellet obtained from a 50 ml overnight *E. coli* culture using the QIAfilter Plasmid Midi DNA purification kit from Qiagen, following the manufacturer's instructions. The dAb genes were excised from the pDOM4 vector by mixing: 10 μl of 10×SalI buffer; 1 μl of 100× BSA; 20 μg of purified DNA fragment; 2.5 μl of SalI enzyme (10 U/μl); 2.5 μl of NotI enzyme (10 U/μl); the digestion mix was made up to a final volume of 100 μl using sterile water. The digestion mix was incubated for 5 hours at 37° C.

The digested DNA samples were electrophoresed on a 1.5% agarose gel and the band corresponding to the dAb V-genes (~324 bp to 372 bp) was excised from the gel. The dAb gene DNA was purified from the gel slice using the QIAquick Gel Extraction kit from Qiagen, following the manufacturer's instructions.

The expression vector pDOM5 was digested with SalI and NotI as follows: 10 μl of 10×SalI buffer; 1 μl of 100× BSA; 20 μg of plasmid pDOM5; 1.5 μl of SalI enzyme (10 U/μl); 1.5 μl of NotI enzyme (10 U/μl); the digestion mix was made up to a final volume of 100 μl using sterile water. The digestion mix was incubated for 2 hours at 37° C. The digested vector fragment was purified using the QIAquick PCR Purification Kit.

The digested pDOM5 and digested dAb genes were ligated by mixing: 2 μl of 10× T4 DNA ligase buffer; 400 ng of digested pDOM5 vector; 100 ng of digested dAb genes; 1 μl of T4 DNA ligase (400 U/μl); the ligation mix was made up to 20 μl with sterile water. The ligation mixes were incubated for 2 hours at 25° C.

Two microlitres of the ligation mix was transferred to the bottom of a pre-chilled (on ice) 0.2 cm electroporation cuvette to which 100 μl of electrocompetent *E. coli* HB2151 cells were added. The DNA/cell mixture was incubated on ice for 1-2 min, then electroporated at 2.5 kV (25 μF, 200 Ω). One millilitre of 2×TY was immediately added to the cuvette and the cells gently resuspended. The resuspended cells were transferred to a 14 ml disposable culture tube and incubated for 1 hour at 37° C. with shaking at 250 rpm. Dilutions of the cells from $10^{-0}$ to $10^{-3}$ were plated on regular 9 cm diameter plates containing TYE supplemented with 5% glucose and 50 μg/ml carbenicillin. The cells are incubated overnight at 37° C. in an inverted position. Reagents, equipment and sources from which they are available are provided in Table 3.

TABLE 3

| Equipment/Reagent | Suggested or required supplier | Instrument setting, reagent preparation |
|---|---|---|
| QIAfilter Plasmid Midi DNA purification kit | Qiagen Ltd Cat. No.: 12143 | Supplied as kit |
| SalI restriction endonuclease + 10x SalI buffer | New England Biolabs Cat. No.: R0138S | |
| NotI restriction endonuclease + 10x NotI buffer + 100x BSA | New England Biolabs Cat. No.: R0189S | |
| QIAquick Gel Extraction kit | Qiagen Ltd Cat. No.: 28706 | Supplied as kit |
| Expression plasmid pDOM5 | | |
| T4 DNA ligase + 10x T4 DNA ligase buffer | New England Biolabs Cat. No.: M0202L | The T4 DNA ligase buffer should be stored aliquotted at −20° C. Repeated freeze-thawing should be avoided to minimise the hydrolysis of ATP in the buffer. |

Example 4

Microwell Expression of Soluble dAbs

Following cloning of the selected phage dAb outputs into pDOM5, individual bacterial colonies were inoculated as microwell cultures and induced using IPTG to express dAb protein which was analysed for inhibitory activity using the CD40L receptor binding assay. Reagents, equipment and sources from which they are available are provided in Table 4.

Individual bacterial colonies were carefully picked to ensure that contamination from neighbouring colonies was avoided. The picked colonies were used to inoculate 96 well cell culture plates containing 100 μl per well of 2×TY supplemented with 5% glucose and 50 μg/ml carbenicillin. The lids were placed on the cell culture plates which were incubated overnight in a HiGro orbital shaker (GeneMachines, 935 Washington St, San Carlos, Calif. 94070, USA) under a humidified atmosphere at 37° C. with shaking at 450 rpm (4 mm shaking orbital diameter), with gas (30% $O_2$+70% $N_2$) pulsed for 10 seconds every 5 minutes at a flow rate of 5 SLPM (standard litres per minute). [These plates are referred to as Master Plates].

Following overnight growth, a 96 well transfer device was used to transfer between 1-5 μl of the bacterial culture into a fresh 96 well culture plate containing 100 μl per well of 2×TY supplemented with 0.1% glucose and 50 μg/ml carbenicillin.

The freshly inoculated plates were incubated at 37° C. for 3 to 4 h (shaking at 450 rpm, gas (30% $O_2$+70% $N_2$) pulsed for 10 seconds every 5 minutes at a flow rate of 5 SLPM) until the culture $OD_{600}$ reached approximately 1.0. The cultures were then induced by the addition of 100 μl per well of 2×TY containing 50 μg/ml carbenicillin and 2 mM IPTG (final IPTG concentration of 1 mM) and incubated overnight at 30° C. with shaking at 450 rpm, with gas (30% $O_2$+70% $N_2$) pulsed for 10 seconds every 5 minutes at a flow rate of 5 SLPM. [These plates are referred to a Induction Plates].

Glycerol stocks of the original Master Plates were made by the addition of 100 μl per well of 2×TY containing 50% sterile glycerol. These plates were stored at −80° C. Following overnight incubation of the Induction Plates, the bacterial cells were pelleted by centrifugation at 1,800 g for 10 min at 4° C. The supernatant (containing expressed dAb) was then analysed to determine if dabs were capable of inhibiting binding of CD40L to CD40-Fc fusion in a receptor binding assay.

TABLE 4

| Equipment/Reagent | Suggested or required supplier | Instrument setting, reagent preparation |
|---|---|---|
| 96 Well Cell Culture Cluster with round bottom and lid, Non-pyrogenic, Polystyrene | Corning Incorporated, Costar. Number: 3799 | |
| 2xTY | | 16 g Tryptone, 10 g Yeast Extract and 5 g NaCl in 1 litre. Autoclave (121° C., 15 min) and store at RT |

Example 5

Expression of dAb in *E. coli* at 50 ml

To generate greater quantities of dAb protein for analysis, 50 ml cultures were used for induction. A single colony of the desired dAb (for example DOM-24) grown on TYE plates was inoculated into 10 ml 2×TY supplemented with 5% glucose and 50 μg/ml carbenicillin in a 30 ml universal tube and grown overnight at 37° C. with shaking at 250 rpm. Five hundred microlitres of the overnight culture was added into 50 ml of 2×TY supplemented with 0.1% glucose and 50 μg/ml carbenicillin and grown at 37° C. with shaking at 250 rpm. The $OD_{600}$ of the culture was monitored regularly in comparison with sterile 2×TY and at an $OD_{600}$ of 0.9 the culture was induced by the addition of 1 M IPTG to a final concentration of 1 mM. The inoculated culture was incubated at 30° C. with shaking at 250 rpm overnight. The next day, the culture was centrifuged at 6000 g for 15 min at 4° C. and the clarified supernatant mixed with 100 μl of protein-A streamline or protein-L agarose (pre-washed with 5 mM $MgSO_4$) overnight at 4° C. The supernatant/bead mixture was then centrifuged at 180 g at 4° C. for 2 minutes. The supernatant was decanted and the retained beads washed with 10 ml of PBS containing 0.5M NaCl. The bead solution was transferred into a 96 well Whatman filter plate and the beads washed once with 400 μl of PBS containing 0.5M NaCl, then once with 400 μl of PBS, followed by centrifugation for 2 minutes at 180 g after each washing step. dAb protein was eluted using 70 μl of 0.1 M glycine (pH 2.0) and the solution neutralised by the addition of 40 μl of 1 M Tris-HCl (pH 8.0). The purified dAb concentration was determinate by $OD_{280}$.

Reagents, equipment and sources from which they are available are provided in Table 5.

TABLE 5

| Equipment/Reagent | Suggested or required supplier | Instrument setting, reagent preparation |
|---|---|---|
| TYE | | 15 g Bacto-Agar, 8 g NaCl, 10 g Tryptone, 5 g Yeast Extract in 1 litre water. Autoclave (121° C., 15 min) and store at RT |
| 2xTY | | 16 g Tryptone, 10 g Yeast Extract and 5 g NaCl in 1 litre. Autoclave (121° C., 15 min) and store at RT |
| 1 M IPTG | | stock made up in MQ water is sterile filtered through 0.22 μM filter and stored in aliquots at −20° C. |
| Carbenicillin | | 50 mg/ml stock made in water, 0.2 μm filter sterilised and stored in aliquots at −20° C. |
| 40% glucose solution | | 0.2 μm filter sterilise, store at RT |
| 5 mM $MgSO_4$ | | prepare fresh from 1 M stock solution, 0.2 μm filter sterilise and store at RT |
| 0.5M NaCl/PBS | | Autoclave or 0.2 μm filter sterilise and store at RT |
| Protein A agarose | Sigma P3476 | store 4° C. |
| Protein L agarose | Sigma P3351 | store 4° C. |
| Streamline rProtein A | Amersham Biosciences, cat no. 17-1281-02 (300 ml) | store 4° C. |
| 1 M Tris-HCl, pH 8.0 | | 0.2 μm filter sterilise or autoclave and store at RT |
| 0.2 M Glycine, pH2.0 | | 0.2 μm filter sterilise and store at 4° C. |

Example 6

CD40L Receptor Binding Assay

Figure 7:
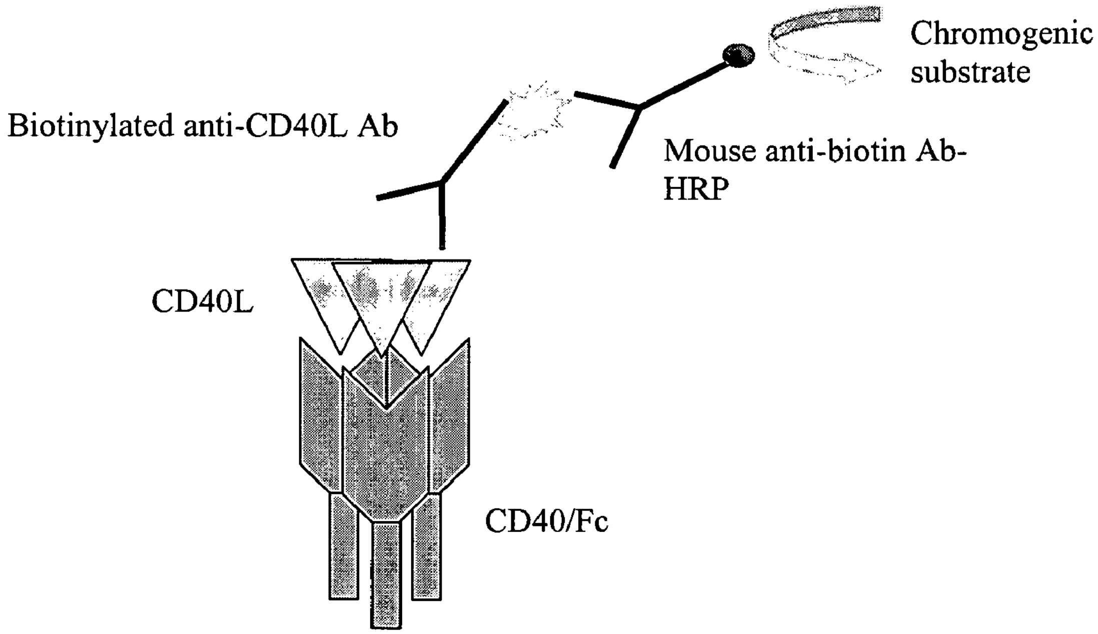
FIG. 7 shows a schematic representation of the CD40L binding assay used herein, e.g., in Example 6.

The CD40L assay was used to measure the binding of CD40L to CD40 and the ability of binding entities (eg, monovalent antibody fragments such a dAbs) to block this interaction, as described below and shown schematically in FIG. 7. (The soluble proteins from R&D Systems are CD40/Fc=homodimer and CD40L=homotrimer).

A 96 well Nunc Maxisorp assay plate was coated overnight at 4° C. with 100 μl per well of recombinant human CD40/Fc (R&D Systems) at 0.5 μg/ml in carbonate buffer. The plate was washed 3 times with 300 μl of 0.05% Tween/PBS and 3 times with 300 μl of PBS using a Tecan plate washer. The wells were blocked using 200 μl of PBS containing 2% (w/v) BSA and incubated for a minimum of 1 h at room temperature. The wells were washed as above, then 50 μl of purified dAb protein (or unpurified supernatant containing dAb from a micro-culture expression) was added to each well. To each well 50 μl of CD40L, at 6 ng/ml in diluent (for a final concentration of 3 ng/ml), was also added and the plate incubated for 1 hr at room temperature.

The plate was washed as described previously and 100 μl biotinylated anti-CD40L antibody, 0.5 μg/ml in diluent, was added and incubated for 1 hr at room temperature. The plate was washed as described above, then 100 μl HRP conjugated anti-biotin antibody (1:5000 dilution in diluent) added to each well and the plate incubated for 1 hr at room temperature. The plate was washed again as described above using a Tecan plate washer and the assay developed using 100 μl of Sure-Blue 1-Component TMB MicroWell Peroxidase solution (the plate was left at room temperature for up to 20 min). The reaction was stopped by the addition of 100 μl 1 M hydrochloric acid. The $OD_{450nm}$ of the plate was assayed within 30 minutes of acid addition. The $OD_{450nm}$ is proportional to the amount of bound streptavidin-HRP conjugate, therefore the greater the degree of dAb inhibition the lower the $OD_{450nm}$ of the resulting signal. Reagents, equipment and sources from which they are available are provided in Table 6.

Controls

The following controls were included:

0 ng/ml CD40L (diluent only)

3 ng/ml CD40L 3 ng/ml CD40L with 1 μg/ml anti-CD40L antibody

TABLE 6

| Equipment/Reagent | Suggest or required supplier (specify) | Reagent preparation |
|---|---|---|
| F96 Maxisorp 96 well immunoplate | Nunc, Cat No: 439454 | |
| 0.2M sodium carbonate bicarbonate buffer pH9.4 | Pierce, Cat No: 28382 | Dissolve 1 sachet in 500 ml deionised water and keep solution at 4° C. |
| Recombinant human CD40/Fc chimera | R&D Systems, Cat No: 1493-CD | Stock 50 μg/ml at−80° C. |
| Phosphate buffered saline (PBS) | Sigma, Cat No: P4417 | 10x solution 100 tablets/L water. |
| Wash buffer | | 0.05% Tween-20/PBS |
| Diluent | | 0.1% BSA, 0.05% Tween-20 in PBS |
| Block | | 2% BSA in PBS |
| Recombinant human CD40L | R&D Systems, Cat No: 617-CL | Stock 50 μg/ml at−80° C. |
| Neutralising anti-CD40L antibody | Calbiochem, Cat No: 217595 | Stock 1 mg/ml at 4° C. |
| Biotinylated anti-CD40L antibody | R&D Systems, Cat No: BAF617 | Stock 50 μg/ml at −80° C. |
| Anti-biotin-HRP conjugate | Stratech, Cat No: 200-032-096 | Stock 800 μg/ml at −80 C., diluted 1:5000 in antibody diluent. Keep for 1 week only. |

TABLE 6-continued

| Equipment/Reagent | Suggest or required supplier (specify) | Reagent preparation |
|---|---|---|
| SureBlue TMB 1-component microwell peroxidase substrate | KPL, Cat No: 52-00-00 | at 4° C. |

Example 7

Results

Receptor binding data for the most potent inhibitors is summarised in FIGS. 2, 3, and 4, and in Table 7, below. Table 8, below, provides DNA and translated amino acid sequence of unique dAbs identified in the receptor binding assay as inhibiting CD40L binding to CD40.

Figure 2:
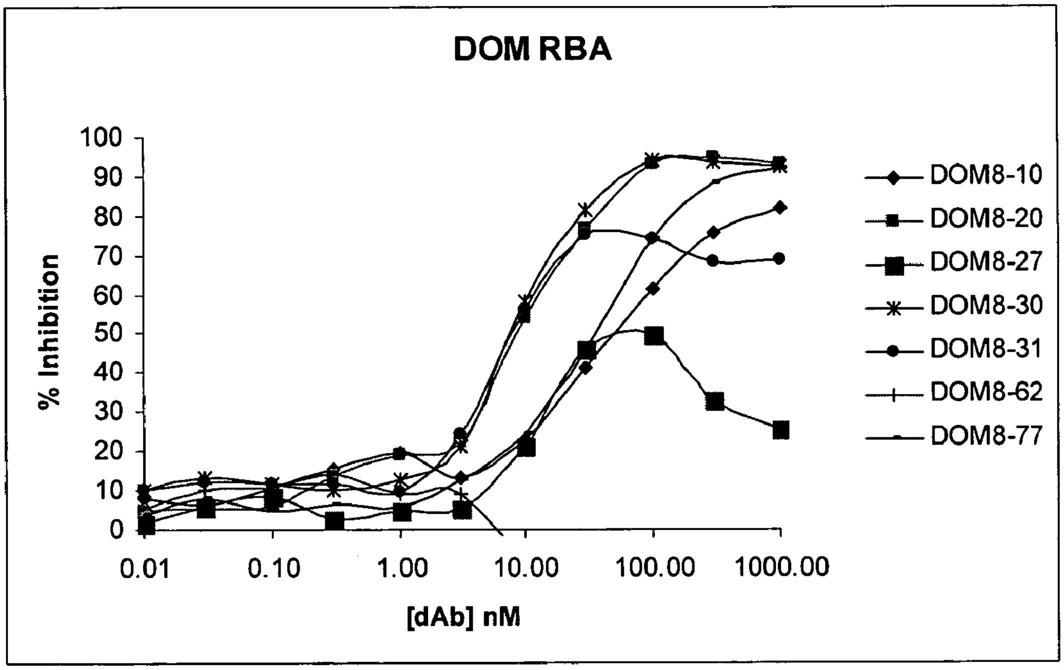
FIG. 2 shows a graphical representation of a dose response receptor binding assay (RBA) readout, analysing the inhibition of CD40L binding to CD40-Fc by dAbs DOM-10, -20, -27, -30, -31, -62, -77, titrated from 1 μM down to 10 pM. dAbs DOM-20, -30, and -31 are the most potent with $IC_{50}$ values of approximately 8 nM.

FIG. 2 shows a dose response receptor binding assay (RBA) readout, analysing the inhibition of CD40L binding to CD40-Fc by dAbs DOM-10, -20, -27, -30, -31, -62, -77, titrated from 1 μM down to 10 pM. dAbs DOM-20, -30, and -31 are the most potent, with $IC_{50}$ values of approximately 8 nM.

Figure 3:
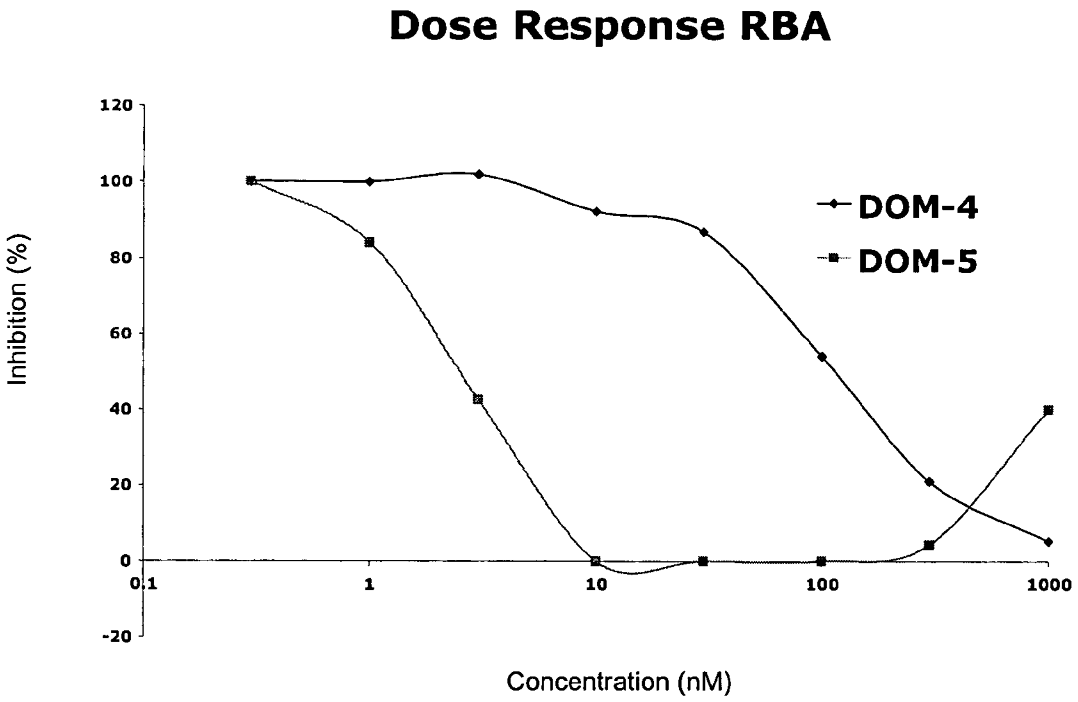
FIG. 3 shows a graphical representation of a dose response receptor binding assay readout, analysing the inhibition of CD40L binding to CD40-Fc by dAbs DOM-4 and DOM-5, titrated from 1 μM down to 500 pM. The $IC_{50}$ values for dAbs DOM-5 and DOM-4 are approximately 3 nM and 100 nM respectively.

FIG. 3 shows a dose response receptor binding assay readout, analysing the inhibition of CD40L binding to CD40-Fc by dAbs DOM-4 and DOM-5, titrated from 1 μM down to 500 pM. The $IC_{50}$ values for dAbs DOM-5 and DOM-4 are approximately 3 nM and 100 nM respectively.

Figure 4:
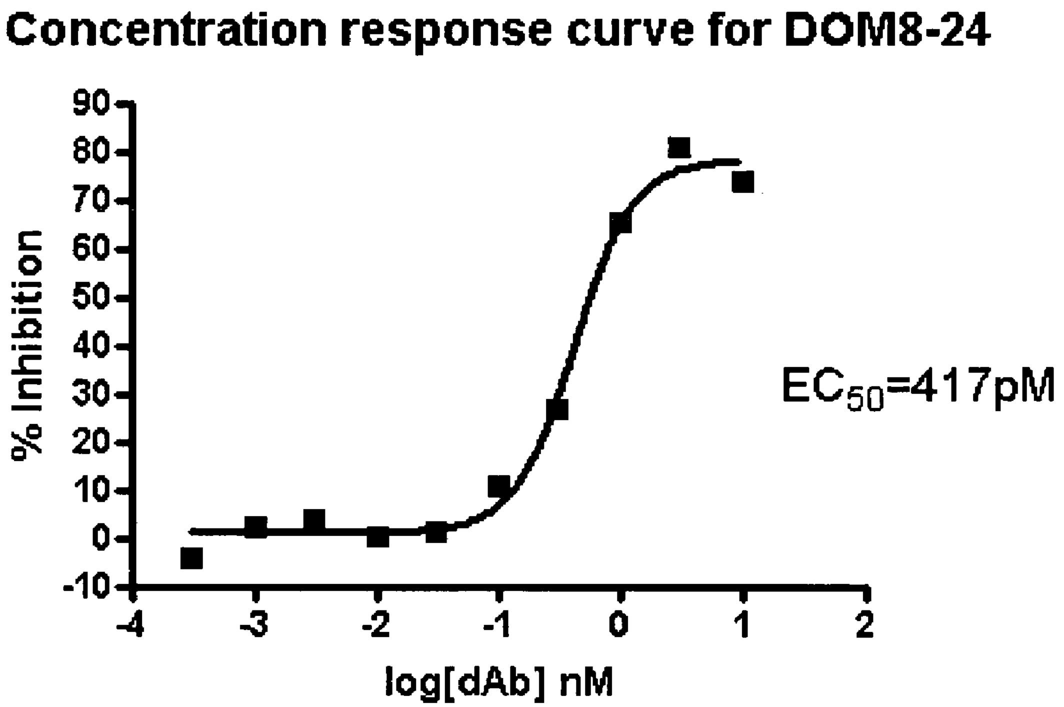
FIG. 4 shows a graphical representation of a dose response receptor binding assay readout, analysing the inhibition of CD40L binding to CD40-Fc by dAb DOM-24, titrated from 100 nM down to 0.5 pM. The data were curve-fitted using GraphPad Prism software.

FIG. 4 shows a dose response receptor binding assay readout, analysing the inhibition of CD40L binding to CD40-Fc by dAb DOM-24, titrated from 100 nM down to 0.5 pM. The data were curve-fitted using GraphPad Prism software.

TABLE 7

| Clone Name | dAb Type | $IC_{50}$ (nM) |
|---|---|---|
| DOM-2 | VH | 800 |
| DOM-4 | VH | 100 |
| DOM-5 | VH | 3 |
| DOM-7 | VH | 1500 |
| DOM-8 | VK | 900 |
| DOM-10 | VH | 50 |
| DOM-20 | VH | 8 |
| DOM-24 | VH | 0.417 |
| DOM-27 | VH | 100 approx. |
| DOM-30 | VH | 8 |
| DOM-31 | VH | 8 |
| DOM-77 | VH | 40 |

TABLE 8

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| DOM-2 | SEQ ID NO: 7 |
| | E V Q L L E S G G G L V Q P G G S L R L S C A A S G F T F S D Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTTCT GATTATGAGA |
| | CTCCACGTCG ACAACCTCAG ACCCCCTCCG AACCATGTCG GACCCCCCAG GGACGCAGAG AGGACACGTC GGAGGCCTAA GTGGAAAAGA CTAATACTCT |
| | . M W V R Q A P G K G L E W V S T I T S D G I S T Y Y A D S V K G R . |
| 101 | TGATGTGGGT CCGCCAGGCT CCAGGGAAGG GTCTAGAGTG GGTCTCAACT ATTACTTCGG ATGGTATTTC TACATACTAC GCAGACTCCG TGAAGGGCCG |
| | ACTACACCCA GGCGGTCCGA GGTCCCTTCC CAGATCTCAC CCAGAGTTGA TAATGAAGCC TACCATAAAG ATGTATGATG CGTCTGAGGC ACTTCCCGGC |
| | . F T I F R D N S K N T L Y L Q M N S L R A E D T A V Y Y C A K S G |
| 201 | GTTCACCATC TTCCGCGACA ATTCCAAGAA CACGCTGTAT CTGCAAATGA ACAGCCTGCG TGCCGAGGAT ACCGCGGTAT ATTACTGTGC GAAAAGTGGG |
| | CAAGTGGTAG AAGGCGCTGT TAAGGTTCTT GTGCGACATA GACGTTTACT TGTCGGACGC ACGGCTCCTA TGGCGCCATA TAATGACACG CTTTTCACCC |
| | R F F D Y W G Q G T L V T V S S |
| 301 | AGGTTTTTTG ACTACTGGGG TCAGGGAACC CTGGTCACCG TCTCGAGC (SEQ ID NO: 94) |
| | TCCAAAAAAC TGATGACCCC AGTCCCTTGG GACCAGTGGC AGAGCTCG (SEQ ID NO: 95) |
| DOM-4 | SEQ ID NO: 8 |
| | E V Q L L E S G G G L V Q P G G S L R L S C A A S G F T F D N Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGAT AATTATGAGA |
| | CTCCACGTCG ACAACCTCAG ACCCCCTCCG AACCATGTCG GACCCCCCAG GGACGCAGAG AGGACACGTC GGAGGCCTAA GTGGAAACTA TTAATACTCT |
| | . T W V R Q A P G K G L E W V S S I T S D G T S T Y Y A D S V K G R . |
| 101 | TGACGTGGGT CCGCCAGGCT CCAGGGAAGG GTCTAGAGTG GGTCTCATCT ATTACGAGTG ATGGTACTTC GACATACTAC GCAGACTCCG TGAAGGGCCG |
| | ACTGCACCCA GGCGGTCCGA GGTCCCTTCC CAGATCTCAC CCAGAGTAGA TAATGCTCAC TACCATGAAG CTGTATGATG CGTCTGAGGC ACTTCCCGGC |
| | . F T I S R D N S K N T L Y L Q M N S L R A E D T A V Y Y C A K P N |
| 201 | GTTCACCATC TCCCGCGACA ATTCCAAGAA CACGCTGTAT CTGCAAATGA ACAGCCTGCG TGCCGAGGAT ACCGCGGTAT ATTACTGTGC GAAACCTAAT |
| | CAAGTGGTAG AGGGCGCTGT TAAGGTTCTT GTGCGACATA GACGTTTACT TGTCGGACGC ACGGCTCCTA TGGCGCCATA TAATGACACG CTTTGGATTA |
| | P P F D Y W G Q G T L V T V S S |
| 301 | CCGCCGTTTG ACTACTGGGG TCAGGGAACC CTGGTCACCG TCTCGAGC (SEQ ID NO: 96) |
| | GGCGGCAAAC TGATGACCCC AGTCCCTTGG GACCAGTGGC AGAGCTCG (SEQ ID NO: 97) |
| DOM-5 | SEQ ID NO: 9 |
| | E V Q L L E S G G G L V Q P G G S L R L S C A A S G F T F D G Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGAT GGGTATGAGA |
| | CTCCACGTCG ACAACCTCAG ACCCCCTCCG AACCATGTCG GACCCCCCAG GGACGCAGAG AGGACACGTC GGAGGCCTAA GTGGAAACTA CCCATACTCT |
| | . A W V R Q A P G K G L E W V S S I T S D G T S T Y Y A D S V K G R . |
| 101 | TGGCGTGGGT CCGCCAGGCT CCAGGGAAGG GTCTAGAGTG GGTCTCATCT ATTACGAGTG ATGGTACGAG TACATACTAC GCAGACTCCG TGAAGGGCCG |
| | ACCGCACCCA GGCGGTCCGA GGTCCCTTCC CAGATCTCAC CCAGAGTAGA TAATGCTCAC TACCATGCTC ATGTATGATG CGTCTGAGGC ACTTCCCGGC |
| | . F T I S R D N S K N T L Y L Q M N S L R A E D T A V Y Y C A K P G |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGGG |
| | CAAGTGGTAG AGGGCGCTGT TAAGGTTCTT GTGCGACATA GACGTTTACT TGTCGGACGC ACGGCTCCTG TGGCGCCATA TAATGACACG CTTTGGCCCC |

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| | L R F D Y W G Q G T L V T V S S |
| 301 | CTGCGTTTTG ACTACTGGGG TCAGGGAACC CTGGTCACCG TCTCGAGC (SEQ ID NO: 98) |
| | GACGCAAAAC TGATGACCCC AGTCCCTTGG GACCAGTGGC AGAGCTCG (SEQ ID NO: 99) |
| DOM-7 | SEQ ID NO: 10 |
| | E V Q L L E S G G G L V Q P G G S L R L S C A A S G F T F N L Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTAAT TTGTATGAGA |
| | CTCCACGTCG ACAACCTCAG ACCCCCTCCG AACCATGTCG GACCCCCCAG GGACGCAGAG AGGACACGTC GGAGGCCTAA GTGGAAATTA AACATACTCT |
| | . T W V R Q A P G K G L E W V S S I T S D G V S T Y Y A D S V K G R . |
| 101 | TGACTTGGGT CCGCCAGGCT CCAGGGAAGG GTCTAGAGTG GGTCTCATCT ATTACTAGTG ATGGTGTTTC TACATACTAC GCAGACTCCG TGAAGGGCCG |
| | ACTGAACCCA GGCGGTCCGA GGTCCCTTCC CAGATCTCAC CCAGAGTAGA TAATGATCAC TACCACAAAG ATGTATGATG CGTCTGAGGC ACTTCCCGGC |
| | . F T I S R D N S K N T L Y L Q M N S L R A E D T A V Y Y C A K A G |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAAGCTGGG |
| | CAAGTGGTAG AGGGCGCTGT TAAGGTTCTT GTGCGACATA GACGTTTACT TGTCGGACGC ACGGCTCCTG TGGCGCCATA TAATGACACG CTTTCGACCC |
| | V I F D Y W G Q G T L V T V S S |
| 301 | GTGATTTTTG ACTACTGGGG TCAGGGAACC CTGGTCACCG TCTCGAGC (SEQ ID NO: 100) |
| | CACTAAAAAC TGATGACCCC AGTCCCTTGG GACCAGTGGC AGAGCTCG (SEQ ID NO: 101) |
| DOM-8 | SEQ ID NO: 11 |
| | D I Q M T Q S P S S L S A S V G D R V T I T C R A S Q F I D T S L E . |
| 1 | GACATCCAGA TGACCCAGTC TCCATCCTCC CTGTCTGCAT CTGTAGGAGA CCGTGTCACC ATCACTTGCC GGGCAAGTCA GTTTATTGAT ACGTCGTTAG |
| | CTGTAGGTCT ACTGGGTCAG AGGTAGGAGG GACAGACGTA GACATCCTCT GGCACAGTGG TAGTGAACGG CCCGTTCAGT CAAATAACTA TGCAGCAATC |
| | . W Y Q Q K P G K A P K L L I Y D G S H L Q S G V P S R F S G S G S . |
| 101 | AGTGGTATCA GCAGAAACCA GGGAAAGCCC CTAAGCTCCT GATCTATGAT GGGTCCCATT TGCAAAGTGG GGTCCCATCA CGTTTCAGTG GCAGTGGATC |
| | TCACCATAGT CGTCTTTGGT CCCTTTCGGG GATTCGAGGA CTAGATACTA CCCAGGGTAA ACGTTTCACC CCAGGGTAGT GCAAAGTCAC CGTCACCTAG |
| | . G T D F T L T I S S L Q P E D L A T Y Y C Q Q Y W V L P L T F G Q |
| 201 | TGGGACAGAT TTCACTCTCA CCATCAGCAG TCTGCAACCT GAAGATTTAG CTACGTACTA CTGTCAACAG TATTGGGTTC TTCCTCTGAC GTTCGGCCAA |
| | ACCCTGTCTA AAGTGAGAGT GGTAGTCGTC AGACGTTGGA CTTCTAAATC GATGCATGAT GACAGTTGTC ATAACCCAAG AAGGAGACTG CAAGCCGGTT |
| | G T K V E I K R |
| 301 | GGGACCAAGG TGGAAATCAA ACGG (SEQ ID NO: 102) |
| | CCCTGGTTCC ACCTTTAGTT TGCC (SEQ ID NO: 103) |
| DOM-10 | SEQ ID NO: 12 |
| | E V Q L L E S G G G L V Q P G G S L R L S C A A S G F T F I A Y D M . |
| 1 | GAGGTGCAGC TGTTGGAGTC TGGGGGAGGC TTAGTACAGC CTGGGGGGTC CCTGCGTCTC TCCTGTGCAG CCTCCGGATT CACCTTTATT GCTTATGATA |
| | CTCCACGTCG ACAACCTCAG ACCCCCTCCG AATCATGTCG GACCCCCCAG GGACGCAGAG AGGACACGTC GGAGGCCTAA GTGGAAATAA CGAATACTAT |
| | . S W V R Q A P G K G L E W V S W I D E W G L Q T Y Y A D S V K G R . |
| 101 | TGAGTTGGGT CCGCCAGGCT CCAGGGAAGG GTCTGGAGTG GGTCTCATGG ATTGATGAGT GGGGTCTGCA GACATACTAC GCAGACTCCG TGAAGGGCCG |
| | ACTCAACCCA GGCGGTCCGA GGTCCCTTCC CAGACCTCAC CCAGAGTACC TAACTACTCA CCCCAGACGT CTGTATGATG CGTCTGAGGC ACTTCCCGGC |
| | . F T I S R D N S K N T L Y L Q M N S L R A E D T A V Y Y C A K K T |

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201      GTTCACCATC TCCCGCGACA ATTCCAAGAA CACGCTGTAT CTGCAAATGA ACAGCCTGCG TGCCGAGGAC ACCGCGGTAT ATTACTGTGC GAAAAAGACG
         CAAGTGGTAG AGGGCGCTGT TAAGGTTCTT GTGCGACATA GACGTTTACT TGTCGGACGC ACGGCTCCTG TGGCGCCATA TAATGACACG CTTTTTCTGC

          P  E  E  F   D  Y  W   G  Q  G   T  L  V  T   V  S  S
301      CCTGAGGAGT TTGACTACTG GGGTCAGGGA ACCCTGGTCA CCGTCTCGAG C (SEQ ID NO: 104)
         GGACTCCTCA AACTGATGAC CCCAGTCCCT TGGGACCAGT GGCAGAGCTC G (SEQ ID NO: 105)

DOM-11   SEQ ID NO: 13
          E  V  Q  L   L  E  S   G  G  G   L  V  Q  P   G  G  S   L  R  L   S  C  A  A   S  G  F   T  F  G   D  Y  E  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTGGT GATTATGAGA
         CTCCACGTCG ACAACCTCAG ACCCCCTCCG AACCATGTCG GACCCCCCAG GGACGCAGAG AGGACACGTC GGAGGCCTAA GTGGAAACCA CTAATACTCT

         .  S  W  V   R  Q  A   P  G  K  G   L  E  W   V  S  G   I  D  G  E   G  S  D   T  Y  Y   A  D  S  V   K  G  R .
101      TGAGTTGGGT CCGCCAGGCT CCAGGGAAGG GTCTAGAGTG GGTCTCAGGG ATTGATGGTG AGGGTTCTGA TACATACTAC GCAGACTCCG TGAAGGGCCG
         ACTCAACCCA GGCGGTCCGA GGTCCCTTCC CAGATCTCAC CCAGAGTCCC TAACTACCAC TCCCAAGACT ATGTATGATG CGTCTGAGGC ACTTCCCGGC

         .  F  T   I  S  R  D  N   S  K  N   T  L  Y   L  Q  M  N   S  L  R   A  E  D   T  A  V  Y   Y  C  A   K  P  G
201      GTTCACCATC TCCCGCGACA ATTCCAAGAA CACGCTGTAT CTGCAAATGA ACAGCCTGCG TGCCGAGGAT ACCGCGGTAT ATTACTGTGC GAAACCGGGG
         CAAGTGGTAG AGGGCGCTGT TAAGGTTCTT GTGCGACATA GACGTTTACT TGTCGGACGC ACGGCTCCTA TGGCGCCATA TAATGACACG CTTTGGCCCC

          R  S  F  D   Y  W  G   Q  G  T   L  V  T  V   S  S
301      AGGAGTTTTG ACTACTGGGG TCAGGGAACC CTGGTCACCG TCTCGAGC (SEQ ID NO: 106)
         TCCTCAAAAC TGATGACCCC AGTCCCTTGG GACCAGTGGC AGAGCTCG (SEQ ID NO: 107)

DOM-12   SEQ ID NO: 14
          E  V  Q  L   L  E  S   G  G  G   L  V  Q  P   G  G  S   L  R  L   S  C  A  A   S  G  F   T  F  R   L  Y  E  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTAGG TTGTATGAGA
         CTCCACGTCG ACAACCTCAG ACCCCCTCCG AACCATGTCG GACCCCCCAG GGACGCAGAG AGGACACGTC GGAGGCCTAA GTGGAAATCC AACATACTCT

         .  A  W  V   R  Q  A   P  G  K  G   L  E  W   V  S  G   I  D  I  L   G  S  R   T  Y  Y   A  D  S  V   K  G  R .
101      TGGCGTGGGT CCGCCAGGCT CCAGGGAAGG GTCTAGAGTG GGTCTCAGGG ATTGATATTT TGGGTTCGAG GACATACTAC GCAGACTCCG TGAAGGGCCG
         ACCGCACCCA GGCGGTCCGA GGTCCCTTCC CAGATCTCAC CCAGAGTCCC TAACTATAAA ACCCAAGCTC CTGTATGATG CGTCTGAGGC ACTTCCCGGC

         .  F  T  I   S  R  D  N   S  K  N   T  L  Y   L  Q  M  N   S  L  R   A  E  D   T  A  V  Y   Y  C  A   K  D  L
201      GTTCACCATC TCCCGCGACA ATTCCAAGAA CACGCTGTAT CTGCAAATGA ACAGCCTGCG TGCCGAGGAT ACCGCGGTAT ATTACTGTGC GAAAGATCTG
         CAAGTGGTAG AGGGCGCTGT TAAGGTTCTT GTGCGACATA GACGTTTACT TGTCGGACGC ACGGCTCCTA TGGCGCCATA TAATGACACG CTTTCTAGAC

          S  W  Q  G   F  D  Y   W  G  Q   G  T  L  V   T  V  S   S
301      TCGTGGCAGG GTTTTGACTA CTGGGGTCAG GGAACCCTGG TCACCGTCTC GAGC (SEQ ID NO: 108)
         AGCACCGTCC CAAAACTGAT GACCCCAGTC CCTTGGGACC AGTGGCAGAG CTCG (SEQ ID NO: 109)

DOM-13   SEQ ID NO: 15
          E  V  Q  L   L  E  S   G  G  G   L  V  Q  P   G  G  S   L  R  L   S  C  A  A   S  G  F   T  F  S   Y  Y  S  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTTCT TATTATTCGA
         CTCCACGTCG ACAACCTCAG ACCCCCTCCG AACCATGTCG GACCCCCCAG GGACGCAGAG AGGACACGTC GGAGGCCTAA GTGGAAAAGA ATAATAAGCT

         .  Y  W  V   R  Q  A   P  G  K  G   L  E  W   V  S  S   I  S  P  F   G  W  G   T  Y  Y   A  D  S  V   K  G  R .
101      TGTATTGGGT CCGCCAGGCT CCAGGGAAGG GTCTAGAGTG GGTCTCATCG ATTTCGCCTT TTGGTTGGGG TACATACTAC GCAGACTCCG TGAAGGGCCG
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
           ACATAACCCA GGCGGTCCGA GGTCCCTTCC CAGATCTCAC CCAGAGTAGC TAAAGCGGAA AACCAACCCC ATGTATGATG CGTCTGAGGC ACTTCCCGGC

            .  F  T  I   S  R  D  N   S  K  D   T  L  Y   L  Q  M  N   S  L  R   A  E  D   T  A  V  Y   Y  C  A   K  Y  G
201        GTTCACCATC TCCCGCGACA ATTCCAAGGA CACGCTGTAT CTGCAAATGA ACAGCCTGCG TGCCGAGGAC ACCGCGGTAT ATTACTGTGC GAAATATGGG
           CAAGTGGTAG AGGGCGCTGT TAAGGTTCCT GTGCGACATA GACGTTTACT TGTCGGACGC ACGGCTCCTG TGGCGCCATA TAATGACACG CTTTATACCC

            E  T  S  G   P  I  S   E  N  F   D  Y  W  G   Q  G  T   L  V  T   V  S  S
301        GAGACGAGTG GTCCGATTTC TGAGAATTTT GACTACTGGG GTCAGGGAAC CCTGGTCACC GTCTCGAGC (SEQ ID NO: 110)
           CTCTGCTCAC CAGGCTAAAG ACTCTTAAAA CTGATGACCC CAGTCCCTTG GGACCAGTGG CAGAGCTCG (SEQ ID NO: 111)

DOM-14     SEQ ID NO: 16
            E  V  Q  L   L  E  S   G  G  G   L  V  Q   P  G  G  S   L  R  L   S  C  A  A   S  G  F   T  F  W   S  Y  D  M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTTGG TCTTATGATA
           CTCCACGTCG ACAACCTCAG ACCCCCTCCG AACCATGTCG GACCCCCCAG GGACGCAGAG AGGACACGTC GGAGGCCTAA GTGGAAAACC AGAATACTAT

            .  T  W  V   R  Q  A   P  G  K  G   L  E  W   V  S  S   I  M  A  S   G  D  D   T  Y  Y   A  D  S  V   K  G  R .
101        TGACGTGGGT CCGCCAGGCT CCAGGGAAGG GTCTAGAGTG GGTCTCATCT ATTATGGCTT CGGGTGATGA TACATACTAC GCAGACTCCG TGAAGGGCCG
           ACTGCACCCA GGCGGTCCGA GGTCCCTTCC CAGATCTCAC CCAGAGTAGA TAATACCGAA GCCCACTACT ATGTATGATG CGTGTGAGGC ACTTCCCGGC

            .  F  T  I   S  R  D  N   S  K  N   T  L  Y   L  Q  M  N   S  L  R   A  E  D   T  A  V  Y   Y  C  A   K  W  D
201        GTTCACCATC TCCCGCGACA ACTCCAAGAA CACGCTGTAT CTGCAAATGA ACAGCCTGCG TGCCGAGGAT ACCGCGGTAT ATTACTGTGC GAAATGGGAT
           CAAGTGGTAG AGGGCGCTGT TAAGGTTCTT GTGCGACATA GACGTTTACT TGTCGGACGC ACGGCTCCTA TGGCGCCATA TAATGACACG CTTTACCCTA

            R  D  F  D   Y  W  G   Q  G  T   L  V  T  V   S  S
301        CGGGATTTTG ACTACTGGGG TCAGGGAACC CTGGTCACCG TCTCGAGC (SEQ ID NO: 112)
           GCCCTAAAAC TGATGACCCC AGTCCCTTGG GACCAGTGGC AGAGCTCG (SEQ ID NO: 113)

DOM-15     SEQ ID NO: 17
            E  V  Q  L   L  E  S   G  G  G   L  V  Q  P   G  G  S   L  R  L   S  C  A  A  S   G  F   T  F  E   E  Y  V  M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTGAG GAGTATGTTA
           CTCCACGTCG ACAACCTCAG ACCCCCTCCG AACCATGTCG GACCCCCCAG GGACGCAGAG AGGACACGTC GGAGGCCTAA GTGGAAACTC CTCATACAAT

            .  S  W  V   R  Q  A   P  G  K  G   L  E  W   V  S  T   I  S  P  I   G  L  T   T  Y  Y   A  D  S  V   K  G  R .
101        TGTCGTGGGT CCGCCAGGCT CCAGGGAAGG GTCTGGAGTG GGTCTCAACT ATTTCTCCTA TTGGTCTGAC TACATACTAC GCAGACTCCG TGAAGGGCCG
           ACAGCACCCA GGCGGTCCGA GGTCCCTTCC CAGACCTCAC CCAGAGTTGA TAAAGAGGAT AACCAGACTG ATGTATGATG CGTCTGAGGC ACTTCCCGGC

            .  F  T  I   S  R  D  N   S  K  N   T  L  Y   L  Q  M  N   S  L  R  A  E  D   T  A  V  Y   Y  C  A   E  F  P
201        GTTCACCATC TCCCGCGACA ATTCCAAGAA CACGCTGTAT CTGCAAATGA ACAGCCTGCG TGCCGAGGAC ACCGCGGTAT ATTACTGTGC GGAATTTCCT
           CAAGTGGTAG AGGGCGCTGT TAAGGTTCTT GTGCGACATA GACGTTTACT TGTCGGACGC ACGGCTCCTG TGGCGCCATA TAATGACACG CCTTAAAGGA

            L  I  I  L   P  D  F   D  Y  W   G  Q  G  T   L  V  T   V  S  S
301        TTGATTATTC TTCCTGATTT TGACTACTGG GGTCAGGGAA CCCTGGTCAC CGTCTCGAGC (SEQ ID NO: 114)
           AACTAATAAG AAGGACTAAA ACTGATGACC CCAGTCCCTT GGGACCAGTG GCAGAGCTCG (SEQ ID NO: 115)

DOM-16     SEQ ID NO: 18
            E  V  Q  L   L  E  S   G  G  G   L  V  Q  P   G  G  S   L  R  L   S  C  A  A   S  G  F   T  F  M   E  Y  A  M .
  1        GAGGTGCAGC TGTTGGAGTC TGGGGGAGGC CTGGTACAGC CTGGGGGGTC CCTGCGTCTC TCCTGTGCAG CCTCCGGATT CACCTTTATG GAGTATGCGA
           CTCCACGTCG ACAACCTCAG ACCCCCTCCG GACCATGTCG GACCCCCCAG GGACGCAGAG AGGACACGTC GGAGGCCTAA GTGGAAATAC CTCATACGCT
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| | . I W V R Q A P G K G L E W V S I I S P L G L S T Y Y A D S V K G R . |
| 101 | TGATTTGGGT CCGCCAGGCT CCAGGGAAGG GTCTAGAGTG GGTCTCAATT ATCTCTCCGC TTGGTTTGTC TACATACTAC GCAGACTCCG TGAAGGGCCG |
| | ACTAAACCCA GGCGGTCCGA GGTCCCTTCC CAGATCTCAC CCAGAGTTAA TAAAGAGGCG AACCAAACAG ATGTATGATG CGTCTGAGGC ACTTCCCGGC |
| | . F T I S R D N S K N T L Y L Q M N S L R A E D T A V Y Y C A K Y Q |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAATATCAG |
| | CAAGTGGTAG AGGGCGCTGT TAAGGTTCTT GTGCGACATA GACGTTTACT TGTCGGACGC ACGGCTCCTG TGGCGCCATA TAATGACACG CTTTATAGTC |
| | D S S D S Q Y T N F D Y W G Q G T L V T V S S |
| 301 | GATTCGTCTG ATAGTCAGTA TACGAATTTT GACTACTGGG GTCAGGGAAC CCTGGTCACC GTCTCGAGC (SEQ ID NO: 116) |
| | CTAAGCAGAC TATCAGTCAT ATGCTTAAAA CTGATGACCC CAGTCCCTTG GGACCAGTGG CAGAGCTCG (SEQ ID NO: 117) |
| DOM-17 | SEQ ID NO: 19 |
| | E V Q L L E S G G G L V Q P G G S L R L S C A A S G F T F E D Y G M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGAG GATTATGGGA |
| | CTCCACGTCG ACAACCTCAG ACCCCCTCCG AACCATGTCG GACCCCCCAG GGACGCAGAG AGGACACGTC GGAGGCCTAA GTGGAAACTC CTAATACCCT |
| | . G W A R Q A P G K G L E W V S S I G P L G L W T Y Y A D S A K G R . |
| 101 | TGGGGTGGGC CCGCCAGGCT CCAGGGAAGG GTCTAGAGTG GGTCTCAAGT ATTGGTCCTC TGGGTCTTTG GACATACTAC GCAGACTCCG CGAAGGGCCG |
| | ACCCCACCCG GGCGGTCCGA GGTCCCTTCC CAGATCTCAC CCAGAGTTCA TAACCAGGAG ACCCAGAAAC CTGTATGATG CGTCTGAGGC GCTTCCCGGC |
| | . F T I S R D N S K N T L Y L Q M N S L R A E D T A V Y Y C A K S P |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAATCTCCG |
| | CAAGTGGTAG AGGGCGCTGT TAAGGTTCTT GTGCGACATA GACGTTTACT TGTCGGACGC ACGGCTCCTG TGGCGCCATA TAATGACACG CTTTAGAGGC |
| | L E G L I T N F D Y W G Q G T L V T V S S |
| 301 | CTTGAGGGTT TGATTACGAA TTTTGACTAC TGGGGTCAGG GAACCCTGGT CACCGTCTCG AGC (SEQ ID NO: 118) |
| | GAACTCCCAA ACTAATGCTT AAAACTGATG ACCCCAGTCC CTTGGGACCA GTGGCAGAGC TCG (SEQ ID NO: 119) |
| DOM-18 | SEQ ID NO: 20 |
| | E V Q L L E S G G G L V Q P G G S L R L S C A A S G F T F P E Y D M . |
| 1 | GAGGTGCAGC TGCTGGAGTC TGGGGGAGGC TTGGTACAGC CTGGGGGGTC CCTGCGTCTC TCCTGTGCAG CCTCCGGATT CACCTTTCCT GAGTATGATA |
| | CTCCACGTCG ACAACCTCAG ACCCCCTCCG AACCATGTCG GACCCCCCAG GGACGCAGAG AGGACACGTC GGAGGCCTAA GTGGAAAGGA CTCATACTAT |
| | . T W V R Q A P G K G L E W V S Y I S S D G Y S T Y Y A D S V K G R . |
| 101 | TGACGTGGGT CCGCCAGGCT CCAGGGAAGG GTCTGGAGTG GGTCTCATAT ATTAGTTCTG ATGGTTATTC TACATACTAC GCAGACTCCG TGAAGGGCCG |
| | ACTGCACCCA GGCGGTCCGA GGTCCCTTCC CAGACCTCAC CCAGAGTATA TAATCAAGAC TACCAATAAG ATGTATGATG CGTCTGAGGC ACTTCCCGGC |
| | . F T I S R D N S K N T L Y L Q M N S L R A E D T A V Y Y C A K P H |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGCAT |
| | CAAGTGGTAG AGGGCGCTGT TAAGGTTCTT GTGCGACATA GACGTTTACT TGTCGGACGC ACGGCTCCTG TGGCGCCATA TAATGACACG CTTTGGCGTA |
| | G S P R E F D Y W G Q G T L V T V S S |
| 301 | GGGAGTCCGC GGGAGTTTGA CTACTGGGGT CAGGGAACCC TGGTCACCGT CTCGAGC (SEQ ID NO: 120) |
| | CCCTCAGGCG CCCTCAAACT GATGACCCCA GTCCCTTGGG ACCAGTGGCA GAGCTCG (SEQ ID NO: 121) |
| DOM-19 | SEQ ID NO: 21 |

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
                 E V Q L  L E S  G G G  L V Q P  G G S  L R L  S C A A  S G F  P F P  Q Y Q M .
  1             GAGGTGCAGC TGTTGGAGTC TGGGGGAGGC TTGGTACAGC CTGGGGGGTC CCTGCGTCTC TCCTGTGCAG CCTCCGGATT CCCCTTTCCG CAGTATCAGA
                CTCCACGTCG ACAACCTCAG ACCCCCTCCG AACCATGTCG GACCCCCCAG GGACGCAGAG AGGACACGTC GGAGGCCTAA GGGGAAAGGC GTCATAGTCT

                . A W V  R Q A  P G K G  L E W  V S M  I T S D  G L D  T Y Y  A D S V  K G R .
101             TGGCGTGGGT CCGCCAGGCT CCAGGGAAGG GTCTAGAGTG GGTCTCAATG ATTACTTCTG ATGGTCTTGA TACATATTAC GCAGACTCCG TGAAGGGCCG
                ACCGCACCCA GGCGGTCCGA GGTCCCTTCC CAGATCTCAC CCAGAGTTAC TAATGAAGAC TACCAGAACT ATGTATAATG CGTCTGAGGC ACTTCCCGGC

                . F T I  S R D N  S K N  T L Y  L Q M N  S L R  A E D  T A V Y  Y C A  K P E
201             GTTCACCATC TCCCGCGACA ATTCCAAGAA CACGCTGTAT CTGCAAATGA ACAGCCTGCG TGCCGAGGAT ACCGCGGTAT ATTACTGTGC GAAACCTGAG
                CAAGTGGTAG AGGGCGCTGT TAAGGTTCTT GTGCGACATA GACGTTTACT TGTCGGACGC ACGGCTCCTA TGGCGCCATA TAATGACACG CTTTGGACTC

                 P L F D  Y W G  Q G T  L V T V  S S
301             CCTCTTTTTG ACTACTGGGG TCAGGGAACC CTGGTCACCG TCTCGAGC (SEQ ID NO: 122)
                GGAGAAAAAC TGATGACCCC AGTCCCTTGG GACCAGTGGC AGAGCTCG (SEQ ID NO: 123)

DOM-20          SEQ ID NO: 22
                 E V Q L  L E S  G G G  L V Q P  G G S  L R L  S C A A  S G F  T F S  G Y Q M .
  1             GAGGTGCAGC TGTTGGAGTC TGGGGGAGGC TTGGTACAGC CTGGGGGGTC CCTGCGTCTC TCCTGTGCAG CCTCCGGATT CACCTTTTCG GGTTATCAGA
                CTCCACGTCG ACAACCTCAG ACCCCCTCCG AACCATGTCG GACCCCCCAG GGACGCAGAG AGGACACGTC GGAGGCCTAA GTGGAAAAGC CCAATAGTCT

                . A W V  R Q A  P G K G  L E W  V S G  I S S E  G L T  T Y Y  A D S V  K G R .
101             TGGCTTGGGT CCGCCAGGCT CCAGGGAAGG GTCTAGAGTG GGTCTCAGGT ATTAGTTCGG AGGGTCTTAC TACATACTAC GCAGACTCCG TGAAGGGCCG
                ACCGAACCCA GGCGGTCCGA GGTCCCTTCC CAGATCTCAC CCAGAGTCCA TAATCAAGCC TCCCAGAATG ATGTATGATG CGTCTGAGGC ACTTCCCGGC

                . F T I  S R D N  S K N  T L Y  L Q M N  S L R  A E D  T A V Y  Y C A  K L G
201             GTTCACCATC TCCCGCGACA ATTCCAAGAA CACGCTGTAT CTGCAAATGA ACAGCCTGCG TGCCGAGGAC ACCGCGGTAT ATTACTGTGC GAAATTGGGG
                CAAGTGGTAG AGGGCGCTGT TAAGGTTCTT GTGCGACATA GACGTTTACT TGTCGGACGC ACGGCTCCTG TGGCGCCATA TAATGACACG CTTTAACCCC

                 R R F D  Y W G  Q G T  L V T V  S S
301             CGTAGGTTTG ACTACTGGGG TCAGGGAACC CTGGTCACCG TCTCGAGC (SEQ ID NO: 124)
                GCATCCAAAC TGATGACCCC AGTCCCTTGG GACCAGTGGC AGAGCTCG (SEQ ID NO: 125)

DOM-21          SEQ ID NO: 23
                 E V Q L  L E S  G G G  L V Q P  G G S  L R L  S C A A  S G F  T F A  N Y E M .
  1             GAGGTGCAGC TGTTGGAGTC TGGGGGAGGC TTGGTACAGC CTGGGGGGTC CCTGCGTCTC TCCTGTGCAG CCTCCGGATT CACCTTTGCG AATTATGAGA
                CTCCACGTCG ACAACCTCAG ACCCCCTCCG AACCATGTCG GACCCCCCAG GGACGCAGAG AGGACACGTC GGAGGCCTAA GTGGAAACGC TTAATACTCT

                . G W A  R Q A  P G K G  L E W  V S V  I S E W  G Y S  T Y Y  A D S A  K G R .
101             TGGGGTGGGC CCGCCAGGCT CCAGGGAAGG GTCTAGAGTG GGTCTCAGTT ATTTCTGAGT GGGGTTATTC TACATACTAC GCAGACTCCG CGAAGGGCCG
                ACCCCACCCG GGCGGTCCGA GGTCCCTTCC CAGATCTCAC CCAGAGTCAA TAAAGACTCA CCCCAATAAG ATGTATGATG CGTCTGAGGC GCTTCCCGGC

                . F T I  S R D N  S K N  T L Y  L Q M N  S L R  A E D  T A V Y  Y C A  K L V
201             GTTCACCATC TCCCGCGACA ATTCCAAGAA CACGCTGTAT CTGCAAATGA ACAGCCTGCG TGCCGAGGAC ACCGCGGTAT ATTACTGTGC GAAACTTGTG
                CAAGTGGTAG AGGGCGCTGT TAAGGTTCTT GTGCGACATA GACGTTTACT TGTCGGACGC ACGGCTCCTG TGGCGCCATA TAATGACACG CTTTGAACAC

                 G G T Q  Y E F  D Y W  G Q G T  L V T  V S S
301             GGTGGGACTC AGTATGAGTT TGACTACTGG GGTCAGGGAA CCCTGGTCAC CGTCTCGAGC (SEQ ID NO: 126)
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| | CCACCCTGAG TCATACTCAA ACTGATGACC CCAGTCCCTT GGGACCAGTG GCAGAGCTCG (SEQ ID NO: 127) |
| DOM-22 | SEQ ID NO: 24 |
| | E V Q L L E S G G G L V Q P G G S L R L S C A A S G F T F H N Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTCAT AATTATGAGA |
| | CTCCACGTCG ACAACCTCAG ACCCCCTCCG AACCATGTCG GACCCCCCAG GGACGCAGAG AGGACACGTC GGAGGCCTAA GTGGAAAGTA TTAATACTCT |
| | . S W V R Q A P G K G L E W V S S I S S G G S S T Y Y A D S V K G R . |
| 101 | TGTCGTGGGT CCGCCAGGCT CCAGGGAAGG GTCTAGAGTG GGTCTCAAGT ATTTCTTCGG GTGGTTCTTC TACATACTAC GCAGACTCCG TGAAGGGCCG |
| | ACAGCACCCA GGCGGTCCGA GGTCCCTTCC CAGATCTCAC CCAGAGTTCA TAAAGAAGCC CACCAAGAAG ATGTATGATG CGTCTGAGGC ACTTCCCGGC |
| | . F T I S R D N S K N T L Y L Q M N S L R A E D T A V Y Y C A K P G |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGGG |
| | CAAGTGGTAG AGGGCGCTGT TAAGGTTCTT GTGCGACATA GACGTTTACT TGTCGGACGC ACGGCTCCTG TGGCGCCATA TAATGACACG CTTTGGCCCC |
| | V K F D Y W G Q G T L V T V S S |
| 301 | GTTAAGTTTG ACTACTGGGG TCAGGGAACC CTGGTCACCG TCTCGAGC (SEQ ID NO: 128) |
| | CAATTCAAAC TGATGACCCC AGTCCCTTGG GACCAGTGGC AGAGCTCG (SEQ ID NO: 129) |
| DOM-23 | SEQ ID NO: 25 |
| | E V Q L L E S G G G L V Q P G G S L R L S C A A S G F T F G L Y E M . |
| 1 | GAGGTGCAGC TGTTGGAGTC CGGGGGAGGC TTGGTACAGC CTGGGGGGTC CCTGCGTCTC TCCTGTGCAG CCTCCGGATT CACCTTGGG CTGTATGAGA |
| | CTCCACGTCG ACAACCTCAG GCCCCCTCCG AACCATGTCG GACCCCCCAG GGACGCAGAG AGGACACGTC GGAGGCCTAA GTGGAAACCC GACATACTCT |
| | . T W V R Q A P G K G L E W V S S I T G D G I S T Y Y A D S V K G R . |
| 101 | TGACGTGGGT CCGCCAGGCT CCAGGGAAGG GTCTAGAGTG GGTCTCAAGT ATTACGGGTG ATGGTATTTC GACATACTAC GCAGACTCCG TGAAGGGCCG |
| | ACTGCACCCA GGCGGTCCGA GGTCCCTTCC CAGATCTCAC CCAGAGTTCA TAATGCCCAC TACCATAAAG CTGTATGATG CGTCTGAGGC ACTTCCCGGC |
| | . F T I S R D N S R N T L Y L Q M N S L R A E D T A V Y Y C A K A G |
| 201 | GTTCACCATC TCCCGCGACA ATTCCAGGAA CACGCTGTAT CTGCAAATGA ACAGCCTGCG TGCCGAGGAC ACCGCGGTAT ATTACTGTGC GAAAGCTGGG |
| | CAAGTGGTAG AGGGCGCTGT TAAGGTCCTT GTGCGACATA GACGTTTACT TGTCGGACGC ACGGCTCCTG TGGCGCCATA TAATGACACG CTTTCGACCC |
| | R K F D Y W G Q G T L V T V S S |
| 301 | AGGAAGTTTG ACTACTGGGG TCAGGGAACC CTGGTCACCG TCTCGAGC (SEQ ID NO: 130) |
| | TCCTTCAAAC TGATGACCCC AGTCCCTTGG GACCAGTGGC AGAGCTCG (SEQ ID NO: 131) |
| DOM-24 | SEQ ID NO: 26 |
| | E V Q L L E S G G G L V Q P G G S L R L S C A A S G F T F S N Y Q M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTAGT AATTATCAGA |
| | CTCCACGTCG ACAACCTCAG ACCCCCTCCG AACCATGTCG GACCCCCCAG GGACGCAGAG AGGACACGTC GGAGGCCTAA GTGGAAATCA TTAATAGTCT |
| | . A W V R Q A P G K G L E W V S S I T S E G G S T Y Y A D S V K G R . |
| 101 | TGGCGTGGGT CCGCCAGGCT CCAGGGAAGG GTCTAGAGTG GGTCTCAAGT ATTACTAGTG AGGGTGGTTC GACATACTAC GCAGACTCCG TGAAGGGCCG |
| | ACCGCACCCA GGCGGTCCGA GGTCCCTTCC CAGATCTCAC CCAGAGTTCA TAATGATCAC TCCCACCAAG CTGTATGATG CGTCTGAGGC ACTTCCCGGC |
| | . F T I S R D N S K N T L Y L Q M N S L R A E D T A V Y Y C A K P G |
| 201 | GTTCACCATC TCCCGCGACA ATTCCAAGAA CACACTGTAT CTGCAAATGA ACAGCCTGCG TGCCGAGGAC ACCGCGGTAT ATTACTGTGC GAAACCGGGT |
| | CAAGTGGTAG AGGGCGCTGT TAAGGTTCTT GTGTGACATA GACGTTTACT TGTCGGACGC ACGGCTCCTG TGGCGCCATA TAATGACACG CTTTGGCCCA |

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
            K  N  F  D   Y  W  G   Q  G  T   L  V  T  V   S  S
301        AAGAATTTTG ACTACTGGGG TCAGGGAACC CTGGTCACCG TCTCGAGC (SEQ ID NO: 132)
           TTCTTAAAAC TGATGACCCC AGTCCCTTGG GACCAGTGGC AGAGCTCG (SEQ ID NO: 133)

DOM-25     SEQ ID NO: 27
            E  V  Q  L   L  E  S   G  G  G   L  V  Q  P   G  G  S   L  R  L   S  C  A  A   S  G  F   T  F  D   N  Y  E  M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTGAT AATTATGAGA
           CTCCACGTCG ACAACCTCAG ACCCCCTCCG AACCATGTCG GACCCCCCAG GGACGCAGAG AGGACACGTC GGAGGCCTAA GTGGAAACTA TTAATACTCT

           .  T  W  V   R  Q  A   P  G  K  G   L  E  W   V  S  T   I  T  S  Q   G  T  S   T  Y  Y   A  D  S  V   K  G  R .
101        TGACGTGGGT CCGCCAGGCT CCAGGGAAGG GTCTAGAGTG GGTCTCAACT ATTACGTCGC AGGGTACTAG TACATACTAC GCAGACTCCG TGAAGGGCCG
           ACTGCACCCA GGCGGTCCGA GGTCCCTTCC CAGATCTCAC CCAGAGTTGA TAATGCAGCG TCCCATGATC ATGTATGATG CGTCTGAGGC ACTTCCCGGC

           .  F  T  I   S  R  D  N   S  K  N   T  L  Y   L  Q  M  N   S  L  R   A  E  D   T  A  V  Y   Y  C  A   K  P  D
201        GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGAT
           CAAGTGGTAG AGGGCGCTGT TAAGGTTCTT GTGCGACATA GACGTTTACT TGTCGGACGC ACGGCTCCTG TGGCGCCATA TAATGACACG CTTTGGACTA

            R  S  F  D   Y  W  G   Q  G  T   L  V  T  V   S  S
301        CGTTCTTTTG ACTACTGGGG TCAGGGAACC CTGGTCACCG TCTCGAGC (SEQ ID NO: 134)
           GCAAGAAAAC TGATGACCCC AGTCCCTTGG GACCAGTGGC AGAGCTCG (SEQ ID NO: 135)

DOM-26     SEQ ID NO: 28
            E  V  Q  L   L  E  S   G  G  G   L  V  Q  P   G  G  S   L  R  L   S  C  A  A   S  G  F   T  F  R   S  Y  E  M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTCGT AGTTATGAGA
           CTCCACGTCG ACAACCTCAG ACCCCCTCCG AACCATGTCG GACCCCCCAG GGACGCAGAG AGGACACGTC GGAGGCCTAA GTGGAAAGCA TCAATACTCT

           .  T  W  V   R  Q  A   P  G  K  G   L  E  W   V  S  S   I  T  S  D   G  G  T   T  Y  Y   A  D  S  V   K  G  R .
101        TGACTTGGGT CCGCCAGGCT CCAGGGAAGG GTCTGGAGTG GGTCTCATCT ATTACGTCGG ATGGTGGTAC TACATACTAC GCAGACTCCG TGAAGGGCCG
           ACTGAACCCA GGCGGTCCGA GGTCCCTTCC CAGACCTCAC CCAGAGTAGA TAATGCAGCC TACCACCATG ATGTATGATG CGTCTGAGGC ACTTCCCGGC

           .  F  T  I   S  R  D  N   S  K  N   T  L  Y   L  Q  M  N   S  L  R   A  E  D   T  A  V  Y   Y  C  A   K  P  D
201        GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGAT
           CAAGTGGTAG AGGGCGCTGT TAAGGTTCTT GTGCGACATA GACGTTTACT TGTCGGACGC ACGGCTCCTG TGGCGCCATA TAATGACACG CTTTGGACTA

            K  T  F  D   Y  W  G   Q  G  T   L  V  T  V   S  S
301        AAGACGTTTG ACTACTGGGG TCAGGGAACC CTGGTCACCG TCTCGAGC (SEQ ID NO: 136)
           TTCTGCAAAC TGATGACCCC AGTCCCTTGG GACCAGTGGC AGAGCTCG (SEQ ID NO: 137)

DOM-27     SEQ ID NO: 29
            E  V  Q  L   L  E  S   G  G  G   L  V  Q  P   G  G  S   L  R  L   S  C  A  A   S  G  F   T  F  N   L  Y  E  M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTAAT TTGTATGAGA
           CTCCACGTCG ACAACCTCAG ACCCCCTCCG AACCATGTCG GACCCCCCAG GGACGCAGAG AGGACACGTC GGAGGCCTAA GTGGAAATTA AACATACTCT

           .  T  W  V   R  Q  A   P  G  K  G   L  E  W   V  S  S   I  T  S  D   G  V  S   T  Y  Y   A  D  S  V   K  G  R .
101        TGACTTGGGT CCGCCAGGCT CCAGGGAAGG GTCTAGAGTG GGTCTCATCT ATTACTAGTG ATGGTGTTTC TACATACTAC GCAGACTCCG TGAAGGGCCG
           ACTGAACCCA GGCGGTCCGA GGTCCCTTCC CAGATCTCAC CCAGAGTAGA TAATGATCAC TACCACAAAG ATGTATGATG CGTCTGAGGC ACTTCCCGGC
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
              .  F  T  I   S  R  D  N   S  K  N   T  L  Y   L  Q  M  N   S  L  R   A  E  D   T  A  V  Y   Y  C  A   K  P  D
201           GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGAT
              CAAGTGGTAG AGGGCGCTGT TAAGGTTCTT GTGCGACATA GACGTTTACT TGTCGGACGC ACGGCTCCTG TGGCGCCATA TAATGACACG CTTTGGCCTA

               S  P  F  D   Y  W  G   Q  G  T   L  V  T  V   S  S
301           TCTCCGTTTG ACTACTGGGG TCAGGGAACC CTGGTCACCG TCTCGAGC (SEQ ID NO: 138)
              AGAGGCAAAC TGATGACCCC AGTCCCTTGG GACCAGTGGC AGAGCTCG (SEQ ID NO: 139)

DOM-28        SEQ ID NO: 30
               E  V  Q  L   L  E  S   G  G  G   L  V  Q  P   G  G  S   L  R  L   S  C  A  A   S  G  F   T  F  G   H  Y  D  M .
  1           GAGGTGCAGC TGTTGGAGTC TGGGGTAGGC TTGGTACAGC CTGGGGGGTC CCTGCGTCTC TCCTGTGCAG CCTCCGGATT CACCTTTGGG CATTATGATA
              CTCCACGTCG ACAACCTCAG ACCCCCTCCG AACCATGTCG GACCCCCCAG GGACGCAGAG AGGACACGTC GGAGGCCTAA GTGGAAACCC GTAATACTAT

              .  A  W  V   R  Q  A   P  G  K  G   L  E  W   V  S  T   I  S  D  N   G  N  G   T  Y  Y   A  D  S  V   K  G  R .
101           TGGCTTGGGT CCGCCAGGCT CCAGGGAAGG GTCTAGAGTG GGTCTCAACT ATTAGTGATA ATGGTAATGG GACATACTAC GCAGACTCCG TGAAGGGCCG
              ACCGAACCCA GGCGGTCCGA GGTCCCTTCC CAGATCTCAC CCAGAGTTGA TAATCACTAT TACCATTACC CTGTATGATG CGTCTGAGGC ACTTCCCGGC

              .  F  T  I   S  R  D  N   S  K  N   T  L  Y   L  Q  M  N   S  L  R   A  E  D   T  A  V  Y   Y  C  A   K  P  G
201           GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGGG
              CAAGTGGTAG AGGGCGCTGT TAAGGTTCTT GTGCGACATA GACGTTTACT TGTCGGACGC ACGGCTCCTG TGGCGCCATA TAATGACACG CTTTGGCCCC

               R  D  F  D   Y  W  G   Q  G  T   L  V  T  V   S  S
301           CGTGATTTTG ACTACTGGGG TCAGGGAACC CTGGTCACCG TCTCGAGC (SEQ ID NO: 140)
              GCACTAAAAC TGATGACCCC AGTCCCTTGG GACCAGTGGC AGAGCTCG (SEQ ID NO: 141)

DOM-29        SEQ ID NO: 31
               E  V  Q  L   L  E  S   G  G  G   L  V  Q  P   G  G  S   L  R  L   S  C  A  A   S  G  F   T  F  G   R  Y  Q  M .
  1           GAGGTGCAGC TGTTGGAGTC TGGGGGAGGC TTGGTACAGC CTGGGGGGTC CCTGCGTCTC TCCTGTGCAG CCTCCGGATT CACCTTTGGT CGTTATCAGA
              CTCCACGTCG ACAACCTCAG ACCCCCTCCG AACCATGTCG GACCCCCCAG GGACGCAGAG AGGACACGTC GGAGGCCTAA GTGGAAACCA GCAATAGTCT

              .  A  W  V   R  Q  A   P  G  K  G   L  E  W   V  S  S   I  S  S  D   G  G  G   T  Y  Y   A  D  S  V   K  G  R .
101           TGGCTTGGGT CCGCCAGGCT CCAGGGAAGG GTCTAGAGTG GGTCTCATCT ATTTCTTCTG ATGGTGGGGG GACATACTAC GCAGACTCCG TGAAGGGCCG
              ACCGAACCCA GGCGGTCCGA GGTCCCTTCC CAGATCTCAC CCAGAGTAGA TAAAGAAGAC TACCACCCCC CTGTATGATG CGTCTGAGGC ACTTCCCGGC

              .  F  T  I   S  R  D  N   S  K  N   T  L  Y   L  Q  M  N   S  L  R   A  E  D   T  A  V  Y   Y  C  A   K  P  G
201           GTTCACCATC TCCCGCGACA ATTCCAAGAA CACGCTGTAT CTGCAAATGA ACAGCCTGCG TGCCGAGGAT ACCGCGGTAT ATTACTGTGC GAAACCTGGG
              CAAGTGGTAG AGGGCGCTGT TAAGGTTCTT GTGCGACATA GACGTTTACT TGTCGGACGC ACGGCTCCTA TGGCGCCATA TAATGACACG CTTTGGACCC

               R  A  F  D   Y  W  G   Q  G  T   L  V  T  V   S  S
301           CGGGCGTTTG ACTACTGGGG TCAGGGAACC CTGGTCACCG TCTCGAGC (SEQ ID NO: 142)
              GCCCGCAAAC TGATGACCCC AGTCCCTTGG GACCAGTGGC AGAGCTCG (SEQ ID NO: 143)

DOM-30        SEQ ID NO: 32
               E  V  Q  L   L  E  S   G  G  G   L  V  Q  P   G  G  S   L  R  L   S  C  A  A   S  G  F   T  F  A   R  Y  Q  M .
  1           GAGGTGCAGC TGTTGGAGTC TGGGGGAGGC TTGGTACAGC CTGGGGGGTC CCTGCGTCTC TCCTGTGCAG CCTCCGGATT CACCTTTGCG AGGTATCAGA
              CTCCACGTCG ACAACCTCAG ACCCCCTCCG AACCATGTCG GACCCCCCAG GGACGCAGAG AGGACACGTC GGAGGCCTAA GTGGAAACGC TCCATAGTCT

              .  A  W  V   R  Q  A   P  G  K  G   L  E  W   V  S  T   I  S  D  D   G  D  S   T  Y  Y   A  D  S  V   K  G  R .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
101     TGGCTTGGGT CCGCCAGGCT CCAGGGAAGG GTCTGGAGTG GGTCTCAACT ATTTCTGATG ATGGTGATTC GACATACTAC GCAGACTCCG TGAAGGGCCG
        ACCGAACCCA GGCGGTCCGA GGTCCCTTCC CAGACCTCAC CCAGAGTTGA TAAAGACTAC TACCACTAAG CTGTATGATG CGTCTGAGGC ACTTCCCGGC

         .  F  T  I   S  R  D N   S  K  N   T  L  Y   L  Q  M  N   S  L  R   A  E  D   T  A  V  Y   Y  C  A   K  L  D
201     GTTCACCATC TCCCGCGACA ATTCCAAGAA CACGCTGTAT CTGCAAATGA ACAGCCTGCG TGCCGAGGAC ACCGCGGTAT ATTACTGTGC GAAACTGGAT
        CAAGTGGTAG AGGGCGCTGT TAAGGTTCTT GTGCGACATA GACGTTTACT TGTCGGACGC ACGGCTCCTG TGGCGCCATA TAATGACACG CTTTGACCTA

         K  L  F  D   Y  W  G   Q  G  T   L  V  T  V   S  S
301     AAGTTGTTTG ACTACTGGGG TCAGGGAACC CTGGTCACCG TCTCGAGC (SEQ ID NO: 144)
        TTCAACAAAC TGATGACCCC AGTCCCTTGG GACCAGTGGC AGAGCTCG (SEQ ID NO: 145)

DOM-31  SEQ ID NO: 33
         E  V  Q  L   L  E  S   G  G  G   L  V  Q  P   G  G  S   L  R  L   S  C  A  A   S  G  F   T  F  E   E  Y  Q  M .
1       GAGGTGCAGC TGTTGGAGTC TGGGGGAGGC TTGGTACAGC CTGGGGGGTC CCTGCGTCTC TCCTGTGCAG CCTCCGGATT CACCTTTGAG GAGTATCAGA
        CTCCACGTCG ACAACCTCAG ACCCCCTCCG AACCATGTCG GACCCCCCAG GGACGCAGAG AGGACACGTC GGAGGCCTAA GTGGAAACTC CTCATAGTCT

         .  A  W  V   R  Q  A   P  G  K  G   L  E  W   V  S  T   I  S  D  D   G  S  S   T  Y  Y   A  D  S  V   K  G  R .
101     TGGCGTGGGT CCGCCAGGCT CCAGGGAAGG GTCTAGAGTG GGTCTCAACG ATTTCGGATG ATGGTTCTTC GACATACTAC GCAGACTCCG TGAAGGGCCG
        ACCGCACCCA GGCGGTCCGA GGTCCCTTCC CAGATCTCAC CCAGAGTTGC TAAAGCCTAC TACCAAGAAG CTGTATGATG CGTCTGAGGC ACTTCCCGGC

         .  F  T  I   S  R  D  N   S  K  N   T  L  Y   L  Q  M  N   S  L  R   A  E  D   T  A  V  Y   Y  C  A   K  P  D
201     GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGAT
        CAAGTGGTAG AGGGCGCTGT TAAGGTTCTT GTGCGACATA GACGTTTACT TGTCGGACGC ACGGCTCCTG TGGCGCCATA TAATGACACG CTTTGGACTA

         L  Y  F  D   Y  W  G   Q  G  T   L  V  T  V   S  S
301     CTTTATTTTG ACTACTGGGG TCAGGGAACC CTGGTCACCG TCTCGAGC (SEQ ID NO: 146)
        GAAATAAAAC TGATGACCCC AGTCCCTTGG GACCAGTGGC AGAGCTCG (SEQ ID NO: 147)

DOM-32  SEQ ID NO: 34
         E  V  Q  L   L  E  S   G  G  G   L  V  Q  P   G  G  S   L  R  L   S  C  A  A   S  G  F   T  F  E   V  Y  Q  M .
1       GAGGTGCAGC TGTTGGAGTC TGGGGGAGGC TTGGTACAGC CTGGGGGGTC CCTGCGTCTC TCCTGTGCAG CCTCCGGATT CACCTTTGAG GTGTATCAGA
        CTCCACGTCG ACAACCTCAG ACCCCCTCCG AACCATGTCG GACCCCCCAG GGACGCAGAG AGGACACGTC GGAGGCCTAA GTGGAAACTC CACATAGTCT

         .  G  W  V   R  Q  A   P  G  K  G   L  E  W   V  S  F   I  V  P  G   G  D  L   T  Y  Y   A  D  S  V   K  G  R .
101     TGGGTTGGGT CCGCCAGGCT CCAGGGAAGG GTCTAGAGTG GGTCTCATTT ATTGTGCCTG GGGGTGATTT GACATACTAC GCAGACTCCG TGAAGGGCCG
        ACCCAACCCA GGCGGTCCGA GGTCCCTTCC CAGATCTCAC CCAGAGTAAA TAACACGGAC CCCCACTAAA CTGTATGATG CGTCTGAGGC ACTTCCCGGC

         .  F  T  I   S  R  D  N   S  K  N   T  L  Y   L  Q  M  N   S  L  R   A  E  D   T  A  V  Y   Y  C  A   E  T  W
201     GTTCACCATC TCCCGCGACA ATTCCAAGAA CACGCTGTAT CTGCAAATGA ACAGCCTGCG TGCCGAGGAC ACCGCGGTAT ATTACTGTGC CGAAACGTGG
        CAAGTGGTAG AGGGCGCTGT TAAGGTTCTT GTGCGACATA GACGTTTACT TGTCGGACGC ACGGCTCCTG TGGCGCCATA TAATGACACG CCTTTGCACC

         P  E  F  D   Y  W  G   Q  G  T   L  V  T  V   S  S
301     CCGGAGTTTG ACTACTGGGG TCAGGGAACC CTGGTCACCG TCTCGAGC (SEQ ID NO: 148)
        GGCCTCAAAC TGATGACCCC AGTCCCTTGG GACCAGTGGC AGAGCTCG (SEQ ID NO: 149)

DOM-33  SEQ ID NO: 35
         D  I  Q  M   T  Q  S   P  S  S   L  S  A  S   V  G  D   R  V  T   I  T  C  R   A  S  Q   T  I  G   E  S  L  H .
1       GACATCCAGA TGACCCAGTC TCCATCCTCC CTGTCTGCAT CTGTAGGAGA CCGTGTCACC ATCACTTGCC GGGCAAGTCA GACGATTGGG GAGAGTTTAC
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
            CTGTAGGTCT ACTGGGTCAG AGGTAGGAGG GACAGACGTA GACATCCTCT GGCACAGTGG TAGTGAACGG CCCGTTCAGT CTGCTAACCC CTCTCAAATG

            . W Y Q  Q K P  G K A P  R L L  I Y F  A S L L  Q S G  V P S  R F S G  S G S .
101         ATTGGTACCA GCAGAAACCA GGGAAAGCCC CTAGGCTCCT GATCTATTTT GCTTCCCTGT TGCAAAGTGG GGTCCCATCG CGTTTCAGTG GCAGTGGATC
            TAACCATGGT CGTCTTTGGT CCCTTTCGGG GATCCGAGGA CTAGATAAAA CGAAGGGACA ACGTTTCACC CCAGGGTAGC GCAAAGTCAC CGTCACCTAG

            . G T D  F T L T  I S S  L Q P  E D F A  T Y Y  C Q Q  H H M L  P S T  F G Q
201         TGGGACAGAT TTTACTCTCA CCATCAGCAG TCTGCAACCT GAAGATTTTG CTACGTACTA CTGTCAACAG CATCATATGC TTCCTTCTAC GTTCGGCCAA
            ACCCTGTCTA AAATGAGAGT GGTAGTCGTC AGACGTTGGA CTTCTAAAAC GATGCATGAT GACAGTTGTC GTAGTATACG AAGGAAGATG CAAGCCGGTT

             G T K V  E I K  R
301         GGGACCAAGG TGGAAATCAA ACGG (SEQ ID NO: 150)
            CCCTGGTTCC ACCTTTAGTT TGCC (SEQ ID NO: 151)

DOM-34      SEQ ID NO: 36
             D I Q M  T Q S  P S S  L S A S  V G D  R V T  I T C R  A S Q  W I G  D S L S .
  1         GACATCCAGA TGACCCAGTC TCCATCCTCC CTGTCTGCAT CTGTAGGAGA CCGTGTCACC ATCACTTGCC GGGCAAGTCA GTGGATTGGT GATAGTTTAT
            CTGTAGGTCT ACTGGGTCAG AGGTAGGAGG GACAGACGTA GACATCCTCT GGCACAGTGG TAGTGAACGG CCCGTTCAGT CACCTAACCA CTATCAAATA

            . W Y Q  Q K P  G K A P  K L L  I Y F  A S Y L  Q S G  V P T  R F S G  S G S .
101         CTTGGTACCA GCAGAAACCA GGGAAAGCCC CTAAGCTCCT GATCTATTTT GCTTCCTATT TGCAAAGTGG GGTCCCAACA CGTTTCAGTG GCAGTGGATC
            GAACCATGGT CGTCTTTGGT CCCTTTCGGG GATTCGAGGA CTAGATAAAA CGAAGGATAA ACGTTCACC CCAGGGTTGT GCAAAGTCAC CGTCACCTAG

            . G T D  F T L T  I S S  L Q P  E D F A  T Y Y  C Q Q  Y F E N  P V T  F G Q
201         TGGGACAGAT TTCACTCTCA CCATCAGCAG TCTGCAACCT GAAGATTTTG CTACGTACTA CTGTCAACAG TATTTTGAGA ATCCTGTTAC GTTCGGCCAA
            ACCCTGTCTA AAGTGAGAGT GGTAGTCGTC AGACGTTGGA CTTCTAAAAC GATGCATGAT GACAGTTGTC ATAAAACTCT TAGGACAATG CAAGCCGGTT

             G T K V  G I K  R
301         GGGACCAAGG TGGGAATCAA ACGG (SEQ ID NO: 152)
            CCCTGGTTCC ACCCTTAGTT TGCC (SEQ ID NO: 153)

DOM-35      SEQ ID NO: 37
             D I Q M  T Q S  P S S  L S A S  V G D  R V T  I T C R  A S Q  F I G  D S L S .
  1         GACATCCAAA TGACCCAGTC TCCATCCTCC CTGTCTGCAT CTGTAGGAGA CCGTGTCACC ATCACTTGCC GGGCAAGTCA GTTTATTGGT GATTCTTTAT
            CTGTAGGTTT ACTGGGTCAG AGGTAGGAGG GACAGACGTA GACATCCTCT GGCACAGTGG TAGTGAACGG CCCGTTCAGT CAAATAACCA CTAAGAAATA

            . W Y Q  Q K P  G K A P  K L L  I Y F  S S I L  Q S G  V P S  R F S G  S G S .
101         CTTGGTACCA GCAGAAACCA GGGAAAGCCC CTAAGCTCCT GATCTATTTT TCTTCCATTT TGCAAAGTGG GGTCCCATCA CGTTTCAGTG GCAGTGGATC
            GAACCATGGT CGTCTTTGGT CCCTTTCGGG GATTCGAGGA CTAGATAAAA AGAAGGTAAA ACGTTTCACC CCAGGGTAGT GCAAAGTCAC CGTCACCTAG

            . G T D  F T L T  I S S  L Q P  E D F A  T Y Y  C Q Q  Y M D I  P I T  F G Q
201         TGGGACAGAT TTCACTCTCA CCATCAGCAG TCTGCAACCT GAAGATTTTG CTACGTACTA CTGTCAACAG TATATGGATA TTCCTATTAC GTTCGGCCAA
            ACCCTGTCTA AAGTGAGAGT GGTAGTCGTC AGACGTTGGA CTTCTAAAAC GATGCATGAT GACAGTTGTC ATATACCTAT AAGGATAATG CAAGCCGGTT

             G T K V  E I K  R
301         GGGACCAAGG TGGAAATCAA ACGG (SEQ ID NO: 154)
            CCCTGGTTCC ACCTTTAGTT TGCC (SEQ ID NO: 155)
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
DOM-36   SEQ ID NO: 38
          D  I  Q  M   T  Q  S   P  S  S   L  S  A  S   V  G  D   R  V  T   I  T  C  R   A  S  Q   D  I  D   H  N  L  E .
  1      GACATCCAGA TGACCCAGTC TCCATCCTCC CTGTCTGCAT CTGTAGGAGA CCGTGTCACC ATCACTTGCC GGGCAAGTCA GGATATTGAT CATAATTTAG
         CTGTAGGTCT ACTGGGTCAG AGGTAGGAGG GACAGACGTA GACATCCTCT GGCACAGTGG TAGTGAACGG CCCGTTCAGT CCTATAACTA GTATTAAATC

         . W  Y  Q   Q  K  P   G  K  A  P   K  L  L   I  Y  D   S  S  M  L   Q  S  G   V  P  S   R  F  S  G   S  G  S .
101      AGTGGTATCA GCAGAAACCA GGGAAAGCCC CTAAGCTCCT GATCTATGAT AGTTCCATGT TGCAAAGTGG GGTCCCATCA CGTTTCAGTG GCAGTGGATC
         TCACCATAGT CGTCTTTGGT CCCTTTCGGG GATTCGAGGA CTAGATACTA TCAAGGTACA ACGTTTCACC CCAGGGTAGT GCAAAGTCAC CGTCACCTAG

         . G  T  D   F  T  L  T   I  S  S   L  Q  P   E  D  F  A   T  Y  Y   C  Q  Q   Y  H  S  I   P  V  T   F  G  Q
201      TGGGACAGAT TTCACTCTCA CCATCAGCAG TCTGCAACCT GAAGATTTTG CTACGTACTA CTGTCAACAG TATCATTCTA TTCCTGTTAC GTTCGGCCAA
         ACCCTGTCTA AAGTGAGAGT GGTAGTCGTC AGACGTTGGA CTTCTAAAAC GATGCATGAT GACAGTTGTC ATAGTAAGAT AAGGACAATG CAAGCCGGTT

          G  T  K  V   E  I  K   R
301      GGGACCAAGG TGGAAATCAA ACGG (SEQ ID NO: 156)
         CCCTGGTTCC ACCTTTAGTT TGCC (SEQ ID NO: 157)

DOM-37   SEQ ID NO: 39
          D  I  Q  M   T  Q  S   P  S  S   L  S  A  S   V  G  D   R  V  T   I  T  C  R   A  S  Q   Q  I  E   T  N  L  E .
  1      GACATCCAGA TGACCCAGTC TCCATCCTCC CTGTCTGCAT CTGTAGGAGA CCGTGTCACC ATCACTTGCC GGGCAAGTCA GCAGATTGAG ACGAATTTAG
         CTGTAGGTCT ACTGGGTCAG AGGTAGGAGG GACAGACGTA GACATCCTCT GGCACAGTGG TAGTGAACGG CCCGTTCAGT CGTCTAACTC TGCTTAAATC

         . W  Y  Q   Q  K  P   G  K  A  P   K  L  L   I  Y  D   G  S  W  L   Q  S  G   V  P  S   R  F  S  G   S  G  S .
101      AGTGGTATCA GCAGAAACCA GGGAAAGCCC CTAAGCTCCT GATCTATGAT GGTTCCTGGT TGCAAAGTGG GGTCCCATCA CGTTTCAGTG GCAGTGGATC
         TCACCATAGT CGTCTTTGGT CCCTTTCGGG GATTCGAGGA CTAGATACTA CCAAGGACCA ACGTTTCACC CCAGGGTAGT GCAAAGTCAC CGTCACCTAG

         . G  T  D   F  T  L  T   I  S  S   L  Q  P   E  D  F  A   T  Y  Y   C  Q  Q   Y  H  S  L   P  A  T   F  G  Q
201      TGGGACAGAT TTCACTCTCA CCATCAGCAG TCTGCAACCT GAAGATTTTG CTACGTACTA CTGTCAACAG TATCATAGTT TGCCTGCTAC GTTCGGCCAA
         ACCCTGTCTA AAGTGAGAGT GGTAGTCGTC AGACGTTGGA CTTCTAAAAC GATGCATGAT GACAGTTGTC ATAGTATCAA ACGGACGATG CAAGCCGGTT

          G  T  K  V   E  I  K   R
301      GGGACCAAGG TGGAAATCAA ACGG (SEQ ID NO: 158)
         CCCTGGTTCC ACCTTTAGTT TGCC (SEQ ID NO: 159)

DOM-38   SEQ ID NO: 40
          D  I  Q  M   T  Q  S   P  S  S   L  S  A  S   V  G  D   R  V  T   I  T  C  R   A  S  Q   D  I  G   N  N  L  E .
  1      GACATCCAGA TGACCCAGTC TCCATCCTCC CTGTCTGCAT CTGTAGGAGA CCGTGTCACC ATCACTTGCC GGGCAAGTCA GGATATTGGT AATAATTTAG
         CTGTAGGTCT ACTGGGTCAG AGGTAGGAGG GACAGACGTA GACATCCTCT GGCACAGTGG TAGTGAACGG CCCGTTCAGT CCTATAACCA TTATTAAATC

         . W  Y  Q   Q  K  P   G  K  A  P   R  L  L   I  Y  H   G  S  W  L   Q  S  G   V  P  S   R  F  S  G   S  G  S .
101      AGTGGTACCA GCAGAAACCA GGGAAAGCCC CTAGGCTCCT GATCTATCAT GGGTCCTGGT TGCAAAGTGG GGTCCCATCG CGTTTCAGTG GCAGTGGATC
         TCACCATGGT CGTCTTTGGT CCCTTTCGGG GATCCGAGGA CTAGATAGTA CCCAGGACCA ACGTTTCACC CCAGGGTAGC GCAAAGTCAC CGTCACCTAG

         . G  T  D   F  T  L   T  I  S  S   L  Q  P   E  D  F  A   T  Y  Y   C  Q  Q   Y  D  F  N   P  T  T   F  G  Q
201      TGGGACAGAT TTCACTCTTA CCATCAGCAG TCTGCAACCT GAAGATTTTG CTACGTACTA CTGTCAACAG TATGATTTTA ATCCTACTAC GTTCGGCCAA
         ACCCTGTCTA AAGTGAGAAT GGTAGTCGTC AGACGTTGGA CTTCTAAAAC GATGCATGAT GACAGTTGTC ATACTAAAAT TAGGATGATG CAAGCCGGTT

          G  T  K  V   E  I  K   R
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| 301 | GGGACCAAGG TGGAAATCAA ACGG (SEQ ID NO: 160) |
| | CCCTGGTTCC ACCTTTAGTT TGCC (SEQ ID NO: 161) |
| DOM 39 | SEQ ID NO: 41 |
| | D I Q M T Q S P S S L S A S V G D C V T I T C R A S Q N I D G L L W . |
| 1 | GACATCCAGA TGACCCAGTC TCCATCCTCC CTGTCTGCAT CTGTAGGAGA CTGTGTCACC ATCACTTGCC GGGCAAGTCA GAATATTGAT GGTCTGTTAT |
| | CTGTAGGTCT ACTGGGTCAG AGGTAGGAGG GACAGACGTA GACATCCTCT GACACAGTGG TAGTGAACGG CCCGTTCAGT CTTATAACTA CCAGACAATA |
| | . W Y Q Q K P G K A P K L L I Y A G S G L Q S G V P S R F S G S G S . |
| 101 | GGTGGTATCA GCAGAAACCA GGGAAAGCCC CTAAGCTCCT GATCTATGCG GGGTCCGGGT TGCAAAGTGG GGTCCCATCA CGTTTCAGTG GCAGTGGATC |
| | CCACCATAGT CGTCTTTGGT CCCTTTCGGG GATTCGAGGA CTAGATACGC CCCAGGCCCA ACGTTTCACC CCAGGGTAGT GCAAAGTCAC CGTCACCTAG |
| | . G T D F T L T I S S L Q P E D F A T Y Y C Q Q K A F E P F T F G Q |
| 201 | TGGGACAGAT TTCACTCTCA CCATCAGCAG TCTGCAACCT GAAGATTTTG CTACGTACTA CTGTCAACAG AAGGCTTTTG AGCCTTTTAC GTTCGGCCAA |
| | ACCCTGTCTA AAGTGAGAGT GGTAGTCGTC AGACGTTGGA CTTCTAAAAC GATGCATGAT GACAGTTGTC TTCCGAAAAC TCGGAAAATG CAAGCCGGTT |
| | G T K V E I K R |
| 301 | GGGACCAAGG TGGAAATCAA ACGG (SEQ ID NO: 162) |
| | CCCTGGTTCC ACCTTTAGTT TGCC (SEQ ID NO: 163) |
| DOM-40 | SEQ ID NO: 42 |
| | E V Q L L E S G G G L V Q P G G S L R L S C A A S G F T F K A Y D M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTAAG GCGTATGATA |
| | CTCCACGTCG ACAACCTCAG ACCCCCTCCG AACCATGTCG GACCCCCCAG GGACGCAGAG AGGACACGTC GGAGGCCTAA GTGGAAATTC CGCATACTAT |
| | . G W V R Q A P G K G L E W V S Q I G R D G S F T Y Y A D S V K G R . |
| 101 | TGGGTTGGGT CCGCCAGGCT CCAGGGAAGG GTCTAGAGTG GGTCTCACAG ATTGGGAGGG ATGGTTCTTT TACATACTAC GCAGACTCCG TGAAGGGCCG |
| | ACCCAACCCA GGCGGTCCGA GGTCCCTTCC CAGATCTCAC CCAGAGTGTC TAACCCTCCC TACCAAGAAA ATGTATGATG CGTCTGAGGC ACTTCCCGGC |
| | . F T I S R D N S K N T L Y L Q M N S L R A E D T A V Y Y C A K P R |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTCGT |
| | CAAGTGGTAG AGGGCGCTGT TAAGGTTCTT GTGCGACATA GACGTTTACT TGTCGGACGC ACGGCTCCTG TGGCGCCATA TAATGACACG CTTTGGAGCA |
| | R Y A I F T F D R G Q G T L V T V S S |
| 301 | CGGTATGCTA TTTTTACTTT TGATCGGGGT CAGGGAACCC TGGTCACCGT CTCGAGC (SEQ ID NO: 164) |
| | GCCATACGAT AAAAATGAAA ACTAGCCCCA GTCCCTTGGG ACCAGTGGCA GAGCTCG (SEQ ID NO: 165) |
| DOM-41 | SEQ ID NO: 43 |
| | E V Q L L E S G G G L V Q P G G S L R L S C A A S G F T F F E Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTTTT GAGTATGAGA |
| | CTCCACGTCG ACAACCTCAG ACCCCCTCCG AACCATGTCG GACCCCCCAG GGACGCAGAG AGGACACGTC GGAGGCCTAA GTGGAAAAAA CTCATACTCT |
| | . T W V R Q A P G K G L E W V S S I A N D G S T T Y Y A D S V K G R . |
| 101 | TGACGTGGGT CCGCCAGGCT CCAGGGAAGG GTCTAGAGTG GGTCTCATCT ATTGCGAATG ATGGTTCGAC TACATACTAC GCAGACTCCG TGAAGGGCCG |
| | ACTGCACCCA GGCGGTCCGA GGTCCCTTCC CAGATCTCAC CCAGAGTAGA TAACGCTTAC TACCAAGCTG ATGTATGATG CGTCTGAGGC ACTTCCCGGC |
| | . F T I S R D N S K N T L Y L Q M N S L R A E D T A V Y Y C A K P D |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGAT |

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| | CAAGTGGTAG AGGGCGCTGT TAAGGTTCTT GTGCGACATA GACGTTTACT TGTCGGACGC ACGGCTCCTG TGGCGCCATA TAATGACACG CTTTGGACTA |
| | R Q F D Y W G Q G T L V T V S S |
| 301 | CGGCAGTTTG ACTACTGGGG TCAGGGAACC CTGGTCACCG TCTCGAGC (SEQ ID NO: 166)<br>GCCGTCAAAC TGATGACCCC AGTCCCTTGG GACCAGTGGC AGAGCTCG (SEQ ID NO: 167) |
| DOM-42 | SEQ ID NO: 44 |
| | E V Q L L E S G G G L V Q P G G S L R L S C A A S G F T F G P Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGGT CCGTATGAGA<br>CTCCACGTCG ACAACCTCAG ACCCCCTCCG AACCATGTCG GACCCCCCAG GGACGCAGAG AGGACACGTC GGAGGCCTAA GTGGAAACCA GGCATACTCT |
| | . T W V R Q A P G K G L E W V S S I V G D G L D T Y Y A D S V K G R . |
| 101 | TGACTTGGGT CCGCCAGGCT CCAGGGAAGG GTCTAGAGTG GGTCTCATCG ATTGTTGGTG ATGGTCTGGA TACATACTAC GCAGACTCCG TGAAGGGCCG<br>ACTGAACCCA GGCGGTCCGA GGTCCCTTCC CAGATCTCAC CCAGAGTAGC TAACAACCAC TACCAGACCT ATGTATGATG CGTCTGAGGC ACTTCCCGGC |
| | . F T I S R D N S K N T L Y L Q M N S L R A E D T A V Y Y C A K P D |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGAT<br>CAAGTGGTAG AGGGCGCTGT TAAGGTTCTT GTGCGACATA GACGTTTACT TGTCGGACGC ACGGCTCCTG TGGCGCCATA TAATGACACG CTTTGGCCTA |
| | R V F D Y W G Q G T L V T V S S |
| 301 | CGGGTTTTTG ACTACTGGGG TCAGGGAACC CTGGTCACCG TCTCGAGC (SEQ ID NO: 168)<br>GCCCAAAAAC TGATGACCCC AGTCCCTTGG GACCAGTGGC AGAGCTCG (SEQ ID NO: 169) |
| DOM-43 | SEQ ID NO: 45 |
| | E V Q L L E S G G G L V Q P G G S L R L S C A A S G F T F A S Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGCT TCTTATGAGA<br>CTCCACGTCG ACAACCTCAG ACCCCCTCCG AACCATGTCG GACCCCCCAG GGACGCAGAG AGGACACGTC GGAGGCCTAA GTGGAAACGA AGAATACTCT |
| | . A W V R Q A P G K G L E W V S S I G S D G G P T Y Y A D S V K G R . |
| 101 | TGGCGTGGGT CCGCCAGGCT CCAGGGAAGG GTCTAGAGTG GGTCTCATCG ATTGGTAGTG ATGGTGGGCC GACATACTAC GCAGACTCCG TGAAGGGCCG<br>ACCGCACCCA GGCGGTCCGA GGTCCCTTCC CAGATCTCAC CCAGAGTAGC TAACCATCAC TACCACCCGG CTGTATGATG CGTCTGAGGC ACTTCCCGGC |
| | . F T I S R D N S K N T L Y L Q M N S L R A E D S A V Y Y C A K P D |
| 201 | GTTCACCATC TCCCGCGACA ATTCCAAGAA CACGCTGTAT CTGCAAATGA ACAGCCTGCG TGCCGAGGAC TCCGCGGTAT ATTACTGTGC GAAACCTGAT<br>CAAGTGGTAG AGGGCGCTGT TAAGGTTCTT GTGCGACATA GACGTTTACT TGTCGGACGC ACGGCTCCTG AGGCGCCATA TAATGACACG CTTTGGACTA |
| | R A F D Y W G Q G T L V T V S S |
| 301 | AGGGCTTTTG ACTACTGGGG TCAGGGAACC CTGGTCACCG TCTCGAGC (SEQ ID NO: 170)<br>TCCCGAAAAC TGATGACCCC AGTCCCTTGG GACCAGTGGC AGAGCTCG (SEQ ID NO: 171) |
| DOM-44 | SEQ ID NO: 46 |
| | E V Q L L E S G G G L V Q P G G S L R L S C A A S G F T F T S Y E M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTACG TCTTATGAGA<br>CTCCACGTCG ACAACCTCAG ACCCCCTCCG AACCATGTCG GACCCCCCAG GGACGCAGAG AGGACACGTC GGAGGCCTAA GTGGAAATGC AGAATACTCT |
| | . G W V R Q A P G K G L E W V S S I E P T G I T T Y Y A D S V K G R . |
| 101 | TGGGGTGGGT CCGCCAGGCT CCAGGGAAGG GTCTAGAGTG GGTCTCATCT ATTGAGCCTA CTGGTATTAC GACATACTAC GCAGACTCCG TGAAGGGCCG<br>ACCCCACCCA GGCGGTCCGA GGTCCCTTCC CAGATCTCAC CCAGAGTAGA TAACTCGGAT GACCATAATG CTGTATGATG CGTCTGAGGC ACTTCCCGGC |

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
             . F T I  S R D N  S K N  T L Y  L Q M N  S L R  A E D  T A V Y  Y C A  K P H
201          GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTCAT
             CAAGTGGTAG AGGGCGCTGT TAAGGTTCTT GTGCGACATA GACGTTTACT TGTCGGACGC ACGGCTCCTG TGGCGCCATA TAATGACACG CTTTGGAGTA

              F T E L  G F D  Y W G  Q G T L  V T V S S
301          TTTACTGAGC TTGGTTTTGA CTACTGGGGT CAGGGAACCC TGGTCACCGT CTCGAGC (SEQ ID NO: 172)
             AAATGACTCG AACCAAAACT GATGACCCCA GTCCCTTGGG ACCAGTGGCA GAGCTCG (SEQ ID NO: 173)

DOM-45       SEQ ID NO: 47
              E V Q L  L E S  G G G  L V Q P  G G S  L R L  S C A A  S G F  T F G  N Y A M .
1            GAGGTGCAGC TGTTGGAGTC TGGGGGAGGC TTGGTACAGC CTGGGGGGTC CCTGCGTCTC TCCTGTGCAG CCTCCGGATT CACCTTTGGT AATTATGCGA
             CTCCACGTCG ACAACCTCAG ACCCCCTCCG AACCATGTCG GACCCCCCAG GGACGCAGAG AGGACACGTC GGAGGCCTAA GTGGAAACCA TTAATACGCT

             . A W V  R Q A  P G K G  L E W  V S K  I G A Q  G L H  T Y Y  A G S V  K G R .
101          TGGCGTGGGT CCGCCAGGCT CCAGGGAAGG GTCTAGAGTG GGTCTCAAAG ATTGGGGCGC AGGGTCTTCA TACATACTAC GCAGGCTCCG TGAAGGGCCG
             ACCGCACCCA GGCGGTCCGA GGTCCCTTCC CAGATCTCAC CCAGAGTTTC TAACCCCGCG TCCCAGAAGT ATGTATGATG CGTCCGAGGC ACTTCCCGGC

             . F T I  S R D N  S K N  T L Y  L Q M N  S L R  A E D  T A V Y  Y C A  K Q T
201          GTTCACCATC TCCCGCGACA ATTCCAAGAA CACGCTGTAT CTGCAAATGA ACAGCCTGCG TGCCGAGGAC ACCGCGGTAT ATTACTGTGC GAAACAGACG
             CAAGTGGTAG AGGGCGCTGT TAAGGTTCTT GTGCGACATA GACGTTTACT TGTCGGACGC ACGGCTCCTG TGGCGCCATA TAATGACACG CTTTGTCTGC

              T M D Y  E R F  D Y W  G Q G T  L V T  V S S
301          ACGATGGATT ATGAGAGGTT TGACTACTGG GGTCAGGGAA CCCTGGTCAC CGTCTCGAGC (SEQ ID NO: 174)
             TGCTACCTAA TACTCTCCAA ACTGATGACC CCAGTCCCTT GGGACCAGTG GCAGAGCTCG (SEQ ID NO: 175)

DOM 46       SEQ ID NO: 48
              E V Q L  L E S  G G G  L V Q P  G G S  L R L  S C A A  S G F  T F E  L Y A M .
1            GAGGTGCAGC TGTTGGAGTC TGGGGGAGGC TTGGTACAGC CTGGGGGGTC CCTGCGTCTC TCCTGTGCAG CCTCCGGATT CACCTTTGAG TTGTATGCTA
             CTCCACGTCG ACAACCTCAG ACCCCCTCCG AACCATGTCG GACCCCCCAG GGACGCAGAG AGGACACGTC GGAGGCCTAA GTGGAAACTC AACATACGAT

             . A W V  R Q A  P G K G  L E W  V S G  I G A V  G E T  T Y Y  A D S V  K G R .
101          TGGCGTGGGT CCGCCAGGCT CCAGGGAAGG GTCTAGAGTG GGTCTCAGGT ATTGGTGCTG TGGGTGAGAC TACATACTAC GCAGACTCCG TGAAGGGCCG
             ACCGCACCCA GGCGGTCCGA GGTCCCTTCC CAGATCTCAC CCAGAGTCCA TAACCACGAC ACCCACTCTG ATGTATGATG CGTCTGAGGC ACTTCCCGGC

             . F T I  S R D N  S K N  T L Y  L Q M N  S L R  A E D  T A V Y  Y C A  K E A
201          GTTCACCATC TCCCGCGACA ATTCCAAGAA CACGCTGTAT CTGCAAATGA ACAGCCTGCG TGCCGAGGAC ACCGCGGTAT ATTACTGTGC GAAAGAGGCT
             CAAGTGGTAG AGGGCGCTGT TAAGGTTCTT GTGCGACATA GACGTTTACT TGTCGGACGC ACGGCTCCTG TGGCGCCATA TAATGACACG CTTTCTCCGA

              N N L S  D N L  V F D  Y W G Q  G T L  V T V  S S
301          AATAATCTTT CTGATAATCT TGTGTTTGAC TACTGGGGTC AGGGAACCCT GGTCACCGTC TCGAGC (SEQ ID NO: 176)
             TTATTAGAAA GACTATTAGA ACACAAACTG ATGACCCCAG TCCCTTGGGA CCAGTGGCAG AGCTCG (SEQ ID NO: 177)

DOM 47       SEQ ID NO: 49
              D I Q M  T Q S  P S S  L S A S  V G D  R V T  I T C R  A S Q  W I G  D S L S .
1            GACATCCAGA TGACCCAGTC TCCATCCTCC CTGTCTGCAT CTGTAGGAGA CCGTGTCACC ATCACTTGCC GGGCAAGTCA GTGGATTGGG GATTCGTTAA
             CTGTAGGTCT ACTGGGTCAG AGGTAGGAGG GACAGACGTA GACATCCTCT GGCACAGTGG TAGTGAACGG CCCGTTCAGT CACCTAACCC CTAAGCAATT
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
            . W Y Q   Q K P   G K A P   K L L   I Y F   G S Y L   Q S G   V P S   R F S G   S G S .
101         GTTGGTACCA GCAGAAACCA GGGAAAGCCC CTAAGCTCCT GATCTATTTT GGTTCCTATT TGCAAAGTGG GGTCCCATCA CGTTTCAGTG GCAGTGGATC
            CAACCATGGT CGTCTTTGGT CCCTTTCGGG GATTCGAGGA CTAGATAAAA CCAAGGATAA ACGTTTCACC CCAGGGTAGT GCAAAGTCAC CGTCACCTAG

            . G T D   F T L T   I S S   L Q P   E D F A   T Y Y   C Q Q   Y L H T   P S T   F G Q
201         TGGGACAGAT TTCACTCTCA CCATCAGCAG TCTGCAACCT GAAGATTTTG CTACGTACTA CTGTCAACAG TATTTGCATA CTCCTTCGAC GTTCGGCCAA
            ACCCTGTCTA AAGTGAGAGT GGTAGTCGTC AGACGTTGGA CTTCTAAAAC GATGCATGAT GACAGTTGTC ATAAACGTAT GAGGAAGCTG CAAGCCGGTT

             G T K V   E I K   R
301         GGGACCAAGG TGGAAATCAA ACGG (SEQ ID NO: 178)
            CCCTGGTTCC ACCTTTAGTT TGCC (SEQ ID NO: 179)

DOM-48      SEQ ID NO: 50
             D I Q M   T Q S   P S S   L S A S   V G D   R V T   I T C R   A S Q   W I G   D S L S .
  1         GACATCCAGA TGACCCAGTC TCCATCCTCC CTGTCTGCAT CTGTAGGAGA CCGTGTCACC ATCACTTGCC GGGCAAGTCA GTGGATTGGG GATTCGTTAA
            CTGTAGGTCT ACTGGGTCAG AGGTAGGAGG GACAGACGTA GACATCCTCT GGCACAGTGG TAGTGAACGG CCCGTTCAGT CACCTAACCC CTAAGCAATT

            . W Y Q   Q K P   G K A P   K L L   I Y F   G S Y L   Q N G   V P S   R F S G   S G S .
101         GTTGGTACCA GCAGAAACCA GGGAAAGCCC CTAAGCTCCT GATCTATTTT GGTTCCTATT TGCAAAATGG GGTCCCATCA CGTTTCAGTG GCAGTGGATC
            CAACCATGGT CGTCTTTGGT CCCTTTCGGG GATTCGAGGA CTAGATAAAA CCAAGGATAA ACGTTTTACC CCAGGGTAGT GCAAAGTCAC CGTCACCTAG

            . G T D   F T L T   I S S   L Q P   E D F A   T Y Y   C Q Q   Y M I T   P T T   F G Q
201         TGGGACAGAT TTCACTCTCA CCATCAGCAG TCTGCAACCT GAAGATTTTG CTACGTACTA CTGTCAACAG TATATGATTA CTCCTACTAC GTTCGGCCAA
            ACCCTGTCTA AAGTGAGAGT GGTAGTCGTC AGACGTTGGA CTTCTAAAAC GATGCATGAT GACAGTTGTC ATATACTAAT GAGGATGATG CAAGCCGGTT

             G T K V   E I K   R
301         GGGACCAAGG TGGAAATCAA ACGG (SEQ ID NO: 180)
            CCCTGGTTCC ACCTTTAGTT TGCC (SEQ ID NO: 181)

DOM-49      SEQ ID NO: 51
             D V Q M   T Q S   P S S   L S A S   V G D   R V T   I T C R   A S Q   W I G   D S L S .
  1         GACGTCCAGA TGACCCAGTC TCCATCCTCC CTGTCTGCAT CTGTAGGAGA CCGTGTCACC ATCACTTGCC GGGCAAGTCA GTGGATTGGG GATTCGTTAA
            CTGCAGGTCT ACTGGGTCAG AGGTAGGAGG GACAGACGTA GACATCCTCT GGCACAGTGG TAGTGAACGG CCCGTTCAGT CACCTAACCC CTAAGCAATT

            . W Y Q   Q K P   G K A P   K L L   I Y F   G S Y L   Q S G   V P S   R F S G   S G S .
101         GTTGGTACCA GCAGAAACCA GGGAAAGCCC CTAAGCTCCT GATCTATTTT GGTTCCTATT TGCAAAGTGG GGTCCCATCA CGTTTCAGTG GCAGTGGATC
            CAACCATGGT CGTCTTTGGT CCCTTTCGGG GATTCGAGGA CTAGATAAAA CCAAGGATAA ACGTTTCACC CCAGGGTAGT GCAAAGTCAC CGTCACCTAG

            . G T D   F T L T   I S S   L Q P   E D F A   T Y Y   C Q Q   Y M S A   P S T   F G Q
201         TGGGACAGAT TTCACTCTCA CCATCAGCAG TCTGCAACCT GAAGATTTTG CTACGTACTA CTGTCAACAG TATATGAGTG CTCCTTCTAC GTTCGGCCAA
            ACCCTGTCTA AAGTGAGAGT GGTAGTCGTC AGACGTTGGA CTTCTAAAAC GATGCATGAT GACAGTTGTC ATATACTCAC GAGGAAGATG CAAGCCGGTT

             G T K V   E I K   R
301         GGGACCAAGG TGGAAATCAA ACGG (SEQ ID NO: 182)
            CCCTGGTTCC ACCTTTAGTT TGCC (SEQ ID NO: 183)

DOM-50      SEQ ID NO: 52
             D I Q M   T Q S   P S S   L S A S   V G D   R V T   I T C R   A S Q   W I G   D S L S .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
1        GACATCCAGA TGACCCAGTC TCCATCCTCC CTGTCTGCAT CTGTAGGAGA CCGTGTCACC ATCACTTGCC GGGCAAGTCA GTGGATTGGG GATTCGTTAA
         CTGTAGGTCT ACTGGGTCAG AGGTAGGAGG GACAGACGTA GACATCCTCT GGCACAGTGG TAGTGAACGG CCCGTTCAGT CACCTAACCC CTAAGCAATT

         . W Y Q  Q K P  G K A P  K L L  I Y F  G S Y L  Q S G  V P S  R F S G  S G S .
101      GTTGGTACCA GCAGAAACCA GGGAAAGCCC CTAAGCTCCT GATCTATTTT GGTTCCTATT TGCAAAGTGG GGTCCCATCA CGTTTCAGTG GCAGTGGATC
         CAACCATGGT CGTCTTTGGT CCCTTTCGGG GATTCGAGGA CTAGATAAAA CCAAGGATAA ACGTTTCACC CCAGGGTAGT GCAAAGTCAC CGTCACCTAG

         . G T D  F T L T  I S S  L Q P  E D S A  T Y Y  C Q Q  Y Q Y V  P S T  F G Q
201      TGGGACAGAT TTCACTCTCA CCATCAGCAG TCTGCAACCT GAAGATTCTG CTACGTACTA CTGTCAACAG TATCAGTATG TTCCTTCTAC GTTCGGCCAA
         ACCCTGTCTA AAGTGAGAGT GGTAGTCGTC AGACGTTGGA CTTCTAAGAC GATGCATGAT GACAGTTGTC ATAGTCATAC AAGGAAGATG CAAGCCGGTT

          G T K V  E I K  Q
301      GGGACCAAGG TGGAAATCAA ACAG (SEQ ID NO: 184)
         CCCTGGTTCC ACCTTTAGTT TGTC (SEQ ID NO: 185)

DOM-51   SEQ ID NO: 53
          D I Q M  T Q S  P S S  L S A S  V G D  R V T  I T C R  A S Q  P I V  D E L D .
1        GACATCCAGA TGACCCAGTC TCCATCCTCC CTGTCTGCAT CTGTAGGAGA CCGTGTCACC ATCACTTGCC GGGCAAGTCA GCCTATTGTT GATGAGTTAG
         CTGTAGGTCT ACTGGGTCAG AGGTAGGAGG GACAGACGTA GACATCCTCT GGCACAGTGG TAGTGAACGG CCCGTTCAGT CGGATAACAA CTACTCAATC

         . W Y Q  Q K P  G K A P  K L L  I Y A  A S I L  Q S G  V P S  R F S G  S G S .
101      ATTGGTACCA GCAGAAACCA GGGAAAGCCC CTAAGCTCCT GATCTATGCT GCGTCCATTT TGCAAAGTGG GGTCCCATCA CGTTTCAGTG GCAGTGGATC
         TAACCATGGT CGTCTTTGGT CCCTTTCGGG GATTCGAGGA CTAGATACGA CGCAGGTAAA ACGTTTCACC CCAGGGTAGT GCAAAGTCAC CGTCACCTAG

         . G T D  F T L T  I S S  L Q P  E D F A  T Y Y  C H Q  W S T Y  P T T  F G Q
201      TGGGACAGAT TTCACTCTCA CCATCAGCAG TCTGCAACCT GAAGATTTTG CTACGTACTA CTGTCATCAG TGGTCTACTT ATCCTACGAC GTTCGGCCAA
         ACCCTGTCTA AAGTGAGAGT GGTAGTCGTC AGACGTTGGA CTTCTAAAAC GATGCATGAT GACAGTAGTC ACCAGATGAA TAGGATGCTG CAAGCCGGTT

          G T K V  E I K  R
301      GGGACCAAGG TGGAAATTAA ACGG (SEQ ID NO: 186)
         CCCTGGTTCC ACCTTTAATT TGCC (SEQ ID NO: 187)

DOM-52   SEQ ID NO: 54
          D I Q M  T Q S  P S S  L S A S  V G D  R V T  I T C R  A S Q  D I G  S A L R .
1        GACATCCAGA TGACCCAGTC TCCATCCTCC CTGTCTGCAT CTGTAGGTGA CCGTGTCACC ATCACTTGCC GGGCAAGTCA GGATATTGGG TCTGCGTTAA
         CTGTAGGTCT ACTGGGTCAG AGGTAGGAGG GACAGACGTA GACATCCACT GGCACAGTGG TAGTGAACGG CCCGTTCAGT CCTATAACCC AGACGCAATT

         . W Y Q  Q K P  G K A P  K L L  I Y L  G S D L  Q S G  V P S  R F S G  S G S .
101      GGTGGTATCA GCAGAAACCA GGGAAAGCCC CTAAGCTCCT GATCTATTTG GGTTCCGATT TGCAAAGTGG GGTCCCATCA CGTTTCAGTG GCAGTGGATC
         CCACCATAGT CGTCTTTGGT CCCTTTCGGG GATTCGAGGA CTAGATAAAC CCAAGGCTAA ACGTTTCACC CCAGGGTAGT GCAAAGTCAC CGTCACCTAG

         . G T D  F T L T  I S S  L Q P  E D F A  T Y Y  C Q Q  T Q Y F  P T T  F G Q
201      TGGGACAGAT TTCACTCTCA CCATCAGCAG TCTGCAACCT GAAGATTTTG CTACGTACTA CTGTCAACAG ACGCAGTATT TTCCTACGAC GTTCGGCCAA
         ACCCTGTCTA AAGTGAGAGT GGTAGTCGTC AGACGTTGGA CTTCTAAAAC GATGCATGAT GACAGTTGTC TGCGTCATAA AAGGATGCTG CAAGCCGGTT

          G T K V  E I K  R
301      GGGACCAAGG TGGAAATCAA ACGG (SEQ ID NO: 188)
         CCCTGGTTCC ACCTTTAGTT TGCC (SEQ ID NO: 189)
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
DOM-53   SEQ ID NO: 55
          D  I  Q  M   T  Q  S   P  S  S   L  S  A  S   V  G  D   R  V  T   I  T  C  R   A  S  Q   A  I  Y   G  G  L  R .
  1      GACATCCAGA TGACCCAGTC TCCATCCTCC CTGTCTGCAT CTGTAGGAGA CCGTGTCACC ATCACTTGCC GGGCAAGTCA GGCGATTTAT GGGGGGTTAC
         CTGTAGGTCT ACTGGGTCAG AGGTAGGAGG GACAGACGTA GACATCCTCT GGCACAGTGG TAGTGAACGG CCCGTTCAGT CCGCTAAATA CCCCCCAATG

         . W  Y  Q   Q  K  P   G  K  A  P   K  L  L   I  Y  G   E  S  M  L   Q  S  G   V  P  S   R  F  S  G   S  G  S .
101      GGTGGTACCA GCAGAAACCA GGGAAAGCCC CTAAGCTCCT GATCTATGGG GAGTCCATGT TGCAAAGTGG GGTCCCATCA CGTTTCAGTG GCAGTGGATC
         CCACCATGGT CGTCTTTGGT CCCTTTCGGG GATTCGAGGA CTAGATACCC CTCAGGTACA ACGTTTCACC CCAGGGTAGT GCAAAGTCAC CGTCACCTAG

         . G  T  D   F  T  L  T   I  S  S   L  H  P   E  D  F  A   T  Y  Y   C  Q  Q   V  Y  H  K   P  F  T   F  G  Q
201      TGGGACAGAT TTCACTCTCA CCATCAGCAG TCTGCATCCT GAAGATTTTG CTACGTACTA CTGTCAACAG GTTTATCATA AGCCTTTTAC GTTCGGCCAA
         ACCCTGTCTA AAGTGAGAGT GGTAGTCGTC AGACGTAGGA CTTCTAAAAC GATGCATGAT GACAGTTGTC CAAATAGTAT TCGGAAAATG CAAGCCGGTT

          G  T  K  V   E  I  K   R
301      GGGACCAAGG TGGAAATCAA ACGG (SEQ ID NO: 190)
         CCCTGGTTCC ACCTTTAGTT TGCC (SEQ ID NO: 191)

DOM-54   SEQ ID NO: 56
          E  V  Q  L   L  E  S   G  G  G   L  V  Q  P   G  G  S   L  R  L   S  C  A  A   S  G  F   T  F  T   A  Y  R  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTACG GCGTATAGGA
         CTCCACGTCG ACAACCTCAG ACCCCCTCCG AACCATGTCG GACCCCCCAG GGACGCAGAG AGGACACGTC GGAGGCCTAA GTGGAAATGC CGCATATCCT

         . A  W  V   R  Q  A   P  G  K  G   L  E  W   V  S  W   I  S  P  S   G  S  G   T  Y  Y   A  D  S  V   K  G  R .
101      TGGCTTGGGT CCGCCAGGCT CCAGGGAAGG GTCTAGAGTG GGTCTCATGG ATTTCGCCTT CTGGTTCGGG GACATACTAC GCAGACTCCG TGAAGGGCCG
         ACCGAACCCA GGCGGTCCGA GGTCCCTTCC CAGATCTCAC CCAGAGTACC TAAAGCGGAA GACCAAGCCC CTGTATGATG CGTCTGAGGC ACTTCCCGGC

         . F  T  I   S  R  D  N   S  K  N   T  L  Y   L  Q  M  N   S  L  R   A  E  D   T  A  V  Y   Y  C  A   K  T  L
201      GTTCACCATC TCCCGCGACA ATTCCAAGAA CACGCTGTAT CTGCAAATGA ACAGCCTGCG TGCCGAGGAC ACCGCGGTAT ATTACTGTGC GAAAACTTTG
         CAAGTGGTAG AGGGCGCTGT TAAGGTTCTT GTGCGACATA GACGTTTACT TGTCGGACGC ACGGCTCCTG TGGCGCCATA TAATGACACG CTTTGAAAC

          T  D  S  P   S  G  H   Y  E  F   D  Y  W  G   Q  G  T   L  V  T   V  S  S
301      ACGGATTCGC CGTCGGGGCA TTATGAGTTT GACTACTGGG GTCAGGGAAC CCTGGTCACC GTCTCGAGC (SEQ ID NO: 192)
         TGCCTAAGCG GCAGCCCCGT AATACTCAAA CTGATGACCC CAGTCCCTTG GGACCAGTGG CAGAGCTCG (SEQ ID NO: 193)

DOM-55   SEQ ID NO: 57
          E  V  Q  L   L  E  S   G  G  G   L  V  Q  P   G  G  S   L  R  L   S  C  A  A   S  G  F   T  F  A   R  Y  E  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTGCG CGGTATGAGA
         CTCCACGTCG ACAACCTCAG ACCCCCTCCG AACCATGTCG GACCCCCCAG GGACGCAGAG AGGACACGTC GGAGGCCTAA GTGGAAACGC GCCATACTCT

         . G  W  V   R  Q  A   P  G  K  G   L  E  W   V  S  R   I  T  A  Q   G  L  G   T  Y  Y   A  D  S  V   K  G  R .
101      TGGGGTGGGT CCGCCAGGCT CCAGGGAAGG GTCTAGAGTG GGTCTCACGG ATTACTGCTC AGGGTCTTGG GACATACTAC GCAGACTCCG TGAAGGGCCG
         ACCCCACCCA GGCGGTCCGA GGTCCCTTCC CAGATCTCAC CCAGAGTGCC TAATGACGAG TCCCAGAACC CTGTATGATG CGTCTGAGGC ACTTCCCGGC

         . F  T  I   S  R  D  N   S  K  N   T  L  Y   L  Q  M  N   S  L  R   A  E  D   T  A  V  Y   Y  C  A   K  Y  L
201      GTTCACCATC TCCCGCGACA ACTCCAAGAA CACGCTGTAT CTGCAAATGA ACAGCCTGCG TGCCGAGGAT ACCGCGGTAT ATTACTGTGC GAAATATCTT
         CAAGTGGTAG AGGGCGCTGT TGAGGTTCTT GTGCGACATA GACGTTTACT TGTCGGACGC ACGGCTCCTA TGGCGCCATA TAATGACACG CTTTATAGAA
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| | T D F S S G H Q E F D Y W G Q G T L V T V S S |
| 301 | ACTGATTTTA GTAGTGGGCA TCAGGAGTTT GACTACTGGG GTCAGGGAAC CCTGGTCACC GTCTCGAGC (SEQ ID NO: 194) |
| | TGACTAAAAT CATCACCCGT AGTCCTCAAA CTGATGACCC CAGTCCCTTG GGACCAGTGG CAGAGCTCG (SEQ ID NO: 195) |
| DOM-56 | SEQ ID NO: 58 |
| | E V Q L L E S G G G L V Q P G G S L R L S C A A S G F T F N D Y T M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTAAT GATTATACTA |
| | CTCCACGTCG ACAACCTCAG ACCCCCTCCG AACCATGTCG GACCCCCCAG GGACGCAGAG AGGACACGTC GGAGGCCTAA GTGGAAATTA CTAATATGAT |
| | . G W V R Q A P G K G L E W V S W I H G T G G Q T Y Y A D S V K G R . |
| 101 | TGGGTTGGGT CCGCCAGGCT CCAGGGAAGG GTCTAGAGTG GGTCTCATGG ATTCATGGGA CTGGTGGTCA GACATACTAC GCAGACTCCG TGAAGGGCCG |
| | ACCCAACCCA GGCGGTCCGA GGTCCCTTCC CAGATCTCAC CCAGAGTACC TAAGTACCCT GACCACCAGT CTGTATGATG CGTCTGAGGC ACTTCCCGGC |
| | . F T I S R D N S K N T L Y L Q M N S L R A E D T A V Y Y C A K A L |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAAGCTTTG |
| | CAAGTGGTAG AGGGCGCTGT TAAGGTTCTT GTGCGACATA GACGTTTACT TGTCGGACGC ACGGCTCCTG TGGCGCCATA TAATGACACG CTTTCGAAAC |
| | A D R S G G V V E F D Y W G Q G T L V T V S S |
| 301 | GCTGATAGGA GTGGGGGGGT TGTTGAGTTT GACTACTGGG GTCAGGGAAC CCTGGTCACC GTCTCGAGC (SEQ ID NO: 196) |
| | CGACTATCCT CACCCCCCCA ACAACTCAAA CTGATGACCC CAGTCCCTTG GGACCAGTGG CAGAGCTCG (SEQ ID NO: 197) |
| DOM-57 | SEQ ID NO: 59 |
| | E V Q L L E S G G G L V Q P G G S L R L S C A A S G F T F S E Y D M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTTCT GAGTATGATA |
| | CTCCACGTCG ACAACCTCAG ACCCCCTCCG AACCATGTCG GACCCCCCAG GGACGCAGAG AGGACACGTC GGAGGCCTAA GTGGAAAAGA CTCATACTAT |
| | . Y W V R Q A P G K G L E W V S W I D T D G G D T Y Y A D S V K G R . |
| 101 | TGTATTGGGT CCGCCAGGCT CCAGGGAAGG GTCTAGAGTG GGTCTCATGG ATTGATACTG ATGGTGGGGA TACATACTAC GCAGACTCCG TGAAGGGCCG |
| | ACATAACCCA GGCGGTCCGA GGTCCCTTCC CAGATCTCAC CCAGAGTACC TAACTATGAC TACCACCCCT ATGTATGATG CGTCTGAGGC ACTTCCCGGC |
| | . F T I S R D N S K N T L Y L Q M N S L R A E D T A V Y Y C A K P G |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGGT |
| | CAAGTGGTAG AGGGCGCTGT TAAGGTTCTT GTGCGACATA GACGTTTACT TGTCGGACGC ACGGCTCCTG TGGCGCCATA TAATGACACG CTTTGGACCA |
| | L K F D Y W G Q G T L V T V S S |
| 301 | CTGAAGTTTG ACTACTGGGG TCAGGGAACC CTGGTCACCG TCTCGAGC (SEQ ID NO: 198) |
| | GACTTCAAAC TGATQACCCC AGTCCCTTGG GACCAGTGGC AGAGCTCG (SEQ ID NO: 199) |
| DOM-58 | SEQ ID NO: 60 |
| | E V Q L L E S G G G L V Q P G G S L R L S C A A S G F T F E V Y T M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGAG GTTTATACTA |
| | CTCCACGTCG ACAACCTCAG ACCCCCTCCG AACCATGTCG GACCCCCCAG GGACGCAGAG AGGACACGTC GGAGGCCTAA GTGGAAACTC CAAATATGAT |
| | . A W V R Q A P G K G L E W V S T I D E S G R D T Y Y A D S V K G R . |
| 101 | TGGCGTGGGT CCGCCAGGCT CCAGGGAAGG GTCTGGAGTG GGTCTCAACG ATTGATGAGT CTGGTCGTGA TACATACTAC GCAGACTCCG TGAAGGGCCG |
| | ACCGCACCCA GGCGGTCCGA GGTCCCTTCC CAGACCTCAC CCAGAGTTGC TAACTACTCA GACCAGCACT ATGTATGATG CGTCTGAGGC ACTTCCCGGC |
| | . F T I S R D N S K N T L Y L Q M N S L R A E D T A V Y Y C A K P G |

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
201     GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGGT
        CAAGTGGTAG AGGGCGCTGT TAAGGTTCTT GTGCGACATA GACGTTTACT TGTCGGACGC ACGGCTCCTG TGGCGCCATA TAATGACACG CTTTGGACCA

         V  W  F  D   Y  W  G   Q  G  T   L  V  T  V   S  S
301     GTTTGGTTTG ACTACTGGGG TCAGGGAACC CTGGTCACCG TCTCGAGC (SEQ ID NO: 200)
        CAAACCAAAC TGATGACCCC AGTCCCTTGG GACCAGTGGC AGAGCTCG (SEQ ID NO: 201)

DOM-59  SEQ ID NO: 61
         E  V  Q  L   L  E  S   G  G  G   L  V  Q  P   G  G  S   L  R  L   S  C  A  A   S  G  F   T  F  L   D  Y  A  M .
1       GAGGTGCAGC TGTTGGAGTC TGGGGGAGGC TTGGTACAGC CTGGGGGGTC CCTGCGTCTC TCCTGTGCAG CCTCCGGATT CACCTTTCTG GATTATGCGA
        CTCCACGTCG ACAACCTCAG ACCCCCTCCG AACCATGTCG GACCCCCCAG GGACGCAGAG AGGACACGTC GGAGGCCTAA GTGGAAAGAC CTAATACGCT

        .  G  W  V   R  Q  A   P  G  K  G   L  E  W   V  S  T   I  S  P  M   G  M  G   T  Y  Y   A  D  S  V   K  G  R .
101     TGGGTTGGGT CCGCCAGGCT CCAGGGAAGG GTCTGGAGTG GGTCTCAACT ATTTCTCCGA TGGGTATGGG TACATACTAC GCAGACTCCG TGAAGGGCCG
        ACCCAACCCA GGCGGTCCGA GGTCCCTTCC CAGACCTCAC CCAGAGTTGA TAAAGAGGCT ACCCATACCC ATGTATGATG CGTCTGAGGC ACTTCCCGGC

        .  F  T  I   S  R  D  N   S  K  N   T  L  Y   L  Q  M  N   S  L  R   A  E  D   T  A  V  Y   Y  C  A   K  S  S
201     GTTCACCATC TCCCGCGACA ATTCCAAGAA CACGCTGTAT CTGCAAATGA ACAGCCTGCG TGCCGAGGAC ACCGCGGTAT ATTACTGTGC GAAATCGAGT
        CAAGTGGTAG AGGGCGCTGT TAAGGTTCTT GTGCGACATA GACGTTTACT TGTCGGACGC ACGGCTCCTG TGGCGCCATA TAATGACACG CTTTAGCTCA

         A  I  S  F   T  S  D   I  S  N   F  D  Y  W   G  Q  G   T  L  V   T  V  S  S
301     GCTATTTCGT TTACTTCTGA TATTTCTAAT TTTGACTACT GGGGTCAGGG AACCCTGGTC ACCGTCTCGA GC (SEQ ID NO: 202)
        CGATAAAGCA AATGAAGACT ATAAAGATTA AAACTGATGA CCCCAGTCCC TTGGGACCAG TGGCAGAGCT CG (SEQ ID NO: 203)

DOM-61  SEQ ID NO: 62
         E  V  Q  L   L  E  S   G  G  G   L  V  Q  P   G  G  S   L  R  L   S  C  A  A   S  G  F   T  F  A   A  Y  A  M .
1       GAGGTGCAGC TGTTGGAGTC TGGGGGAGGC TTGGTACAGC CTGGGGGGTC CCTGCGTCTC TCCTGTGCAG CCTCCGGATT CACCTTTGCT GCTTATGCTA
        CTCCACGTCG ACAACCTCAG ACCCCCTCCG AACCATGTCG GACCCCCCAG GGACGCAGAG AGGACACGTC GGAGGCCTAA GTGGAAACGA CGAATACGAT

        .  T  W  V   R  Q  A   P  G  K  G   L  E  W   V  S  Y   I  S  P  N   G  T  A   T  Y  Y   A  D  S  V   K  G  R .
101     TGACGTGGGT CCGCCAGGCT CCAGGGAAGG GTCTAGAGTG GGTCTCATAT ATTAGTCCGA ATGGTACGGC GACATACTAC GCAGACTCCG TGAAGGGCCG
        ACTGCACCCA GGCGGTCCGA GGTCCCTTCC CAGATCTCAC CCAGAGTATA TAATCAGGCT TACCATGCCG CTGTATGATG CGTCTGAGGC ACTTCCCGGC

        .  F  T  I   S  R  D  N   S  K N   T  L  Y   L  Q  M  N   S  L  R   A  E  D   T  A  V  Y   Y  C  A   E  Y  V
201     GTTCACCATC TCCCGCGACA ATTCCAAGAA CACGCTGTAT CTGCAAATGA ACAGCCTGCG TGCCGAGGAC ACCGCGGTAT ATTACTGTGC GGAATATGTG
        CAAGTGGTAG AGGGCGCTGT TAAGGTTCTT GTGCGACATA GACGTTTACT TGTCGGACGC ACGGCTCCTG TGGCGCCATA TAATGACACG CCTTATACAC

         G  M  R  W   N  S  F   D  Y  W   G  Q  G  T   L  V  T   V  S  S
301     GGGATGCGTT GGAATTCTTT TGACTACTGG GGTCAGGGAA CCCTGGTCAC CGTCTCGAGC (SEQ ID NO: 204)
        CCCTACGCAA CCTTAAGAAA ACTGATGACC CCAGTCCCTT GGGACCAGTG GCAGAGCTCG (SEQ ID NO: 205)

DOM-62  SEQ ID NO: 63
         E  V  Q  L   L  E  S   G  G  G   L  V  Q  P   G  G  S   L  R  L   S  C  A  A   S  G  F   T  F  S   S  Y  E  M .
1       GAGGTGCAGC TGTTGGAGTC TGGGGGAGGC TTGGTACAGC CTGGGGGGTC CCTGCGTCTC TCCTGTGCAG CCTCCGGATT CACCTTTTCG AGTTATGAGA
        CTCCACGTCG ACAACCTCAG ACCCCCTCCG AACCATGTCG GACCCCCCAG GGACGCAGAG AGGACACGTC GGAGGCCTAA GTGGAAAAGC TCAATACTCT

        .  A  W  V   R  Q  A   P  G  K  G   L  E  W   V  S  S   I  T  S  L   G  T  S   T  Y  Y   A  D  S  V   K  G  R .
101     TGGCTTGGGT CCGCCAGGCT CCAGGGAAGG GTCTAGAGTG GGTCTCATCT ATTACGAGTC TTGGTACTTC TACATACTAC GCAGACTCCG TGAAGGGCCG
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
           ACCGAACCCA GGCGGTCCGA GGTCCCTTCC CAGATCTCAC CCAGAGTAGA TAATGCTCAG AACCATGAAG ATGTATGATG CGTCTGAGGC ACTTCCCGGC

           . F T I  S R D N  S K N  T L Y  L Q M N  S L R  A E D  T A V Y  Y C A  K P G
201        GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGGT
           CAAGTGGTAG AGGGCGCTGT TAAGGTTCTT GTGCGACATA GACGTTTACT TGTCGGACGC ACGGCTCCTG TGGCGCCATA TAATGACACG CTTTGGCCCA

            R K F D  Y W G  Q G T  L V T V  S S
301        AGGAAGTTTG ACTACTGGGG TCAGGGAACC CTGGTCACCG TCTCGAGC (SEQ ID NO: 206)
           TCCTTCAAAC TGATGACCCC AGTCCCTTGG GACCAGTGGC AGAGCTCG (SEQ ID NO: 207)

DOM-65     SEQ ID NO: 64
            E V Q L  L E S  G G G  L V Q P  G G S  L R L  S C A A  S G F  T F N  E Y E M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTAAT GAGTATGAGA
           CTCCACGTCG ACAACCTCAG ACCCCCTCCG AACCATGTCG GACCCCCCAG GGACGCAGAG AGGACACGTC GGAGGCCTAA GTGGAAATTA CTCATACTCT

           . T W V  R Q A  P G K G  L E W  V S T  I T S E  G S G  T Y Y  A D S V  K G R .
101        TGACGTGGGT CCGCCAGGCT CCAGGGAAGG GTCTAGAGTG GGTCTCAACG ATTACTAGTG AGGGTAGTGG GACATACTAC GCAGACTCCG TAAAGGGCCG
           ACTGCACCCA GGCGGTCCGA GGTCCCTTCC CAGATCTCAC CCAGAGTTGC TAATGATCAC TCCCATCACC CTGTATGATG CGTCTGAGGC ATTTCCCGGC

           . F T I  S R D N  S K N  T L Y  L Q M N  S L R  A E D  T A V Y  Y C A  K P N
201        GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTAAT
           CAAGTGGTAG AGGGCGCTGT TAAGGTTCTT GTGCGACATA GACGTTTACT TGTCGGACGC ACGGCTCCTG TGGCGCCATA TAATGACACG CTTTGGATTA

            G K F D  Y W G  Q G T  L V T V  S S
301        GGTAAGTTTG ACTACTGGGG TCAGGGAACC CTGGTCACCG TCTCGAGC (SEQ ID NO: 208)
           CCATTCAAAC TGATGACCCC AGTCCCTTGG GACCAGTGGC AGAGCTCG (SEQ ID NO: 209)

DOM-66     SEQ ID NO: 65
            E V Q L  L E S  G G G  L V Q P  G G S  L R L  S C A A  S G F  T F S  D Y E M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTTCT GATTATGAGA
           CTCCACGTCG ACAACCTCAG ACCCCCTCCG AACCATGTCG GACCCCCCAG GGACGCAGAG AGGACACGTC GGAGGCCTAA GTGGAAAAGA CTAATACTCT

           . L W V  R Q A  P G K G  L E W  V S T  I T S E  G H S  T Y Y A D S V  K G R .
101        TGTTGTGGGT CCGCCAGGCT CCAGGGAAGG GTCTGGAGTG GGTCTCAACT ATTACTAGTG AGGGTCATTC TACATACTAC GCAGACTCCG TGAAGGGCCG
           ACAACACCCA GGCGGTCCGA GGTCCCTTCC CAGACCTCAC CCAGAGTTGA TAATGATCAC TCCCAGTAAG ATGTATGATG CGTCTGAGGC ACTTCCCGGC

           . F T I  S R D N  S K N  T L Y  L Q M N  S L R  A E D  T A V Y  Y C A  K P G
201        GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGGG
           CAAGTGGTAG AGGGCGCTGT TAAGGTTCTT GTGCGACATA GACGTTTACT TGTCGGACGC ACGGCTCCTG TGGCGCCATA TAATGACACG CTTTGGACCC

            T S F D  Y W G  Q G T  L V T V  S S
301        ACTTCGTTTG ACTACTGGGG TCAGGGAACC CTGGTCACCG TCTCGAGC (SEQ ID NO: 210)
           TGAAGCAAAC TGATGACCCC AGTCCCTTGG GACCAGTGGC AGAGCTCG (SEQ ID NO: 211)

DOM-67     SEQ ID NO: 66
            E V Q L  L E S  G G G  L V Q P  G G S  L R L  S C A A  S G F  T F S  D Y E M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTAGT GATTATGAGA
           CTCCACGTCG ACAACCTCAG ACCCCCTCCG AACCATGTCG GACCCCCCAG GGACGCAGAG AGGACACGTC GGAGGCCTAA GTGGAAATCA CTAATACTCT
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
            . S W V  R Q A  P G K G  L E W  V S T  I D S D  G S F  T Y Y  A D S V  K G R .
101         TGAGTTGGGT CCGCCAGGCT CCAGGGAAGG GTCTAGAGTG GGTCTCAACG ATTGATTCTG ATGGTAGTTT TACATACTAC GCAGACTCCG TGAAGGGCCG
            ACTCAACCCA GGCGGTCCGA GGTCCCTTCC CAGATCTCAC CCAGAGTTGC TAACTAAGAC TACCATCAAA ATGTATGATG CGTCTGAGGC ACTTCCCGGC

            . F T I  S R D N  S K N  T L Y  L Q M N  S L R  A E D  T A V Y  Y C A  K P G
201         GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGGT
            CAAGTGGTAG AGGGCGCTGT TAAGGTTCTT GTGCGACATA GACGTTTACT TGTCGGACGC ACGGCTCCTG TGGCGCCATA TAATGACACG CTTTGGCCCA

             V K F D  Y W G  Q G T  L V T V  S S
301         GTGAAGTTTG ACTACTGGGG TCAGGGAACC CTGGTCACCG TCTCGAGC (SEQ ID NO: 212)
            CACTTCAAAC TGATGACCCC AGTCCCTTGG GACCAGTGGC AGAGCTCG (SEQ ID NO: 213)

DOM-68      SEQ ID NO: 67
             E V Q L  L E S  G G G  L V Q P  G G S  L R L  S C A A  S G F  T F K  D Y E M .
  1         GAGGTGCAGC TGTTGGAGTC TGGGGGAGGC TTGGTACAGC CTGGGGGGTC CCTGCGTCTC TCCTGTGCAG CCTCCGGATT CACCTTTAAG GATTATGAGA
            CTCCACGTCG ACAACCTCAG ACCCCCTCCG AACCATGTCG GACCCCCCAG GGACGCAGAG AGGACACGTC GGAGGCCTAA GTGGAAATTC CTAATACTCT

            . T W V  R Q A  P G K G  L E W  V S S  I S S T  G Q S  T Y Y  A D S V  K G R .
101         TGACTTGGGT CCGCCAGGCT CCAGGGAAGG GTCTAGAGTG GGTCTCATCT ATTTCTTCTA CTGGTCAGTC TACATACTAC GCAGACTCCG TGAAGGGCCG
            ACTGAACCCA GGCGGTCCGA GGTCCCTTCC CAGATCTCAC CCAGAGTAGA TAAAGAAGAT GACCAGTCAG ATGTATGATG CGTCTGAGGC ACTTCCCGGC

            . F T I  S R D N  S K N  T L Y  L Q M N  S L R  A E D  T A V Y  Y C A  K P G
201         GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGGT
            CAAGTGGTAG AGGGCGCTGT TAAGGTTCTT GTGCGACATA GACGTTTACT TGTCGGACGC ACGGCTCCTG TGGCGCCATA TAATGACACG CTTTGGCCCA

             N K F D  Y W G  Q G T  L V T V  S S
301         AATAAGTTTG ACTACTGGGG TCAGGGAACC CTGGTCACCG TCTCGAGC (SEQ ID NO: 214)
            TTATTCAAAC TGATGACCCC AGTCCCTTGG GACCAGTGGC AGAGCTCG (SEQ ID NO: 215)

DOM-69      SEQ ID NO: 68
             E V Q L  L E S  G G G  L V Q P  G G S  L R L  S C A A  S G F  T F L  D Y G M .
  1         GAGGTGCAGC TGTTGGAGTC TGGGGGAGGC TTGGTACAGC CTGGGGGGTC CCTGCGTCTC TCCTGTGCAG CCTCCGGATT CACCTTTCTT GATTATGGTA
            CTCCACGTCG ACAACCTCAG ACCCCCTCCG AACCATGTCG GACCCCCCAG GGACGCAGAG AGGACACGTC GGAGGCCTAA GTGGAAAGAA CTAATACCAT

            . A W V  R Q A  P G K G  L E W  V S A  I S P L  G L S  T Y Y  A D S V  K S R .
101         TGGCTTGGGT CCGCCAGGCT CCAGGGAAGG GTCTAGAGTG GGTCTCAGCT ATTTCGCCTC TTGGTCTTAG TACATACTAC GCAGACTCCG TGAAGAGCCG
            ACCGAACCCA GGCGGTCCGA GGTCCCTTCC CAGATCTCAC CCAGAGTCGA TAAAGCGGAG AACCAGAATC ATGTATGATG CGTCTGAGGC ACTTCTCGGC

            . F T I  S R D N  S K N  T L Y  L Q M N  S L R  A E D  T A V Y  Y C A  K E V
201         GTTCACCATC TCCCGCGACA ATTCCAAGAA CACGCTGTAT CTGCAAATGA ACAGCCTGCG TGCCGAGGAT ACCGCGGTAT ATTACTGTGC GAAAGAGGTG
            CAAGTGGTAG AGGGCGCTGT TAAGGTTCTT GTGCGACATA GACGTTTACT TGTCGGACGC ACGGCTCCTA TGGCGCCATA TAATGACACG CTTTCTCCAC

             R V G R  G V H  P P K  F D Y W  G Q G  T L V  T V S S
301         AGGGTGGGTA GGGGTGTTCA TCCTCCGAAG TTTGACTACT GGGGTCAGGG AACCCTGGTC ACCGTCTCGA GC (SEQ ID NO: 216)
            TCCCACCCAT CCCCACAAGT AGGAGGCTTC AAACTGATGA CCCCAGTCCC TTGGGACCAG TGGCAGAGCT CG (SEQ ID NO: 217)

DOM-70      SEQ ID NO: 69
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
             E  V  Q  L   L  E  S   G  G  G   L  V  Q  P   G  G  S   L  R  L   S  C  A  A   S  G  F   T  F  E   N  Y  A  M .
1            GAGGTGCAGC TGTTGGAGTC TGGGGGAGGC TTGGTACAGC CTGGGGGGTC CCTGCGTCTC TCCTGTGCAG CCTCCGGATT CACCTTTGAG AATTATGCTA
             CTCCACGTCG ACAACCTCAG ACCCCCTCCG AACCATGTCG GACCCCCCAG GGACGCAGAG AGGACACGTC GGAGGCCTAA GTGGAAACTC TTAATACGAT

             .  S  W  V   R  Q  A   P  G  K  G   L  E  W   V  S  T   I  A  P  L   G  V  P   T  Y  Y   A  D  S  V   K  G  R .
101          TGTCGTGGGT CCGCCAGGCT CCAGGGAAGG GTCTAGAGTG GGTCTCAACG ATTGCTCCGC TGGGTGTTCC GACATACTAC GCAGACTCCG TGAAGGGCCG
             ACAGCACCCA GGCGGTCCGA GGTCCCTTCC CAGATCTCAC CCAGAGTTGC TAACGAGGCG ACCCACAAGG CTGTATGATG CGTCTGAGGC ACTTCCCGGC

             .  F  T  I   S  R  D  N   S  K  N   T  L  Y   L  Q  M  N   S  L  R   A  E  D   T  A  V  Y   Y  C  A   K  K  K
201          GTTCACCATC TCCCGCGACA ATTCCAAGAA CACGCTGTAT CTGCAAATGA ACAGCCTGCG TGCCGAGGAT ACCGCGGTAT ATTACTGTGC GAAAAAGAAG
             CAAGTGGTAG AGGGCGCTGT TAAGGTTCTT GTGCGACATA GACGTTTACT TGTCGGACGC ACGGCTCCTA TGGCGCCATA TAATGACACG CTTTTTCTTC

             V  G  A  W   L  Q  S   R  S  F   D  Y  W  G   Q  G  T   L  V  T   V  S  S
301          GTTGGGGCGT GGCTGCAGTC GCGGAGTTTT GACTACTGGG GTCAGGGAAC CCTGGTCACC GTCTCGAGC (SEQ ID NO: 218)
             CAACCCCGCA CCGACGTCAG CGCCTCAAAA CTGATGACCC CAGTCCCTTG GGACCAGTGG CAGAGCTCG (SEQ ID NO: 219)

DOM-71       SEQ ID NO: 70
             E  V  Q  L   L  E  S   G  G  G   L  V  Q  P   G  G  S   L  R  L   S  C  A  A   S  G  F   T  F  E   G  Y  P  M .
1            GAGGTGCAGC TGTTGGAGTC TGGGGGAGGC TTGGTACAGC CTGGGGGGTC CCTGCGTCTC TCCTGTGCAG CCTCCGGATT CACCTTTGAG GGTTATCCTA
             CTCCACGTCG ACAACCTCAG ACCCCCTCCG AACCATGTCG GACCCCCCAG GGACGCAGAG AGGACACGTC GGAGGCCTAA GTGGAAACTC CCAATAGGAT

             .  S  W  V   R  Q  A   P  G  K  G   L  E  W   V  S  T   I  S  P  L   G  P  D   T  Y  Y   A  D  S  V   K  G  R .
101          TGTCGTGGGT CCGCCAGGCT CCAGGGAAGG GTCTAGAGTG GGTCTCAACT ATTAGTCCTT TGGGTCCTGA TACATACTAC GCAGACTCCG TGAAGGGCCG
             ACAGCACCCA GGCGGTCCGA GGTCCCTTCC CAGATCTCAC CCAGAGTTGA TAATCAGGAA ACCCAGGACT ATGTATGATG CGTCTGAGGC ACTTCCCGGC

             .  F  T  I   S  R  D  N   S  K  N   T  L  Y   L  Q  M  N   S  L  R   A  E  D   T  A  V  Y   Y  C  A   K  L  L
201          GTTCACCATC TCCCGCGACA ATTCCAAGAA CACGCTGTAT CTGCAAATGA ACAGCCTGCG TGCCGAGGAT ACCGCGGTAT ATTACTGTGC GAAACTGTTG
             CAAGTGGTAG AGGGCGCTGT TAAGGTTCTT GTGCGACATA GACGTTTACT TGTCGGACGC ACGGCTCCTA TGGCGCCATA TAATGACACG CTTTGACAAC

             M  G  E  Y   L  N  S   R  T  F   D  Y  W  G   Q  G  T   L  V  T   V  S  S
301          ATGGGGGAGT ATTTGAATTC TAGGACGTTT GACTACTGGG GTCAGGGAAC CCTGGTCACC GTCTCGAGC (SEQ ID NO: 220)
             TACCCCCTCA TAAACTTAAG ATCCTGCAAA CTGATGACCC CAGTCCCTTG GGACCAGTGG CAGAGCTCG (SEQ ID NO: 221)

DOM-72       SEQ ID NO: 71
             E  V  Q  L   L  E  S   G  G  G   L  V  Q  P   G  G  S   L  R  L   S  C  A  A   S  G  F   T  F  E   A  Y  P  M .
1            GAGGTGCAGC TGTTGGAGTC TGGGGGAGGC TTGGTACAGC CTGGGGGGTC CCTGCGTCTC TCCTGTGCAG CCTCCGGATT CACCTTTGAG GCGTATCCTA
             CTCCACGTCG ACAACCTCAG ACCCCCTCCG AACCATGTCG GACCCCCCAG GGACGCAGAG AGGACACGTC GGAGGCCTAA GTGGAAACTC CGCATAGGAT

             .  S  W  V   R  Q  A   P  G  K  G   L  E  W   V  S  S   I  S  P  L   G  L  W   T  Y  Y   A  D  S  V   K  G  R .
101          TGTCGTGGGT CCGCCAGGCT CCAGGGAAGG GTCTAGAGTG GGTCTCAAGT ATTTCCCCTC TTGGTTTGTG GACATACTAC GCAGACTCCG TGAAGGGCCG
             ACAGCACCCA GGCGGTCCGA GGTCCCTTCC CAGATCTCAC CCAGAGTTCA TAAAGGGGAG AACCAAACAC CTGTATGATG CGTCTGAGGC ACTTCCCGGC

             .  F  T  I   S  R  D  N   S  K  N   T  L  Y   L  Q  M  N   S  L  R   A  E  D   T  A  V  Y   Y  C  A   K  L  S
201          GTTCACCATC TCCCGCGACA ATTCCAAGAA CACGCTGTAT CTGCAAATGA ACAGCCTGCG TGCCGAGGAC ACCGCGGTAT ATTACTGTGC GAAACTTAGT
             CAAGTGGTAG AGGGCGCTGT TAAGGTTCTT GTGCGACATA GACGTTTACT TGTCGGACGC ACGGCTCCTG TGGCGCCATA TAATGACACG CTTTGAATCA

             A  G  A  E   T  H  V   Y  R  L   F  D  Y  W   G  Q  G   T  L  V   T  V  S  S
301          GCTGGGGCGG AGACTCATGT TTATCGGCTT TTTGACTACT GGGGTCAGGG AACCCTGGTC ACCGTCTCGA GC (SEQ ID NO: 222)
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
          CGACCCCGCC TCTGAGTACA AATAGCCGAA AAACTGATGA CCCCAGTCCC TTGGGACCAG TGGCAGAGCT CG (SEQ ID NO: 223)

DOM-73    SEQ ID NO: 72
           E  V  Q  L   L  E  S   G  G  G   L  V  Q  P   G  G  S   L  R  L   S  C  A  A   S  G  F   T  F  S   K  Y  D  M .
 1        GAGGTGCAGC TGTTGGAGTC TGGGGGAGGC TTGGTACAGC CTGGGGGGTC CCTGCGTCTC TCCTGTGCAG CCTCCGGATT CACCTTTTCT AAGTATGATA
          CTCCACGTCG ACAACCTCAG ACCCCCTCCG AACCATGTCG GACCCCCCAG GGACGCAGAG AGGACACGTC GGAGGCCTAA GTGGAAAAGA TTCATACTAT

          .  S  W  V   R  Q  A   P  G  K  G   L  E  W   V  S  T   I  L  E  D   G  L  T   T  Y  Y   A  D  S  V   K  G  R .
101       TGTCTTGGGT CCGCCAGGCT CCAGGGAAGG GTCTAGAGTG GGTCTCAACT ATTCTGGAGG ATGGTCTGAC TACATACTAC GCAGACTCCG TGAAGGGCCG
          ACAGAACCCA GGCGGTCCGA GGTCCCTTCC CAGATCTCAC CCAGAGTTGA TAAGACCTCC TACCAGACTG ATGTATGATG CGTCTGAGGC ACTTCCCGGC

          .  F  T  I   S  R  D  N   S  K  N   T  L  Y   L  Q  M  N   S  L  R   A  E  D   T  A  V  Y   Y  C  A   K  P  G
201       GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGGG
          CAAGTGGTAG AGGGCGCTGT TAAGGTTCTT GTGCGACATA GACGTTTACT TGTCGGACGC ACGGCTCCTG TGGCGCCATA TAATGACACG CTTTGGCCCC

           R  L  F  D   Y  W  G   Q  G  T   L  V  T  V   S  S
301       CGTTTGTTTG ACTACTGGGG TCAGGGAACC CTGGTCACCG TCTCGAGC (SEQ ID NO: 224)
          GCAAACAAAC TGATGACCCC AGTCCCTTGG GACCAGTGGC AGAGCTCG (SEQ ID NO: 225)

DOM-74    SEQ ID NO: 73
           E  V  Q  L   L  E  S   G  G  G   L  V  Q  P   G  G  S   L  R  L   S  C  A  A   S  G  F   T  F  S   D  Y  P  M .
 1        GAGGTGCAGC TGTTGGAGTC TGGGGGAGGC TTGGTACAGC CTGGGGGGTC CCTGCGTCTC TCCTGTGCAG CCTCCGGATT CACCTTTTCG GATTATCCTA
          CTCCACGTCG ACAACCTCAG ACCCCCTCCG AACCATGTCG GACCCCCCAG GGACGCAGAG AGGACACGTC GGAGGCCTAA GTGGAAAAGC CTAATAGGAT

          .  T  W  V   R  Q  A   P  G  K  G   L  E  W   V  S  T   I  L  S  P   G  T  E   T  Y  Y   A  D  S  V   K  G  R .
101       TGACGTGGGT CCGCCAGGCT CCAGGGAAGG GTCTGGAGTG GGTCTCAACT ATTCTGTCTC CGGGTACGGA GACATACTAC GCAGACTCCG TGAAGGGCCG
          ACTGCACCCA GGCGGTCCGA GGTCCCTTCC CAGACCTCAC CCAGAGTTGA TAAGACAGAG GCCCATGCCT CTGTATGATG CGTCTGAGGC ACTTCCCGGC

          .  F  T  I   S  R  D  N   S  K  N   T  L  Y   L  Q  M  N   S  L  R   A  E  D   T  A  V  Y   Y  C  A   K  A  E
201       GTTCACCATC TCCCGCGACA ATTCCAAGAA CACGCTGTAT CTGCAAATGA ACAGCCTGCG TGCCGAGGAC ACCGCGGTAT ATTACTGTGC GAAAGCTGAG
          CAAGTGGTAG AGGGCGCTGT TAAGGTTCTT GTGCGACATA GACGTTTACT TGTCGGACGC ACGGCTCCTG TGGCGCCATA TAATGACACG CTTTCGACTC

          K  D  F  D   Y  W  G   Q  G  T   L  V  T  V   S  S
301       AAGGATTTTG ACTACTGGGG TCAGGGAACC CTGGTCACCG TCTCGAGC (SEQ ID NO: 226)
          TTCCTAAAAC TGATGACCCC AGTCCCTTGG GACCAGTGGC AGAGCTCG (SEQ ID NO: 227)

DOM-75    SEQ ID NO: 74
                                             AvaI
                                            -----
           E  V  Q  L   L  E  S   G  G  G   L  V  Q  P   G  G  S   L  R  L   S  C  A  A   S  G  F   T  F  L   Q  Y  P  M .
 1        GAGGTGCAGC TGTTGGAGTC TGGGGGAGGC TTGGTACAGC CTGGGGGGTC CCTGCGTCTC TCCTGTGCAG CCTCGGGATT CACCTTTTTG CAGTATCCGA
          CTCCACGTCG ACAACCTCAG ACCCCCTCCG AACCATGTCG GACCCCCCAG GGACGCAGAG AGGACACGTC GGAGCCCTAA GTGGAAAAAC GTCATAGGCT

          .  G  W  V   R  Q  A   P  G  K  G   L  E  W   V  S  T   I  S  P  V   G  L  T   T  Y  Y   A  D  S  V   K  G  R .
101       TGGGTTGGGT CCGCCAGGCT CCAGGGAAGG GTCTAGAGTG GGTCTCAACT ATTTCTCCTG TTGGTTTGAC TACATACTAC GCAGACTCCG TGAAGGGCCG
          ACCCAACCCA GGCGGTCCGA GGTCCCTTCC CAGATCTCAC CCAGAGTTGA TAAAGAGGAC AACCAAACTG ATGTATGATG CGTCTGAGGC ACTTCCCGGC

          .  F  T  I   S  R  D  N   S  K  N   T  L  Y   L  Q  M  N   S  L  R   A  E  D   T  A  V  Y   Y  C  A   K  L  F
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
201      GTTCACCATC TCCCGCGACA ATTCCAAGAA CACGCTGTAT CTGCAAATGA ACAGCCTGCG TGCCGAGGAT ACCGCGGTAT ATTACTGTGC GAAATTGTTT
         CAAGTGGTAG AGGGCGCTGT TAAGGTTCTT GTGCGACATA GACGTTTACT TGTCGGACGC ACGGCTCCTA TGGCGCCATA TAATGACACG CTTTAACAAA

          E  G  S  R   I  Q  R   D  V  G   F  D  Y  W   G  Q  G   T  L  V   T  V  S  S
301      GAGGGGTCGA GGATTCAGCG TGATGTGGGT TTTGACTACT GGGGTCAGGG AACCCTGGTC ACCGTCTCGA GC (SEQ ID NO: 228)
         CTCCCCAGCT CCTAAGTCGC ACTACACCCA AAACTGATGA CCCCAGTCCC TTGGGACCAG TGGCAGAGCT CG (SEQ ID NO: 229)

DOM-77   SEQ ID NO: 75
          E  V  Q  L   L  E  S   G  G  G   L  V  Q  P   G  G  S   L  R  L   S  C  A  A   S  G  F   T  F  E   E  Y  G  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTGAG GAGTATGGTA
         CTCCACGTCG ACAACCTCAG ACCCCCTCCG AACCATGTCG GACCCCCCAG GGACGCAGAG AGGACACGTC GGAGGCCTAA GTGGAAACTC CTCATACCAT

         .  A  W  V   R  Q  A   P  G  K  G   L  E  W   V  S  T   I  S  P  L   G  I  S   T  Y  Y   A  D  S  V   K  G  R .
101      TGGCGTGGGT CCGCCAGGCT CCAGGGAAGG GTCTAGAGTG GGTCTCAACT ATTTCTCCGC TGGGTATTTC GACATACTAC GCAGACTCCG TGAAGGGCCG
         ACCGCACCCA GGCGGTCCGA GGTCCCTTCC CAGATCTCAC CCAGAGTTGA TAAAGAGGCG ACCCATAAAG CTGTATGATG CGTCTGAGGC ACTTCCCGGC

         .  F  T  I   S  R  D  N   S  K  N   T  L  Y   L  Q  M  N   S  L  R   A  E  D   T  A  V  Y   Y  C  A   K  H  A
201      GTTCACCATC TCCCGCGACA ATTCCAAGAA CACGCTGTAT CTGCAAATGA ACAGCCTGCG TGCCGAGGAC ACCGCGGTAT ATTACTGTGC GAAACATGCT
         CAAGTGGTAG AGGGCGCTGT TAAGGTTCTT GTGCGACATA GACGTTTACT TGTCGGACGC ACGGCTCCTG TGGCGCCATA TAATGACACG CTTTGTACGA

          T  S  Q  E   S  L  R   S  F  D   Y  W  G  Q   G  T  L   V  T  V   S  S
301      ACGTCTCAGG AGTCTTTGCG GTCTTTTGAC TACTGGGGTC AGGGAACCCT GGTCACCGTC TCGAGC (SEQ ID NO: 230)
         TGCAGAGTCC TCAGAAACGC CAGAAAACTG ATGACCCCAG TCCCTTGGGA CCAGTGGCAG AGCTCG (SEQ ID NO: 231)

DOM-78   SEQ ID NO: 76
          E  V  Q  L   L  E  S   G  G  G   L  V  Q  P   G  G  S   L  R  L   S  C  A  A   S  G  F   T  F  E   R  Y  Q  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTGAG AGGTATCAGA
         CTCCACGTCG ACAACCTCAG ACCCCCTCCG AACCATGTCG GACCCCCCAG GGACGCAGAG AGGACACGTC GGAGGCCTAA GTGGAAACTC TCCATAGTCT

         .  A  W  V   R  Q  A   P  G  K  G   L  E  W   V  S  T   I  S  S  D   G  G  G   T  Y  Y   A  D  S  V   K  G  R .
101      TGGCGTGGGT CCGCCAGGCT CCGGGGAAGG GTCTAGAGTG GGTCTCAACG ATTAGTTCTG ATGGTGGGGG GACATACTAC GCAGACTCCG TGAAGGGCCG
         ACCGCACCCA GGCGGTCCGA GGCCCCTTCC CAGATCTCAC CCAGAGTTGC TAATCAAGAC TACCACCCCC CTGTATGATG CGTCTGAGGC ACTTCCCGGC

         .  F  T  I   S  R  D  N   S  K  N   T  L  Y   L  Q  M  N   S  L  R   A  E  D   T  A  V  Y   Y  C  A   K  P  G
201      GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGGT
         CAAGTGGTAG AGGGCGCTGT TAAGGTTCTT GTGCGACATA GACGTTTACT TGTCGGACGC ACGGCTCCTG TGGCGCCATA TAATGACACG CTTTGGACCA

          H  R  F  D   Y  W  G   Q  G  T   L  V  T  V   S  S
301      CATCGGTTTG ACTACTGGGG TCAGGGAACC CTGGTCACCG TCTCGAGC (SEQ ID NO: 232)
         GTAGCCAAAC TGATGACCCC AGTCCCTTGG GACCAGTGGC AGAGCTCG (SEQ ID NO: 233)

DOM-80   SEQ ID NO: 77
          E  V  Q  L   L  E  S   G  G  G   L  V  Q  P   G  G  S   L  R  L   S  C  A  A   S  G  F   T  F  G   R  Y  Q  M .
  1      GAGGTGCAGC TGTTGGAGTC TGGGGGAGGC TTGGTACAGC CTGGGGGGTC CCTGCGTCTC TCCTGTGCAG CCTCCGGATT CACCTTTGGT CGTTATCAGA
         CTCCACGTCG ACAACCTCAG ACCCCCTCCG AACCATGTCG GACCCCCCAG GGACGCAGAG AGGACACGTC GGAGGCCTAA GTGGAAACCA GCAATAGTCT

         .  A  W  V   R  Q  A   P  G  K  G   L  E  W   V  S  S   I  S  S  D   G  G  G   T  Y  Y   A  D  S  V   K  G  R .
101      TGGCTTGGGT CCGCCAGGCT CCAGGGAAGG GTCTAGAGTG GGTCTCATCT ATTTCTTCTG ATGGTGGGGG GACATACTAC GCAGACTCCG TGAAGGGCCG
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

| | |
|---|---|
| | ACCGAACCCA GGCGGTCCGA GGTCCCTTCC CAGATCTCAC CCAGAGTAGA TAAAGAAGAC TACCACCCCC CTGTATGATG CGTCTGAGGC ACTTCCCGGC |
| | . F T I S R D N S K N T L Y L Q M N S L R A E D T A V Y Y C A K P S |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGTCT |
| | CAAGTGGTAG AGGGCGCTGT TAAGGTTCTT GTGCGACATA GACGTTTACT TGTCGGACGC ACGGCTCCTG TGGCGCCATA TAATGACACG CTTTGGCAGA |
| | R R F D Y W G Q G T L V T V S S |
| 301 | CGTCGGTTTG ACTACTGGGG TCAGGGAACC CTGGTCACCG TCTCGAGC (SEQ ID NO: 234) |
| | GCAGCCAAAC TGATGACCCC AGTCCCTTGG GACCAGTGGC AGAGCTCG (SEQ ID NO: 235) |
| DOM-81 | SEQ ID NO: 78 |
| | E V Q L L E S G G G L V Q P G G F L R L S C A A S G F T F E L Y P M . |
| 1 | GAGGTGCAGC TGTTGGAGTC TGGGGGAGGC TTGGTACAGC CTGGGGGGTT CCTGCGTCTC TCCTGTGCAG CCTCCGGATT CACCTTTGAG TTGTATCCGA |
| | CTCCACGTCG ACAACCTCAG ACCCCCTCCG AACCATGTCG GACCCCCCAA GGACGCAGAG AGGACACGTC GGAGGCCTAA GTGGAAACTC AACATAGGCT |
| | . A W V R Q A P G K G L E W V S S I S P V G F L T Y Y A D S V K G R . |
| 101 | TGGCGTGGGT CCGCCAGGCT CCAGGGAAGG GTCTGGAGTG GGTCTCATCG ATTTCTCCGG TTGGTTTTCT GACATACTAC GCAGACTCCG TGAAGGGCCG |
| | ACCGCACCCA GGCGGTCCGA GGTCCCTTCC CAGACCTCAC CCAGAGTAGC TAAAGAGGCC AACCAAAAGA CTGTATGATG CGTCTGAGGC ACTTCCCGGC |
| | . F T I S R D N S K N T L Y L Q M N S L R A E D T A V Y Y C A K G H |
| 201 | GTTCACCATC TCCCGCGACA ATTCCAAGAA CACGCTGTAT CTGCAAATGA ACAGCCTGCG TGCCGAGGAT ACCGCGGTAT ATTACTGTGC GAAAGGGCAT |
| | CAAGTGGTAG AGGGCGCTGT TAAGGTTCTT GTGCGACATA GACGTTTACT TGTCGGACGC ACGGCTCCTA TGGCGCCATA TAATGACACG CTTTCCCGTA |
| | E G S Y T P R S A F D Y W G Q G T L V T V S S |
| 301 | GAGGGGTCGT ATACTCCGCG GTCGGCTTTT GACTACTGGG GTCAGGGAAC CCTGGTCACC GTCTCGAGC (SEQ ID NO: 236) |
| | CTCCCCAGCA TATGAGGCGC CAGCCGAAAA CTGATGACCC CAGTCCCTTG GGACCAGTGG CAGAGCTCG (SEQ ID NO: 237) |
| DOM-82 | SEQ ID NO: 79 |
| | E V Q L L E S G G G L V Q P G G S L R L S C A A S G F T F V A Y P M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGTG GCGTATCCTA |
| | CTCCACGTCG ACAACCTCAG ACCCCCTCCG AACCATGTCG GACCCCCCAG GGACGCAGAG AGGACACGTC GGAGGCCTAA GTGGAAACAC CGCATAGGAT |
| | . A W V R Q A P G K G L E W V S T I A P L G G N T Y Y A D S V K G R . |
| 101 | TGGCGTGGGT CCGCCAGGCT CCAGGGAAGG GTCTGGAGTG GGTCTCAACT ATTGCGCCTC TGGGTGGTAA TACATACTAC GCAGACTCCG TGAAGGGCCG |
| | ACCGCACCCA GGCGGTCCGA GGTCCCTTCC CAGACCTCAC CCAGAGTTGA TAACGCGGAG ACCCACCATT ATGTATGATG CGTCTGAGGC ACTTCCCGGC |
| | . F T I S R D N S K N T L Y L Q M N S L R A E D T A V Y Y C A K R P |
| 201 | GTTCACCATC TCCCGCGACA ATTCCAAGAA CACGCTGTAT CTGCAAATGA ACAGCCTGCG TGCCGAGGAC ACCGCGGTAT ATTACTGTGC GAAACGGCCG |
| | CAAGTGGTAG AGGGCGCTGT TAAGGTTCTT GTGCGACATA GACGTTTACT TGTCGGACGC ACGGCTCCTG TGGCGCCATA TAATGACACG CTTTGCCGGC |
| | E G L Q I D S Q N F D Y W G Q G T L V T V S S |
| 301 | GAGGGGCTGC AGATTGATTC TCAGAATTTT GACTACTGGG GTCAGGGAAC CCTGGTCACC GTCTCGAGC (SEQ ID NO: 238) |
| | CTCCCCGACG TCTAACTAAG AGTCTTAAAA CTGATGACCC CAGTCCCTTG GGACCAGTGG CAGAGCTCG (SEQ ID NO: 239) |
| DOM-83 | SEQ ID NO: 80 |
| | E V Q L L E S G G G L V Q P G G S L R L S C A A S G F T F A L Y Q M . |
| 1 | GAGGTGCAGC TGTTGGAGTC TGGGGGAGGC TTGGTACAGC CTGGGGGGTC CCTGCGTCTC TCCTGTGCAG CCTCCGGATT CACCTTTGCG TTGTATCAGA |
| | CTCCACGTCG ACAACCTCAG ACCCCCTCCG AACCATGTCG GACCCCCCAG GGACGCAGAG AGGACACGTC GGAGGCCTAA GTGGAAACGC AACATAGTCT |

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
           . A  W  V   R  Q  A   P  G  K  G   L  E  W   V  S  S   I  D  S  S   G  S  D   T  Y  Y   A  D  S  V   K  G  R .
101        TGGCTTGGGT CCGCCAGGCT CCAGGGAAGG GTCTAGAGTG GGTCTCATCG ATTGATTCTT CTGGTAGTGA TACATACTAC GCAGACTCCG TGAAGGGCCG
           ACCGAACCCA GGCGGTCCGA GGTCCCTTCC CAGATCTCAC CCAGAGTAGC TAACTAAGAA GACCATCACT ATGTATGATG CGTCTGAGGC ACTTCCCGGC

           . F  T  I   S  R  D  N   S  K  N   T  L  Y   L  Q  M  N   S  L  R   A  E  D   T  A  V  Y   Y  C  A   K  P  E
201        GTTCACCATC TCCCGCGACA ATTCCAAGAA CACGCTGTAT CTGCAAATGA ACAGCCTGCG TGCCGAGGAC ACCGCGGTAT ATTACTGTGC GAAACCTGAG
           CAAGTGGTAG AGGGCGCTGT TAAGGTTCTT GTGCGACATA GACGTTTACT TGTCGGACGC ACGGCTCCTG TGGCGCCATA TAATGACACG CTTTGGACTC

            R  D  F  D   Y  W  G   Q  G  T  L  V  T  V   S  S
301        CGTGATTTTG ACTACTGGGG TCAGGGAACC CTGGTCACCG TCTCGAGC (SEQ ID NO: 240)
           GCACTAAAAC TGATGACCCC AGTCCCTTGG GACCAGTGGC AGAGCTCG (SEQ ID NO: 241)

DOM-84     SEQ ID NO: 81
            E  V  Q  L   L  E  S   G  G  G   L  V  Q  P   G  G  S   L  R  L   S  C  A  A   S  G  F   T  F  R   Q  Y  Q  M .
  1        GAGGTGCAGC TGTTGGAGTC TGGGGGAGGC TTGGTACAGC CTGGGGGGTC CCTGCGTCTC TCCTGTGCAG CCTCCGGATT CACCTTTAGG CAGTACCAGA
           CTCCACGTCG ACAACCTCAG ACCCCCTCCG AACCATGTCG GACCCCCCAG GGACGCAGAG AGGACACGTC GGAGGCCTAA GTGGAAATCC GTCATGGTCT

           . A  W  A   R  Q  A   P  G  K  G   L  E  W   V  S  T   I  A  S  D   G  V  S   T  Y  Y   A  D  S  V   K  G  R .
101        TGGCTTGGGC CCGCCAGGCT CCAGGGAAGG GTCTAGAGTG GGTCTCAACG ATTGCGTCGG ATGGTGTTTC TACATACTAC GCAGACTCCG TGAAGGGCCG
           ACCGAACCCG GGCGGTCCGA GGTCCCTTCC CAGATCTCAC CCAGAGTTGC TAACGCAGCC TACCACAAAG ATGTATGATG CGTCTGAGGC ACTTCCCGGC

           . F  T  I   S  R  D  N   S  K  N   T  L  Y   L  Q  M  N   S  L  R   A  E  D   T  A  V  Y   Y  C  A   K  V  G
201        GTTCACCATC TCCCGCGACA ATTCCAAGAA CACGCTGTAT CTGCAAATGA ACAGCCTGCG TGCCGAGGAC ACCGCGGTAT ATTACTGTGC GAAAGTTGGT
           CAAGTGGTAG AGGGCGCTGT TAAGGTTCTT GTGCGACATA GACGTTTACT TGTCGGACGC ACGGCTCCTG TGGCGCCATA TAATGACACG CTTTCAACCA

            R  D  F  D   Y  W  G   Q  G  T   L  V  T  V   S  S
301        CGTGATTTTG ACTACTGGGG TCAGGGAACC CTGGTCACCG TCTCGAGC (SEQ ID NO: 242)
           GCACTAAAAC TGATGACCCC AGTCCCTTGG GACCAGTGGC AGAGCTCG (SEQ ID NO: 243)

DOM-116    SEQ ID NO: 82
            D  I  Q  M   T  Q  S   P  S  S   L  S  A  S   V  G  D   R  V  T   I  T  C  R   A  S  Q   P  I  G   P  D  L  L .
  1        GACATCCAGA TGACCCAGTC TCCATCCTCC CTGTCTGCAT CTGTAGGAGA CCGTGTCACC ATCACTTGCC GGGCAAGTCA GCCTATTGGT CCTGATTTAC
           CTGTAGGTCT ACTGGGTCAG AGGTAGGAGG GACAGACGTA GACATCCTCT GGCACAGTGG TAGTGAACGG CCCGTTCAGT CGGATAACCA GGACTAAATG

           . W  Y  Q   Q  K  P   G  K  A  P   K  L  L   I  Y  Q   T  S  I  L   Q  S  G   V  P  S   R  F  S  G   S  G  S .
101        TGTGGTACCA GCAGAAACCA GGGAAAGCCC CTAAGCTCCT GATCTATCAG ACGTCCATTT TGCAAAGTGG GGTCCCATCA CGTTTCAGTG GCAGTGGATC
           ACACCATGGT CGTCTTTGGT CCCTTTCGGG GATTCGAGGA CTAGATAGTC TGCAGGTAAA ACGTTTCACC CCAGGGTAGT GCAAAGTCAC CGTCACCTAG

           . G  T  D   F  T  L  T   I  S  S   L  Q  P   E  D  F  A   T  Y  Y   C  Q  Q   Y  W  A  F   P  V  T   F  G  Q
201        TGGGACAGAT TTCACTCTCA CCATCAGCAG TCTGCAACCT GAAGATTTTG CTACGTACTA CTGTCAACAG TATTGGGCTT TTCCTGTGAC GTTCGGCCAA
           ACCCTGTCTA AAGTGAGAGT GGTAGTCGTC AGACGTTGGA CTTCTAAAAC GATGCATGAT GACAGTTGTC ATAACCCGAA AAGGACACTG CAAGCCGGTT

            G  T  K  V   E  I  K   R
301        GGGACCAAGG TGGAAATCAA ACGG (SEQ ID NO: 244)
           CCCTGGTTCC ACCTTTAGTT TGCC (SEQ ID NO: 245)
```

Example 8

PEGylation of DOM8-24

Site specific maleimide-PEGylation of DOM8-24 requires a solvent accessible cysteine to be provided on the surface of the protein, in this example, at the C-terminus. The cysteine residue, once reduced to give the free thiol, can then be used to specifically couple the protein to PEG via a wide range of chemistries such as maleimide or another thiol to give a disulphide. A wide range of chemical modified PEGs of different sizes and branched formats are available from Nektar (formally known as Shearwater Corp). This allows the basic dAb-cys monomer to be formatted in a variety of ways for example as a PEGylated monomer, dimer, trimer, tetramer etc. The size of the PEGs is given in kDa but can also be referred to as K (i.e. "40K PEG"=40 kDa PEG).

PCR Construction of DOM8-24cys

The site of attachment for the PEG may be placed elsewhere on the surface of the dAb as long as the targeted amino acid is solvent accessible and the resultant PEGylated protein still maintains antigen binding. Thus it is also possible to engineer the cys into any one of frameworks 1-4 of the dAb for PEGylation and still maintain some antigen binding. The following oligonucleotides were used to specifically PCR DOM8-24 with a SalI and BamHI sites for cloning and also to introduce a C-terminal cysteine residue.

```
      SalI
  1 Ala Ser Thr Glu Val Gln Leu Leu Glu Ser Gly Gly Gly Leu Val
    GCG TCG ACG GAG GTG CAG CTG TTG GAG TCT GGG GGA GGC TTG GTA
    CGC AGC TGC CTC CAC GTC GAC AAC CTC AGA CCC CCT CCG AAC CAT

 46 Gln Pro Gly Gly Ser Leu Arg Leu Ser Cys Ala Ala Ser Gly Phe
    CAG CCT GGG GGG TCC CTG CGT CTC TCC TGT GCA GCC TCC GGA TTC
    GTC GGA CCC CCC AGG GAC GCA GAG AGG ACA CGT CGG AGG CCT AAG

 91 Thr Phe Ser Asn Tyr Gln Met Ala Trp Val Arg Gln Ala Pro Gly
    ACC TTT AGT AAT TAT CAG ATG GCG TGG GTC CGC CAG GCT CCA GGG
    TGG AAA TCA TTA ATA GTC TAC CGC ACC CAG GCG GTC CGA GGT CCC

136 Lys Gly Leu Glu Trp Val Ser Ser Ile Thr Ser Glu Gly Gly Ser
    AAG GGT CTA GAG TGG GTC TCA AGT ATT ACT AGT GAG GGT GGT TCG
    TTC CCA GAT CTC ACC CAG AGT TCA TAA TGA TCA CTC CCA CCA AGC

181 Thr Tyr Tyr Ala Asp Ser Val Lys Gly Arg Phe Thr Ile Ser Arg
    ACA TAC TAC GCA GAC TCC GTG AAG GGC CGG TTC ACC ATC TCC CGC
    TGT ATG ATG CGT CTG AGG CAC TTC CCG GCC AAG TGG TAG AGG GCG

226 Asp Asn Ser Lys Asn Thr Leu Tyr Leu Gln Met Asn Ser Leu Arg
    GAC AAT TCC AAG AAC ACA CTG TAT CTG CAA ATG AAC AGC CTG CGT
    CTG TTA AGG TTC TTG TGT GAC ATA GAC GTT TAC TTG TCG GAC GCA

271 Ala Glu Asp Thr Ala Val Tyr Tyr Cys Ala Lys Pro Gly Lye Asn
    GCC GAG GAC ACC GCG GTA TAT TAC TGT GCG AAA CCG GGT AAG AAT
    CGG CTC CTG TGG CGC CAT ATA ATG ACA CGC TTT GGC CCA TTC TTA

316 Phe Asp Tyr Trp Gly Gln Gly Thr Leu Val Thr Val Ser Cys ***
    TTT GAC TAC TGG GGT CAG GGA ACC CTG GTC ACC GTC TCG TGC TAA
    AAA CTG ATG ACC CCA GTC CCT TGG GAC CAG TGG CAG AGC ACG ATT

        BamHI
361 *** Gly Ser (SEQ ID NO: 85)
    TAA GGA TCC (SEQ ID NO: 83)
    ATT CCT AGG (SEQ ID NO: 84)
```

The DNA sequence of the PCR primers used to amplify the engineered dAb are shown below.

```
Forward primer
                                          (SEQ ID NO: 86)
5'-AGTGCGTCGACGGAGGTGCAGCTGTTGGAGTCT-3'

Reverse primer
                                          (SEQ ID NO: 87)
5'-AAAGGATCCTTATTAGCACGAGACGGTGACCAGGGTTCCCTG-3'
```

The PCR reaction (50 μL volume) was set up as follows: 200 μM dNTP's, 0.4 μM of each primer, 5 μL of 10× PfuTurbo buffer (Stratagene), 100 ng of template plasmid (DOM8-24), 1 μL of PfuTurbo enzyme (Stratagene) and the volume adjusted to 50 μL using sterile water. The following PCR conditions were used: initial denaturing step 94° C. for 2 mins, then 25 cycles of 94° C. for 30 secs, 64° C. for 30 sec and 72° C. for 30 sec. A final extension step was also included of 72° C. for 5 mins. The PCR product was purified and digested with SalI and BamHI and ligated into the vector (pDOM5) which had also been cut with the same restriction enzymes. Correct clones were verified by DNA sequencing.

Expression and Purification of DOM8-24

DOM8-24 vector was transformed into HB2151 electro-competent cells. Cells carrying the dAb plasmid were selected for using 100 μg/mL carbenicillin. Cultures were set up in 2 L baffled flasks containing 500 mL of terrific broth (Sigma-Aldrich) and 100 μg/mL carbenicillin. The cultures were grown at 30° C. at 200 rpm to an O.D.600 of 1-1.5 and then induced with 1 mM IPTG (isopropyl-beta-D-thiogalactopyranoside, from Melford Laboratories). The expression of the dAb was allowed to continue for 12-16 hrs at 30° C. It was found that most of the dAb was present in the culture media. Therefore, the cells were separated from the media by centrifugation (8,000×g for 30 mins), and the supernatant used to purify the dAb. Per litre of supernatant, 10 mL of Streamline Protein A (Amersham Biosciences) was added and the dAb allowed to batch bind with stirring for 3 hours at room temperature, or overnight at 4° C. The resin was then allowed to settle under gravity for an hour before the supernatant removed. The agarose was then packed into a XK 16 column (Amersham Pharmacia) and was washed with 10 column volumes of 2×PBS. The bound dAb was eluted with 100 mM glycine pH 3.0 and protein containing fractions were then neutralized by the addition of ⅕ volume of 1 M Tris pH 8.0.

PEGylation of DOM8-24cys Using MAL Activated PEG Monomer PEGylation

The cysteine residue which had been engineered onto the surface of the VH dAb was specifically modified with a single linear or branched PEG-MAL to give monomeric modified protein. mPEG-MAL formats which may be used to PEGylate a monomeric VH or Vk dAb. The PEGs may be of MW from 500 to 60,000 (eg, from 2,000 to 40,000) in size.

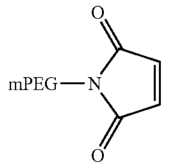

mPEG-MAL

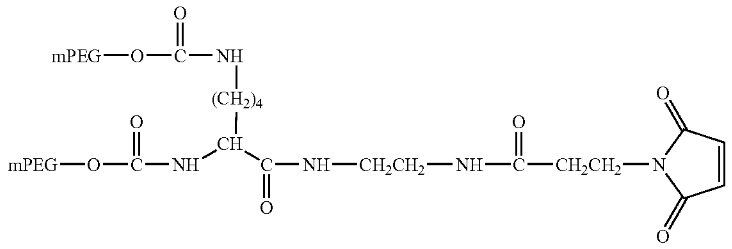

mPEG2-MAL 2.5 ml of 500 μM DOM8-24cys was reduced with 5 mM dithiothreitol and left at room temperature for 20 minutes. The sample was then buffer exchanged using a PD-10 column (Amersham Pharmacia). The column had been pre-equilibrated with 5 mM EDTA, 20 mM sodium phosphate pH 6.5, 10% glycerol, and the sample applied and eluted following the manufactures guidelines. The eluted sample (3.5 ml of ~360 μM dAb) was placed on ice until required. A four fold molar excess of 30K PEG-MAL or 40K PEG2-MAL (Nektar) was weighed out and added directly to the reduced dAb solution and gently mixed until the polymer had dissolved. The reaction was left to proceed at room temperature for 3 hours.

Purification of 30K and 40K PEGylated DOM8-24cys Monomer

The PEGylated dAb was purified using cation exchange chromatography as the isoelectric point (pI) of the protein is ~8.40 μL of 40% glacial acetic acid was added per mL of the 30K or 40K PEG DOM8-24cys reaction to reduce the pH to ~4. The sample was then applied to a 1 mL Resource S cation exchange column (Amersham Pharmacia), which had been pre-equilibrated with 50 mM sodium acetate pH 4.0. The PEGylated material was separated from the unmodified dAb by running a linear sodium chloride gradient from 0 to 500 mM over 20 column volumes. Fractions containing PEGylated dAb only were identified using SDS-PAGE and then pooled and the pH increased to 8 by the addition of ⅕ volume of 1M Tris pH 8.0

In Vitro Functional Binding Assay: CD40 Ligand Receptor Assay (CD40L RBA)

Figure 9:
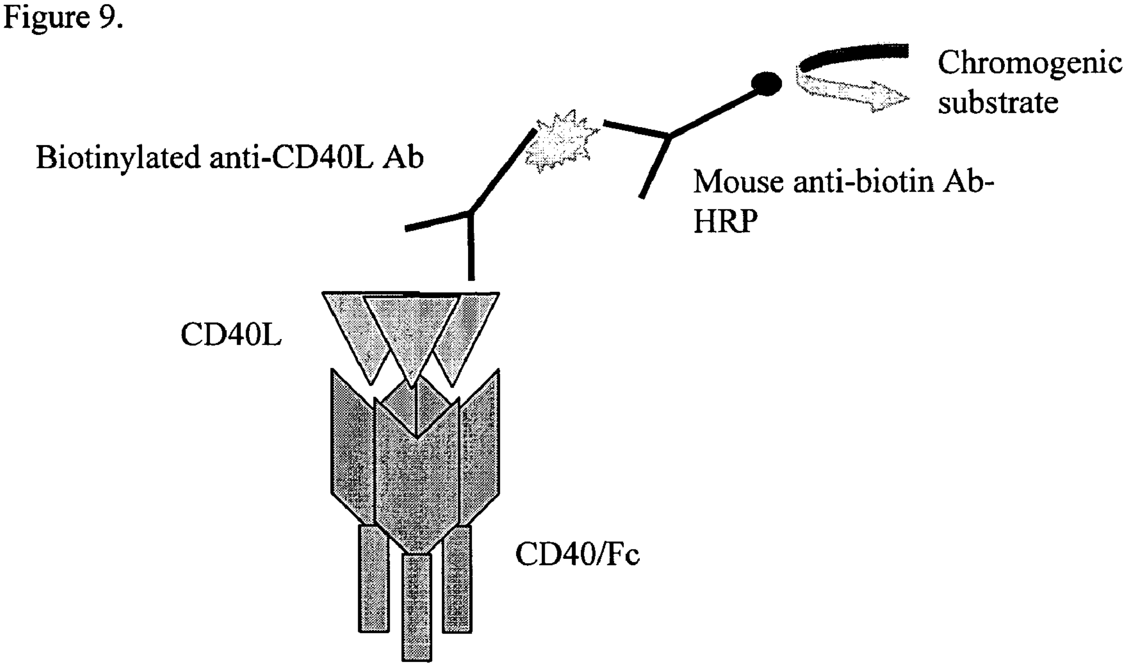
FIG. 9 is a schematic showing the CD40L RBA. The soluble proteins obtained from R&D Systems are CD40/Fc=homodimer and CD40L=homotrimer).

The CD40L assay was used to measure the binding of CD40L to CD40 and the ability of binding entities (including monovalent antibody fragments such a dAbs) to block this interaction, as shown below in FIG. 9.

A 96 well Nunc Maxisorp assay plate was coated overnight at 4° C. with 100 μl per well of recombinant human CD40/Fc (R&D Systems) at 0.5 μg/ml in carbonate buffer. The plate was washed 3 times with 300 μl of 0.05% Tween/PBS and 3 times with 300 μl of PBS using a Tecan plate washer. The wells were blocked using 200 μl of PBS containing 2% (w/v) BSA and incubated for a minimum of 1 h at room temperature. The wells were washed as above, then 50 μl of purified dAb protein was added to each well. To each well 50 μl of CD40L, at 6 ng/ml in diluent (for a final concentration of 3 ng/ml), was also added and the plate incubated for 1 hr at room temperature. The plate was washed as described previously and 100 μl biotinylated anti-CD40L antibody, 0.5 μg/ml in diluent, was added and incubated for 1 hr at room temperature. The plate was washed as described above, then 100 μl HRP conjugated anti-biotin antibody (1:5000 dilution in diluent) added to each well and the plate incubated for 1 hr at room temperature. The plate was washed again as described above using a Tecan plate washer and the assay developed using 100 μl of SureBlue 1-Component TMB MicroWell Peroxidase solution (the plate was left at room temperature for up to 20 min). The reaction was stopped by the addition of 100 μl 1 M hydrochloric acid. The $OD_{450nm}$ of the plate was assayed within 30 minutes of acid addition. The $OD_{450nm}$ is proportional to the amount of bound streptavidin-HRP conjugate, therefore the greater the degree of dAb inhibition the lower the $OD_{450nm}$ of the resulting signal. The following controls were included; 0 ng/ml CD40L (diluent only), 3 ng/ml CD40L and 3 ng/ml CD40L with 1 μg/ml anti-CD40L antibody.

Figure 10:
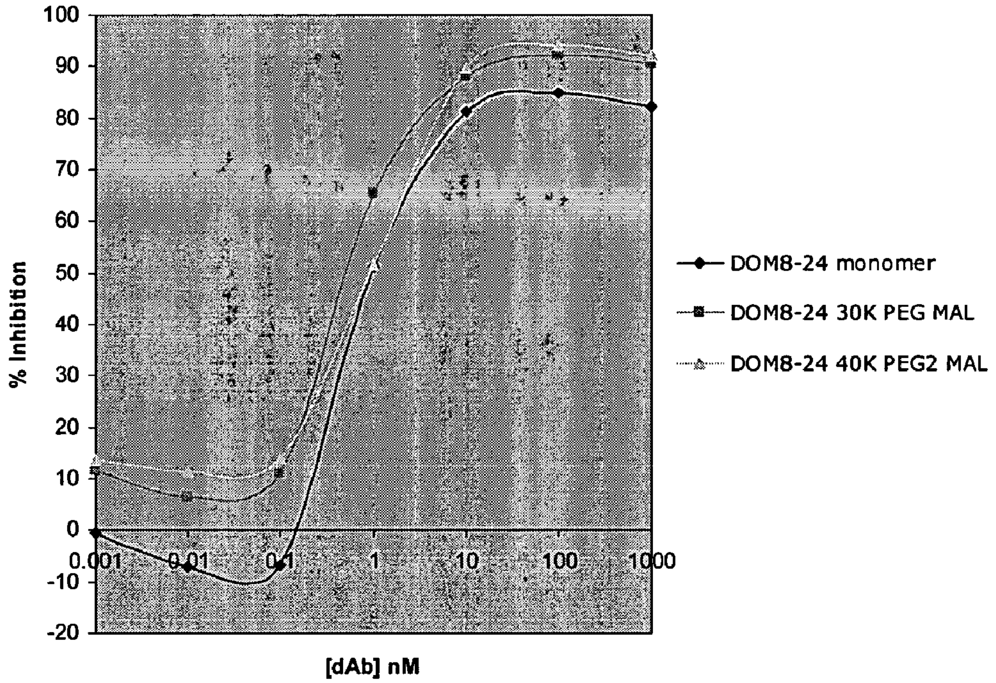
FIG. 10 shows the results of a receptor binding assay which demonstrates the affinity of PEGylated DOM8-24cys with either 30K PEG MAL or 40K PEG2-MAL.

The results of the CD40L RBA are shown in FIG. 10. It can be seen that PEGylated DOM8-24cys has a similar affinity for CD40L as the unmodified protein. The size of the polymer attached (either 30 or 40K) does not seem to significantly affect the IC 50 of ~1 nM.

Example 9

Generation and Expression of a Dual Specific dAb Dimer (DOM7h-26-DOM-24)

A dual specific dAb dimer was constructed essentially as described in WO2004/003019 and as described below.

A PCR fragment introducing 5' NotI and 3' EcoRI restriction sites into the DOM-24 DNA sequence was generated using the primers VH-5'-NotI (5'-GTATGTCTGGCGGCCG-CAGAGGTGCAGCTGTTGGAGTCTGGGG-GAGGCTTG-3'; SEQ ID NO: 90) and VH-NO-XhoI (5'-TAGAATTCTTATTAGCTGGAGACGGTGACCAGGGT-3'; SEQ ID NO: 91). The PCR product was electrophoresed on a 1% agarose gel and the appropriate band was excised and gel cleaned using the Qiagen Gel Extraction Kit. The purified DNA was digested with NotI and EcoRI for 1 hour at 37° C. and then the digested DNA fragment purified using the Qiagen PCR Cleanup Kit. The digested PCR product was ligated using T4 DNA ligase into the vector pCH3, derived from pPICz-alpha (Invitrogen Ltd, Paisley, UK), which had been previously been digested with NotI and EcoRI, thereby enabling the ligation of the DOM-24 DNA sequence 3' relative to the anti-human serum albumin dAb DNA sequence (DOM7h-26). One micro-litre of the ligation mix was used to electroporate 50 μl of *E. coli* TOP10F' (0.2 mm diameter cuvettes; 25 μFD; 200Ω; 2.500 kV) using a Biorad Genepulser II with pulse controller module. The electroporated cells were immediately resuspended in 1 ml low salt LB medium (10 g/l tryptone; 5 g/l yeast extract; 5 g/l NaCl; pH to 7.5 with 4 M NaOH; then autoclaved at 121° C. for 15 min) and 100 μl of the cell suspension plated onto low salt LB agar plates (10 g/l tryptone; 5 g/l yeast extract; 5 g/l NaCl; pH to 7.5 with 4 M NaOH; 15 g/l agar; then autoclaved at 121° C. for 15 min) supplemented with 25 μg/ml zeocin (Invitrogen Ltd, Paisley, UK) and grown at 37° C. overnight.

Several individual clones from the overnight growth plate were analysed by DNA sequencing using the alpha-factor sequencing primer (5'-TACTATTGCCAGCATTGCTGC-3'; SEQ ID NO: 92) and the reverse 3' AOX1 primer (5'-GCAAATGGCATTCTGACATCC-3': SEQ ID NO: 93). A plasmid prep derived from a single clone containing the desired DNA sequence was made by inoculating 100 ml of low salt LB medium supplemented with 25 μg/ml zeocin and grown overnight at 37° C. with shaking at 250 rpm, followed by purification of the plasmid DNA using a Qiagen Plasmid Midi Prep Kit (Qiagen).

The concentration and purity of the DNA was determined by measuring the absorbance at 280 nm and 260 nm. Between 10 and 50 μg of DNA was digested with PmeI, SacI or BstXI restriction enzymes and the DNA digestion confirmed by analysis on a 0.8% agarose gel. The digested DNA was purified using the Qiagen Qiaex II Kit (Qiagen) and the DNA eluted into 10 μl purified water per 20 μl of Qiaex II resin.

Competent yeast cells were made by streaking the wild type *Pichia pastoris* strain X33 onto a YPD agar plate (for 1 litre of media: 20 g peptone from meat type 1; 10 g yeast extract; 20 g agar dissolved in 900 ml water and sterilise by autoclaving at 121° C. for 15 minutes; followed by the aseptic addition of 100 ml of 20% destrose and the desired amount of zeocin once the media had cooled below 50° C.) and grown at 30° C. for 36-48 h until colonies appeared. A single colony was inoculated into 5 ml of YPD medium (as for YPD agar, without the addition of 20 g agar) and grown overnight in a 50 ml baffled flask at 30° C. with shaking at 250 rpm. Five hundred millilitres of YPD medium in a 2 l baffled flask was inoculated with 0.1-0.5 ml of the overnight culture and grown at 30° C. with shaking at 250 rpm overnight to an OD600 of approximately 1.3-1.5. The culture was cooled on ice then the *Pichia* harvested by centrifugation at 1500 g for 5 min at 4° C. The supernatant was discarded and the pellet resuspended in 500 ml ice cold ultrapure water. The *Pichia* were recovered again by centrifugation at 1500 g for 5 min at 4° C. The pellet was resuspended and centrifuged for a further three times, the first time in 250 ml ice cold ultrapure water, then twice in 20 ml ice cold 1M sorbitol. The competent *Pichia* were kept on ice for up to 6 hours prior to use.

To transform the *Pichia* by electroporation, between 10 to 20 μg of linearised vector in 10 μl of water was mixed with 80 μl of competent *Pichia* in a precooled microfuge tube and incubate on ice for 5 min. The *Pichia* mixture was then transferred to a precooled 0.2 cm gap electroporation cuvette, and electroporated: 25 μF, resistance set to infinity, 0.54 kV in a Biorad Genepulser II with pulse controller module. Immediately 1 ml ice cold 1 M sorbitol was added to the electroporation cuvette and the electroporated *Pichia* transferred into a 15 ml polypropylene tube. This culture was incubated at 30° C. without shaking for 2 hours to allow the cells to recover. The cells were then plated onto YPDS agar plates (YPD agar supplemented with 1 M sorbitol) and zeocin added to final concentrations of 100 μg/ml, 500 μg/ml, 1000 μg/ml, and 2000 μg/ml. The plates were incubated at 30° C. in the dark for 2-10 days until colonies appeared. Several clones were picked from each plate and restreaked onto YPD plates supplemented with the same amount of zeocin as they were originally selected against. For small to medium scale shaking flask expression the Mut status of each X33 clone was not determined.

Individual restreaked colonies were used to inoculate 50 ml of BMGY medium (for 1 litre of medium: 20 g peptone from meat type 1; 10 g yeast extract were dissolved in 700 ml with water and sterilise by autoclaving at 121° C. for 15 minutes; followed by the aseptic addition of 100 ml 1 M KPO4 pH 6.0; 100 ml 10% glycerol; and 100 ml 10×YNB (Yeast Nitrogen Base); 2 ml of 500× biotin) in a 250 ml flask and grown at 30° C. with shaking at 250 rpm until an OD600 of 2 to 6 was attained. The *Pichia* was recovered by centrifugation at 1500 g for 5 min at room temperature. The resulting pellet was resuspended in 20 ml BMMH medium (as for BMGY medium except the 100 ml 10% glycerol was replaced with 100 ml of 5% methanol), and returned to a fresh 250 ml baffled flask and incubated at 30° C. with shaking at 250 rpm for up to 5 days post induction. At 24 h intervals, 0.5 ml samples were recovered and assessed by analysis of the supernatant by SDS-PAGE.

Dimer dAb was purified from the culture supernatant using Streamline protein-A matrix (Amersham Biosciences). Following binding of the dimer dAb, the matrix was transferred to an empty 20 ml chromatography column containing a frit and the supernatant allowed to flow through the column, retaining the matrix. The matrix was washed with 10 times the matrix volume of high salt buffer (10 mM Phosphate buffer, 2.7 mM KCl, 487 mM NaCl, pH 7.4). The bound protein was eluted with 0.1 M glycine pH 3 supplemented with 0.15 M NaCl and 0.8 ml fractions were collected which were immediately neutralised with the addition of 0.2 ml of 1 M Tris-HCl pH 8.0.

Simultaneous Antigen Binding of the Dual Specific dAb Dimer

Figure 11:
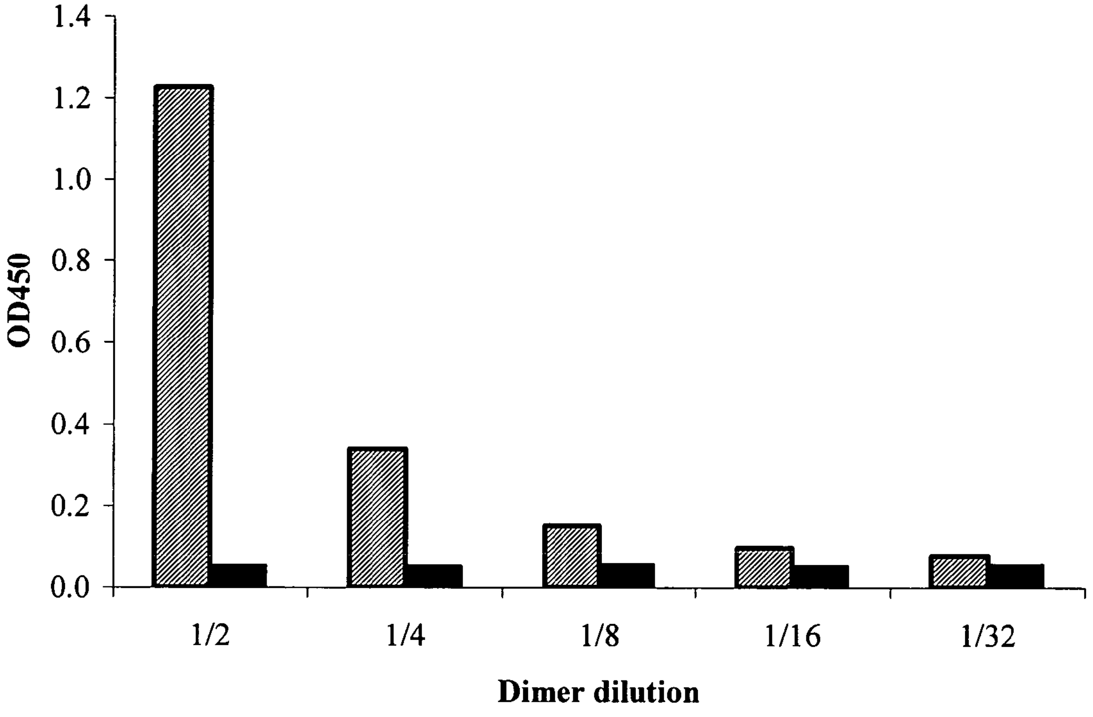
FIG. 11 shows the results of an assay to assess the simultaneous binding of a dual specific dimer to HSA and CD40L (shaded bars). Binding to control BSA antigen is also shown (solid bars).

To demonstrate that the dual specific dimeric dAb was functional and could bind both antigens simultaneously, an antigen binding ELISA was performed. Fifty microlitres per well of human serum albumin at 100 μg/ml in PBS was coated on to a Maxisorb ELISA plate (Nunc) overnight at 4° C. The plate was washed 3 times with 250 μl/well of PBS supplemented with 0.1% (v/v) Tween 20 (Sigma). The plate was then blocked for 1 h at room temperature with 200 μl per well of PBSM (PBS supplemented with 2% (w/v) low fat milk powder). The plate was washed as before, then 50 μl per well of doubling dilutions of the dimer dAb in PBSM were added and incubated for 1 hour at room temperature. The plate was washed as before then 50 μl per well of a 5 nM solution of biotinylated CD40L in PBSM added and incubated for 1 hour at room temperature. The plate was washed as before then 50 μl per well of streptavidin-HRP (Amersham Biosciences) diluted 1 in 4000 in PBSM was added and incubated for 1 hour at room temperature. The plate was washed 4 times with 250 μl/well of PBS supplemented with 0.1% (v/v) Tween 20, followed by two washes with 250 μl/well of PBS. The ELISA was developed by adding 50 μl per well of SureBlue 1-Component TMB MicroWell Peroxidase solution (KPL, Gaithersberg, Md.) and incubated at room temperature for several minutes until the desired colour intensity was obtained. The reaction was stopped by the addition of 100 μl of 1 M hydrochloric acid and read at 450 nm (FIG. 11).

Generation and Expression of a Dual Specific Fab (DOM7h-2:CK DOM-24:CH)

The produce a dual specific Fab the method used was essentially the same method as described for the dual specific dAb dimer (DOM7h-26-DOM-24) except that the DNA for the DOM7h-2 and DOM-24 dAbs were cloned into separate pPICz-alpha based vectors containing the human CK or human CH1 domain respectively. Each of the two vectors were designed to enable the expression of a single polypeptide consisting of the CH1 or CK domain fused in frame to the 3' end of the appropriate dAb. To obtain expression of the complete Fab fragment, competent *Pichia pastoris* strain X33 were cotransformed with two linearised vectors. Purification was as described for the dimer Fab.

Simultaneous Antigen Binding of the Dual Specific Fab

Figure 12:
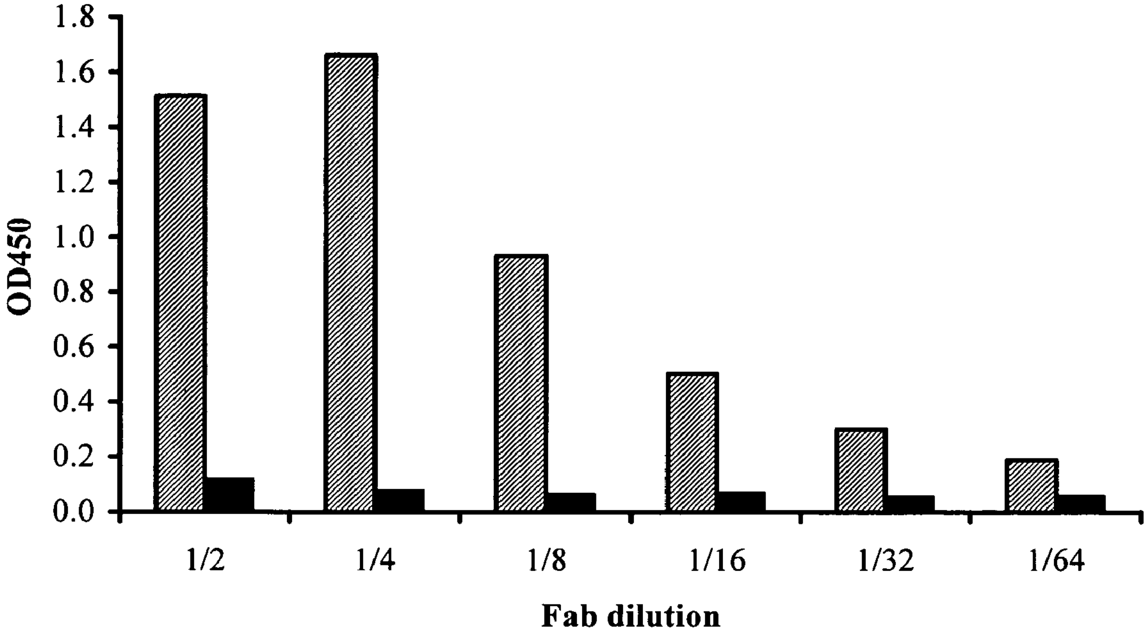
FIG. 12 shows the results of an assay to assess the simultaneous binding of a dual specific Fab to HSA and CD40L (shaded bars). Binding to control skimmed mild powder antigen is also shown (solid bars).
Figure 13:
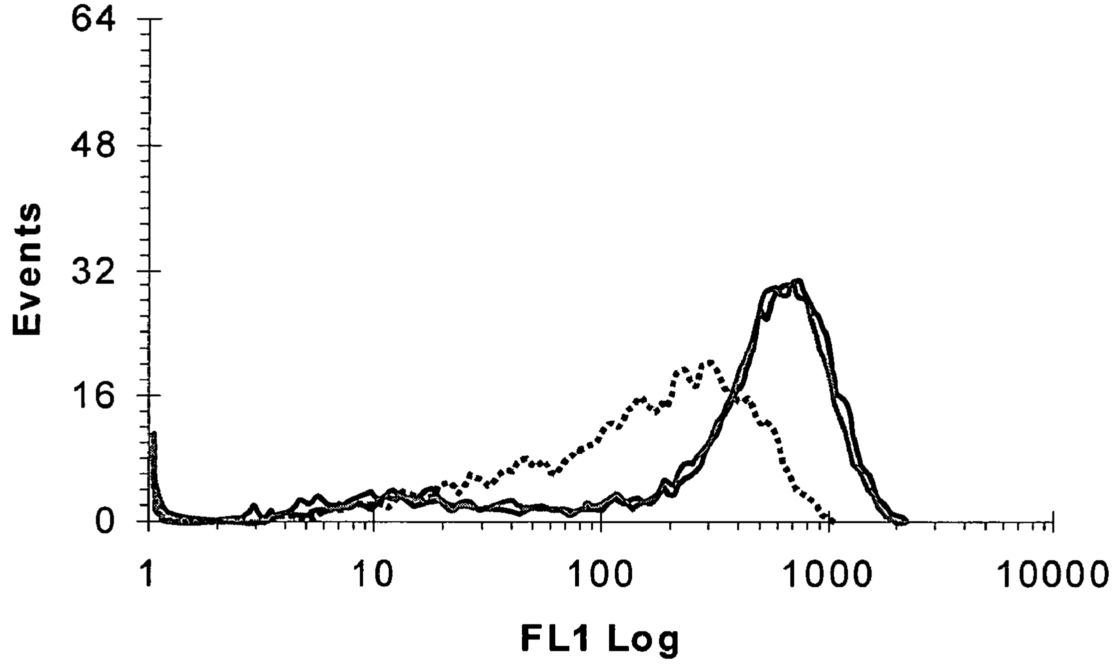
FIG. 13 shows the results of FACS analysis of the inhibitory effect of monomeric DOM-24 (grey dotted line). Control stimulated cells ae shown as the solid black line and a control dAb is shown as the grey solid line.

The simultaneous antigen binding of the dual specific Fab was carried out using the same assay as described for the dual specific dAb dimer above. The results are shown in FIG. 12.

Inhibition of CD40 Mediated CD54 Upregulation Disruption of CD40/CD40L Interaction in L3055 Cells.

Monomeric dAb molecules were assayed for their ability to disrupt the binding of cellularly associated CD40L to CD40. This was determined by measuring the level inhibition of CD40 mediated CD54 upregulation on group 1 Burkitt lymphoma cell line L3055 by FACS. CD40 displayed on the L3055 cells was stimulated by CD40L expressed on the surface of fibroblasts (typically mouse L-cells) transfected with the CD40L gene as previously described by Garrone et al., 1995 (Garrone P., Neidhardt E. V., Garcia E., Galibert L., van Kooten C., Banchereau J. (1995) J Exp Med 182, 1265-1273.)

Samples containing the dAbs were preincubated with the L-cells cells for 1 hour prior to the addition of the L3055 cells. Both cell lines were co-cultured for 22 hours following which the L-cells were stained for FACS analysis, as described by Baker et al., 1998 (Baker, M. P., Eliopoulos, A. G., Young, L. S., Armitage, R. J., Gregory, C. D., Gordon, J. (1998) Blood, 92 (8), 2830-2843) and by Challa et al., 2002 (Challa, A., Eliopoulos, A. G., Holder, M. J., Burguete, A. S., Pound, J. D., Chamba, A., Grafton, G., Armitage, R. J., Gregory, C. D., Martinez-Valdez, H., Young, L. and Gordon, J. (2002) Blood, 99 (9), 3411-3418.

The FACS analysis of DOM-24 (monomeric form) at a concentration of 12 μm showed inhibition.

Figure 14:
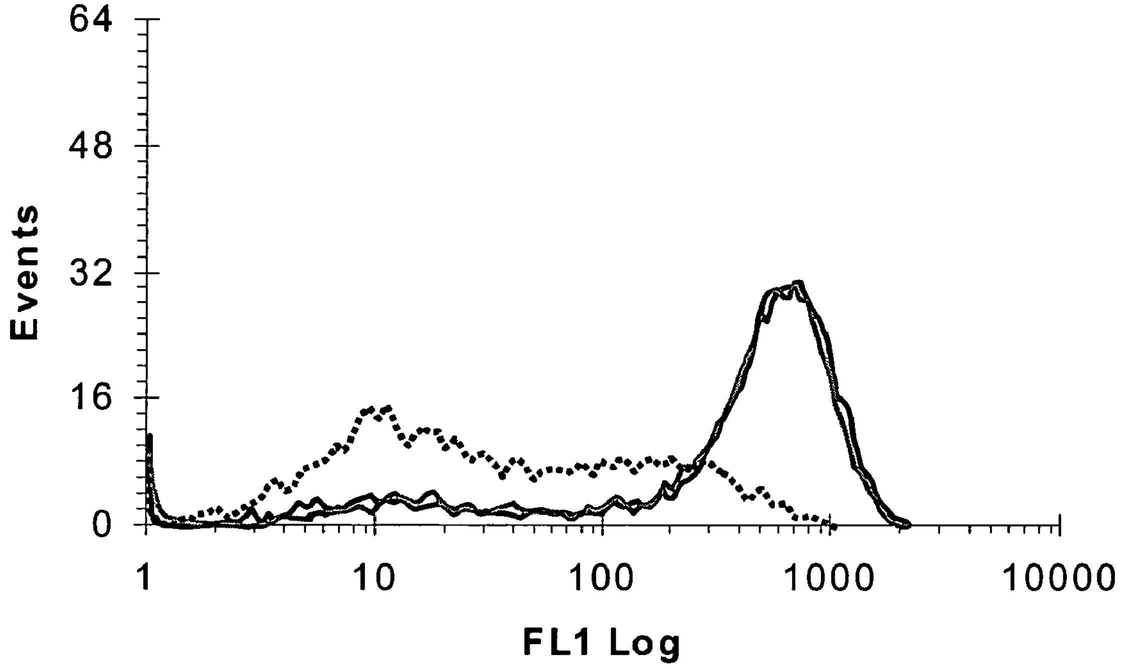
FIG. 14 shows the results of FACS analysis of the inhibitory effect of the Vk dAb DOM-116 (dotted line). Control stimulated cells are shown as the solid black line and a control dAb is shown as the grey solid line.

FACS analysis of the Vk DOM-116 at a concentration of 9 μM showed inhibition compared with a control blank dAb and the stimulated cell trace (FIG. 14).

Effect of Anti-CD40L Therapy on Primary Immune Response to KLH Immunisation.

To show the effect of anti-CD40L therapy on the primary immune response to KLH immunization a similar study to that described by Gobburu, J. V. S. et al., 1998 can be carried out (Gobburu, J. V. S., Tenhoor, C., Rogge, M. C., Frazier, D. E., Thomas, D., Benjamin, C., Hess, D. M., & Jusko, W. J. (1998) JPET, 286, 925-930.

A study example could be as follows: Cynomolgus monkeys are injected with an anti-CD40L antibody or dAb format at a dosing of 10 mg/kg at time 0 h, 168 h and 336 h. At 24 h the animals receive a single intradermal injection of 100 μg highly purified keyhole limpet hemocyanin (KLH). The serum is tested for a KLH response prior to the start and following completion of the study. The animals are allowed to recover for a suitable time to ensure that the dAb molecule has cleared the circulation, then injected with KLH (without dAb) to determine if the animal can raise an immune response against KLH. Alternative antigens can be used for the study if an earlier response to KLH is detected prior to the start of the study.

The immune response to KLH will be measured by a suitable ELISA, RIA or antibody titer assay. It is anticipated that the results would show that that the PEGlyated monomeric DOM-24 would suppress the animals immune response to KLH. This would be shown in the reduction of the antibody titer compared to a positive control. The results could be normalized such that the positive control was deemed to be 100 and the reduction in immune response after the administration of the dAbs would be in the range of 10 to 90% i.e. 90 to 10 units.

```
Sequence of the DOM7h-26-DOM-24
LEKREVQLLESGGGLVQPGGSLRLSCTASGFTFDEYNMSWVRQAPGKGLEWVSTILPH    (SEQ ID NO: 88)

GDRTYYADSVKGRFTISRDNSKNTLYLQMNSLRAEDTAVYYCAKQDPLYRFDYWGQG

TLVTVSSAAAEVQLLESGGGLVQPGGSLRLSCAASGFTFSNYQMAWVRQAPGKGLEW

VSSITSEGGSTYYADSVKGRFTISRDNSKNTLYLQMNSLRAEDTAVYYCAKPGKNFDY

WGQGTLVTVSS

Sequence of the DOM7h-26
DIQMTQSPSSLSASVGDRVTITCRASQKIATYLNWYQQKPGKAPKLLIYRSSSLQSAVPS  (SEQ ID NO: 89)

RFSGSGSGTVFTLTISSLQPEDFATYYCQQTYAVPPTFGQGTKVEIKR
```

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. An isolated antibody single variable domain polypeptide which has an amino acid sequence at least 85% identical to a sequence selected from the group consisting of SEQ ID NOs 7-82, which antibody polypeptide specifically and monovalently binds CD40L.

2. The antibody single variable domain polypeptide of claim 1 which inhibits binding of CD40L to CD40 with an $IC_{50}$ in the range of 20 pM to 1.5 μM.

3. A composition comprising the isolated antibody single variable domain polypeptide of claim 1 which is fused to an isolated antibody variable polypeptide which binds a ligand other than CD40L.

4. The composition of claim 3 wherein said isolated antibody single variable domain polypeptide which binds a ligand other than CD40L binds a ligand selected from the group consisting of HSA, TNFα, IL-1, IL-2, IL-4, IL-6, IL-8, IL-12, IL-18, IFN-γ, CD2, CD4, CD8, CTLA4, LFA-1, LFA-3 and VLA-4.

5. The antibody single variable domain polypeptide of claim 1 which is free of an Fc domain.

6. The antibody single variable domain polypeptide of claim 5 wherein the presence of said antibody polypeptide in a standard platelet aggregation assay does not result in aggregation of more than 25% over the aggregation observed in a negative control assay.

7. The antibody single variable domain polypeptide of claim 1 which dissociates from human CD40L with a Kd in the range of 50 nM to 20 pM, inclusive, as determined by surface plasmon resonance.

8. The antibody single variable domain polypeptide of claim 1 wherein said polypeptide inhibits the binding of CD40L to CD40.

9. The antibody single variable domain polypeptide of claim 1 wherein binding of said polypeptide to CD40L does not increase CD40 activity by more than 5%.

10. The antibody single variable domain polypeptide of claim 1 wherein binding of said polypeptide to CD40L does not increase JNK phosphorylation in Jurkat T-cells by more than 5%.

11. The antibody single variable domain polypeptide of claim 1 wherein binding of said polypeptide to CD40L does not increase IFN-γ secretion by Jurkat T-cells co-stimulated with anti-CD3 antibody by more than 5%.

12. The antibody single variable domain polypeptide of claim 1 wherein said single-antibody single variable domain is a $V_H$ or a $V_L$ domain.

13. A PEG-linked antibody single variable domain polypeptide comprising the antibody single variable domain polypeptide of claim 1 linked to PEG.

14. The PEG-linked antibody single variable domain polypeptide of claim 13 which has a hydrodynamic size of at least 24 kD.

15. The PEG-linked antibody single variable domain polypeptide of claim 13 wherein said PEG is linked to said antibody at a cysteine or lysine residue.

16. The PEG-linked antibody single variable domain polypeptide of claim 13 wherein the total PEG size is in the range of from 20 to 60 kD.

17. The PEG-linked antibody single variable domain polypeptide of claim 13 which has a hydrodynamic size of at least 200 kD.

18. The PEG-linked antibody single variable domain polypeptide of claim 13 which has an increased in vivo half-life relative to the same polypeptide composition lacking linked polyethylene glycol.

19. The PEG-linked antibody single variable domain polypeptide of claim 13 wherein the tα-half life of the polypeptide composition is increased by 10% or more.

20. The PEG-linked antibody single variable domain polypeptide of claim 13 wherein the tα-half life of the polypeptide composition is in the range of 0.25 minutes to 12 hours.

21. The PEG-linked antibody single variable domain polypeptide of claim 13 wherein the tβ-half life of the polypeptide composition is increased by 10% or more.

22. The PEG-linked antibody single variable domain polypeptide of claim 13 wherein the tβ-half life is in the range of 12 to 48 hours.

23. The antibody single variable domain polypeptide of claim 1 wherein said antibody polypeptide is linked to human serum albumin (HSA).

24. The antibody single variable domain polypeptide of claim 23 which has an increased in vivo half-life relative to the same antibody single variable domain polypeptide lacking linked HSA.

25. The antibody single variable domain polypeptide of claim 23 wherein the tα-half life of the polypeptide composition is increased by 10% or more.

26. The antibody single variable domain polypeptide of claim 23 wherein the tα-half life of the polypeptide composition is in the range of 0.25 minutes to 12 hours.

27. The antibody single variable domain polypeptide of claim 23 wherein the tβ-half life of the polypeptide composition is increased by 10% or more.

28. The antibody single variable domain polypeptide of claim 23 wherein the tβ-half life is in the range of 12 to 48 hours.

29. The antibody single variable domain polypeptide of claim 1 which comprises an amino acid sequence selected from the group consisting of SEQ ID NOs 7-82.

30. The antibody single variable domain polypeptide of claim 23 which further comprises an antibody single variable domain polypeptide which binds a ligand other than CD40L.

31. The composition of claim 30 wherein said antibody single variable domain polypeptide which binds a ligand other than CD40L binds a ligand selected from the group consisting of HSA, TNFα, IL-1, IL-2, IL-4, IL-6, IL-8, IL-12, IL-18, IFN-γ, CD2, CD4, CD8, CTLA4, LFA-1, LFA-3 and VLA-4.

32. The antibody single variable domain polypeptide of claim 1 comprising a $V_H$ domain that is not a camelid or murine immunoglobulin variable domain.

33. The antibody single variable domain polypeptide of claim 32 comprising a $V_H$ domain that does not contain one or more amino acids that are specific to Camelid immunoglobulin variable domains as compared to human $V_H$ domains.

34. A pharmaceutical formulation comprising the antibody single variable domain polypeptide of claim 1.

35. An isolated antibody single variable domain polypeptide comprising the sequence of SEQ ID NO: 26 or a sequence at least 85% identical thereto, wherein said isolated antibody single variable domain polypeptide binds CD40L.

36. An isolated antibody single variable domain polypeptide comprising the sequence of SEQ ID NO: 26, wherein said isolated antibody single variable domain polpeptide binds CD40L.

37. An isolated antibody single variable domain polypeptide consisting of the sequence of SEQ ID NO: 26.

38. An isolated antibody single variable domain polypeptide comprising the sequence of SEQ ID NO: 85, wherein said isolated antibody single variable domain polypeptide binds CD40L.

39. The isolated antibody single variable domain polypeptide of claim 1 wherein said antibody single variable domain polypeptide is a human antibody single variable domain polypeptide.

40. The pharmaceutical formulation of claim 34, wherein said pharmaceutical formulation is an extended release formulation.

* * * * *

UNITED STATES PATENT AND TRADEMARK OFFICE

CERTIFICATE OF CORRECTION

PATENT NO. : 7,563,443 B2
APPLICATION NO. : 11/102512
DATED : July 21, 2009
INVENTOR(S) : Grant et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this
Twenty-third Day of August, 2011

David J. Kappos
*Director of the United States Patent and Trademark Office*

```
                    SEQUENCE LISTING


<160> NUMBER OF SEQ ID NOS: 247

<210> SEQ ID NO 1
<211> LENGTH: 116
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115


<210> SEQ ID NO 2
<211> LENGTH: 288
<212> TYPE: DNA
<213> ORGANISM: Homo sapiens

<400> SEQUENCE: 2

gaggtgcagc tgttggagtc tgggggaggc ttggtacagc ctggggggtc cctgcgtctc      60

tcctgtgcag cctccggatt cacctttagc agctatgcca tgagctgggt ccgccaggct     120

ccagggaagg gtctagagtg ggtctcagct attagtggta gtggtggtag cacatactac     180

gcagactccg tgaagggccg gttcaccatc tcccgtgaca attccaagaa cacgctgtat     240

ctgcaaatga acagcctgcg tgccgaggac accgcggtat attactgt                  288


<210> SEQ ID NO 3
<211> LENGTH: 108
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105


<210> SEQ ID NO 4
<211> LENGTH: 324
<212> TYPE: DNA
<213> ORGANISM: Homo sapiens

<400> SEQUENCE: 4

gacatccaga tgacccagtc tccatcctcc ctgtctgcat ctgtaggaga ccgtgtcacc      60

atcacttgcc gggcaagtca gagcattagc agctatttaa attggtacca gcagaaacca     120

gggaaagccc ctaagctcct gatctatgct gcatccagtt tgcaaagtgg ggtcccatca     180

cgtttcagtg gcagtggatc tgggacagat ttcactctca ccatcagcag tctgcaacct     240

gaagattttg ctacgtacta ctgtcaacag agttacagta cccctaatac gttcggccaa     300

gggaccaagg tggaaatcaa acgg                                            324


<210> SEQ ID NO 5
<211> LENGTH: 120
<212> TYPE: PRT
<213> ORGANISM: Homo sapiens

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Ile Ser Asp Glu
            20                  25                  30

Asp Met Gly Trp Val Arg Gln Ala Pro Gly Lys Gly Leu Glu Trp Val
        35                  40                  45

Ser Ser Ile Tyr Gly Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ala Leu Glu Pro Leu Ser Glu Pro Leu Gly Phe Trp Gly Gln
            100                 105                 110

Gly Thr Leu Val Thr Val Ser Ser
        115                 120


<210> SEQ ID NO 6
<211> LENGTH: 108
<212> TYPE: PRT
<213> ORGANISM: Artificial
<220> FEATURE:
<223> OTHER INFORMATION: Primary amino acid sequence of Vk dummy

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

-continued

```
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105


<210> SEQ ID NO 7
<211> LENGTH: 116
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Met Trp Val Arg Gln Ala Pro Gly Lys Gly Leu Glu Trp Val
        35                  40                  45

Ser Thr Ile Thr Ser Asp Gly Ile Ser Thr Tyr Tyr Ala Asp Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Arg Phe Phe Asp Tyr Trp Gly Gln Gly Thr Leu Val
            100                 105                 110

Thr Val Ser Ser
        115


<210> SEQ ID NO 8
<211> LENGTH: 116
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Glu Met Thr Trp Val Arg Gln Ala Pro Gly Lys Gly Leu Glu Trp Val
        35                  40                  45

Ser Ser Ile Thr Ser Asp Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asn Pro Pro Phe Asp Tyr Trp Gly Gln Gly Thr Leu Val
            100                 105                 110

Thr Val Ser Ser
        115
```

-continued

<210> SEQ ID NO 9
<211> LENGTH: 116
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Gly Tyr
20 25 30

Glu Met Ala Trp Val Arg Gln Ala Pro Gly Lys Gly Leu Glu Trp Val
35 40 45

Ser Ser Ile Thr Ser Asp Gly Thr Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Leu Arg Phe Asp Tyr Trp Gly Gln Gly Thr Leu Val
100 105 110

Thr Val Ser Ser
115

<210> SEQ ID NO 10
<211> LENGTH: 116
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asn Leu Tyr
20 25 30

Glu Met Thr Trp Val Arg Gln Ala Pro Gly Lys Gly Leu Glu Trp Val
35 40 45

Ser Ser Ile Thr Ser Asp Gly Val Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ala Gly Val Ile Phe Asp Tyr Trp Gly Gln Gly Thr Leu Val
100 105 110

Thr Val Ser Ser
115

<210> SEQ ID NO 11
<211> LENGTH: 108
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1 5 10 15

Asp Arg Val Thr Ile Thr Cys Arg Ala Ser Gln Phe Ile Asp Thr Ser
20 25 30

Leu Glu Trp Tyr Gln Gln Lys Pro Gly Lys Ala Pro Lys Leu Leu Ile
35 40 45

-continued

```
Tyr Asp Gly Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Tyr Trp Val Leu Pro Leu
                85                  90                  95

Thr Phe Gly Gln Gly Thr Lys Val Glu Ile Lys Arg
            100                 105


<210> SEQ ID NO 12
<211> LENGTH: 117
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Ala Tyr
            20                  25                  30

Asp Met Ser Trp Val Arg Gln Ala Pro Gly Lys Gly Leu Glu Trp Val
        35                  40                  45

Ser Trp Ile Asp Glu Trp Gly Leu Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Thr Pro Glu Glu Phe Asp Tyr Trp Gly Gln Gly Thr Leu
            100                 105                 110

Val Thr Val Ser Ser
        115


<210> SEQ ID NO 13
<211> LENGTH: 116
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Glu Met Ser Trp Val Arg Gln Ala Pro Gly Lys Gly Leu Glu Trp Val
        35                  40                  45

Ser Gly Ile Asp Gly Glu Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Ser Phe Asp Tyr Trp Gly Gln Gly Thr Leu Val
            100                 105                 110

Thr Val Ser Ser
        115


<210> SEQ ID NO 14
```

-continued

```
<211> LENGTH: 118
<212> TYPE: PRT
<213> ORGANISM: Homo sapiens

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Leu Tyr
            20                  25                  30

Glu Met Ala Trp Val Arg Gln Ala Pro Gly Lys Gly Leu Glu Trp Val
        35                  40                  45

Ser Gly Ile Asp Ile Leu Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ser Trp Gln Gly Phe Asp Tyr Trp Gly Gln Gly Thr
            100                 105                 110

Leu Val Thr Val Ser Ser
        115


<210> SEQ ID NO 15
<211> LENGTH: 123
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ser Met Tyr Trp Val Arg Gln Ala Pro Gly Lys Gly Leu Glu Trp Val
        35                  40                  45

Ser Ser Ile Ser Pro Phe Gly Trp Gly Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gly Glu Thr Ser Gly Pro Ile Ser Glu Asn Phe Asp Tyr
            100                 105                 110

Trp Gly Gln Gly Thr Leu Val Thr Val Ser Ser
        115                 120


<210> SEQ ID NO 16
<211> LENGTH: 116
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Ser Tyr
            20                  25                  30

Asp Met Thr Trp Val Arg Gln Ala Pro Gly Lys Gly Leu Glu Trp Val
        35                  40                  45
```

-continued

```
Ser Ser Ile Met Ala Ser Gly Asp Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Asp Arg Asp Phe Asp Tyr Trp Gly Gln Gly Thr Leu Val
            100                 105                 110

Thr Val Ser Ser
        115


<210> SEQ ID NO 17
<211> LENGTH: 120
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Glu Tyr
            20                  25                  30

Val Met Ser Trp Val Arg Gln Ala Pro Gly Lys Gly Leu Glu Trp Val
        35                  40                  45

Ser Thr Ile Ser Pro Ile Gly Leu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Phe Pro Leu Ile Ile Leu Pro Asp Phe Asp Tyr Trp Gly Gln
            100                 105                 110

Gly Thr Leu Val Thr Val Ser Ser
        115                 120


<210> SEQ ID NO 18
<211> LENGTH: 123
<212> TYPE: PRT
<213> ORGANISM: Homo sapiens

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Glu Tyr
            20                  25                  30

Ala Met Ile Trp Val Arg Gln Ala Pro Gly Lys Gly Leu Glu Trp Val
        35                  40                  45

Ser Ile Ile Ser Pro Leu Gly Leu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gln Asp Ser Ser Asp Ser Gln Tyr Thr Asn Phe Asp Tyr
            100                 105                 110

Trp Gly Gln Gly Thr Leu Val Thr Val Ser Ser
        115                 120
```

-continued

<210> SEQ ID NO 19
<211> LENGTH: 121
<212> TYPE: PRT
<213> ORGANISM: Homo sapiens

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asp Tyr
            20                  25                  30

Gly Met Gly Trp Ala Arg Gln Ala Pro Gly Lys Gly Leu Glu Trp Val
        35                  40                  45

Ser Ser Ile Gly Pro Leu Gly Leu Trp Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Leu Glu Gly Leu Ile Thr Asn Phe Asp Tyr Trp Gly
            100                 105                 110

Gln Gly Thr Leu Val Thr Val Ser Ser
        115                 120
```

<210> SEQ ID NO 20
<211> LENGTH: 119
<212> TYPE: PRT
<213> ORGANISM: Homo sapiens

<400> SEQUENCE: 20

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Glu Tyr
            20                  25                  30

Asp Met Thr Trp Val Arg Gln Ala Pro Gly Lys Gly Leu Glu Trp Val
        35                  40                  45

Ser Tyr Ile Ser Ser Asp Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Gly Ser Pro Arg Glu Phe Asp Tyr Trp Gly Gln Gly
            100                 105                 110

Thr Leu Val Thr Val Ser Ser
        115
```

<210> SEQ ID NO 21
<211> LENGTH: 116
<212> TYPE: PRT
<213> ORGANISM: Homo sapiens

<400> SEQUENCE: 21

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Pro Gln Tyr
            20                  25                  30

Gln Met Ala Trp Val Arg Gln Ala Pro Gly Lys Gly Leu Glu Trp Val
```

-continued

```
        35                  40                  45

Ser Met Ile Thr Ser Asp Gly Leu Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Glu Pro Leu Phe Asp Tyr Trp Gly Gln Gly Thr Leu Val
            100                 105                 110

Thr Val Ser Ser
        115


<210> SEQ ID NO 22
<211> LENGTH: 116
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gln Met Ala Trp Val Arg Gln Ala Pro Gly Lys Gly Leu Glu Trp Val
        35                  40                  45

Ser Gly Ile Ser Ser Glu Gly Leu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Arg Arg Phe Asp Tyr Trp Gly Gln Gly Thr Leu Val
            100                 105                 110

Thr Val Ser Ser
        115


<210> SEQ ID NO 23
<211> LENGTH: 120
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asn Tyr
            20                  25                  30

Glu Met Gly Trp Ala Arg Gln Ala Pro Gly Lys Gly Leu Glu Trp Val
        35                  40                  45

Ser Val Ile Ser Glu Trp Gly Tyr Ser Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Val Gly Gly Thr Gln Tyr Glu Phe Asp Tyr Trp Gly Gln
            100                 105                 110

Gly Thr Leu Val Thr Val Ser Ser
```

-continued

```
        115                 120


<210> SEQ ID NO 24
<211> LENGTH: 116
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asn Tyr
            20                  25                  30

Glu Met Ser Trp Val Arg Gln Ala Pro Gly Lys Gly Leu Glu Trp Val
        35                  40                  45

Ser Ser Ile Ser Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Val Lys Phe Asp Tyr Trp Gly Gln Gly Thr Leu Val
            100                 105                 110

Thr Val Ser Ser
        115


<210> SEQ ID NO 25
<211> LENGTH: 116
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Leu Tyr
            20                  25                  30

Glu Met Thr Trp Val Arg Gln Ala Pro Gly Lys Gly Leu Glu Trp Val
        35                  40                  45

Ser Ser Ile Thr Gly Asp Gly Ile Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Arg Lys Phe Asp Tyr Trp Gly Gln Gly Thr Leu Val
            100                 105                 110

Thr Val Ser Ser
        115


<210> SEQ ID NO 26
<211> LENGTH: 116
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Gln Met Ala Trp Val Arg Gln Ala Pro Gly Lys Gly Leu Glu Trp Val
        35                  40                  45

Ser Ser Ile Thr Ser Glu Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Lys Asn Phe Asp Tyr Trp Gly Gln Gly Thr Leu Val
            100                 105                 110

Thr Val Ser Ser
        115


<210> SEQ ID NO 27
<211> LENGTH: 116
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Glu Met Thr Trp Val Arg Gln Ala Pro Gly Lys Gly Leu Glu Trp Val
        35                  40                  45

Ser Thr Ile Thr Ser Gln Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Arg Ser Phe Asp Tyr Trp Gly Gln Gly Thr Leu Val
            100                 105                 110

Thr Val Ser Ser
        115


<210> SEQ ID NO 28
<211> LENGTH: 116
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Glu Met Thr Trp Val Arg Gln Ala Pro Gly Lys Gly Leu Glu Trp Val
        35                  40                  45

Ser Ser Ile Thr Ser Asp Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Lys Thr Phe Asp Tyr Trp Gly Gln Gly Thr Leu Val
            100                 105                 110
```

-continued

```
Thr Val Ser Ser
        115


<210> SEQ ID NO 29
<211> LENGTH: 116
<212> TYPE: PRT
<213> ORGANISM: Homo sapiens

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Leu Tyr
            20                  25                  30

Glu Met Thr Trp Val Arg Gln Ala Pro Gly Lys Gly Leu Glu Trp Val
        35                  40                  45

Ser Ser Ile Thr Ser Asp Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Ser Pro Phe Asp Tyr Trp Gly Gln Gly Thr Leu Val
            100                 105                 110

Thr Val Ser Ser
        115


<210> SEQ ID NO 30
<211> LENGTH: 116
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly His Tyr
            20                  25                  30

Asp Met Ala Trp Val Arg Gln Ala Pro Gly Lys Gly Leu Glu Trp Val
        35                  40                  45

Ser Thr Ile Ser Asp Asn Gly Asn Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Asp Phe Asp Tyr Trp Gly Gln Gly Thr Leu Val
            100                 105                 110

Thr Val Ser Ser
        115


<210> SEQ ID NO 31
<211> LENGTH: 116
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Gly Arg Tyr
            20                  25                  30

Gln Met Ala Trp Val Arg Gln Ala Pro Gly Lys Gly Leu Glu Trp Val
        35                  40                  45

Ser Ser Ile Ser Ser Asp Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Ala Phe Asp Tyr Trp Gly Gln Gly Thr Leu Val
            100                 105                 110

Thr Val Ser Ser
        115


<210> SEQ ID NO 32
<211> LENGTH: 116
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
            20                  25                  30

Gln Met Ala Trp Val Arg Gln Ala Pro Gly Lys Gly Leu Glu Trp Val
        35                  40                  45

Ser Thr Ile Ser Asp Asp Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asp Lys Leu Phe Asp Tyr Trp Gly Gln Gly Thr Leu Val
            100                 105                 110

Thr Val Ser Ser
        115


<210> SEQ ID NO 33
<211> LENGTH: 116
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Glu Tyr
            20                  25                  30

Gln Met Ala Trp Val Arg Gln Ala Pro Gly Lys Gly Leu Glu Trp Val
        35                  40                  45

Ser Thr Ile Ser Asp Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Lys Pro Asp Leu Tyr Phe Asp Tyr Trp Gly Gln Gly Thr Leu Val
            100                 105                 110

Thr Val Ser Ser
        115


<210> SEQ ID NO 34
<211> LENGTH: 116
<212> TYPE: PRT
<213> ORGANISM: Homo sapiens

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Val Tyr
            20                  25                  30

Gln Met Gly Trp Val Arg Gln Ala Pro Gly Lys Gly Leu Glu Trp Val
        35                  40                  45

Ser Phe Ile Val Pro Gly Gly Asp Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Thr Trp Pro Glu Phe Asp Tyr Trp Gly Gln Gly Thr Leu Val
            100                 105                 110

Thr Val Ser Ser
        115


<210> SEQ ID NO 35
<211> LENGTH: 108
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Gly Glu Ser
            20                  25                  30

Leu His Trp Tyr Gln Gln Lys Pro Gly Lys Ala Pro Arg Leu Leu Ile
        35                  40                  45

Tyr Phe Ala Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His His Met Leu Pro Ser
                85                  90                  95

Thr Phe Gly Gln Gly Thr Lys Val Glu Ile Lys Arg
            100                 105


<210> SEQ ID NO 36
<211> LENGTH: 108
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asp Ser
```

-continued

```
            20                  25                  30

Leu Ser Trp Tyr Gln Gln Lys Pro Gly Lys Ala Pro Lys Leu Leu Ile
        35                  40                  45

Tyr Phe Ala Ser Tyr Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Glu Asn Pro Val
                85                  90                  95

Thr Phe Gly Gln Gly Thr Lys Val Gly Ile Lys Arg
            100                 105


<210> SEQ ID NO 37
<211> LENGTH: 108
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Ile Gly Asp Ser
            20                  25                  30

Leu Ser Trp Tyr Gln Gln Lys Pro Gly Lys Ala Pro Lys Leu Leu Ile
        35                  40                  45

Tyr Phe Ser Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Asp Ile Pro Ile
                85                  90                  95

Thr Phe Gly Gln Gly Thr Lys Val Glu Ile Lys Arg
            100                 105


<210> SEQ ID NO 38
<211> LENGTH: 108
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp His Asn
            20                  25                  30

Leu Glu Trp Tyr Gln Gln Lys Pro Gly Lys Ala Pro Lys Leu Leu Ile
        35                  40                  45

Tyr Asp Ser Ser Met Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Ile Pro Val
                85                  90                  95

Thr Phe Gly Gln Gly Thr Lys Val Glu Ile Lys Arg
            100                 105


<210> SEQ ID NO 39
<211> LENGTH: 108
<212> TYPE: PRT
```

-continued

<213> ORGANISM: Homo sapiens

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gln Ile Glu Thr Asn
            20                  25                  30

Leu Glu Trp Tyr Gln Gln Lys Pro Gly Lys Ala Pro Lys Leu Leu Ile
        35                  40                  45

Tyr Asp Gly Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Leu Pro Ala
                85                  90                  95

Thr Phe Gly Gln Gly Thr Lys Val Glu Ile Lys Arg
            100                 105
```

<210> SEQ ID NO 40
<211> LENGTH: 108
<212> TYPE: PRT
<213> ORGANISM: Homo sapiens

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Asn
            20                  25                  30

Leu Glu Trp Tyr Gln Gln Lys Pro Gly Lys Ala Pro Arg Leu Leu Ile
        35                  40                  45

Tyr His Gly Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Phe Asn Pro Thr
                85                  90                  95

Thr Phe Gly Gln Gly Thr Lys Val Glu Ile Lys Arg
            100                 105
```

<210> SEQ ID NO 41
<211> LENGTH: 108
<212> TYPE: PRT
<213> ORGANISM: Homo sapiens

<400> SEQUENCE: 41

```
Asp Ile Gln Met Thr Gln Ser Pro Ser Ser Leu Ser Ala Ser Val Gly
1               5                   10                  15

Asp Cys Val Thr Ile Thr Cys Arg Ala Ser Gln Asn Ile Asp Gly Leu
            20                  25                  30

Leu Trp Trp Tyr Gln Gln Lys Pro Gly Lys Ala Pro Lys Leu Leu Ile
        35                  40                  45

Tyr Ala Gly Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Ala Phe Glu Pro Phe
                85                  90                  95
```

-continued

```
Thr Phe Gly Gln Gly Thr Lys Val Glu Ile Lys Arg
            100                 105


<210> SEQ ID NO 42
<211> LENGTH: 119
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Asp Met Gly Trp Val Arg Gln Ala Pro Gly Lys Gly Leu Glu Trp Val
        35                  40                  45

Ser Gln Ile Gly Arg Asp Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Arg Tyr Ala Ile Phe Thr Phe Asp Arg Gly Gln Gly
            100                 105                 110

Thr Leu Val Thr Val Ser Ser
        115


<210> SEQ ID NO 43
<211> LENGTH: 116
<212> TYPE: PRT
<213> ORGANISM: Homo sapiens

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Glu Tyr
            20                  25                  30

Glu Met Thr Trp Val Arg Gln Ala Pro Gly Lys Gly Leu Glu Trp Val
        35                  40                  45

Ser Ser Ile Ala Asn Asp Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Arg Gln Phe Asp Tyr Trp Gly Gln Gly Thr Leu Val
            100                 105                 110

Thr Val Ser Ser
        115


<210> SEQ ID NO 44
<211> LENGTH: 116
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Gly Pro Tyr
            20                  25                  30

Glu Met Thr Trp Val Arg Gln Ala Pro Gly Lys Gly Leu Glu Trp Val
        35                  40                  45

Ser Ser Ile Val Gly Asp Gly Leu Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Arg Val Phe Asp Tyr Trp Gly Gln Gly Thr Leu Val
            100                 105                 110

Thr Val Ser Ser
        115


<210> SEQ ID NO 45
<211> LENGTH: 116
<212> TYPE: PRT
<213> ORGANISM: Homo sapiens

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ser Tyr
            20                  25                  30

Glu Met Ala Trp Val Arg Gln Ala Pro Gly Lys Gly Leu Glu Trp Val
        35                  40                  45

Ser Ser Ile Gly Ser Asp Gly Gly Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Lys Pro Asp Arg Ala Phe Asp Tyr Trp Gly Gln Gly Thr Leu Val
            100                 105                 110

Thr Val Ser Ser
        115


<210> SEQ ID NO 46
<211> LENGTH: 119
<212> TYPE: PRT
<213> ORGANISM: Homo sapiens

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Glu Met Gly Trp Val Arg Gln Ala Pro Gly Lys Gly Leu Glu Trp Val
        35                  40                  45

Ser Ser Ile Glu Pro Thr Gly Ile Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Lys Pro His Phe Thr Glu Leu Gly Phe Asp Tyr Trp Gly Gln Gly
            100                 105                 110

Thr Leu Val Thr Val Ser Ser
        115


<210> SEQ ID NO 47
<211> LENGTH: 120
<212> TYPE: PRT
<213> ORGANISM: Homo sapiens

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ala Trp Val Arg Gln Ala Pro Gly Lys Gly Leu Glu Trp Val
        35                  40                  45

Ser Lys Ile Gly Ala Gln Gly Leu His Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Thr Thr Met Asp Tyr Glu Arg Phe Asp Tyr Trp Gly Gln
            100                 105                 110

Gly Thr Leu Val Thr Val Ser Ser
        115                 120


<210> SEQ ID NO 48
<211> LENGTH: 122
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Leu Tyr
            20                  25                  30

Ala Met Ala Trp Val Arg Gln Ala Pro Gly Lys Gly Leu Glu Trp Val
        35                  40                  45

Ser Gly Ile Gly Ala Val Gly Glu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ala Asn Asn Leu Ser Asp Asn Leu Val Phe Asp Tyr Trp
            100                 105                 110

Gly Gln Gly Thr Leu Val Thr Val Ser Ser
        115                 120


<210> SEQ ID NO 49
<211> LENGTH: 108
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Trp Ile Gly Asp Ser
            20                  25                  30

Leu Ser Trp Tyr Gln Gln Lys Pro Gly Lys Ala Pro Lys Leu Leu Ile
        35                  40                  45

Tyr Phe Gly Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu His Thr Pro Ser
                85                  90                  95

Thr Phe Gly Gln Gly Thr Lys Val Glu Ile Lys Arg
            100                 105


<210> SEQ ID NO 50
<211> LENGTH: 108
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asp Ser
            20                  25                  30

Leu Ser Trp Tyr Gln Gln Lys Pro Gly Lys Ala Pro Lys Leu Leu Ile
        35                  40                  45

Tyr Phe Gly Ser Tyr Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Ile Thr Pro Thr
                85                  90                  95

Thr Phe Gly Gln Gly Thr Lys Val Glu Ile Lys Arg
            100                 105


<210> SEQ ID NO 51
<211> LENGTH: 108
<212> TYPE: PRT
<213> ORGANISM: Homo sapiens

<400> SEQUENCE: 51

Asp Val Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asp Ser
            20                  25                  30

Leu Ser Trp Tyr Gln Gln Lys Pro Gly Lys Ala Pro Lys Leu Leu Ile
        35                  40                  45

Tyr Phe Gly Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Ser Ala Pro Ser
                85                  90                  95

Thr Phe Gly Gln Gly Thr Lys Val Glu Ile Lys Arg
            100                 105
```

-continued

<210> SEQ ID NO 52
<211> LENGTH: 108
<212> TYPE: PRT
<213> ORGANISM: Homo sapiens

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asp Ser
            20                  25                  30

Leu Ser Trp Tyr Gln Gln Lys Pro Gly Lys Ala Pro Lys Leu Leu Ile
        35                  40                  45

Tyr Phe Gly Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Gln Tyr Val Pro Ser
                85                  90                  95

Thr Phe Gly Gln Gly Thr Lys Val Glu Ile Lys Gln
            100                 105
```

<210> SEQ ID NO 53
<211> LENGTH: 108
<212> TYPE: PRT
<213> ORGANISM: Homo sapiens

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Val Asp Glu
            20                  25                  30

Leu Asp Trp Tyr Gln Gln Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Trp Ser Thr Tyr Pro Thr
                85                  90                  95

Thr Phe Gly Gln Gly Thr Lys Val Glu Ile Lys Arg
            100                 105
```

<210> SEQ ID NO 54
<211> LENGTH: 108
<212> TYPE: PRT
<213> ORGANISM: Homo sapiens

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ala
            20                  25                  30

Leu Arg Trp Tyr Gln Gln Lys Pro Gly Lys Ala Pro Lys Leu Leu Ile
        35                  40                  45

Tyr Leu Gly Ser Asp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln Thr Gln Tyr Phe Pro Thr
                85                  90                  95

Thr Phe Gly Gln Gly Thr Lys Val Glu Ile Lys Arg
            100                 105


<210> SEQ ID NO 55
<211> LENGTH: 108
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Tyr Gly Gly
            20                  25                  30

Leu Arg Trp Tyr Gln Gln Lys Pro Gly Lys Ala Pro Lys Leu Leu Ile
        35                  40                  45

Tyr Gly Glu Ser Met Leu Gln Ser Gly Val Pro Ser Arg Phe Ser Gly
    50                  55                  60

Ser Gly Ser Gly Thr Asp Phe Thr Leu Thr Ile Ser Ser Leu His Pro
65                  70                  75                  80

Glu Asp Phe Ala Thr Tyr Tyr Cys Gln Gln Val Tyr His Lys Pro Phe
                85                  90                  95

Thr Phe Gly Gln Gly Thr Lys Val Glu Ile Lys Arg
            100                 105


<210> SEQ ID NO 56
<211> LENGTH: 123
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ala Tyr
            20                  25                  30

Arg Met Ala Trp Val Arg Gln Ala Pro Gly Lys Gly Leu Glu Trp Val
        35                  40                  45

Ser Trp Ile Ser Pro Ser Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Thr Asp Ser Pro Ser Gly His Tyr Glu Phe Asp Tyr
            100                 105                 110

Trp Gly Gln Gly Thr Leu Val Thr Val Ser Ser
        115                 120


<210> SEQ ID NO 57
<211> LENGTH: 123
<212> TYPE: PRT
<213> ORGANISM: Homo sapiens

<400> SEQUENCE: 57

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ala Arg Tyr
            20                  25                  30

Glu Met Gly Trp Val Arg Gln Ala Pro Gly Lys Gly Leu Glu Trp Val
        35                  40                  45

Ser Arg Ile Thr Ala Gln Gly Leu Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Leu Thr Asp Phe Ser Ser Gly His Gln Glu Phe Asp Tyr
            100                 105                 110

Trp Gly Gln Gly Thr Leu Val Thr Val Ser Ser
        115                 120


<210> SEQ ID NO 58
<211> LENGTH: 123
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Gly Trp Val Arg Gln Ala Pro Gly Lys Gly Leu Glu Trp Val
        35                  40                  45

Ser Trp Ile His Gly Thr Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Leu Ala Asp Arg Ser Gly Gly Val Val Glu Phe Asp Tyr
            100                 105                 110

Trp Gly Gln Gly Thr Leu Val Thr Val Ser Ser
        115                 120


<210> SEQ ID NO 59
<211> LENGTH: 116
<212> TYPE: PRT
<213> ORGANISM: Homo sapiens

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Asp Met Tyr Trp Val Arg Gln Ala Pro Gly Lys Gly Leu Glu Trp Val
        35                  40                  45

Ser Trp Ile Asp Thr Asp Gly Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Lys Pro Gly Leu Lys Phe Asp Tyr Trp Gly Gln Gly Thr Leu Val
            100                 105                 110

Thr Val Ser Ser
        115


<210> SEQ ID NO 60
<211> LENGTH: 116
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Val Tyr
            20                  25                  30

Thr Met Ala Trp Val Arg Gln Ala Pro Gly Lys Gly Leu Glu Trp Val
        35                  40                  45

Ser Thr Ile Asp Glu Ser Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Val Trp Phe Asp Tyr Trp Gly Gln Gly Thr Leu Val
            100                 105                 110

Thr Val Ser Ser
        115


<210> SEQ ID NO 61
<211> LENGTH: 124
<212> TYPE: PRT
<213> ORGANISM: Homo sapiens

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Asp Tyr
            20                  25                  30

Ala Met Gly Trp Val Arg Gln Ala Pro Gly Lys Gly Leu Glu Trp Val
        35                  40                  45

Ser Thr Ile Ser Pro Met Gly Met Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ala Ile Ser Phe Thr Ser Asp Ile Ser Asn Phe Asp
            100                 105                 110

Tyr Trp Gly Gln Gly Thr Leu Val Thr Val Ser Ser
        115                 120


<210> SEQ ID NO 62
<211> LENGTH: 120
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
```

-continued

```
1               5                   10                  15

Ser Leu Arg Leu Ser Cys Ala Ala Ser Gly Phe Thr Phe Ala Ala Tyr
            20                  25                  30

Ala Met Thr Trp Val Arg Gln Ala Pro Gly Lys Gly Leu Glu Trp Val
        35                  40                  45

Ser Tyr Ile Ser Pro Asn Gly Thr Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Tyr Val Gly Met Arg Trp Asn Ser Phe Asp Tyr Trp Gly Gln
            100                 105                 110

Gly Thr Leu Val Thr Val Ser Ser
        115                 120


<210> SEQ ID NO 63
<211> LENGTH: 116
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Ala Trp Val Arg Gln Ala Pro Gly Lys Gly Leu Glu Trp Val
        35                  40                  45

Ser Ser Ile Thr Ser Leu Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Lys Phe Asp Tyr Trp Gly Gln Gly Thr Leu Val
            100                 105                 110

Thr Val Ser Ser
        115


<210> SEQ ID NO 64
<211> LENGTH: 116
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Glu Tyr
            20                  25                  30

Glu Met Thr Trp Val Arg Gln Ala Pro Gly Lys Gly Leu Glu Trp Val
        35                  40                  45

Ser Thr Ile Thr Ser Glu Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95

Ala Lys Pro Asn Gly Lys Phe Asp Tyr Trp Gly Gln Gly Thr Leu Val
            100                 105                 110

Thr Val Ser Ser
        115


<210> SEQ ID NO 65
<211> LENGTH: 116
<212> TYPE: PRT
<213> ORGANISM: Homo sapiens

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Leu Trp Val Arg Gln Ala Pro Gly Lys Gly Leu Glu Trp Val
        35                  40                  45

Ser Thr Ile Thr Ser Glu Gly His Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Thr Ser Phe Asp Tyr Trp Gly Gln Gly Thr Leu Val
            100                 105                 110

Thr Val Ser Ser
        115


<210> SEQ ID NO 66
<211> LENGTH: 116
<212> TYPE: PRT
<213> ORGANISM: Homo sapiens

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Ser Trp Val Arg Gln Ala Pro Gly Lys Gly Leu Glu Trp Val
        35                  40                  45

Ser Thr Ile Asp Ser Asp Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Val Lys Phe Asp Tyr Trp Gly Gln Gly Thr Leu Val
            100                 105                 110

Thr Val Ser Ser
        115


<210> SEQ ID NO 67
<211> LENGTH: 116
<212> TYPE: PRT
<213> ORGANISM: Homo sapiens

<400> SEQUENCE: 67
```

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asp Tyr
            20                  25                  30

Glu Met Thr Trp Val Arg Gln Ala Pro Gly Lys Gly Leu Glu Trp Val
        35                  40                  45

Ser Ser Ile Ser Ser Thr Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Asn Lys Phe Asp Tyr Trp Gly Gln Gly Thr Leu Val
            100                 105                 110

Thr Val Ser Ser
        115


<210> SEQ ID NO 68
<211> LENGTH: 124
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Asp Tyr
            20                  25                  30

Gly Met Ala Trp Val Arg Gln Ala Pro Gly Lys Gly Leu Glu Trp Val
        35                  40                  45

Ser Ala Ile Ser Pro Leu Gly Leu Ser Thr Tyr Tyr Ala Asp Ser Val
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Arg Val Gly Arg Gly Val His Pro Pro Lys Phe Asp
            100                 105                 110

Tyr Trp Gly Gln Gly Thr Leu Val Thr Val Ser Ser
        115                 120


<210> SEQ ID NO 69
<211> LENGTH: 123
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asn Tyr
            20                  25                  30

Ala Met Ser Trp Val Arg Gln Ala Pro Gly Lys Gly Leu Glu Trp Val
        35                  40                  45

Ser Thr Ile Ala Pro Leu Gly Val Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Lys Lys Lys Val Gly Ala Trp Leu Gln Ser Arg Ser Phe Asp Tyr
            100                 105                 110

Trp Gly Gln Gly Thr Leu Val Thr Val Ser Ser
        115                 120


<210> SEQ ID NO 70
<211> LENGTH: 123
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Gly Tyr
            20                  25                  30

Pro Met Ser Trp Val Arg Gln Ala Pro Gly Lys Gly Leu Glu Trp Val
        35                  40                  45

Ser Thr Ile Ser Pro Leu Gly Pro Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Leu Met Gly Glu Tyr Leu Asn Ser Arg Thr Phe Asp Tyr
            100                 105                 110

Trp Gly Gln Gly Thr Leu Val Thr Val Ser Ser
        115                 120


<210> SEQ ID NO 71
<211> LENGTH: 124
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Pro Met Ser Trp Val Arg Gln Ala Pro Gly Lys Gly Leu Glu Trp Val
        35                  40                  45

Ser Ser Ile Ser Pro Leu Gly Leu Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Ala Gly Ala Glu Thr His Val Tyr Arg Leu Phe Asp
            100                 105                 110

Tyr Trp Gly Gln Gly Thr Leu Val Thr Val Ser Ser
        115                 120


<210> SEQ ID NO 72
<211> LENGTH: 116
<212> TYPE: PRT
<213> ORGANISM: Homo sapiens
```

-continued

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asp Met Ser Trp Val Arg Gln Ala Pro Gly Lys Gly Leu Glu Trp Val
        35                  40                  45

Ser Thr Ile Leu Glu Asp Gly Leu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Leu Phe Asp Tyr Trp Gly Gln Gly Thr Leu Val
            100                 105                 110

Thr Val Ser Ser
        115
```

<210> SEQ ID NO 73
<211> LENGTH: 116
<212> TYPE: PRT
<213> ORGANISM: Homo sapiens

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Pro Met Thr Trp Val Arg Gln Ala Pro Gly Lys Gly Leu Glu Trp Val
        35                  40                  45

Ser Thr Ile Leu Ser Pro Gly Thr Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Glu Lys Asp Phe Asp Tyr Trp Gly Gln Gly Thr Leu Val
            100                 105                 110

Thr Val Ser Ser
        115
```

<210> SEQ ID NO 74
<211> LENGTH: 124
<212> TYPE: PRT
<213> ORGANISM: Homo sapiens

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Gln Tyr
            20                  25                  30

Pro Met Gly Trp Val Arg Gln Ala Pro Gly Lys Gly Leu Glu Trp Val
        35                  40                  45

Ser Thr Ile Ser Pro Val Gly Leu Thr Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Phe Glu Gly Ser Arg Ile Gln Arg Asp Val Gly Phe Asp
            100                 105                 110

Tyr Trp Gly Gln Gly Thr Leu Val Thr Val Ser Ser
        115                 120


<210> SEQ ID NO 75
<211> LENGTH: 122
<212> TYPE: PRT
<213> ORGANISM: Homo sapiens

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Glu Tyr
            20                  25                  30

Gly Met Ala Trp Val Arg Gln Ala Pro Gly Lys Gly Leu Glu Trp Val
        35                  40                  45

Ser Thr Ile Ser Pro Leu Gly Ile Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ala Thr Ser Gln Glu Ser Leu Arg Ser Phe Asp Tyr Trp
            100                 105                 110

Gly Gln Gly Thr Leu Val Thr Val Ser Ser
        115                 120


<210> SEQ ID NO 76
<211> LENGTH: 116
<212> TYPE: PRT
<213> ORGANISM: Homo sapiens

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Arg Tyr
            20                  25                  30

Gln Met Ala Trp Val Arg Gln Ala Pro Gly Lys Gly Leu Glu Trp Val
        35                  40                  45

Ser Thr Ile Ser Ser Asp Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly His Arg Phe Asp Tyr Trp Gly Gln Gly Thr Leu Val
            100                 105                 110

Thr Val Ser Ser
        115


<210> SEQ ID NO 77
<211> LENGTH: 116
```

-continued

<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Gly Arg Tyr
20 25 30

Gln Met Ala Trp Val Arg Gln Ala Pro Gly Lys Gly Leu Glu Trp Val
35 40 45

Ser Ser Ile Ser Ser Asp Gly Gly Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Ser Arg Arg Phe Asp Tyr Trp Gly Gln Gly Thr Leu Val
100 105 110

Thr Val Ser Ser
115

<210> SEQ ID NO 78
<211> LENGTH: 123
<212> TYPE: PRT
<213> ORGANISM: Homo sapiens

<400> SEQUENCE: 78

Glu Val Gln Leu Leu Glu Ser Gly Gly Gly Leu Val Gln Pro Gly Gly
1 5 10 15

Phe Leu Arg Leu Ser Cys Ala Ala Ser Gly Phe Thr Phe Glu Leu Tyr
20 25 30

Pro Met Ala Trp Val Arg Gln Ala Pro Gly Lys Gly Leu Glu Trp Val
35 40 45

Ser Ser Ile Ser Pro Val Gly Phe Leu Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly His Glu Gly Ser Tyr Thr Pro Arg Ser Ala Phe Asp Tyr
100 105 110

Trp Gly Gln Gly Thr Leu Val Thr Val Ser Ser
115 120

<210> SEQ ID NO 79
<211> LENGTH: 123
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Val Ala Tyr
20 25 30

Pro Met Ala Trp Val Arg Gln Ala Pro Gly Lys Gly Leu Glu Trp Val
35 40 45

Ser Thr Ile Ala Pro Leu Gly Gly Asn Thr Tyr Tyr Ala Asp Ser Val

-continued

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Pro Glu Gly Leu Gln Ile Asp Ser Gln Asn Phe Asp Tyr
            100                 105                 110

Trp Gly Gln Gly Thr Leu Val Thr Val Ser Ser
        115                 120


<210> SEQ ID NO 80
<211> LENGTH: 116
<212> TYPE: PRT
<213> ORGANISM: Homo sapiens

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Leu Tyr
            20                  25                  30

Gln Met Ala Trp Val Arg Gln Ala Pro Gly Lys Gly Leu Glu Trp Val
        35                  40                  45

Ser Ser Ile Asp Ser Ser Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Glu Arg Asp Phe Asp Tyr Trp Gly Gln Gly Thr Leu Val
            100                 105                 110

Thr Val Ser Ser
        115


<210> SEQ ID NO 81
<211> LENGTH: 116
<212> TYPE: PRT
<213> ORGANISM: Homo sapiens

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Gln Tyr
            20                  25                  30

Gln Met Ala Trp Ala Arg Gln Ala Pro Gly Lys Gly Leu Glu Trp Val
        35                  40                  45

Ser Thr Ile Ala Ser Asp Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Arg Asp Phe Asp Tyr Trp Gly Gln Gly Thr Leu Val
            100                 105                 110

Thr Val Ser Ser
        115
```

-continued

<210> SEQ ID NO 82
<211> LENGTH: 108
<212> TYPE: PRT
<213> ORGANISM: Homo sapiens

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Gly Pro Asp
            20                  25                  30

Leu Leu Trp Tyr Gln Gln Lys Pro Gly Lys Ala Pro Lys Leu Leu Ile
        35                  40                  45

Tyr Gln Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Ala Phe Pro Val
                85                  90                  95

Thr Phe Gly Gln Gly Thr Lys Val Glu Ile Lys Arg
            100                 105
```

<210> SEQ ID NO 83
<211> LENGTH: 369
<212> TYPE: DNA
<213> ORGANISM: Homo sapiens

<400> SEQUENCE: 83

```
gcgtcgacgg aggtgcagct gttggagtct gggggaggct tggtacagcc tggggggtcc     60

ctgcgtctct cctgtgcagc ctccggattc acctttagta attatcagat ggcgtgggtc    120

cgccaggctc cagggaaggg tctagagtgg gtctcaagta ttactagtga gggtggttcg    180

acatactacg cagactccgt gaagggccgg ttcaccatct cccgcgacaa ttccaagaac    240

acactgtatc tgcaaatgaa cagcctgcgt gccgaggaca ccgcggtata ttactgtgcg    300

aaaccgggta agaattttga ctactggggt cagggaaccc tggtcaccgt ctcgtgctaa    360

taaggatcc                                                            369
```

<210> SEQ ID NO 84
<211> LENGTH: 369
<212> TYPE: DNA
<213> ORGANISM: Homo sapiens

<400> SEQUENCE: 84

```
cgcagctgcc tccacgtcga caacctcaga ccccctccga accatgtcgg acccccccagg     60

gacgcagaga ggacacgtcg gaggcctaag tggaaatcat taatagtcta ccgcacccag    120

gcggtccgag gtcccttccc agatctcacc cagagttcat aatgatcact cccaccaagc    180

tgtatgatgc gtctgaggca cttcccggcc aagtggtaga gggcgctgtt aaggttcttg    240

tgtgacatag acgtttactt gtcggacgca cggctcctgt ggcgccatat aatgacacgc    300

tttggcccat tcttaaaact gatgacccca gtcccttggg accagtggca gagcacgatt    360

attcctagg                                                            369
```

<210> SEQ ID NO 85
<211> LENGTH: 123
<212> TYPE: PRT
<213> ORGANISM: Homo sapiens
<220> FEATURE:
<221> NAME/KEY: MISC_FEATURE -continued
<222> LOCATION: (120)..(121)
<223> OTHER INFORMATION: X corresponds to stop codon in coding sequence

<400> SEQUENCE: 85

Ala Ser Thr Glu Val Gln Leu Leu Glu Ser Gly Gly Gly Leu Val Gln
1 5 10 15

Pro Gly Gly Ser Leu Arg Leu Ser Cys Ala Ala Ser Gly Phe Thr Phe
20 25 30

Ser Asn Tyr Gln Met Ala Trp Val Arg Gln Ala Pro Gly Lys Gly Leu
35 40 45

Glu Trp Val Ser Ser Ile Thr Ser Glu Gly Gly Ser Thr Tyr Tyr Ala
50 55 60

Asp Ser Val Lys Gly Arg Phe Thr Ile Ser Arg Asp Asn Ser Lys Asn
65 70 75 80

Thr Leu Tyr Leu Gln Met Asn Ser Leu Arg Ala Glu Asp Thr Ala Val
85 90 95

Tyr Tyr Cys Ala Lys Pro Gly Lys Asn Phe Asp Tyr Trp Gly Gln Gly
100 105 110

Thr Leu Val Thr Val Ser Cys Xaa Xaa Gly Ser
115 120

<210> SEQ ID NO 86
<211> LENGTH: 33
<212> TYPE: DNA
<213> ORGANISM: Artificial
<220> FEATURE:
<223> OTHER INFORMATION: DOM8-24 forward PCR primer

<400> SEQUENCE: 86
agtgcgtcga cggaggtgca gctgttggag tct 33

<210> SEQ ID NO 87
<211> LENGTH: 42
<212> TYPE: DNA
<213> ORGANISM: Artificial
<220> FEATURE:
<223> OTHER INFORMATION: DOM8-24 reverse PCR primer

<400> SEQUENCE: 87
aaaggatcct tattagcacg agacggtgac cagggttccc tg 42

<210> SEQ ID NO 88
<211> LENGTH: 241
<212> TYPE: PRT
<213> ORGANISM: Homo sapiens

<400> SEQUENCE: 88

Leu Glu Lys Arg Glu Val Gln Leu Leu Glu Ser Gly Gly Gly Leu Val
1 5 10 15

Gln Pro Gly Gly Ser Leu Arg Leu Ser Cys Thr Ala Ser Gly Phe Thr
20 25 30

Phe Asp Glu Tyr Asn Met Ser Trp Val Arg Gln Ala Pro Gly Lys Gly
35 40 45

Leu Glu Trp Val Ser Thr Ile Leu Pro His Gly Asp Arg Thr Tyr Tyr
50 55 60

Ala Asp Ser Val Lys Gly Arg Phe Thr Ile Ser Arg Asp Asn Ser Lys
65 70 75 80

Asn Thr Leu Tyr Leu Gln Met Asn Ser Leu Arg Ala Glu Asp Thr Ala
85 90 95

-continued

```
Val Tyr Tyr Cys Ala Lys Gln Asp Pro Leu Tyr Arg Phe Asp Tyr Trp
            100                 105                 110

Gly Gln Gly Thr Leu Val Thr Val Ser Ser Ala Ala Ala Glu Val Gln
        115                 120                 125

Leu Leu Glu Ser Gly Gly Gly Leu Val Gln Pro Gly Gly Ser Leu Arg
    130                 135                 140

Leu Ser Cys Ala Ala Ser Gly Phe Thr Phe Ser Asn Tyr Gln Met Ala
145                 150                 155                 160

Trp Val Arg Gln Ala Pro Gly Lys Gly Leu Glu Trp Val Ser Ser Ile
                165                 170                 175

Thr Ser Glu Gly Gly Ser Thr Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Pro
    210                 215                 220

Gly Lys Asn Phe Asp Tyr Trp Gly Gln Gly Thr Leu Val Thr Val Ser
225                 230                 235                 240

Ser


<210> SEQ ID NO 89
<211> LENGTH: 108
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ala Thr Tyr
            20                  25                  30

Leu Asn Trp Tyr Gln Gln Lys Pro Gly Lys Ala Pro Lys Leu Leu Ile
        35                  40                  45

Tyr Arg Ser Ser Ser Leu Gln Ser Ala Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Gln Gln Thr Tyr Ala Val Pro Pro
                85                  90                  95

Thr Phe Gly Gln Gly Thr Lys Val Glu Ile Lys Arg
            100                 105


<210> SEQ ID NO 90
<211> LENGTH: 51
<212> TYPE: DNA
<213> ORGANISM: Artificial
<220> FEATURE:
<223> OTHER INFORMATION: VH-5'-NotI PCR primer

<400> SEQUENCE: 90

gtatgtctgg cggccgcaga ggtgcagctg ttggagtctg ggggaggctt g             51


<210> SEQ ID NO 91
<211> LENGTH: 35
<212> TYPE: DNA
<213> ORGANISM: Artificial
<220> FEATURE:
<223> OTHER INFORMATION: VH-NO-XhoI PCR primer

<400> SEQUENCE: 91
```

-continued

```
tagaattctt attagctgga gacggtgacc agggt                              35


<210> SEQ ID NO 92
<211> LENGTH: 21
<212> TYPE: DNA
<213> ORGANISM: Artificial
<220> FEATURE:
<223> OTHER INFORMATION: Alpha factor sequencing primer

<400> SEQUENCE: 92

tactattgcc agcattgctg c                                             21


<210> SEQ ID NO 93
<211> LENGTH: 21
<212> TYPE: DNA
<213> ORGANISM: Artificial
<220> FEATURE:
<223> OTHER INFORMATION: AOX1 reverse primer

<400> SEQUENCE: 93

gcaaatggca ttctgacatc c                                             21


<210> SEQ ID NO 94
<211> LENGTH: 348
<212> TYPE: DNA
<213> ORGANISM: Homo sapiens

<400> SEQUENCE: 94

gaggtgcagc tgttggagtc tgggggaggc ttggtacagc ctggggggtc cctgcgtctc     60

tcctgtgcag cctccggatt caccttttct gattatgaga tgatgtgggt ccgccaggct    120

ccagggaagg gtctagagtg ggtctcaact attacttcgg atggtatttc tacatactac    180

gcagactccg tgaagggccg gttcaccatc ttccgcgaca attccaagaa cacgctgtat    240

ctgcaaatga acagcctgcg tgccgaggat accgcggtat attactgtgc gaaaagtggg    300

aggtttttg actactgggg tcagggaacc ctggtcaccg tctcgagc                348


<210> SEQ ID NO 95
<211> LENGTH: 348
<212> TYPE: DNA
<213> ORGANISM: Homo sapiens

<400> SEQUENCE: 95

ctccacgtcg acaacctcag accccctccg aaccatgtcg gaccccccag ggacgcagag     60

aggacacgtc ggaggcctaa gtggaaaaga ctaatactct actacaccca ggcggtccga    120

ggtcccttcc cagatctcac ccagagttga taatgaagcc taccataaag atgtatgatg    180

cgtctgaggc acttcccggc caagtggtag aaggcgctgt taaggttctt gtgcgacata    240

gacgtttact tgtcggacgc acggctccta tggcgccata taatgacacg cttttcaccc    300

tccaaaaaac tgatgacccc agtcccttgg gaccagtggc agagctcg                348


<210> SEQ ID NO 96
<211> LENGTH: 348
<212> TYPE: DNA
<213> ORGANISM: Homo sapiens

<400> SEQUENCE: 96

gaggtgcagc tgttggagtc tgggggaggc ttggtacagc ctggggggtc cctgcgtctc     60

tcctgtgcag cctccggatt cacctttgat aattatgaga tgacgtgggt ccgccaggct    120
```

-continued

```
ccagggaagg gtctagagtg ggtctcatct attacgagtg atggtacttc gacatactac    180

gcagactccg tgaagggccg gttcaccatc tcccgcgaca attccaagaa cacgctgtat    240

ctgcaaatga acagcctgcg tgccgaggat accgcggtat attactgtgc gaaacctaat    300

ccgccgtttg actactgggg tcagggaacc ctggtcaccg tctcgagc                 348
```

<210> SEQ ID NO 97
<211> LENGTH: 348
<212> TYPE: DNA
<213> ORGANISM: Homo sapiens

<400> SEQUENCE: 97

```
ctccacgtcg acaacctcag accccctccg aaccatgtcg gaccccccag ggacgcagag     60

aggacacgtc ggaggcctaa gtggaaacta ttaatactct actgcaccca ggcggtccga    120

ggtcccttcc cagatctcac ccagagtaga taatgctcac taccatgaag ctgtatgatg    180

cgtctgaggc acttcccggc caagtggtag agggcgctgt taaggttctt gtgcgacata    240

gacgtttact tgtcggacgc acggctccta tggcgccata taatgacacg ctttggatta    300

ggcggcaaac tgatgacccc agtcccttgg gaccagtggc agagctcg                 348
```

<210> SEQ ID NO 98
<211> LENGTH: 348
<212> TYPE: DNA
<213> ORGANISM: Homo sapiens

<400> SEQUENCE: 98

```
gaggtgcagc tgttggagtc tgggggaggc ttggtacagc ctggggggtc cctgcgtctc     60

tcctgtgcag cctccggatt cacctttgat gggtatgaga tggcgtgggt ccgccaggct    120

ccagggaagg gtctagagtg ggtctcatct attacgagtg atggtacgag tacatactac    180

gcagactccg tgaagggccg gttcaccatc tcccgcgaca attccaagaa cacgctgtat    240

ctgcaaatga acagcctgcg tgccgaggac accgcggtat attactgtgc gaaaccgggg    300

ctgcgttttg actactgggg tcagggaacc ctggtcaccg tctcgagc                 348
```

<210> SEQ ID NO 99
<211> LENGTH: 348
<212> TYPE: DNA
<213> ORGANISM: Homo sapiens

<400> SEQUENCE: 99

```
ctccacgtcg acaacctcag accccctccg aaccatgtcg gaccccccag ggacgcagag     60

aggacacgtc ggaggcctaa gtggaaacta cccatactct accgcaccca ggcggtccga    120

ggtcccttcc cagatctcac ccagagtaga taatgctcac taccatgctc atgtatgatg    180

cgtctgaggc acttcccggc caagtggtag agggcgctgt taaggttctt gtgcgacata    240

gacgtttact tgtcggacgc acggctcctg tggcgccata taatgacacg ctttggcccc    300

gacgcaaaac tgatgacccc agtcccttgg gaccagtggc agagctcg                 348
```

<210> SEQ ID NO 100
<211> LENGTH: 348
<212> TYPE: DNA
<213> ORGANISM: Homo sapiens

<400> SEQUENCE: 100

```
gaggtgcagc tgttggagtc tgggggaggc ttggtacagc ctggggggtc cctgcgtctc     60

tcctgtgcag cctccggatt cacctttaat ttgtatgaga tgacttgggt ccgccaggct    120
```

-continued ccagggaagg gtctagagtg ggtctcatct attactagtg atggtgtttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagctggg 300
gtgatttttg actactgggg tcagggaacc ctggtcaccg tctcgagc 348

<210> SEQ ID NO 101
<211> LENGTH: 348
<212> TYPE: DNA
<213> ORGANISM: Homo sapiens

<400> SEQUENCE: 101
ctccacgtcg acaacctcag accccctccg aaccatgtcg gaccccccag ggacgcagag 60
aggacacgtc ggaggcctaa gtggaaatta aacatactct actgaaccca ggcggtccga 120
ggtcccttcc cagatctcac ccagagtaga taatgatcac taccacaaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttcgaccc 300
cactaaaaac tgatgacccc agtcccttgg gaccagtggc agagctcg 348

<210> SEQ ID NO 102
<211> LENGTH: 324
<212> TYPE: DNA
<213> ORGANISM: Homo sapiens

<400> SEQUENCE: 102
gacatccaga tgacccagtc tccatcctcc ctgtctgcat ctgtaggaga ccgtgtcacc 60
atcacttgcc gggcaagtca gtttattgat acgtcgttag agtggtatca gcagaaacca 120
gggaaagccc ctaagctcct gatctatgat gggtcccatt tgcaaagtgg ggtcccatca 180
cgtttcagtg gcagtggatc tgggacagat ttcactctca ccatcagcag tctgcaacct 240
gaagatttag ctacgtacta ctgtcaacag tattgggttc ttcctctgac gttcggccaa 300
gggaccaagg tggaaatcaa acgg 324

<210> SEQ ID NO 103
<211> LENGTH: 324
<212> TYPE: DNA
<213> ORGANISM: Homo sapiens

<400> SEQUENCE: 103
ctgtaggtct actgggtcag aggtaggagg gacagacgta gacatcctct ggcacagtgg 60
tagtgaacgg cccgttcagt caaataacta tgcagcaatc tcaccatagt cgtctttggt 120
ccctttcggg gattcgagga ctagatacta cccagggtaa acgtttcacc ccagggtagt 180
gcaaagtcac cgtcacctag accctgtcta aagtgagagt ggtagtcgtc agacgttgga 240
cttctaaatc gatgcatgat gacagttgtc ataacccaag aaggagactg caagccggtt 300
ccctggttcc acctttagtt tgcc 324

<210> SEQ ID NO 104
<211> LENGTH: 351
<212> TYPE: DNA
<213> ORGANISM: Homo sapiens

<400> SEQUENCE: 104
gaggtgcagc tgttggagtc tgggggaggc ttagtacagc ctggggggtc cctgcgtctc 60

-continued

```
tcctgtgcag cctccggatt cacctttatt gcttatgata tgagttgggt ccgccaggct    120

ccagggaagg gtctggagtg ggtctcatgg attgatgagt ggggtctgca gacatactac    180

gcagactccg tgaagggccg gttcaccatc tcccgcgaca attccaagaa cacgctgtat    240

ctgcaaatga acagcctgcg tgccgaggac accgcggtat attactgtgc gaaaaagacg    300

cctgaggagt ttgactactg gggtcaggga accctggtca ccgtctcgag c             351
```

<210> SEQ ID NO 105
<211> LENGTH: 351
<212> TYPE: DNA
<213> ORGANISM: Homo sapiens

<400> SEQUENCE: 105

```
ctccacgtcg acaacctcag accccctccg aatcatgtcg gaccccccag ggacgcagag     60

aggacacgtc ggaggcctaa gtggaaataa cgaatactat actcaaccca ggcggtccga    120

ggtcccttcc cagacctcac ccagagtacc taactactca ccccagacgt ctgtatgatg    180

cgtctgaggc acttcccggc caagtggtag agggcgctgt taaggttctt gtgcgacata    240

gacgtttact tgtcggacgc acggctcctg tggcgccata taatgacacg ctttttctgc    300

ggactcctca aactgatgac cccagtccct tgggaccagt ggcagagctc g             351
```

<210> SEQ ID NO 106
<211> LENGTH: 348
<212> TYPE: DNA
<213> ORGANISM: Homo sapiens

<400> SEQUENCE: 106

```
gaggtgcagc tgttggagtc tgggggaggc ttggtacagc ctggggggtc cctgcgtctc     60

tcctgtgcag cctccggatt cacctttggt gattatgaga tgagttgggt ccgccaggct    120

ccagggaagg gtctagagtg ggtctcaggg attgatggtg agggttctga tacatactac    180

gcagactccg tgaagggccg gttcaccatc tcccgcgaca attccaagaa cacgctgtat    240

ctgcaaatga acagcctgcg tgccgaggat accgcggtat attactgtgc gaaaccgggg    300

aggagttttg actactgggg tcagggaacc ctggtcaccg tctcgagc                 348
```

<210> SEQ ID NO 107
<211> LENGTH: 348
<212> TYPE: DNA
<213> ORGANISM: Homo sapiens

<400> SEQUENCE: 107

```
ctccacgtcg acaacctcag accccctccg aaccatgtcg gaccccccag ggacgcagag     60

aggacacgtc ggaggcctaa gtggaaacca ctaatactct actcaaccca ggcggtccga    120

ggtcccttcc cagatctcac ccagagtccc taactaccac tcccaagact atgtatgatg    180

cgtctgaggc acttcccggc caagtggtag agggcgctgt taaggttctt gtgcgacata    240

gacgtttact tgtcggacgc acggctccta tggcgccata taatgacacg ctttggcccc    300

tcctcaaaac tgatgacccc agtcccttgg gaccagtggc agagctcg                 348
```

<210> SEQ ID NO 108
<211> LENGTH: 354
<212> TYPE: DNA
<213> ORGANISM: Homo sapiens

<400> SEQUENCE: 108

```
gaggtgcagc tgttggagtc tgggggaggc ttggtacagc ctggggggtc cctgcgtctc     60
```

-continued tcctgtgcag cctccggatt cacctttagg ttgtatgaga tggcgtgggt ccgccaggct 120
ccagggaagg gtctagagtg ggtctcaggg attgatattt tgggttcgag gacatactac 180
gcagactccg tgaagggccg gttcaccatc tcccgcgaca attccaagaa cacgctgtat 240
ctgcaaatga acagcctgcg tgccgaggat accgcggtat attactgtgc gaaagatctg 300
tcgtggcagg gttttgacta ctggggtcag ggaaccctgg tcaccgtctc gagc 354

<210> SEQ ID NO 109
<211> LENGTH: 354
<212> TYPE: DNA
<213> ORGANISM: Homo sapiens

<400> SEQUENCE: 109
ctccacgtcg acaacctcag acccccctccg aaccatgtcg gaccccccag ggacgcagag 60
aggacacgtc ggaggcctaa gtggaaatcc aacatactct accgcaccca ggcggtccga 120
ggtcccttcc cagatctcac ccagagtccc taactataaa acccaagctc ctgtatgatg 180
cgtctgaggc acttcccggc caagtggtag agggcgctgt taaggttctt gtgcgacata 240
gacgtttact tgtcggacgc acggctccta tggcgccata taatgacacg ctttctagac 300
agcaccgtcc caaaactgat gaccccagtc ccttgggacc agtggcagag ctcg 354

<210> SEQ ID NO 110
<211> LENGTH: 369
<212> TYPE: DNA
<213> ORGANISM: Homo sapiens

<400> SEQUENCE: 110
gaggtgcagc tgttggagtc tgggggaggc ttggtacagc ctggggggtc cctgcgtctc 60
tcctgtgcag cctccggatt caccttttct tattattcga tgtattgggt ccgccaggct 120
ccagggaagg gtctagagtg ggtctcatcg atttcgcctt ttggttgggg tacatactac 180
gcagactccg tgaagggccg gttcaccatc tcccgcgaca attccaagga cacgctgtat 240
ctgcaaatga acagcctgcg tgccgaggac accgcggtat attactgtgc gaaatatggg 300
gagacgagtg gtccgatttc tgagaatttt gactactggg gtcagggaac cctggtcacc 360
gtctcgagc 369

<210> SEQ ID NO 111
<211> LENGTH: 369
<212> TYPE: DNA
<213> ORGANISM: Homo sapiens

<400> SEQUENCE: 111
ctccacgtcg acaacctcag acccccctccg aaccatgtcg gaccccccag ggacgcagag 60
aggacacgtc ggaggcctaa gtggaaaaga ataataagct acataaccca ggcggtccga 120
ggtcccttcc cagatctcac ccagagtagc taaagcggaa aaccaacccc atgtatgatg 180
cgtctgaggc acttcccggc caagtggtag agggcgctgt taaggttcct gtgcgacata 240
gacgtttact tgtcggacgc acggctcctg tggcgccata taatgacacg ctttataccc 300
ctctgctcac caggctaaag actcttaaaa ctgatgaccc cagtcccttg ggaccagtgg 360
cagagctcg 369

<210> SEQ ID NO 112
<211> LENGTH: 348
<212> TYPE: DNA

<213> ORGANISM: Homo sapiens

<400> SEQUENCE: 112
gaggtgcagc tgttggagtc tgggggaggc ttggtacagc ctggggggtc cctgcgtctc 60
tcctgtgcag cctccggatt caccttttgg tcttatgata tgacgtgggt ccgccaggct 120
ccagggaagg gtctagagtg ggtctcatct attatggctt cgggtgatga tacatactac 180
gcagactccg tgaagggccg gttcaccatc tcccgcgaca attccaagaa cacgctgtat 240
ctgcaaatga acagcctgcg tgccgaggat accgcggtat attactgtgc gaaatgggat 300
cgggattttg actactgggg tcagggaacc ctggtcaccg tctcgagc 348

<210> SEQ ID NO 113
<211> LENGTH: 348
<212> TYPE: DNA
<213> ORGANISM: Homo sapiens

<400> SEQUENCE: 113
ctccacgtcg acaacctcag accccctccg aaccatgtcg gacccccccag ggacgcagag 60 aggacacgtc ggaggcctaa gtggaaaacc agaatactat actgcaccca ggcggtccga 120
ggtcccttcc cagatctcac ccagagtaga taataccgaa gcccactact atgtatgatg 180
cgtctgaggc acttcccggc caagtggtag agggcgctgt taaggttctt gtgcgacata 240
gacgtttact tgtcggacgc acggctccta tggcgccata taatgacacg ctttacccta 300
gccctaaaac tgatgacccc agtcccttgg gaccagtggc agagctcg 348

<210> SEQ ID NO 114
<211> LENGTH: 360
<212> TYPE: DNA
<213> ORGANISM: Homo sapiens

<400> SEQUENCE: 114
gaggtgcagc tgttggagtc tgggggaggc ttggtacagc ctggggggtc cctgcgtctc 60
tcctgtgcag cctccggatt cacctttgag gagtatgtta tgtcgtgggt ccgccaggct 120
ccagggaagg gtctggagtg ggtctcaact atttctccta ttggtctgac tacatactac 180
gcagactccg tgaagggccg gttcaccatc tcccgcgaca attccaagaa cacgctgtat 240
ctgcaaatga acagcctgcg tgccgaggac accgcggtat attactgtgc ggaatttcct 300
ttgattattc ttcctgattt tgactactgg ggtcagggaa ccctggtcac cgtctcgagc 360

<210> SEQ ID NO 115
<211> LENGTH: 360
<212> TYPE: DNA
<213> ORGANISM: Homo sapiens

<400> SEQUENCE: 115
ctccacgtcg acaacctcag accccctccg aaccatgtcg gacccccccag ggacgcagag 60 aggacacgtc ggaggcctaa gtggaaactc ctcatacaat acagcaccca ggcggtccga 120
ggtcccttcc cagacctcac ccagagttga taaagaggat aaccagactg atgtatgatg 180
cgtctgaggc acttcccggc caagtggtag agggcgctgt taaggttctt gtgcgacata 240
gacgtttact tgtcggacgc acggctcctg tggcgccata taatgacacg ccttaaagga 300
aactaataag aaggactaaa actgatgacc ccagtccctt gggaccagtg gcagagctcg 360

<210> SEQ ID NO 116
<211> LENGTH: 369

-continued

<212> TYPE: DNA
<213> ORGANISM: Homo sapiens

<400> SEQUENCE: 116
gaggtgcagc tgttggagtc tgggggaggc ctggtacagc ctggggggtc cctgcgtctc 60
tcctgtgcag cctccggatt cacctttatg gagtatgcga tgatttgggt ccgccaggct 120
ccagggaagg gtctagagtg ggtctcaatt atttctccgc ttggtttgtc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaatatcag 300
gattcgtctg atagtcagta tacgaatttt gactactggg gtcagggaac cctggtcacc 360
gtctcgagc 369

<210> SEQ ID NO 117
<211> LENGTH: 369
<212> TYPE: DNA
<213> ORGANISM: Homo sapiens

<400> SEQUENCE: 117
ctccacgtcg acaacctcag accccctccg gaccatgtcg gacccccag ggacgcagag 60 aggacacgtc ggaggcctaa gtggaaatac ctcatacgct actaaaccca ggcggtccga 120
ggtcccttcc cagatctcac ccagagttaa taaagaggcg aaccaaacag atgtatgatg 180
cgtctgaggc acttcccggc caagtggtag agggcgctgt taaggttctt gtgcgacata 240
gacgtttact tgtcggacgc acggctcctg tggcgccata taatgacacg ctttatagtc 300
ctaagcagac tatcagtcat atgcttaaaa ctgatgaccc cagtcccttg ggaccagtgg 360
cagagctcg 369

<210> SEQ ID NO 118
<211> LENGTH: 363
<212> TYPE: DNA
<213> ORGANISM: Homo sapiens

<400> SEQUENCE: 118
gaggtgcagc tgttggagtc tgggggaggc ttggtacagc ctggggggtc cctgcgtctc 60
tcctgtgcag cctccggatt cacctttgag gattatggga tggggtgggc ccgccaggct 120
ccagggaagg gtctagagtg ggtctcaagt attggtcctc tgggtctttg gacatactac 180
gcagactccg cgaagggccg gttcaccatc tcccgcgaca attccaagaa cacgctgtat 240
ctgcaaatga acagcctgcg tgccgaggac accgcggtat attactgtgc gaaatctccg 300
cttgagggtt tgattacgaa ttttgactac tggggtcagg gaaccctggt caccgtctcg 360
agc 363

<210> SEQ ID NO 119
<211> LENGTH: 363
<212> TYPE: DNA
<213> ORGANISM: Homo sapiens

<400> SEQUENCE: 119
ctccacgtcg acaacctcag accccctccg aaccatgtcg gacccccag ggacgcagag 60 aggacacgtc ggaggcctaa gtggaaactc ctaataccct accccacccg ggcggtccga 120
ggtcccttcc cagatctcac ccagagttca taaccaggag acccagaaac ctgtatgatg 180
cgtctgaggc gcttcccggc caagtggtag agggcgctgt taaggttctt gtgcgacata 240

-continued gacgtttact tgtcggacgc acggctcctg tggcgccata taatgacacg ctttagaggc 300
gaactcccaa actaatgctt aaaactgatg accccagtcc cttgggacca gtggcagagc 360
tcg 363

<210> SEQ ID NO 120
<211> LENGTH: 357
<212> TYPE: DNA
<213> ORGANISM: Homo sapiens

<400> SEQUENCE: 120
gaggtgcagc tgttggagtc tgggggaggc ttggtacagc ctggggggtc cctgcgtctc 60
tcctgtgcag cctccggatt cacctttcct gagtatgata tgacgtgggt ccgccaggct 120
ccagggaagg gtctggagtg ggtctcatat attagttctg atggttattc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgcat 300
gggagtccgc gggagtttga ctactggggt cagggaaccc tggtcaccgt ctcgagc 357

<210> SEQ ID NO 121
<211> LENGTH: 357
<212> TYPE: DNA
<213> ORGANISM: Homo sapiens

<400> SEQUENCE: 121
ctccacgtcg acaacctcag accccctccg aaccatgtcg gaccccccag ggacgcagag 60
aggacacgtc ggaggcctaa gtggaaagga ctcatactat actgcaccca ggcggtccga 120
ggtcccttcc cagacctcac ccagagtata taatcaagac taccaataag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggcgta 300
ccctcaggcg ccctcaaact gatgacccca gtcccttggg accagtggca gagctcg 357

<210> SEQ ID NO 122
<211> LENGTH: 348
<212> TYPE: DNA
<213> ORGANISM: Homo sapiens

<400> SEQUENCE: 122
gaggtgcagc tgttggagtc tgggggaggc ttggtacagc ctggggggtc cctgcgtctc 60
tcctgtgcag cctccggatt cccctttccg cagtatcaga tggcgtgggt ccgccaggct 120
ccagggaagg gtctagagtg ggtctcaatg attacttctg atggtcttga tacatattac 180
gcagactccg tgaagggccg gttcaccatc tcccgcgaca attccaagaa cacgctgtat 240
ctgcaaatga acagcctgcg tgccgaggat accgcggtat attactgtgc gaaacctgag 300 cctcttttg actactgggg tcagggaacc ctggtcaccg tctcgagc 348

<210> SEQ ID NO 123
<211> LENGTH: 348
<212> TYPE: DNA
<213> ORGANISM: Homo sapiens

<400> SEQUENCE: 123
ctccacgtcg acaacctcag accccctccg aaccatgtcg gaccccccag ggacgcagag 60
aggacacgtc ggaggcctaa ggggaaaggc gtcatagtct accgcaccca ggcggtccga 120
ggtcccttcc cagatctcac ccagagttac taatgaagac taccagaact atgtataatg 180

-continued

```
cgtctgaggc acttcccggc caagtggtag agggcgctgt taaggttctt gtgcgacata    240

gacgtttact tgtcggacgc acggctccta tggcgccata taatgacacg ctttggactc    300

ggagaaaaac tgatgacccc agtcccttgg gaccagtggc agagctcg                 348


<210> SEQ ID NO 124
<211> LENGTH: 348
<212> TYPE: DNA
<213> ORGANISM: Homo sapiens

<400> SEQUENCE: 124

gaggtgcagc tgttggagtc tgggggaggc ttggtacagc ctggggggtc cctgcgtctc     60

tcctgtgcag cctccggatt caccttttcg ggttatcaga tggcttgggt ccgccaggct    120

ccagggaagg gtctagagtg ggtctcaggt attagttcgg agggtcttac tacatactac    180

gcagactccg tgaagggccg gttcaccatc tcccgcgaca attccaagaa cacgctgtat    240

ctgcaaatga acagcctgcg tgccgaggac accgcggtat attactgtgc gaaattgggg    300

cgtaggtttg actactgggg tcagggaacc ctggtcaccg tctcgagc                 348


<210> SEQ ID NO 125
<211> LENGTH: 348
<212> TYPE: DNA
<213> ORGANISM: Homo sapiens

<400> SEQUENCE: 125

ctccacgtcg acaacctcag accccctccg aaccatgtcg gaccccccag ggacgcagag     60

aggacacgtc ggaggcctaa gtggaaaagc ccaatagtct accgaaccca ggcggtccga    120

ggtcccttcc cagatctcac ccagagtcca taatcaagcc tcccagaatg atgtatgatg    180

cgtctgaggc acttcccggc caagtggtag agggcgctgt taaggttctt gtgcgacata    240

gacgtttact tgtcggacgc acggctcctg tggcgccata taatgacacg ctttaacccc    300

gcatccaaac tgatgacccc agtcccttgg gaccagtggc agagctcg                 348


<210> SEQ ID NO 126
<211> LENGTH: 360
<212> TYPE: DNA
<213> ORGANISM: Homo sapiens

<400> SEQUENCE: 126

gaggtgcagc tgttggagtc tgggggaggc ttggtacagc ctggggggtc cctgcgtctc     60

tcctgtgcag cctccggatt cacctttgcg aattatgaga tggggtgggc ccgccaggct    120

ccagggaagg gtctagagtg ggtctcagtt atttctgagt ggggttattc tacatactac    180

gcagactccg cgaagggccg gttcaccatc tcccgcgaca attccaagaa cacgctgtat    240

ctgcaaatga acagcctgcg tgccgaggac accgcggtat attactgtgc gaaacttgtg    300

ggtgggactc agtatgagtt tgactactgg ggtcagggaa ccctggtcac cgtctcgagc    360


<210> SEQ ID NO 127
<211> LENGTH: 360
<212> TYPE: DNA
<213> ORGANISM: Homo sapiens

<400> SEQUENCE: 127

ctccacgtcg acaacctcag accccctccg aaccatgtcg gaccccccag ggacgcagag     60

aggacacgtc ggaggcctaa gtggaaacgc ttaatactct accccacccg ggcggtccga    120
```

-continued ggtcccttcc cagatctcac ccagagtcaa taaagactca ccccaataag atgtatgatg 180
cgtctgaggc gcttcccggc caagtggtag agggcgctgt taaggttctt gtgcgacata 240
gacgtttact tgtcggacgc acggctcctg tggcgccata taatgacacg ctttgaacac 300
ccaccctgag tcatactcaa actgatgacc ccagtccctt gggaccagtg gcagagctcg 360

<210> SEQ ID NO 128
<211> LENGTH: 348
<212> TYPE: DNA
<213> ORGANISM: Homo sapiens

<400> SEQUENCE: 128
gaggtgcagc tgttggagtc tgggggaggc ttggtacagc ctgggggggtc cctgcgtctc 60 tcctgtgcag cctccggatt cacctttcat aattatgaga tgtcgtgggt ccgccaggct 120
ccagggaagg gtctagagtg ggtctcaagt atttcttcgg gtggttcttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
gttaagtttg actactgggg tcagggaacc ctggtcaccg tctcgagc 348

<210> SEQ ID NO 129
<211> LENGTH: 348
<212> TYPE: DNA
<213> ORGANISM: Homo sapiens

<400> SEQUENCE: 129
ctccacgtcg acaacctcag accccctccg aaccatgtcg gacccccccag ggacgcagag 60 aggacacgtc ggaggcctaa gtggaaagta ttaatactct acagcaccca ggcggtccga 120
ggtcccttcc cagatctcac ccagagttca taaagaagcc caccaagaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggcccc 300
caattcaaac tgatgacccc agtcccttgg gaccagtggc agagctcg 348

<210> SEQ ID NO 130
<211> LENGTH: 348
<212> TYPE: DNA
<213> ORGANISM: Homo sapiens

<400> SEQUENCE: 130
gaggtgcagc tgttggagtc cgggggaggc ttggtacagc ctgggggggtc cctgcgtctc 60 tcctgtgcag cctccggatt cacctttggg ctgtatgaga tgacgtgggt ccgccaggct 120
ccagggaagg gtctagagtg ggtctcaagt attacgggtg atggtatttc gacatactac 180
gcagactccg tgaagggccg gttcaccatc tcccgcgaca attccaggaa cacgctgtat 240
ctgcaaatga acagcctgcg tgccgaggac accgcggtat attactgtgc gaaagctggg 300
aggaagtttg actactgggg tcagggaacc ctggtcaccg tctcgagc 348

<210> SEQ ID NO 131
<211> LENGTH: 348
<212> TYPE: DNA
<213> ORGANISM: Homo sapiens

<400> SEQUENCE: 131
ctccacgtcg acaacctcag gccccctccg aaccatgtcg gacccccccag ggacgcagag 60 aggacacgtc ggaggcctaa gtggaaaccc gacatactct actgcaccca ggcggtccga 120

-continued ggtcccttcc cagatctcac ccagagttca taatgcccac taccataaag ctgtatgatg 180
cgtctgaggc acttcccggc caagtggtag agggcgctgt taaggtcctt gtgcgacata 240
gacgtttact tgtcggacgc acggctcctg tggcgccata taatgacacg ctttcgaccc 300
tccttcaaac tgatgacccc agtcccttgg gaccagtggc agagctcg 348

<210> SEQ ID NO 132
<211> LENGTH: 348
<212> TYPE: DNA
<213> ORGANISM: Homo sapiens

<400> SEQUENCE: 132
gaggtgcagc tgttggagtc tgggggaggc ttggtacagc ctggggggtc cctgcgtctc 60
tcctgtgcag cctccggatt cacctttagt aattatcaga tggcgtgggt ccgccaggct 120
ccagggaagg gtctagagtg ggtctcaagt attactagtg agggtggttc gacatactac 180
gcagactccg tgaagggccg gttcaccatc tcccgcgaca attccaagaa cacactgtat 240
ctgcaaatga acagcctgcg tgccgaggac accgcggtat attactgtgc gaaaccgggt 300
aagaattttg actactgggg tcagggaacc ctggtcaccg tctcgagc 348

<210> SEQ ID NO 133
<211> LENGTH: 348
<212> TYPE: DNA
<213> ORGANISM: Homo sapiens

<400> SEQUENCE: 133
ctccacgtcg acaacctcag accccctccg aaccatgtcg gaccccccag ggacgcagag 60
aggacacgtc ggaggcctaa gtggaaatca ttaatagtct accgcaccca ggcggtccga 120
ggtcccttcc cagatctcac ccagagttca taatgatcac tcccaccaag ctgtatgatg 180
cgtctgaggc acttcccggc caagtggtag agggcgctgt taaggttctt gtgtgacata 240
gacgtttact tgtcggacgc acggctcctg tggcgccata taatgacacg ctttggccca 300
ttcttaaaac tgatgacccc agtcccttgg gaccagtggc agagctcg 348

<210> SEQ ID NO 134
<211> LENGTH: 348
<212> TYPE: DNA
<213> ORGANISM: Homo sapiens

<400> SEQUENCE: 134
gaggtgcagc tgttggagtc tgggggaggc ttggtacagc ctggggggtc cctgcgtctc 60
tcctgtgcag cctccggatt cacctttgat aattatgaga tgacgtgggt ccgccaggct 120
ccagggaagg gtctagagtg ggtctcaact attacgtcgc agggtactag tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctgat 300
cgttcttttg actactgggg tcagggaacc ctggtcaccg tctcgagc 348

<210> SEQ ID NO 135
<211> LENGTH: 348
<212> TYPE: DNA
<213> ORGANISM: Homo sapiens

<400> SEQUENCE: 135
ctccacgtcg acaacctcag accccctccg aaccatgtcg gaccccccag ggacgcagag 60

-continued

```
aggacacgtc ggaggcctaa gtggaaacta ttaatactct actgcaccca ggcggtccga    120

ggtcccttcc cagatctcac ccagagttga taatgcagcg tcccatgatc atgtatgatg    180

cgtctgaggc acttcccggc caagtggtag agggcgctgt taaggttctt gtgcgacata    240

gacgtttact tgtcggacgc acggctcctg tggcgccata taatgacacg ctttggacta    300

gcaagaaaac tgatgacccc agtcccttgg gaccagtggc agagctcg                 348
```

```
<210> SEQ ID NO 136
<211> LENGTH: 348
<212> TYPE: DNA
<213> ORGANISM: Homo sapiens

<400> SEQUENCE: 136

gaggtgcagc tgttggagtc tgggggaggc ttggtacagc ctggggggtc cctgcgtctc     60

tcctgtgcag cctccggatt cacctttcgt agttatgaga tgacttgggt ccgccaggct    120

ccagggaagg gtctggagtg ggtctcatct attacgtcgg atggtggtac tacatactac    180

gcagactccg tgaagggccg gttcaccatc tcccgcgaca attccaagaa cacgctgtat    240

ctgcaaatga acagcctgcg tgccgaggac accgcggtat attactgtgc gaaacctgat    300

aagacgtttg actactgggg tcagggaacc ctggtcaccg tctcgagc                 348
```

```
<210> SEQ ID NO 137
<211> LENGTH: 348
<212> TYPE: DNA
<213> ORGANISM: Homo sapiens

<400> SEQUENCE: 137

ctccacgtcg acaacctcag accccctccg aaccatgtcg gaccccccag ggacgcagag     60

aggacacgtc ggaggcctaa gtggaaagca tcaatactct actgaaccca ggcggtccga    120

ggtcccttcc cagacctcac ccagagtaga taatgcagcc taccaccatg atgtatgatg    180

cgtctgaggc acttcccggc caagtggtag agggcgctgt taaggttctt gtgcgacata    240

gacgtttact tgtcggacgc acggctcctg tggcgccata taatgacacg ctttggacta    300

ttctgcaaac tgatgacccc agtcccttgg gaccagtggc agagctcg                 348
```

```
<210> SEQ ID NO 138
<211> LENGTH: 348
<212> TYPE: DNA
<213> ORGANISM: Homo sapiens

<400> SEQUENCE: 138

gaggtgcagc tgttggagtc tgggggaggc ttggtacagc ctggggggtc cctgcgtctc     60

tcctgtgcag cctccggatt cacctttaat ttgtatgaga tgacttgggt ccgccaggct    120

ccagggaagg gtctagagtg ggtctcatct attactagtg atggtgtttc tacatactac    180

gcagactccg tgaagggccg gttcaccatc tcccgcgaca attccaagaa cacgctgtat    240

ctgcaaatga acagcctgcg tgccgaggac accgcggtat attactgtgc gaaaccggat    300

tctccgtttg actactgggg tcagggaacc ctggtcaccg tctcgagc                 348
```

```
<210> SEQ ID NO 139
<211> LENGTH: 348
<212> TYPE: DNA
<213> ORGANISM: Homo sapiens

<400> SEQUENCE: 139

ctccacgtcg acaacctcag accccctccg aaccatgtcg gaccccccag ggacgcagag     60
```

-continued

```
aggacacgtc ggaggcctaa gtggaaatta aacatactct actgaaccca ggcggtccga    120

ggtcccttcc cagatctcac ccagagtaga taatgatcac taccacaaag atgtatgatg    180

cgtctgaggc acttcccggc caagtggtag agggcgctgt taaggttctt gtgcgacata    240

gacgtttact tgtcggacgc acggctcctg tggcgccata taatgacacg ctttggccta    300

agaggcaaac tgatgacccc agtcccttgg gaccagtggc agagctcg                 348
```

<210> SEQ ID NO 140
<211> LENGTH: 348
<212> TYPE: DNA
<213> ORGANISM: Homo sapiens

<400> SEQUENCE: 140

```
gaggtgcagc tgttggagtc tgggggaggc ttggtacagc ctggggggtc cctgcgtctc     60

tcctgtgcag cctccggatt cacctttggg cattatgata tggcttgggt ccgccaggct    120

ccagggaagg gtctagagtg ggtctcaact attagtgata atggtaatgg gacatactac    180

gcagactccg tgaagggccg gttcaccatc tcccgcgaca attccaagaa cacgctgtat    240

ctgcaaatga acagcctgcg tgccgaggac accgcggtat attactgtgc gaaaccgggg    300

cgtgattttg actactgggg tcagggaacc ctggtcaccg tctcgagc                 348
```

<210> SEQ ID NO 141
<211> LENGTH: 348
<212> TYPE: DNA
<213> ORGANISM: Homo sapiens

<400> SEQUENCE: 141

```
ctccacgtcg acaacctcag accccctccg aaccatgtcg gacccccag ggacgcagag      60

aggacacgtc ggaggcctaa gtggaaaccc gtaatactat accgaaccca ggcggtccga    120

ggtcccttcc cagatctcac ccagagttga taatcactat taccattacc ctgtatgatg    180

cgtctgaggc acttcccggc caagtggtag agggcgctgt taaggttctt gtgcgacata    240

gacgtttact tgtcggacgc acggctcctg tggcgccata taatgacacg ctttggcccc    300

gcactaaaac tgatgacccc agtcccttgg gaccagtggc agagctcg                 348
```

<210> SEQ ID NO 142
<211> LENGTH: 348
<212> TYPE: DNA
<213> ORGANISM: Homo sapiens

<400> SEQUENCE: 142

```
gaggtgcagc tgttggagtc tgggggaggc ttggtacagc ctggggggtc cctgcgtctc     60

tcctgtgcag cctccggatt cacctttggt cgttatcaga tggcttgggt ccgccaggct    120

ccagggaagg gtctagagtg ggtctcatct atttcttctg atggtggggg gacatactac    180

gcagactccg tgaagggccg gttcaccatc tcccgcgaca attccaagaa cacgctgtat    240

ctgcaaatga acagcctgcg tgccgaggat accgcggtat attactgtgc gaaacctggg    300

cgggcgtttg actactgggg tcagggaacc ctggtcaccg tctcgagc                 348
```

<210> SEQ ID NO 143
<211> LENGTH: 348
<212> TYPE: DNA
<213> ORGANISM: Homo sapiens

<400> SEQUENCE: 143

-continued

```
ctccacgtcg acaacctcag accccctccg aaccatgtcg gaccccccag ggacgcagag     60

aggacacgtc ggaggcctaa gtggaaacca gcaatagtct accgaaccca ggcggtccga    120

ggtcccttcc cagatctcac ccagagtaga taaagaagac taccaccccc ctgtatgatg    180

cgtctgaggc acttcccggc caagtggtag agggcgctgt taaggttctt gtgcgacata    240

gacgtttact tgtcggacgc acggctccta tggcgccata taatgacacg ctttggaccc    300

gcccgcaaac tgatgacccc agtcccttgg gaccagtggc agagctcg                 348
```

<210> SEQ ID NO 144
<211> LENGTH: 348
<212> TYPE: DNA
<213> ORGANISM: Homo sapiens

<400> SEQUENCE: 144

```
gaggtgcagc tgttggagtc tgggggaggc ttggtacagc ctggggggtc cctgcgtctc     60

tcctgtgcag cctccggatt cacctttgcg aggtatcaga tggcttgggt ccgccaggct    120

ccagggaagg gtctggagtg ggtctcaact atttctgatg atggtgattc gacatactac    180

gcagactccg tgaagggccg gttcaccatc tcccgcgaca attccaagaa cacgctgtat    240

ctgcaaatga acagcctgcg tgccgaggac accgcggtat attactgtgc gaaactggat    300

aagttgtttg actactgggg tcagggaacc ctggtcaccg tctcgagc                 348
```

<210> SEQ ID NO 145
<211> LENGTH: 348
<212> TYPE: DNA
<213> ORGANISM: Homo sapiens

<400> SEQUENCE: 145

```
ctccacgtcg acaacctcag accccctccg aaccatgtcg gaccccccag ggacgcagag     60

aggacacgtc ggaggcctaa gtggaaacgc tccatagtct accgaaccca ggcggtccga    120

ggtcccttcc cagacctcac ccagagttga taaagactac taccactaag ctgtatgatg    180

cgtctgaggc acttcccggc caagtggtag agggcgctgt taaggttctt gtgcgacata    240

gacgtttact tgtcggacgc acggctcctg tggcgccata taatgacacg ctttgaccta    300

ttcaacaaac tgatgacccc agtcccttgg gaccagtggc agagctcg                 348
```

<210> SEQ ID NO 146
<211> LENGTH: 348
<212> TYPE: DNA
<213> ORGANISM: Homo sapiens

<400> SEQUENCE: 146

```
gaggtgcagc tgttggagtc tgggggaggc ttggtacagc ctggggggtc cctgcgtctc     60

tcctgtgcag cctccggatt cacctttgag gagtatcaga tggcgtgggt ccgccaggct    120

ccagggaagg gtctagagtg ggtctcaacg atttcggatg atggttcttc gacatactac    180

gcagactccg tgaagggccg gttcaccatc tcccgcgaca attccaagaa cacgctgtat    240

ctgcaaatga acagcctgcg tgccgaggac accgcggtat attactgtgc gaaacctgat    300

ctttattttg actactgggg tcagggaacc ctggtcaccg tctcgagc                 348
```

<210> SEQ ID NO 147
<211> LENGTH: 348
<212> TYPE: DNA
<213> ORGANISM: Homo sapiens

<400> SEQUENCE: 147

-continued ctccacgtcg acaacctcag accccctccg aaccatgtcg gaccccccag ggacgcagag 60
aggacacgtc ggaggcctaa gtggaaactc ctcatagtct accgcaccca ggcggtccga 120
ggtcccttcc cagatctcac ccagagttgc taaagcctac taccaagaag ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggacta 300
gaaataaaac tgatgacccc agtcccttgg gaccagtggc agagctcg 348

<210> SEQ ID NO 148
<211> LENGTH: 348
<212> TYPE: DNA
<213> ORGANISM: Homo sapiens

<400> SEQUENCE: 148
gaggtgcagc tgttggagtc tgggggaggc ttggtacagc ctggggggtc cctgcgtctc 60
tcctgtgcag cctccggatt cacctttgag gtgtatcaga tgggttgggt ccgccaggct 120
ccagggaagg gtctagagtg ggtctcattt attgtgcctg gggtgattt gacatactac 180 gcagactccg tgaagggccg gttcaccatc tcccgcgaca attccaagaa cacgctgtat 240
ctgcaaatga acagcctgcg tgccgaggac accgcggtat attactgtgc ggaaacgtgg 300
ccggagtttg actactgggg tcagggaacc ctggtcaccg tctcgagc 348

<210> SEQ ID NO 149
<211> LENGTH: 348
<212> TYPE: DNA
<213> ORGANISM: Homo sapiens

<400> SEQUENCE: 149
ctccacgtcg acaacctcag accccctccg aaccatgtcg gaccccccag ggacgcagag 60
aggacacgtc ggaggcctaa gtggaaactc cacatagtct acccaaccca ggcggtccga 120
ggtcccttcc cagatctcac ccagagtaaa taacacggac cccccactaaa ctgtatgatg 180 cgtctgaggc acttcccggc caagtggtag agggcgctgt taaggttctt gtgcgacata 240
gacgtttact tgtcggacgc acggctcctg tggcgccata taatgacacg cctttgcacc 300
ggcctcaaac tgatgacccc agtcccttgg gaccagtggc agagctcg 348

<210> SEQ ID NO 150
<211> LENGTH: 324
<212> TYPE: DNA
<213> ORGANISM: Homo sapiens

<400> SEQUENCE: 150
gacatccaga tgacccagtc tccatcctcc ctgtctgcat ctgtaggaga ccgtgtcacc 60
atcacttgcc gggcaagtca gacgattggg gagagtttac attggtacca gcagaaacca 120
gggaaagccc ctaggctcct gatctatttt gcttccctgt tgcaaagtgg ggtcccatcg 180
cgtttcagtg gcagtggatc tgggacagat tttactctca ccatcagcag tctgcaacct 240
gaagattttg ctacgtacta ctgtcaacag catcatatgc ttccttctac gttcggccaa 300
gggaccaagg tggaaatcaa acgg 324

<210> SEQ ID NO 151
<211> LENGTH: 324
<212> TYPE: DNA
<213> ORGANISM: Homo sapiens -continued

<400> SEQUENCE: 151
ctgtaggtct actgggtcag aggtaggagg gacagacgta gacatcctct ggcacagtgg 60
tagtgaacgg cccgttcagt ctgctaaccc ctctcaaatg taaccatggt cgtctttggt 120
ccctttcggg gatccgagga ctagataaaa cgaagggaca acgtttcacc ccagggtagc 180
gcaaagtcac cgtcacctag accctgtcta aaatgagagt ggtagtcgtc agacgttgga 240
cttctaaaac gatgcatgat gacagttgtc gtagtatacg aaggaagatg caagccggtt 300
ccctggttcc acctttagtt tgcc 324

<210> SEQ ID NO 152
<211> LENGTH: 324
<212> TYPE: DNA
<213> ORGANISM: Homo sapiens

<400> SEQUENCE: 152
gacatccaga tgacccagtc tccatcctcc ctgtctgcat ctgtaggaga ccgtgtcacc 60
atcacttgcc gggcaagtca gtggattggt gatagtttat cttggtacca gcagaaacca 120
gggaaagccc ctaagctcct gatctatttt gcttcctatt tgcaaagtgg ggtcccaaca 180
cgtttcagtg gcagtggatc tgggacagat ttcactctca ccatcagcag tctgcaacct 240
gaagattttg ctacgtacta ctgtcaacag tattttgaga atcctgttac gttcggccaa 300
gggaccaagg tgggaatcaa acgg 324

<210> SEQ ID NO 153
<211> LENGTH: 324
<212> TYPE: DNA
<213> ORGANISM: Homo sapiens

<400> SEQUENCE: 153
ctgtaggtct actgggtcag aggtaggagg gacagacgta gacatcctct ggcacagtgg 60
tagtgaacgg cccgttcagt cacctaacca ctatcaaata gaaccatggt cgtctttggt 120
ccctttcggg gattcgagga ctagataaaa cgaaggataa acgtttcacc ccagggttgt 180
gcaaagtcac cgtcacctag accctgtcta aagtgagagt ggtagtcgtc agacgttgga 240
cttctaaaac gatgcatgat gacagttgtc ataaaactct taggacaatg caagccggtt 300
ccctggttcc acccttagtt tgcc 324

<210> SEQ ID NO 154
<211> LENGTH: 324
<212> TYPE: DNA
<213> ORGANISM: Homo sapiens

<400> SEQUENCE: 154
gacatccaaa tgacccagtc tccatcctcc ctgtctgcat ctgtaggaga ccgtgtcacc 60
atcacttgcc gggcaagtca gtttattggt gattctttat cttggtacca gcagaaacca 120
gggaaagccc ctaagctcct gatctatttt tcttccattt tgcaaagtgg ggtcccatca 180
cgtttcagtg gcagtggatc tgggacagat ttcactctca ccatcagcag tctgcaacct 240
gaagattttg ctacgtacta ctgtcaacag tatatggata ttcctattac gttcggccaa 300
gggaccaagg tggaaatcaa acgg 324

<210> SEQ ID NO 155
<211> LENGTH: 324
<212> TYPE: DNA
<213> ORGANISM: Homo sapiens -continued

<400> SEQUENCE: 155
ctgtaggttt actgggtcag aggtaggagg gacagacgta gacatcctct ggcacagtgg 60
tagtgaacgg cccgttcagt caaataacca ctaagaaata gaaccatggt cgtctttggt 120
ccctttcggg gattcgagga ctagataaaa agaaggtaaa acgtttcacc ccagggtagt 180
gcaaagtcac cgtcacctag accctgtcta aagtgagagt ggtagtcgtc agacgttgga 240
cttctaaaac gatgcatgat gacagttgtc atatacctat aaggataatg caagccggtt 300
ccctggttcc acctttagtt tgcc 324

<210> SEQ ID NO 156
<211> LENGTH: 324
<212> TYPE: DNA
<213> ORGANISM: Homo sapiens

<400> SEQUENCE: 156
gacatccaga tgacccagtc tccatcctcc ctgtctgcat ctgtaggaga ccgtgtcacc 60
atcacttgcc gggcaagtca ggatattgat cataatttag agtggtatca gcagaaacca 120
gggaaagccc ctaagctcct gatctatgat agttccatgt tgcaaagtgg ggtcccatca 180
cgtttcagtg gcagtggatc tgggacagat ttcactctca ccatcagcag tctgcaacct 240
gaagattttg ctacgtacta ctgtcaacag tatcattcta ttcctgttac gttcggccaa 300
gggaccaagg tggaaatcaa acgg 324

<210> SEQ ID NO 157
<211> LENGTH: 324
<212> TYPE: DNA
<213> ORGANISM: Homo sapiens

<400> SEQUENCE: 157
ctgtaggtct actgggtcag aggtaggagg gacagacgta gacatcctct ggcacagtgg 60
tagtgaacgg cccgttcagt cctataacta gtattaaatc tcaccatagt cgtctttggt 120
ccctttcggg gattcgagga ctagatacta tcaaggtaca acgtttcacc ccagggtagt 180
gcaaagtcac cgtcacctag accctgtcta aagtgagagt ggtagtcgtc agacgttgga 240
cttctaaaac gatgcatgat gacagttgtc atagtaagat aaggacaatg caagccggtt 300
ccctggttcc acctttagtt tgcc 324

<210> SEQ ID NO 158
<211> LENGTH: 324
<212> TYPE: DNA
<213> ORGANISM: Homo sapiens

<400> SEQUENCE: 158
gacatccaga tgacccagtc tccatcctcc ctgtctgcat ctgtaggaga ccgtgtcacc 60
atcacttgcc gggcaagtca gcagattgag acgaatttag agtggtatca gcagaaacca 120
gggaaagccc ctaagctcct gatctatgat ggttcctggt tgcaaagtgg ggtcccatca 180
cgtttcagtg gcagtggatc tgggacagat ttcactctca ccatcagcag tctgcaacct 240
gaagattttg ctacgtacta ctgtcaacag tatcatagtt tgcctgctac gttcggccaa 300
gggaccaagg tggaaatcaa acgg 324

<210> SEQ ID NO 159
<211> LENGTH: 324
<212> TYPE: DNA

-continued

<213> ORGANISM: Homo sapiens

<400> SEQUENCE: 159
ctgtaggtct actgggtcag aggtaggagg gacagacgta gacatcctct ggcacagtgg 60
tagtgaacgg cccgttcagt cgtctaactc tgcttaaatc tcaccatagt cgtctttggt 120
ccctttcggg gattcgagga ctagatacta ccaaggacca acgtttcacc ccagggtagt 180
gcaaagtcac cgtcacctag accctgtcta aagtgagagt ggtagtcgtc agacgttgga 240
cttctaaaac gatgcatgat gacagttgtc atagtatcaa acggacgatg caagccggtt 300
ccctggttcc acctttagtt tgcc 324

<210> SEQ ID NO 160
<211> LENGTH: 324
<212> TYPE: DNA
<213> ORGANISM: Homo sapiens

<400> SEQUENCE: 160
gacatccaga tgacccagtc tccatcctcc ctgtctgcat ctgtaggaga ccgtgtcacc 60
atcacttgcc gggcaagtca ggatattggt aataatttag agtggtacca gcagaaacca 120
gggaaagccc ctaggctcct gatctatcat gggtcctggt tgcaaagtgg ggtcccatcg 180
cgtttcagtg gcagtggatc tgggacagat ttcactctta ccatcagcag tctgcaacct 240
gaagattttg ctacgtacta ctgtcaacag tatgatttta atcctactac gttcggccaa 300
gggaccaagg tggaaatcaa acgg 324

<210> SEQ ID NO 161
<211> LENGTH: 324
<212> TYPE: DNA
<213> ORGANISM: Homo sapiens

<400> SEQUENCE: 161
ctgtaggtct actgggtcag aggtaggagg gacagacgta gacatcctct ggcacagtgg 60
tagtgaacgg cccgttcagt cctataacca ttattaaatc tcaccatggt cgtctttggt 120
ccctttcggg gatccgagga ctagatagta cccaggacca acgtttcacc ccagggtagc 180
gcaaagtcac cgtcacctag accctgtcta aagtgagaat ggtagtcgtc agacgttgga 240
cttctaaaac gatgcatgat gacagttgtc atactaaaat taggatgatg caagccggtt 300
ccctggttcc acctttagtt tgcc 324

<210> SEQ ID NO 162
<211> LENGTH: 324
<212> TYPE: DNA
<213> ORGANISM: Homo sapiens

<400> SEQUENCE: 162
gacatccaga tgacccagtc tccatcctcc ctgtctgcat ctgtaggaga ctgtgtcacc 60
atcacttgcc gggcaagtca gaatattgat ggtctgttat ggtggtatca gcagaaacca 120
gggaaagccc ctaagctcct gatctatgcg gggtccgggt tgcaaagtgg ggtcccatca 180
cgtttcagtg gcagtggatc tgggacagat ttcactctca ccatcagcag tctgcaacct 240
gaagattttg ctacgtacta ctgtcaacag aaggcttttg agccttttac gttcggccaa 300
gggaccaagg tggaaatcaa acgg 324

<210> SEQ ID NO 163
<211> LENGTH: 324

-continued

<212> TYPE: DNA
<213> ORGANISM: Homo sapiens

<400> SEQUENCE: 163
ctgtaggtct actgggtcag aggtaggagg gacagacgta gacatcctct gacacagtgg 60
tagtgaacgg cccgttcagt cttataacta ccagacaata ccaccatagt cgtctttggt 120
ccctttcggg gattcgagga ctagatacgc cccaggccca acgtttcacc ccagggtagt 180
gcaaagtcac cgtcacctag accctgtcta aagtgagagt ggtagtcgtc agacgttgga 240
cttctaaaac gatgcatgat gacagttgtc ttccgaaaac tcggaaaatg caagccggtt 300
ccctggttcc acctttagtt tgcc 324

<210> SEQ ID NO 164
<211> LENGTH: 357
<212> TYPE: DNA
<213> ORGANISM: Homo sapiens

<400> SEQUENCE: 164
gaggtgcagc tgttggagtc tgggggaggc ttggtacagc ctggggggtc cctgcgtctc 60
tcctgtgcag cctccggatt cacctttaag gcgtatgata tgggttgggt ccgccaggct 120
ccagggaagg gtctagagtg ggtctcacag attgggaggg atggttcttt tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctcgt 300
cggtatgcta tttttacttt tgatcggggt cagggaaccc tggtcaccgt ctcgagc 357

<210> SEQ ID NO 165
<211> LENGTH: 357
<212> TYPE: DNA
<213> ORGANISM: Homo sapiens

<400> SEQUENCE: 165
ctccacgtcg acaacctcag accccctccg aaccatgtcg gacccccag ggacgcagag 60 aggacacgtc ggaggcctaa gtggaaattc cgcatactat acccaaccca ggcggtccga 120
ggtcccttcc cagatctcac ccagagtgtc taaccctccc taccaagaaa atgtatgatg 180
cgtctgaggc acttcccggc caagtggtag agggcgctgt taaggttctt gtgcgacata 240
gacgtttact tgtcggacgc acggctcctg tggcgccata taatgacacg ctttggagca 300
gccatacgat aaaaatgaaa actagcccca gtcccttggg accagtggca gagctcg 357

<210> SEQ ID NO 166
<211> LENGTH: 348
<212> TYPE: DNA
<213> ORGANISM: Homo sapiens

<400> SEQUENCE: 166
gaggtgcagc tgttggagtc tgggggaggc ttggtacagc ctggggggtc cctgcgtctc 60
tcctgtgcag cctccggatt cacctttttt gagtatgaga tgacgtgggt ccgccaggct 120
ccagggaagg gtctagagtg ggtctcatct attgcgaatg atggttcgac tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctgat 300
cggcagtttg actactgggg tcagggaacc ctggtcaccg tctcgagc 348

<210> SEQ ID NO 167

-continued

<211> LENGTH: 348
<212> TYPE: DNA
<213> ORGANISM: Homo sapiens

<400> SEQUENCE: 167
ctccacgtcg acaacctcag accccctccg aaccatgtcg gaccccccag ggacgcagag 60
aggacacgtc ggaggcctaa gtggaaaaaa ctcatactct actgcaccca ggcggtccga 120
ggtcccttcc cagatctcac ccagagtaga taacgcttac taccaagctg atgtatgatg 180
cgtctgaggc acttcccggc caagtggtag agggcgctgt taaggttctt gtgcgacata 240
gacgtttact tgtcggacgc acggctcctg tggcgccata taatgacacg ctttggacta 300
gccgtcaaac tgatgacccc agtcccttgg gaccagtggc agagctcg 348

<210> SEQ ID NO 168
<211> LENGTH: 348
<212> TYPE: DNA
<213> ORGANISM: Homo sapiens

<400> SEQUENCE: 168
gaggtgcagc tgttggagtc tgggggaggc ttggtacagc ctggggggtc cctgcgtctc 60
tcctgtgcag cctccggatt cacctttggt ccgtatgaga tgacttgggt ccgccaggct 120
ccagggaagg gtctagagtg ggtctcatcg attgttggtg atggtctgga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccggat 300
cgggtttttg actactgggg tcagggaacc ctggtcaccg tctcgagc 348

<210> SEQ ID NO 169
<211> LENGTH: 348
<212> TYPE: DNA
<213> ORGANISM: Homo sapiens

<400> SEQUENCE: 169
ctccacgtcg acaacctcag accccctccg aaccatgtcg gaccccccag ggacgcagag 60
aggacacgtc ggaggcctaa gtggaaacca ggcatactct actgaaccca ggcggtccga 120
ggtcccttcc cagatctcac ccagagtagc taacaaccac taccagacct atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccta 300
gcccaaaaac tgatgacccc agtcccttgg gaccagtggc agagctcg 348

<210> SEQ ID NO 170
<211> LENGTH: 348
<212> TYPE: DNA
<213> ORGANISM: Homo sapiens

<400> SEQUENCE: 170
gaggtgcagc tgttggagtc tgggggaggc ttggtacagc ctggggggtc cctgcgtctc 60
tcctgtgcag cctccggatt cacctttgct tcttatgaga tggcgtgggt ccgccaggct 120
ccagggaagg gtctagagtg ggtctcatcg attggtagtg atggtgggcc gacatactac 180
gcagactccg tgaagggccg gttcaccatc tcccgcgaca attccaagaa cacgctgtat 240
ctgcaaatga acagcctgcg tgccgaggac tccgcggtat attactgtgc gaaacctgat 300
agggcttttg actactgggg tcagggaacc ctggtcaccg tctcgagc 348

-continued

<210> SEQ ID NO 171
<211> LENGTH: 348
<212> TYPE: DNA
<213> ORGANISM: Homo sapiens

<400> SEQUENCE: 171
ctccacgtcg acaacctcag accccctccg aaccatgtcg gaccccccag ggacgcagag 60
aggacacgtc ggaggcctaa gtggaaacga agaatactct accgcaccca ggcggtccga 120
ggtcccttcc cagatctcac ccagagtagc taaccatcac taccacccgg ctgtatgatg 180
cgtctgaggc acttcccggc caagtggtag agggcgctgt taaggttctt gtgcgacata 240
gacgtttact tgtcggacgc acggctcctg aggcgccata taatgacacg ctttggacta 300
tcccgaaaac tgatgacccc agtcccttgg gaccagtggc agagctcg 348

<210> SEQ ID NO 172
<211> LENGTH: 357
<212> TYPE: DNA
<213> ORGANISM: Homo sapiens

<400> SEQUENCE: 172
gaggtgcagc tgttggagtc tgggggaggc ttggtacagc ctggggggtc cctgcgtctc 60
tcctgtgcag cctccggatt cacctttacg tcttatgaga tggggtgggt ccgccaggct 120
ccagggaagg gtctagagtg ggtctcatct attgagccta ctggtattac gacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctcat 300
tttactgagc ttggttttga ctactggggt cagggaaccc tggtcaccgt ctcgagc 357

<210> SEQ ID NO 173
<211> LENGTH: 357
<212> TYPE: DNA
<213> ORGANISM: Homo sapiens

<400> SEQUENCE: 173
ctccacgtcg acaacctcag accccctccg aaccatgtcg gaccccccag ggacgcagag 60
aggacacgtc ggaggcctaa gtggaaatgc agaatactct accccaccca ggcggtccga 120
ggtcccttcc cagatctcac ccagagtaga taactcggat gaccataatg ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggagta 300
aaatgactcg aaccaaaact gatgacccca gtcccttggg accagtggca gagctcg 357

<210> SEQ ID NO 174
<211> LENGTH: 360
<212> TYPE: DNA
<213> ORGANISM: Homo sapiens

<400> SEQUENCE: 174
gaggtgcagc tgttggagtc tgggggaggc ttggtacagc ctggggggtc cctgcgtctc 60
tcctgtgcag cctccggatt cacctttggt aattatgcga tggcgtgggt ccgccaggct 120
ccagggaagg gtctagagtg ggtctcaaag attggggcgc agggtcttca tacatactac 180
gcaggctccg tgaagggccg gttcaccatc tcccgcgaca attccaagaa cacgctgtat 240
ctgcaaatga acagcctgcg tgccgaggac accgcggtat attactgtgc gaaacagacg 300
acgatggatt atgagaggtt tgactactgg ggtcagggaa ccctggtcac cgtctcgagc 360

-continued

<210> SEQ ID NO 175
<211> LENGTH: 360
<212> TYPE: DNA
<213> ORGANISM: Homo sapiens

<400> SEQUENCE: 175
ctccacgtcg acaacctcag accccctccg aaccatgtcg gaccccccag ggacgcagag 60
aggacacgtc ggaggcctaa gtggaaacca ttaatacgct accgcaccca ggcggtccga 120
ggtcccttcc cagatctcac ccagagtttc taaccccgcg tcccagaagt atgtatgatg 180
cgtccgaggc acttcccggc caagtggtag agggcgctgt taaggttctt gtgcgacata 240
gacgtttact tgtcggacgc acggctcctg tggcgccata taatgacacg ctttgtctgc 300
tgctacctaa tactctccaa actgatgacc ccagtccctt gggaccagtg gcagagctcg 360

<210> SEQ ID NO 176
<211> LENGTH: 366
<212> TYPE: DNA
<213> ORGANISM: Homo sapiens

<400> SEQUENCE: 176
gaggtgcagc tgttggagtc tgggggaggc ttggtacagc ctggggggtc cctgcgtctc 60
tcctgtgcag cctccggatt cacctttgag ttgtatgcta tggcgtgggt ccgccaggct 120
ccagggaagg gtctagagtg ggtctcaggt attggtgctg tgggtgagac tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagaggct 300
aataatcttt ctgataatct tgtgtttgac tactggggtc agggaaccct ggtcaccgtc 360
tcgagc 366

<210> SEQ ID NO 177
<211> LENGTH: 366
<212> TYPE: DNA
<213> ORGANISM: Homo sapiens

<400> SEQUENCE: 177
ctccacgtcg acaacctcag accccctccg aaccatgtcg gaccccccag ggacgcagag 60
aggacacgtc ggaggcctaa gtggaaactc aacatacgat accgcaccca ggcggtccga 120
ggtcccttcc cagatctcac ccagagtcca taaccacgac acccactctg atgtatgatg 180
cgtctgaggc acttcccggc caagtggtag agggcgctgt taaggttctt gtgcgacata 240
gacgtttact tgtcggacgc acggctcctg tggcgccata taatgacacg ctttctccga 300
ttattagaaa gactattaga acacaaactg atgaccccag tcccttggga ccagtggcag 360
agctcg 366

<210> SEQ ID NO 178
<211> LENGTH: 324
<212> TYPE: DNA
<213> ORGANISM: Homo sapiens

<400> SEQUENCE: 178
gacatccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaagtgg ggtcccatca 180
cgtttcagtg gcagtggatc tgggacagat ttcactctca ccatcagcag tctgcaacct 240

-continued gaagattttg ctacgtacta ctgtcaacag tatttgcata ctccttcgac gttcggccaa 300
gggaccaagg tggaaatcaa acgg 324

<210> SEQ ID NO 179
<211> LENGTH: 324
<212> TYPE: DNA
<213> ORGANISM: Homo sapiens

<400> SEQUENCE: 179
ctgtaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgtttcacc ccagggtagt 180
gcaaagtcac cgtcacctag accctgtcta aagtgagagt ggtagtcgtc agacgttgga 240
cttctaaaac gatgcatgat gacagttgtc ataaacgtat gaggaagctg caagccggtt 300
ccctggttcc acctttagtt tgcc 324

<210> SEQ ID NO 180
<211> LENGTH: 324
<212> TYPE: DNA
<213> ORGANISM: Homo sapiens

<400> SEQUENCE: 180
gacatccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaaatgg ggtcccatca 180
cgtttcagtg gcagtggatc tgggacagat ttcactctca ccatcagcag tctgcaacct 240
gaagattttg ctacgtacta ctgtcaacag tatatgatta ctcctactac gttcggccaa 300
gggaccaagg tggaaatcaa acgg 324

<210> SEQ ID NO 181
<211> LENGTH: 324
<212> TYPE: DNA
<213> ORGANISM: Homo sapiens

<400> SEQUENCE: 181
ctgtaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgttttacc ccagggtagt 180
gcaaagtcac cgtcacctag accctgtcta aagtgagagt ggtagtcgtc agacgttgga 240
cttctaaaac gatgcatgat gacagttgtc atatactaat gaggatgatg caagccggtt 300
ccctggttcc acctttagtt tgcc 324

<210> SEQ ID NO 182
<211> LENGTH: 324
<212> TYPE: DNA
<213> ORGANISM: Homo sapiens

<400> SEQUENCE: 182
gacgtccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaagtgg ggtcccatca 180

-continued cgtttcagtg gcagtggatc tgggacagat ttcactctca ccatcagcag tctgcaacct 240
gaagattttg ctacgtacta ctgtcaacag tatatgagtg ctccttctac gttcggccaa 300
gggaccaagg tggaaatcaa acgg 324

<210> SEQ ID NO 183
<211> LENGTH: 324
<212> TYPE: DNA
<213> ORGANISM: Homo sapiens

<400> SEQUENCE: 183
ctgcaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgtttcacc ccagggtagt 180
gcaaagtcac cgtcacctag accctgtcta aagtgagagt ggtagtcgtc agacgttgga 240
cttctaaaac gatgcatgat gacagttgtc atatactcac gaggaagatg caagccggtt 300
ccctggttcc acctttagtt tgcc 324

<210> SEQ ID NO 184
<211> LENGTH: 324
<212> TYPE: DNA
<213> ORGANISM: Homo sapiens

<400> SEQUENCE: 184
gacatccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaagtgg ggtcccatca 180
cgtttcagtg gcagtggatc tgggacagat ttcactctca ccatcagcag tctgcaacct 240
gaagattctg ctacgtacta ctgtcaacag tatcagtatg ttccttctac gttcggccaa 300
gggaccaagg tggaaatcaa acag 324

<210> SEQ ID NO 185
<211> LENGTH: 324
<212> TYPE: DNA
<213> ORGANISM: Homo sapiens

<400> SEQUENCE: 185
ctgtaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgtttcacc ccagggtagt 180
gcaaagtcac cgtcacctag accctgtcta aagtgagagt ggtagtcgtc agacgttgga 240
cttctaagac gatgcatgat gacagttgtc atagtcatac aaggaagatg caagccggtt 300
ccctggttcc acctttagtt tgtc 324

<210> SEQ ID NO 186
<211> LENGTH: 324
<212> TYPE: DNA
<213> ORGANISM: Homo sapiens

<400> SEQUENCE: 186
gacatccaga tgacccagtc tccatcctcc ctgtctgcat ctgtaggaga ccgtgtcacc 60
atcacttgcc gggcaagtca gcctattgtt gatgagttag attggtacca gcagaaacca 120
gggaaagccc ctaagctcct gatctatgct gcgtccattt tgcaaagtgg ggtcccatca 180

-continued

```
cgtttcagtg gcagtggatc tgggacagat ttcactctca ccatcagcag tctgcaacct    240

gaagattttg ctacgtacta ctgtcatcag tggtctactt atcctacgac gttcggccaa    300

gggaccaagg tggaaattaa acgg                                           324
```

<210> SEQ ID NO 187
<211> LENGTH: 324
<212> TYPE: DNA
<213> ORGANISM: Homo sapiens

<400> SEQUENCE: 187

```
ctgtaggtct actgggtcag aggtaggagg gacagacgta gacatcctct ggcacagtgg     60

tagtgaacgg cccgttcagt cggataacaa ctactcaatc taaccatggt cgtctttggt    120

ccctttcggg gattcgagga ctagatacga cgcaggtaaa acgtttcacc ccagggtagt    180

gcaaagtcac cgtcacctag accctgtcta aagtgagagt ggtagtcgtc agacgttgga    240

cttctaaaac gatgcatgat gacagtagtc accagatgaa taggatgctg caagccggtt    300

ccctggttcc acctttaatt tgcc                                           324
```

<210> SEQ ID NO 188
<211> LENGTH: 324
<212> TYPE: DNA
<213> ORGANISM: Homo sapiens

<400> SEQUENCE: 188

```
gacatccaga tgacccagtc tccatcctcc ctgtctgcat ctgtaggtga ccgtgtcacc     60

atcacttgcc gggcaagtca ggatattggg tctgcgttaa ggtggtatca gcagaaacca    120

gggaaagccc ctaagctcct gatctatttg ggttccgatt tgcaaagtgg ggtcccatca    180

cgtttcagtg gcagtggatc tgggacagat ttcactctca ccatcagcag tctgcaacct    240

gaagattttg ctacgtacta ctgtcaacag acgcagtatt ttcctacgac gttcggccaa    300

gggaccaagg tggaaatcaa acgg                                           324
```

<210> SEQ ID NO 189
<211> LENGTH: 324
<212> TYPE: DNA
<213> ORGANISM: Homo sapiens

<400> SEQUENCE: 189

```
ctgtaggtct actgggtcag aggtaggagg gacagacgta gacatccact ggcacagtgg     60

tagtgaacgg cccgttcagt cctataaccc agacgcaatt ccaccatagt cgtctttggt    120

ccctttcggg gattcgagga ctagataaac ccaaggctaa acgtttcacc ccagggtagt    180

gcaaagtcac cgtcacctag accctgtcta aagtgagagt ggtagtcgtc agacgttgga    240

cttctaaaac gatgcatgat gacagttgtc tgcgtcataa aaggatgctg caagccggtt    300

ccctggttcc acctttagtt tgcc                                           324
```

<210> SEQ ID NO 190
<211> LENGTH: 324
<212> TYPE: DNA
<213> ORGANISM: Homo sapiens

<400> SEQUENCE: 190

```
gacatccaga tgacccagtc tccatcctcc ctgtctgcat ctgtaggaga ccgtgtcacc     60

atcacttgcc gggcaagtca ggcgatttat ggggggttac ggtggtacca gcagaaacca    120
```

-continued

```
gggaaagccc ctaagctcct gatctatggg gagtccatgt tgcaaagtgg ggtcccatca    180

cgtttcagtg gcagtggatc tgggacagat ttcactctca ccatcagcag tctgcatcct    240

gaagattttg ctacgtacta ctgtcaacag gtttatcata agccttttac gttcggccaa    300

gggaccaagg tggaaatcaa acgg                                           324


<210> SEQ ID NO 191
<211> LENGTH: 324
<212> TYPE: DNA
<213> ORGANISM: Homo sapiens

<400> SEQUENCE: 191

ctgtaggtct actgggtcag aggtaggagg gacagacgta gacatcctct ggcacagtgg     60

tagtgaacgg cccgttcagt ccgctaaata ccccccaatg ccaccatggt cgtctttggt    120

ccctttcggg gattcgagga ctagataccc ctcaggtaca acgtttcacc ccagggtagt    180

gcaaagtcac cgtcacctag accctgtcta aagtgagagt ggtagtcgtc agacgtagga    240

cttctaaaac gatgcatgat gacagttgtc caaatagtat tcggaaaatg caagccggtt    300

ccctggttcc acctttagtt tgcc                                           324


<210> SEQ ID NO 192
<211> LENGTH: 369
<212> TYPE: DNA
<213> ORGANISM: Homo sapiens

<400> SEQUENCE: 192

gaggtgcagc tgttggagtc tgggggaggc ttggtacagc ctggggggtc cctgcgtctc     60

tcctgtgcag cctccggatt cacctttacg gcgtatagga tggcttgggt ccgccaggct    120

ccagggaagg gtctagagtg ggtctcatgg atttcgcctt ctggttcggg gacatactac    180

gcagactccg tgaagggccg gttcaccatc tcccgcgaca attccaagaa cacgctgtat    240

ctgcaaatga acagcctgcg tgccgaggac accgcggtat attactgtgc gaaaactttg    300

acggattcgc cgtcggggca ttatgagttt gactactggg gtcagggaac cctggtcacc    360

gtctcgagc                                                            369


<210> SEQ ID NO 193
<211> LENGTH: 369
<212> TYPE: DNA
<213> ORGANISM: Homo sapiens

<400> SEQUENCE: 193

ctccacgtcg acaacctcag accccctccg aaccatgtcg gacccccccag ggacgcagag     60

aggacacgtc ggaggcctaa gtggaaatgc cgcatatcct accgaaccca ggcggtccga    120

ggtcccttcc cagatctcac ccagagtacc taaagcggaa gaccaagccc ctgtatgatg    180

cgtctgaggc acttcccggc caagtggtag agggcgctgt taaggttctt gtgcgacata    240

gacgtttact tgtcggacgc acggctcctg tggcgccata taatgacacg cttttgaaac    300

tgcctaagcg gcagccccgt aatactcaaa ctgatgaccc cagtcccttg ggaccagtgg    360

cagagctcg                                                            369


<210> SEQ ID NO 194
<211> LENGTH: 369
<212> TYPE: DNA
<213> ORGANISM: Homo sapiens

<400> SEQUENCE: 194
```

-continued

```
gaggtgcagc tgttggagtc tgggggaggc ttggtacagc ctggggggtc cctgcgtctc     60

tcctgtgcag cctccggatt cacctttgcg cggtatgaga tggggtgggt ccgccaggct    120

ccagggaagg gtctagagtg ggtctcacgg attactgctc agggtcttgg gacatactac    180

gcagactccg tgaagggccg gttcaccatc tcccgcgaca actccaagaa cacgctgtat    240

ctgcaaatga acagcctgcg tgccgaggat accgcggtat attactgtgc gaaatatctt    300

actgatttta gtagtgggca tcaggagttt gactactggg gtcagggaac cctggtcacc    360

gtctcgagc                                                            369
```

<210> SEQ ID NO 195
<211> LENGTH: 369
<212> TYPE: DNA
<213> ORGANISM: Homo sapiens

<400> SEQUENCE: 195

```
ctccacgtcg acaacctcag acccccctccg aaccatgtcg gaccccccag ggacgcagag     60

aggacacgtc ggaggcctaa gtggaaacgc gccatactct accccaccca ggcggtccga    120

ggtcccttcc cagatctcac ccagagtgcc taatgacgag tcccagaacc ctgtatgatg    180

cgtctgaggc acttcccggc caagtggtag agggcgctgt tgaggttctt gtgcgacata    240

gacgtttact tgtcggacgc acggctccta tggcgccata taatgacacg ctttatagaa    300

tgactaaaat catcacccgt agtcctcaaa ctgatgaccc cagtcccttg ggaccagtgg    360

cagagctcg                                                            369
```

<210> SEQ ID NO 196
<211> LENGTH: 369
<212> TYPE: DNA
<213> ORGANISM: Homo sapiens

<400> SEQUENCE: 196

```
gaggtgcagc tgttggagtc tgggggaggc ttggtacagc ctggggggtc cctgcgtctc     60

tcctgtgcag cctccggatt cacctttaat gattatacta tgggttgggt ccgccaggct    120

ccagggaagg gtctagagtg ggtctcatgg attcatggga ctggtggtca gacatactac    180

gcagactccg tgaagggccg gttcaccatc tcccgcgaca attccaagaa cacgctgtat    240

ctgcaaatga acagcctgcg tgccgaggac accgcggtat attactgtgc gaaagctttg    300

gctgatagga gtggggggt tgttgagttt gactactggg gtcagggaac cctggtcacc    360

gtctcgagc                                                            369
```

<210> SEQ ID NO 197
<211> LENGTH: 369
<212> TYPE: DNA
<213> ORGANISM: Homo sapiens

<400> SEQUENCE: 197

```
ctccacgtcg acaacctcag acccccctccg aaccatgtcg gaccccccag ggacgcagag     60

aggacacgtc ggaggcctaa gtggaaatta ctaatatgat acccaaccca ggcggtccga    120

ggtcccttcc cagatctcac ccagagtacc taagtaccct gaccaccagt ctgtatgatg    180

cgtctgaggc acttcccggc caagtggtag agggcgctgt taaggttctt gtgcgacata    240

gacgtttact tgtcggacgc acggctcctg tggcgccata taatgacacg ctttcgaaac    300

cgactatcct caccccccca acaactcaaa ctgatgaccc cagtcccttg ggaccagtgg    360
```

-continued cagagctcg 369

<210> SEQ ID NO 198
<211> LENGTH: 348
<212> TYPE: DNA
<213> ORGANISM: Homo sapiens

<400> SEQUENCE: 198
gaggtgcagc tgttggagtc tgggggaggc ttggtacagc ctgggggtc cctgcgtctc 60 tcctgtgcag cctccggatt caccttttct gagtatgata tgtattgggt ccgccaggct 120
ccagggaagg gtctagagtg ggtctcatgg attgatactg atggtgggga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggt 300
ctgaagtttg actactgggg tcagggaacc ctggtcaccg tctcgagc 348

<210> SEQ ID NO 199
<211> LENGTH: 348
<212> TYPE: DNA
<213> ORGANISM: Homo sapiens

<400> SEQUENCE: 199
ctccacgtcg acaacctcag accccctccg aaccatgtcg gaccccccag ggacgcagag 60
aggacacgtc ggaggcctaa gtggaaaaga ctcatactat acataaccca ggcggtccga 120
ggtcccttcc cagatctcac ccagagtacc taactatgac taccacccct atgtatgatg 180
cgtctgaggc acttcccggc caagtggtag agggcgctgt taaggttctt gtgcgacata 240
gacgtttact tgtcggacgc acggctcctg tggcgccata taatgacacg ctttggacca 300
gacttcaaac tgatgacccc agtcccttgg gaccagtggc agagctcg 348

<210> SEQ ID NO 200
<211> LENGTH: 348
<212> TYPE: DNA
<213> ORGANISM: Homo sapiens

<400> SEQUENCE: 200
gaggtgcagc tgttggagtc tgggggaggc ttggtacagc ctgggggtc cctgcgtctc 60 tcctgtgcag cctccggatt cacctttgag gtttatacta tggcgtgggt ccgccaggct 120
ccagggaagg gtctggagtg ggtctcaacg attgatgagt ctggtcgtga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggt 300
gtttggtttg actactgggg tcagggaacc ctggtcaccg tctcgagc 348

<210> SEQ ID NO 201
<211> LENGTH: 348
<212> TYPE: DNA
<213> ORGANISM: Homo sapiens

<400> SEQUENCE: 201
ctccacgtcg acaacctcag accccctccg aaccatgtcg gaccccccag ggacgcagag 60
aggacacgtc ggaggcctaa gtggaaactc caaatatgat accgcaccca ggcggtccga 120
ggtcccttcc cagacctcac ccagagttgc taactactca gaccagcact atgtatgatg 180
cgtctgaggc acttcccggc caagtggtag agggcgctgt taaggttctt gtgcgacata 240
gacgtttact tgtcggacgc acggctcctg tggcgccata taatgacacg ctttggacca 300

```
caaaccaaac tgatgacccc agtcccttgg gaccagtggc agagctcg         348

<210> SEQ ID NO 202
<211> LENGTH: 372
<212> TYPE: DNA
<213> ORGANISM: Homo sapiens

<400> SEQUENCE: 202

gaggtgcagc tgttggagtc tgggggaggc ttggtacagc ctggggggtc cctgcgtctc    60

tcctgtgcag cctccggatt cacctttctg gattatgcga tgggttgggt ccgccaggct   120

ccagggaagg gtctggagtg ggtctcaact atttctccga tgggtatggg tacatactac   180

gcagactccg tgaagggccg gttcaccatc tcccgcgaca attccaagaa cacgctgtat   240

ctgcaaatga acagcctgcg tgccgaggac accgcggtat attactgtgc gaaatcgagt   300

gctatttcgt ttacttctga tatttctaat tttgactact ggggtcaggg aaccctggtc   360

accgtctcga gc                                                       372

<210> SEQ ID NO 203
<211> LENGTH: 372
<212> TYPE: DNA
<213> ORGANISM: Homo sapiens

<400> SEQUENCE: 203

ctccacgtcg acaacctcag accccctccg aaccatgtcg gacccccag ggacgcagag     60

aggacacgtc ggaggcctaa gtggaaagac ctaatacgct acccaaccca ggcggtccga   120

ggtcccttcc cagacctcac ccagagttga taaagaggct acccataccc atgtatgatg   180

cgtctgaggc acttcccggc caagtggtag agggcgctgt taaggttctt gtgcgacata   240

gacgtttact tgtcggacgc acggctcctg tggcgccata taatgacacg ctttagctca   300

cgataaagca aatgaagact ataaagatta aaactgatga ccccagtccc ttgggaccag   360

tggcagagct cg                                                       372

<210> SEQ ID NO 204
<211> LENGTH: 360
<212> TYPE: DNA
<213> ORGANISM: Homo sapiens

<400> SEQUENCE: 204

gaggtgcagc tgttggagtc tgggggaggc ttggtacagc ctggggggtc cctgcgtctc    60

tcctgtgcag cctccggatt cacctttgct gcttatgcta tgacgtgggt ccgccaggct   120

ccagggaagg gtctagagtg ggtctcatat attagtccga atggtacggc gacatactac   180

gcagactccg tgaagggccg gttcaccatc tcccgcgaca attccaagaa cacgctgtat   240

ctgcaaatga acagcctgcg tgccgaggac accgcggtat attactgtgc ggaatatgtg   300

gggatgcgtt ggaattcttt tgactactgg ggtcagggaa ccctggtcac cgtctcgagc   360

<210> SEQ ID NO 205
<211> LENGTH: 360
<212> TYPE: DNA
<213> ORGANISM: Homo sapiens

<400> SEQUENCE: 205

ctccacgtcg acaacctcag accccctccg aaccatgtcg gacccccag ggacgcagag     60

aggacacgtc ggaggcctaa gtggaaacga cgaatacgat actgcaccca ggcggtccga   120
```

-continued ggtcccttcc cagatctcac ccagagtata taatcaggct taccatgccg ctgtatgatg 180
cgtctgaggc acttcccggc caagtggtag agggcgctgt taaggttctt gtgcgacata 240
gacgtttact tgtcggacgc acggctcctg tggcgccata taatgacacg ccttatacac 300
ccctacgcaa ccttaagaaa actgatgacc ccagtccctt gggaccagtg gcagagctcg 360

<210> SEQ ID NO 206
<211> LENGTH: 348
<212> TYPE: DNA
<213> ORGANISM: Homo sapiens

<400> SEQUENCE: 206
gaggtgcagc tgttggagtc tgggggaggc ttggtacagc ctggggggtc cctgcgtctc 60
tcctgtgcag cctccggatt caccttttcg agttatgaga tggcttgggt ccgccaggct 120
ccagggaagg gtctagagtg ggtctcatct attacgagtc ttggtacttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggt 300
aggaagtttg actactgggg tcagggaacc ctggtcaccg tctcgagc 348

<210> SEQ ID NO 207
<211> LENGTH: 348
<212> TYPE: DNA
<213> ORGANISM: Homo sapiens

<400> SEQUENCE: 207
ctccacgtcg acaacctcag accccctccg aaccatgtcg gacccccag ggacgcagag 60 aggacacgtc ggaggcctaa gtggaaaagc tcaatactct accgaaccca ggcggtccga 120
ggtcccttcc cagatctcac ccagagtaga taatgctcag aaccatgaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccca 300
tccttcaaac tgatgacccc agtcccttgg gaccagtggc agagctcg 348

<210> SEQ ID NO 208
<211> LENGTH: 348
<212> TYPE: DNA
<213> ORGANISM: Homo sapiens

<400> SEQUENCE: 208
gaggtgcagc tgttggagtc tgggggaggc ttggtacagc ctggggggtc cctgcgtctc 60
tcctgtgcag cctccggatt cacctttaat gagtatgaga tgacgtgggt ccgccaggct 120
ccagggaagg gtctagagtg ggtctcaacg attactagtg agggtagtgg gacatactac 180
gcagactccg taaagggccg gttcaccatc tcccgcgaca attccaagaa cacgctgtat 240
ctgcaaatga acagcctgcg tgccgaggac accgcggtat attactgtgc gaaacctaat 300
ggtaagtttg actactgggg tcagggaacc ctggtcaccg tctcgagc 348

<210> SEQ ID NO 209
<211> LENGTH: 348
<212> TYPE: DNA
<213> ORGANISM: Homo sapiens

<400> SEQUENCE: 209
ctccacgtcg acaacctcag accccctccg aaccatgtcg gacccccag ggacgcagag 60 aggacacgtc ggaggcctaa gtggaaatta ctcatactct actgcaccca ggcggtccga 120

-continued ggtcccttcc cagatctcac ccagagttgc taatgatcac tcccatcacc ctgtatgatg 180
cgtctgaggc atttcccggc caagtggtag agggcgctgt taaggttctt gtgcgacata 240
gacgtttact tgtcggacgc acggctcctg tggcgccata taatgacacg ctttggatta 300
ccattcaaac tgatgacccc agtcccttgg gaccagtggc agagctcg 348

<210> SEQ ID NO 210
<211> LENGTH: 348
<212> TYPE: DNA
<213> ORGANISM: Homo sapiens

<400> SEQUENCE: 210
gaggtgcagc tgttggagtc tgggggaggc ttggtacagc ctggggggtc cctgcgtctc 60
tcctgtgcag cctccggatt caccttttct gattatgaga tgttgtgggt ccgccaggct 120
ccagggaagg gtctggagtg ggtctcaact attactagtg agggtcattc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggg 300
acttcgtttg actactgggg tcagggaacc ctggtcaccg tctcgagc 348

<210> SEQ ID NO 211
<211> LENGTH: 348
<212> TYPE: DNA
<213> ORGANISM: Homo sapiens

<400> SEQUENCE: 211
ctccacgtcg acaacctcag accccctccg aaccatgtcg gaccccccag ggacgcagag 60
aggacacgtc ggaggcctaa gtggaaaaga ctaatactct acaacaccca ggcggtccga 120
ggtcccttcc cagacctcac ccagagttga taatgatcac tcccagtaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggaccc 300
tgaagcaaac tgatgacccc agtcccttgg gaccagtggc agagctcg 348

<210> SEQ ID NO 212
<211> LENGTH: 348
<212> TYPE: DNA
<213> ORGANISM: Homo sapiens

<400> SEQUENCE: 212
gaggtgcagc tgttggagtc tgggggaggc ttggtacagc ctggggggtc cctgcgtctc 60
tcctgtgcag cctccggatt cacctttagt gattatgaga tgagttgggt ccgccaggct 120
ccagggaagg gtctagagtg ggtctcaacg attgattctg atggtagttt tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggt 300
gtgaagtttg actactgggg tcagggaacc ctggtcaccg tctcgagc 348

<210> SEQ ID NO 213
<211> LENGTH: 348
<212> TYPE: DNA
<213> ORGANISM: Homo sapiens

<400> SEQUENCE: 213
ctccacgtcg acaacctcag accccctccg aaccatgtcg gaccccccag ggacgcagag 60

-continued aggacacgtc ggaggcctaa gtggaaatca ctaatactct actcaaccca ggcggtccga 120
ggtcccttcc cagatctcac ccagagttgc taactaagac taccatcaaa atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccca 300
cacttcaaac tgatgacccc agtcccttgg gaccagtggc agagctcg 348

<210> SEQ ID NO 214
<211> LENGTH: 348
<212> TYPE: DNA
<213> ORGANISM: Homo sapiens

<400> SEQUENCE: 214
gaggtgcagc tgttggagtc tgggggaggc ttggtacagc ctggggggtc cctgcgtctc 60
tcctgtgcag cctccggatt cacctttaag gattatgaga tgacttgggt ccgccaggct 120
ccagggaagg gtctagagtg ggtctcatct atttcttcta ctggtcagtc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggt 300
aataagtttg actactgggg tcagggaacc ctggtcaccg tctcgagc 348

<210> SEQ ID NO 215
<211> LENGTH: 348
<212> TYPE: DNA
<213> ORGANISM: Homo sapiens

<400> SEQUENCE: 215
ctccacgtcg acaacctcag accccctccg aaccatgtcg gaccccccag ggacgcagag 60
aggacacgtc ggaggcctaa gtggaaattc ctaatactct actgaaccca ggcggtccga 120
ggtcccttcc cagatctcac ccagagtaga taaagaagat gaccagtcag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccca 300
ttattcaaac tgatgacccc agtcccttgg gaccagtggc agagctcg 348

<210> SEQ ID NO 216
<211> LENGTH: 372
<212> TYPE: DNA
<213> ORGANISM: Homo sapiens

<400> SEQUENCE: 216
gaggtgcagc tgttggagtc tgggggaggc ttggtacagc ctggggggtc cctgcgtctc 60
tcctgtgcag cctccggatt cacctttctt gattatggta tggcttgggt ccgccaggct 120
ccagggaagg gtctagagtg ggtctcagct atttcgcctc ttggtcttag tacatactac 180
gcagactccg tgaagagccg gttcaccatc tcccgcgaca attccaagaa cacgctgtat 240
ctgcaaatga acagcctgcg tgccgaggat accgcggtat attactgtgc gaaagaggtg 300
agggtgggta ggggtgttca tcctccgaag tttgactact ggggtcaggg aaccctggtc 360
accgtctcga gc 372

<210> SEQ ID NO 217
<211> LENGTH: 372
<212> TYPE: DNA
<213> ORGANISM: Homo sapiens

<400> SEQUENCE: 217

-continued

```
ctccacgtcg acaacctcag accccctccg aaccatgtcg gaccccccag ggacgcagag     60

aggacacgtc ggaggcctaa gtggaaagaa ctaataccat accgaaccca ggcggtccga    120

ggtcccttcc cagatctcac ccagagtcga taaagcggag aaccagaatc atgtatgatg    180

cgtctgaggc acttctcggc caagtggtag agggcgctgt taaggttctt gtgcgacata    240

gacgtttact tgtcggacgc acggctccta tggcgccata taatgacacg ctttctccac    300

tcccacccat ccccacaagt aggaggcttc aaactgatga ccccagtccc ttgggaccag    360

tggcagagct cg                                                        372
```

```
<210> SEQ ID NO 218
<211> LENGTH: 369
<212> TYPE: DNA
<213> ORGANISM: Homo sapiens

<400> SEQUENCE: 218

gaggtgcagc tgttggagtc tgggggaggc ttggtacagc ctggggggtc cctgcgtctc     60

tcctgtgcag cctccggatt cacctttgag aattatgcta tgtcgtgggt ccgccaggct    120

ccagggaagg gtctagagtg ggtctcaacg attgctccgc tgggtgttcc gacatactac    180

gcagactccg tgaagggccg gttcaccatc tcccgcgaca attccaagaa cacgctgtat    240

ctgcaaatga acagcctgcg tgccgaggat accgcggtat attactgtgc gaaaaagaag    300

gttggggcgt ggctgcagtc gcggagtttt gactactggg gtcagggaac cctggtcacc    360

gtctcgagc                                                            369
```

```
<210> SEQ ID NO 219
<211> LENGTH: 369
<212> TYPE: DNA
<213> ORGANISM: Homo sapiens

<400> SEQUENCE: 219

ctccacgtcg acaacctcag accccctccg aaccatgtcg gaccccccag ggacgcagag     60

aggacacgtc ggaggcctaa gtggaaactc ttaatacgat acagcaccca ggcggtccga    120

ggtcccttcc cagatctcac ccagagttgc taacgaggcg acccacaagg ctgtatgatg    180

cgtctgaggc acttcccggc caagtggtag agggcgctgt taaggttctt gtgcgacata    240

gacgtttact tgtcggacgc acggctccta tggcgccata taatgacacg ctttttcttc    300

caaccccgca ccgacgtcag cgcctcaaaa ctgatgaccc cagtcccttg ggaccagtgg    360

cagagctcg                                                            369
```

```
<210> SEQ ID NO 220
<211> LENGTH: 369
<212> TYPE: DNA
<213> ORGANISM: Homo sapiens

<400> SEQUENCE: 220

gaggtgcagc tgttggagtc tgggggaggc ttggtacagc ctggggggtc cctgcgtctc     60

tcctgtgcag cctccggatt cacctttgag ggttatccta tgtcgtgggt ccgccaggct    120

ccagggaagg gtctagagtg ggtctcaact attagtcctt tgggtcctga tacatactac    180

gcagactccg tgaagggccg gttcaccatc tcccgcgaca attccaagaa cacgctgtat    240

ctgcaaatga acagcctgcg tgccgaggat accgcggtat attactgtgc gaaactgttg    300

atgggggagt atttgaattc taggacgttt gactactggg gtcagggaac cctggtcacc    360
```

-continued gtctcgagc 369

<210> SEQ ID NO 221
<211> LENGTH: 369
<212> TYPE: DNA
<213> ORGANISM: Homo sapiens

<400> SEQUENCE: 221
ctccacgtcg acaacctcag accccctccg aaccatgtcg gaccccccag ggacgcagag 60
aggacacgtc ggaggcctaa gtggaaactc ccaataggat acagcaccca ggcggtccga 120
ggtcccttcc cagatctcac ccagagttga taatcaggaa acccaggact atgtatgatg 180
cgtctgaggc acttcccggc caagtggtag agggcgctgt taaggttctt gtgcgacata 240
gacgtttact tgtcggacgc acggctccta tggcgccata taatgacacg ctttgacaac 300
taccccctca taaacttaag atcctgcaaa ctgatgaccc cagtcccttg ggaccagtgg 360
cagagctcg 369

<210> SEQ ID NO 222
<211> LENGTH: 362
<212> TYPE: DNA
<213> ORGANISM: Homo sapiens

<400> SEQUENCE: 222
tgttggagtc tgggggaggc ttggtacagc ctggggggtc cctgcgtctc tcctgtgcag 60
cctccggatt cacctttgag gcgtatccta tgtcgtgggt ccgccaggct ccagggaagg 120
gtctagagtg ggtctcaagt atttcccctc ttggtttgtg gacatactac gcagactccg 180
tgaagggccg gttcaccatc tcccgcgaca attccaagaa cacgctgtat ctgcaaatga 240
acagcctgcg tgccgaggac accgcggtat attactgtgc gaaacttagt gctggggcgg 300
agactcatgt ttatcggctt tttgactact ggggtcaggg aaccctggtc accgtctcga 360
gc 362

<210> SEQ ID NO 223
<211> LENGTH: 372
<212> TYPE: DNA
<213> ORGANISM: Homo sapiens

<400> SEQUENCE: 223
ctccacgtcg acaacctcag accccctccg aaccatgtcg gaccccccag ggacgcagag 60
aggacacgtc ggaggcctaa gtggaaactc cgcataggat acagcaccca ggcggtccga 120
ggtcccttcc cagatctcac ccagagttca taaaggggag aaccaaacac ctgtatgatg 180
cgtctgaggc acttcccggc caagtggtag agggcgctgt taaggttctt gtgcgacata 240
gacgtttact tgtcggacgc acggctcctg tggcgccata taatgacacg ctttgaatca 300
cgaccccgcc tctgagtaca aatagccgaa aaactgatga ccccagtccc ttgggaccag 360
tggcagagct cg 372

<210> SEQ ID NO 224
<211> LENGTH: 348
<212> TYPE: DNA
<213> ORGANISM: Homo sapiens

<400> SEQUENCE: 224
gaggtgcagc tgttggagtc tgggggaggc ttggtacagc ctggggggtc cctgcgtctc 60
tcctgtgcag cctccggatt cacctttttct aagtatgata tgtcttgggt ccgccaggct 120

-continued ccagggaagg gtctagagtg ggtctcaact attctggagg atggtctgac tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
cgtttgtttg actactgggg tcagggaacc ctggtcaccg tctcgagc 348

<210> SEQ ID NO 225
<211> LENGTH: 348
<212> TYPE: DNA
<213> ORGANISM: Homo sapiens

<400> SEQUENCE: 225
ctccacgtcg acaacctcag accccctccg aaccatgtcg gaccccccag ggacgcagag 60
aggacacgtc ggaggcctaa gtggaaaaga ttcatactat acagaaccca ggcggtccga 120
ggtcccttcc cagatctcac ccagagttga taagacctcc taccagactg atgtatgatg 180
cgtctgaggc acttcccggc caagtggtag agggcgctgt taaggttctt gtgcgacata 240
gacgtttact tgtcggacgc acggctcctg tggcgccata taatgacacg ctttggcccc 300
gcaaacaaac tgatgacccc agtcccttgg gaccagtggc agagctcg 348

<210> SEQ ID NO 226
<211> LENGTH: 348
<212> TYPE: DNA
<213> ORGANISM: Homo sapiens

<400> SEQUENCE: 226
gaggtgcagc tgttggagtc tgggggaggc ttggtacagc ctggggggtc cctgcgtctc 60
tcctgtgcag cctccggatt cacctttttcg gattatccta tgacgtgggt ccgccaggct 120
ccagggaagg gtctggagtg ggtctcaact attctgtctc cgggtacgga gacatactac 180
gcagactccg tgaagggccg gttcaccatc tcccgcgaca attccaagaa cacgctgtat 240
ctgcaaatga acagcctgcg tgccgaggac accgcggtat attactgtgc gaaagctgag 300
aaggattttg actactgggg tcagggaacc ctggtcaccg tctcgagc 348

<210> SEQ ID NO 227
<211> LENGTH: 348
<212> TYPE: DNA
<213> ORGANISM: Homo sapiens

<400> SEQUENCE: 227
ctccacgtcg acaacctcag accccctccg aaccatgtcg gaccccccag ggacgcagag 60
aggacacgtc ggaggcctaa gtggaaaagc ctaataggat actgcaccca ggcggtccga 120
ggtcccttcc cagacctcac ccagagttga taagacagag gcccatgcct ctgtatgatg 180
cgtctgaggc acttcccggc caagtggtag agggcgctgt taaggttctt gtgcgacata 240
gacgtttact tgtcggacgc acggctcctg tggcgccata taatgacacg ctttcgactc 300
ttcctaaaac tgatgacccc agtcccttgg gaccagtggc agagctcg 348

<210> SEQ ID NO 228
<211> LENGTH: 372
<212> TYPE: DNA
<213> ORGANISM: Homo sapiens

<400> SEQUENCE: 228
gaggtgcagc tgttggagtc tgggggaggc ttggtacagc ctggggggtc cctgcgtctc 60

-continued

```
tcctgtgcag cctcgggatt cacctttttg cagtatccga tgggttgggt ccgccaggct    120

ccagggaagg gtctagagtg ggtctcaact atttctcctg ttggtttgac tacatactac    180

gcagactccg tgaagggccg gttcaccatc tcccgcgaca attccaagaa cacgctgtat    240

ctgcaaatga acagcctgcg tgccgaggat accgcggtat attactgtgc gaaattgttt    300

gaggggtcga ggattcagcg tgatgtgggt tttgactact ggggtcaggg aaccctggtc    360

accgtctcga gc                                                         372
```

<210> SEQ ID NO 229
<211> LENGTH: 372
<212> TYPE: DNA
<213> ORGANISM: Homo sapiens

<400> SEQUENCE: 229

```
ctccacgtcg acaacctcag accccctccg aaccatgtcg gaccccccag ggacgcagag     60

aggacacgtc ggagccctaa gtggaaaaac gtcataggct acccaaccca ggcggtccga    120

ggtcccttcc cagatctcac ccagagttga taaagaggac aaccaaactg atgtatgatg    180

cgtctgaggc acttcccggc caagtggtag agggcgctgt taaggttctt gtgcgacata    240

gacgtttact tgtcggacgc acggctccta tggcgccata taatgacacg ctttaacaaa    300

ctccccagct cctaagtcgc actacaccca aaactgatga ccccagtccc ttgggaccag    360

tggcagagct cg                                                         372
```

<210> SEQ ID NO 230
<211> LENGTH: 366
<212> TYPE: DNA
<213> ORGANISM: Homo sapiens

<400> SEQUENCE: 230

```
gaggtgcagc tgttggagtc tgggggaggc ttggtacagc ctggggggtc cctgcgtctc     60

tcctgtgcag cctccggatt cacctttgag gagtatggta tggcgtgggt ccgccaggct    120

ccagggaagg gtctagagtg ggtctcaact atttctccgc tgggtatttc gacatactac    180

gcagactccg tgaagggccg gttcaccatc tcccgcgaca attccaagaa cacgctgtat    240

ctgcaaatga acagcctgcg tgccgaggac accgcggtat attactgtgc gaaacatgct    300

acgtctcagg agtctttgcg gtcttttgac tactggggtc agggaaccct ggtcaccgtc    360

tcgagc                                                                366
```

<210> SEQ ID NO 231
<211> LENGTH: 366
<212> TYPE: DNA
<213> ORGANISM: Homo sapiens

<400> SEQUENCE: 231

```
ctccacgtcg acaacctcag accccctccg aaccatgtcg gaccccccag ggacgcagag     60

aggacacgtc ggaggcctaa gtggaaactc ctcataccat accgcaccca ggcggtccga    120

ggtcccttcc cagatctcac ccagagttga taaagaggcg acccataaag ctgtatgatg    180

cgtctgaggc acttcccggc caagtggtag agggcgctgt taaggttctt gtgcgacata    240

gacgtttact tgtcggacgc acggctcctg tggcgccata taatgacacg ctttgtacga    300

tgcagagtcc tcagaaacgc cagaaaactg atgaccccag tcccttggga ccagtggcag    360

agctcg                                                                366
```

-continued

<210> SEQ ID NO 232
<211> LENGTH: 348
<212> TYPE: DNA
<213> ORGANISM: Homo sapiens

<400> SEQUENCE: 232
gaggtgcagc tgttggagtc tgggggaggc ttggtacagc ctggggggtc cctgcgtctc 60
tcctgtgcag cctccggatt cacctttgag aggtatcaga tggcgtgggt ccgccaggct 120
ccggggaagg gtctagagtg ggtctcaacg attagttctg atggtggggg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggt 300
catcggtttg actactgggg tcagggaacc ctggtcaccg tctcgagc 348

<210> SEQ ID NO 233
<211> LENGTH: 348
<212> TYPE: DNA
<213> ORGANISM: Homo sapiens

<400> SEQUENCE: 233
ctccacgtcg acaacctcag accccctccg aaccatgtcg gaccccccag ggacgcagag 60
aggacacgtc ggaggcctaa gtggaaactc tccatagtct accgcaccca ggcggtccga 120
ggccccttcc cagatctcac ccagagttgc taatcaagac taccaccccc ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggacca 300
gtagccaaac tgatgacccc agtcccttgg gaccagtggc agagctcg 348

<210> SEQ ID NO 234
<211> LENGTH: 348
<212> TYPE: DNA
<213> ORGANISM: Homo sapiens

<400> SEQUENCE: 234
gaggtgcagc tgttggagtc tgggggaggc ttggtacagc ctggggggtc cctgcgtctc 60
tcctgtgcag cctccggatt cacctttggt cgttatcaga tggcttgggt ccgccaggct 120
ccagggaagg gtctagagtg ggtctcatct atttcttctg atggtggggg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgtct 300
cgtcggtttg actactgggg tcagggaacc ctggtcaccg tctcgagc 348

<210> SEQ ID NO 235
<211> LENGTH: 348
<212> TYPE: DNA
<213> ORGANISM: Homo sapiens

<400> SEQUENCE: 235
ctccacgtcg acaacctcag accccctccg aaccatgtcg gaccccccag ggacgcagag 60
aggacacgtc ggaggcctaa gtggaaacca gcaatagtct accgaaccca ggcggtccga 120
ggtcccttcc cagatctcac ccagagtaga taaagaagac taccaccccc ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggcaga 300
gcagccaaac tgatgacccc agtcccttgg gaccagtggc agagctcg 348

-continued

<210> SEQ ID NO 236
<211> LENGTH: 369
<212> TYPE: DNA
<213> ORGANISM: Homo sapiens

<400> SEQUENCE: 236
gaggtgcagc tgttggagtc tgggggaggc ttggtacagc ctggggggtt cctgcgtctc 60
tcctgtgcag cctccggatt cacctttgag ttgtatccga tggcgtgggt ccgccaggct 120
ccagggaagg gtctggagtg ggtctcatcg atttctccgg ttggttttct gacatactac 180
gcagactccg tgaagggccg gttcaccatc tcccgcgaca attccaagaa cacgctgtat 240
ctgcaaatga acagcctgcg tgccgaggat accgcggtat attactgtgc gaaagggcat 300
gaggggtcgt atactccgcg gtcggctttt gactactggg gtcagggaac cctggtcacc 360
gtctcgagc 369

<210> SEQ ID NO 237
<211> LENGTH: 369
<212> TYPE: DNA
<213> ORGANISM: Homo sapiens

<400> SEQUENCE: 237
ctccacgtcg acaacctcag accccctccg aaccatgtcg gacccccaa ggacgcagag 60 aggacacgtc ggaggcctaa gtggaaactc aacataggct accgcaccca ggcggtccga 120
ggtcccttcc cagacctcac ccagagtagc taaagaggcc aaccaaaaga ctgtatgatg 180
cgtctgaggc acttcccggc caagtggtag agggcgctgt taaggttctt gtgcgacata 240
gacgtttact tgtcggacgc acggctccta tggcgccata taatgacacg ctttcccgta 300
ctccccagca tatgaggcgc cagccgaaaa ctgatgaccc cagtcccttg ggaccagtgg 360
cagagctcg 369

<210> SEQ ID NO 238
<211> LENGTH: 369
<212> TYPE: DNA
<213> ORGANISM: Homo sapiens

<400> SEQUENCE: 238
gaggtgcagc tgttggagtc tgggggaggc ttggtacagc ctggggggtc cctgcgtctc 60
tcctgtgcag cctccggatt cacctttgtg gcgtatccta tggcgtgggt ccgccaggct 120
ccagggaagg gtctggagtg ggtctcaact attgcgcctc tgggtggtaa tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacggccg 300
gaggggctgc agattgattc tcagaatttt gactactggg gtcagggaac cctggtcacc 360
gtctcgagc 369

<210> SEQ ID NO 239
<211> LENGTH: 369
<212> TYPE: DNA
<213> ORGANISM: Homo sapiens

<400> SEQUENCE: 239
ctccacgtcg acaacctcag accccctccg aaccatgtcg gacccccag ggacgcagag 60 aggacacgtc ggaggcctaa gtggaaacac cgcataggat accgcaccca ggcggtccga 120
ggtcccttcc cagacctcac ccagagttga taacgcggag acccaccatt atgtatgatg 180

-continued cgtctgaggc acttcccggc caagtggtag agggcgctgt taaggttctt gtgcgacata 240
gacgtttact tgtcggacgc acggctcctg tggcgccata taatgacacg ctttgccggc 300
ctccccgacg tctaactaag agtcttaaaa ctgatgaccc cagtcccttg ggaccagtgg 360
cagagctcg 369

<210> SEQ ID NO 240
<211> LENGTH: 348
<212> TYPE: DNA
<213> ORGANISM: Homo sapiens

<400> SEQUENCE: 240
gaggtgcagc tgttggagtc tgggggaggc ttggtacagc ctggggggtc cctgcgtctc 60
tcctgtgcag cctccggatt cacctttgcg ttgtatcaga tggcttgggt ccgccaggct 120
ccagggaagg gtctagagtg ggtctcatcg attgattctt ctggtagtga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctgag 300
cgtgattttg actactgggg tcagggaacc ctggtcaccg tctcgagc 348

<210> SEQ ID NO 241
<211> LENGTH: 348
<212> TYPE: DNA
<213> ORGANISM: Homo sapiens

<400> SEQUENCE: 241
ctccacgtcg acaacctcag accccctccg aaccatgtcg gaccccccag ggacgcagag 60
aggacacgtc ggaggcctaa gtggaaacgc aacatagtct accgaaccca ggcggtccga 120
ggtcccttcc cagatctcac ccagagtagc taactaagaa gaccatcact atgtatgatg 180
cgtctgaggc acttcccggc caagtggtag agggcgctgt taaggttctt gtgcgacata 240
gacgtttact tgtcggacgc acggctcctg tggcgccata taatgacacg ctttggactc 300
gcactaaaac tgatgacccc agtcccttgg gaccagtggc agagctcg 348

<210> SEQ ID NO 242
<211> LENGTH: 348
<212> TYPE: DNA
<213> ORGANISM: Homo sapiens

<400> SEQUENCE: 242
gaggtgcagc tgttggagtc tgggggaggc ttggtacagc ctggggggtc cctgcgtctc 60
tcctgtgcag cctccggatt cacctttagg cagtaccaga tggcttgggc ccgccaggct 120
ccagggaagg gtctagagtg ggtctcaacg attgcgtcgg atggtgtttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagttggt 300
cgtgattttg actactgggg tcagggaacc ctggtcaccg tctcgagc 348

<210> SEQ ID NO 243
<211> LENGTH: 348
<212> TYPE: DNA
<213> ORGANISM: Homo sapiens

<400> SEQUENCE: 243
ctccacgtcg acaacctcag accccctccg aaccatgtcg gaccccccag ggacgcagag 60

-continued aggacacgtc ggaggcctaa gtggaaatcc gtcatggtct accgaacccg ggcggtccga 120
ggtcccttcc cagatctcac ccagagttgc taacgcagcc taccacaaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttcaacca 300
gcactaaaac tgatgacccc agtcccttgg gaccagtggc agagctcg 348

<210> SEQ ID NO 244
<211> LENGTH: 324
<212> TYPE: DNA
<213> ORGANISM: Homo sapiens

<400> SEQUENCE: 244
gacatccaga tgacccagtc tccatcctcc ctgtctgcat ctgtaggaga ccgtgtcacc 60
atcacttgcc gggcaagtca gcctattggt cctgatttac tgtggtacca gcagaaacca 120
gggaaagccc ctaagctcct gatctatcag acgtccattt tgcaaagtgg ggtcccatca 180
cgtttcagtg gcagtggatc tgggacagat ttcactctca ccatcagcag tctgcaacct 240
gaagattttg ctacgtacta ctgtcaacag tattgggctt ttcctgtgac gttcggccaa 300
gggaccaagg tggaaatcaa acgg 324

<210> SEQ ID NO 245
<211> LENGTH: 324
<212> TYPE: DNA
<213> ORGANISM: Homo sapiens

<400> SEQUENCE: 245
ctgtaggtct actgggtcag aggtaggagg gacagacgta gacatcctct ggcacagtgg 60
tagtgaacgg cccgttcagt cggataacca ggactaaatg acaccatggt cgtctttggt 120
ccctttcggg gattcgagga ctagatagtc tgcaggtaaa acgtttcacc ccagggtagt 180
gcaaagtcac cgtcacctag accctgtcta aagtgagagt ggtagtcgtc agacgttgga 240
cttctaaaac gatgcatgat gacagttgtc ataacccgaa aaggacactg caagccggtt 300
ccctggttcc acctttagtt tgcc 324

<210> SEQ ID NO 246
<211> LENGTH: 288
<212> TYPE: DNA
<213> ORGANISM: Homo sapiens

<400> SEQUENCE: 246
ctccacgtcg acaacctcag accccctccg aaccatgtcg gaccccccag ggacgcagag 60
aggacacgtc ggaggcctaa gtggaaatcg tcgatacggt actcgaccca ggcggtccga 120
ggtcccttcc cagatctcac ccagagtcga taatcaccat caccaccatc gtgtatgatg 180
cgtctgaggc acttcccggc caagtggtag agggcactgt taaggttctt gtgcgacata 240
gacgtttact tgtcggacgc acggctcctg tggcgccata taatgaca 288

<210> SEQ ID NO 247
<211> LENGTH: 324
<212> TYPE: DNA
<213> ORGANISM: Homo sapiens

<400> SEQUENCE: 247
ctgtaggtct actgggtcag aggtaggagg gacagacgta gacatcctct ggcacagtgg 60
tagtgaacgg cccgttcagt ctcgtaatcg tcgataaatt taaccatggt cgtctttggt 120

-continued

```
ccctttcggg gattcgagga ctagatacga cgtaggtcaa acgtttcacc ccagggtagt    180

gcaaagtcac cgtcacctag accctgtcta aagtgagagt ggtagtcgtc agacgttgga    240

cttctaaaac gatgcatgat gacagttgtc tcaatgtcat ggggattatg caagccggtt    300

ccctggttcc acctttagtt tgcc                                           324
```